(12) United States Patent
Cabaniols et al.

(10) Patent No.: US 9,365,864 B2
(45) Date of Patent: *Jun. 14, 2016

(54) MEGANUCLEASE RECOMBINATION SYSTEM

(71) Applicant: CELLECTIS, Paris (FR)

(72) Inventors: Jean-Pierre Cabaniols, Saint Leu la Foret (FR); Andre Choulika, Paris (FR); Christophe Delenda, Paris (FR)

(73) Assignee: CELLECTIS, Paris (FR)

( * ) Notice: Subject to any disclaimer, the term of this patent is extended or adjusted under 35 U.S.C. 154(b) by 65 days.

This patent is subject to a terminal disclaimer.

(21) Appl. No.: 13/900,099

(22) Filed: May 22, 2013

(65) Prior Publication Data

US 2014/0004608 A1   Jan. 2, 2014

Related U.S. Application Data

(63) Continuation of application No. 13/125,193, filed as application No. PCT/IB2009/007526 on Oct. 23, 2009, now Pat. No. 8,476,072.

(30) Foreign Application Priority Data

Oct. 23, 2008 (EP) ..................... 08291002

(51) Int. Cl.
   *C12N 15/85* (2006.01)
   *C12N 15/90* (2006.01)
(52) U.S. Cl.
   CPC .............. *C12N 15/85* (2013.01); *C12N 15/902* (2013.01)
(58) Field of Classification Search
   None
   See application file for complete search history.

(56) References Cited

U.S. PATENT DOCUMENTS

| | | | |
|---|---|---|---|
| 2005/0064474 A1* | 3/2005 | Urnov et al. | 435/6 |
| 2005/0208489 A1* | 9/2005 | Carroll et al. | 435/6 |
| 2006/0068395 A1 | 3/2006 | Wood et al. | |
| 2006/0078552 A1 | 4/2006 | Arnould et al. | |
| 2006/0153826 A1 | 7/2006 | Arnould et al. | |
| 2006/0206949 A1 | 9/2006 | Arnould et al. | |
| 2009/0220476 A1 | 9/2009 | Paques | |
| 2009/0222937 A1 | 9/2009 | Arnould et al. | |
| 2009/0271881 A1 | 10/2009 | Arnould et al. | |
| 2010/0086533 A1 | 4/2010 | Montoya et al. | |
| 2010/0146651 A1 | 6/2010 | Smith et al. | |
| 2010/0151556 A1 | 6/2010 | Arnould et al. | |
| 2010/0167357 A1 | 7/2010 | Fajardo Sanchez et al. | |
| 2010/0203031 A1 | 8/2010 | Grizot et al. | |
| 2010/0229252 A1 | 9/2010 | Perez-Michaut | |
| 2011/0072527 A1 | 3/2011 | Duchateau et al. | |
| 2011/0091441 A1 | 4/2011 | Gouble et al. | |
| 2011/0151539 A1 | 6/2011 | Arnould et al. | |
| 2011/0158974 A1 | 6/2011 | Duchateau et al. | |
| 2011/0173710 A1 | 7/2011 | Grizot et al. | |
| 2011/0179506 A1 | 7/2011 | Grizot | |
| 2011/0179507 A1 | 7/2011 | Paques | |
| 2011/0191870 A1 | 8/2011 | Paques | |
| 2011/0207199 A1 | 8/2011 | Paques et al. | |
| 2011/0225664 A1 | 9/2011 | Smith | |
| 2011/0239319 A1 | 9/2011 | Danos et al. | |
| 2012/0159659 A1 | 6/2012 | Arnould et al. | |
| 2012/0171191 A1 | 7/2012 | Choulika et al. | |
| 2012/0244131 A1 | 9/2012 | Delacote et al. | |
| 2012/0258537 A1 | 10/2012 | Duchateau et al. | |
| 2012/0260356 A1 | 10/2012 | Choulika et al. | |
| 2012/0272348 A1 | 10/2012 | Danos et al. | |
| 2012/0288941 A1 | 11/2012 | Arnould et al. | |
| 2012/0288942 A1 | 11/2012 | Arnould et al. | |
| 2012/0288943 A1 | 11/2012 | Arnould et al. | |
| 2012/0301456 A1 | 11/2012 | Tremblay et al. | |
| 2012/0304321 A1 | 11/2012 | Arnould et al. | |
| 2012/0317664 A1 | 12/2012 | Arnould et al. | |
| 2012/0322689 A1 | 12/2012 | Epinat et al. | |
| 2012/0331574 A1 | 12/2012 | Arnould et al. | |
| 2013/0059387 A1 | 3/2013 | Smith et al. | |
| 2013/0061341 A1 | 3/2013 | Arnould et al. | |
| 2013/0067607 A1 | 3/2013 | Arnould et al. | |
| 2013/0203840 A1 | 8/2013 | Arnould et al. | |
| 2013/0209437 A1 | 8/2013 | Paques | |
| 2013/0227715 A1 | 8/2013 | Danos et al. | |
| 2013/0236946 A1 | 9/2013 | Gouble | |

FOREIGN PATENT DOCUMENTS

WO        2004 067753           8/2004
WO    WO 2004067753 A2  *    8/2004

(Continued)

OTHER PUBLICATIONS

Bibikova et al. Stimulation of homologous recombination through targeted cleavage by chimeric nucleases. Molecular and Cellular Biology, vol. 21, No. 1, pp. 289-297, Jan. 2001.*
High. Gene therapy: the moving finger. Nature, vol. 435, pp. 577 and 579, 2005.*
Porteus et al. Gene targeting using zinc finger nucleases. Nature Biotechnology, vol. 23, No. 8, pp. 967-973, Aug. 2005.*
Search Report issued Feb. 10, 2009 in European Patent Application No. 08 29 1002 submitting English translation only.
Office Action issued Mar. 26, 2012 in Chinese Patent Application No. 200980142217.3 submitting English translation only.
Office Action issued Jun. 27, 2012 in European Patent Application No. 09 760 591.9 submitting English translation only.
Office Action issued Jan. 9, 2013 in Chinese Patent Application No. 200980142217.3 submitting English translation only.

(Continued)

*Primary Examiner* — Jennifer Dunston
(74) *Attorney, Agent, or Firm* — Law Office of Salvatore Arrigo and Scott Lee, LLP

(57) ABSTRACT

The invention relates to a set of genetic constructs which allow the efficient and reproducible introduction of a specific nucleotide sequence at a fixed position in the genome by generating a double strand break at a specific position in the genome using a meganuclease and so stimulating a homologous recombination event at this locus between the genomic site and a transfected donor sequence. The present invention also relates to methods using these constructs and to these materials in the form of a kit.

19 Claims, 35 Drawing Sheets

(56) References Cited

FOREIGN PATENT DOCUMENTS

| WO | 2007 093836 | 8/2007 |
|---|---|---|
| WO | 2009118192 A1 | 10/2009 |

OTHER PUBLICATIONS

Florian M Wurm, et al. "Production of recombinant protein therapeutics in cultivated mammalian cells", Nature Biotechnology, XP2514352A, vol. 22, No. 11, Nov. 2004, pp. 1393-1398.
U.S. Appl. No. 14/064,775, filed Oct. 28, 2013, Choulika, et al.
U.S. Appl. No. 90/012,131, filed Feb. 6, 2012, Duchateau, et al.
U.S. Appl. No. 90/011,665, filed May 10, 2011, Duchateau, et al.
U.S. Appl. No. 95/002,160, filed Sep. 7, 2012, Duchateau, et al.
U.S. Appl. No. 12/692,408, filed Jan. 22, 2010, Arnould, et al.
U.S. Appl. No. 90/011,806, filed Jul. 22, 2011, Arnould, et al.
U.S. Appl. No. 13/725,798, filed Dec. 21, 2012, Arnould, et al.
U.S. Appl. No. 13/916,716, Unknown, Paques.
U.S. Appl. No. 12/527,790, filed Aug. 19, 2009, Arnould, et al.
U.S. Appl. No. 13/909,771, filed Jun. 4, 2013, Perez-Michaut.
U.S. Appl. No. 13/904,793, filed May 29, 2013, Gouble, et al.
U.S. Appl. No. 14/744,668, filed Jun. 19, 2015, Choulika, et al.
Cabaniols Jean-Pierre et al. "Robust Cell Line Development Using Meganucleases." Methods in Molecular Biology, vol. 435. pp. 31-45, XP-002514259 (2008).
Khanamad H. et al. "A novel single step double positive double negative selection strategy for beta-globin gene replacement." Biochemical and Biophysical Research Communications, vol. 345, No. 1. pp. 14-20, XP 24925048 (Jun. 23, 2006).
Huang Ying et al. "An efficient and targeted gene integration system for high-level antibody expression." Journal of Immunological Methods, vol. 322, No. 1-2. pp. 28-39, XP 22040562 (Apr. 14, 2007).
Perez Christophe et al. "Factors affecting double-strand break-induced homologous recombination in mammalian cells." Biotechniques, vol. 39, No. 1. pp. 109-115, XP 8065842 (Jul. 1, 2005).
Gouble Agnes et al. "Efficient in toto targeted recombination in mouse liver by meganuclease-induced double-strand break." Journal of Gene Medicine, vol. 8, No. 5. pp. 616-622, XP 2427714 (May 1, 2006).
Anonymous. "Cellectis BioResearch, a subsidiary of Cellectis S. A., announces the market launch of a first revolutionary research kit Considerable time savings in the development of stable cell clones." Cellectis News. XP 2514260 (Dec. 1, 2008).
Cabaniols Jean-Pierre et al. "Targeted gene modification in drug discovery and development." Current Opinion in Pharmacology, vol. 9, No. 5. pp. 657-663, XP 26665562 (Oct. 1, 2009).
Noveen et al. Design of compact multiple cloning sites. Biotechniques, vol. 15, No. 2, pp. 210-212 and 214, 1993.
International Search Report issued Mar. 4, 2010 in PCT/IB09/07526 filed Oct. 23, 2009.
Ahern. Biochemical, reagents kits offer scientists good return on investment. The Scientist, vol. 9, No. 15, p. 20, Jul. 1995, printed as pp. 1/7 to 7/7.

\* cited by examiner

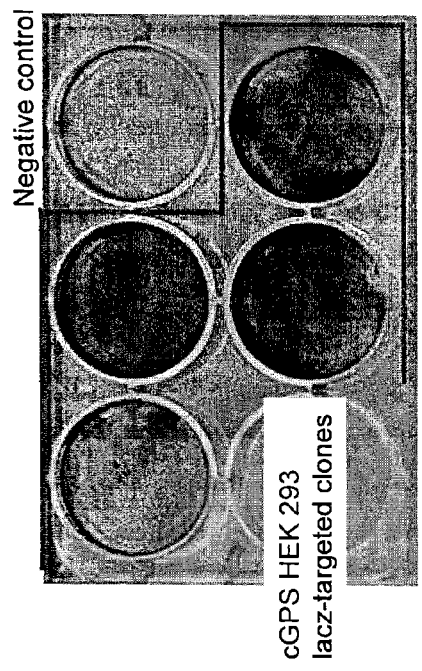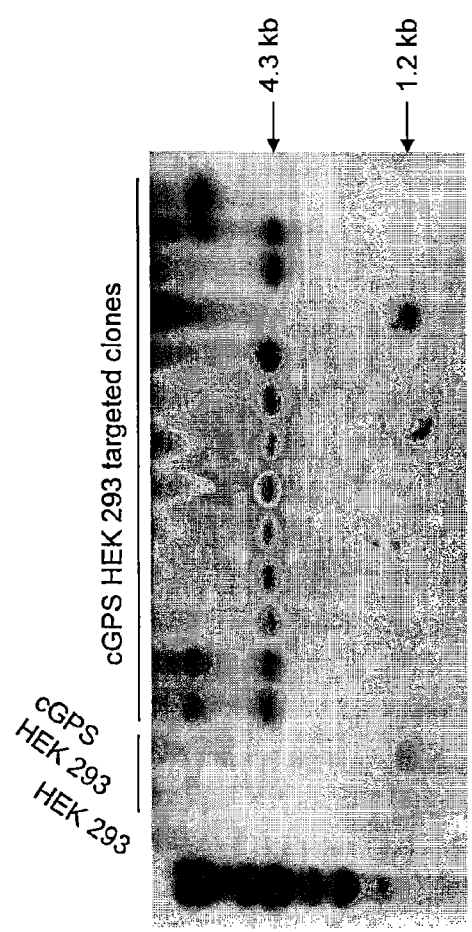
FIG. 12A
FIG. 12B

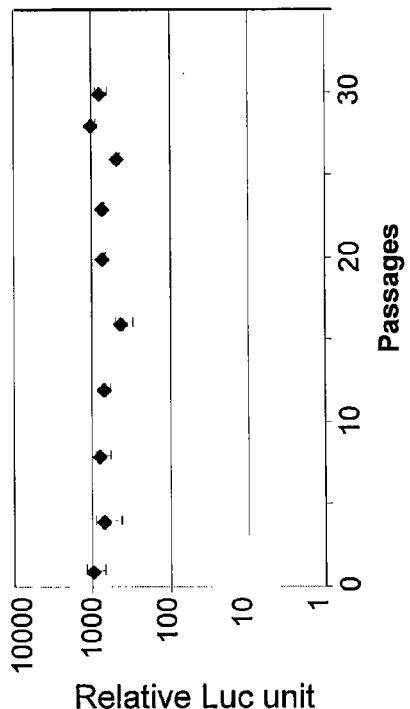
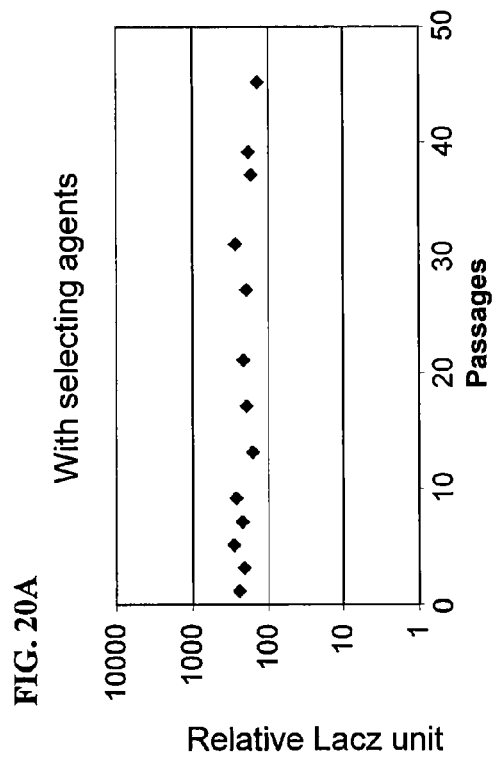
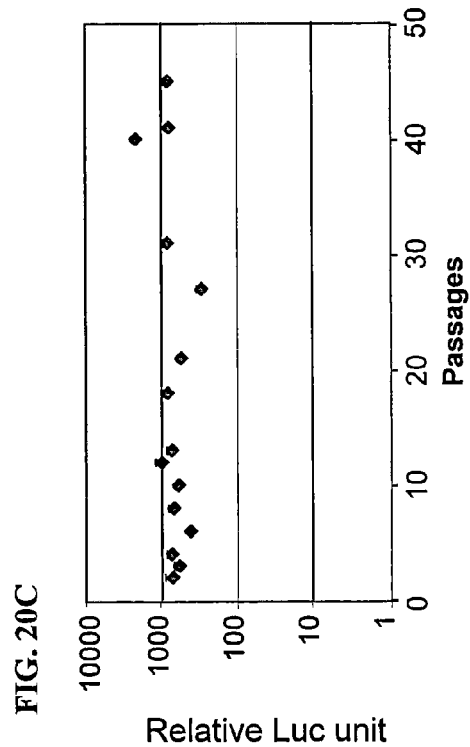
FIG. 20A  FIG. 20B  FIG. 20C  FIG. 20D

MEGANUCLEASE RECOMBINATION SYSTEM

CROSS-REFERENCE TO RELATED APPLICATION

The present application is a continuation of U.S. Ser. No. 13/125,193, filed Jul. 11, 2011, now U.S. Pat. No. 8,476,072, which is a National Stage (371) of PCT/IB09/007526, filed Oct. 23, 2009, which claims foreign priority to EP 08291002.7, filed Oct. 23, 2008.

The invention relates to a set of genetic constructs which allow the efficient and reproducible introduction of a specific nucleotide sequence at a fixed position in the genome. The present invention also relates to methods using these constructs and to these materials in the form of a kit.

Since the first gene targeting experiments in yeast more than 25 years ago (1, 2), homologous recombination has been used to insert, replace or delete genomic sequences in a variety of cells (3-5). However, targeted events occur at a very low frequency in mammalian cells. The frequency of homologous recombination can be significantly increased by a specific DNA double-strand break (DSB) in the targeted locus (6, 7). Such DSBs can be created using Meganucleases, which are sequence-specific endonucleases that recognize large DNA target sites (>12 bp). These proteins can cleave a unique chromosomal sequence without affecting overall genome integrity. Natural Meganucleases are essentially represented by homing endonucleases, a widespread class of proteins found in eukaryotes, bacteria and archae (8). Early studies of the I-SceI and HO homing endonucleases have illustrated how the cleavage activity of these proteins initiates homologous recombination (HR) events in living cells and demonstrated the recombinogenic properties of chromosomal DSBs (9, 10). Since then, Meganuclease-induced recombination has been successfully used for genome engineering purposes in bacteria (11), mammalian cells (6, 7, 12-14), mice (15) and plants (16, 17).

Gene insertion can be used, for example, to introduce genes of interest in specific loci, for heterologous protein production. Recombinant therapeutic proteins are today mostly produced in mammalian cells such as CHO, mouse SP2/0 and NS0 cells, or the human PerC.6 cell line, stably transfected with the gene of interest (18). In the process of selecting highly expressing clones, the level and stability of protein expression are two major criteria. Obtaining reproducible results from one clone to another would be an advantage in terms of improving screening efforts. These principles also apply to the generation of cells for screening of specific drug targets. The same principle can also be applied to the expression of various genes in the same genomic context to comparatively study and analyze the resulting cell lines one to another. Such cell lines can furthermore be subjected to the effect of compounds libraries in screening programs.

At the present time however no means exist to induce a DSB at a locus wherein the insertion/deletion of heterologous sequences can be easily ascertained.

The Inventors have developed a new set of genetic constructs which allow the reproducible integration and expression of a gene of interest (GOI) or a series of genes in otherwise isogenic cell lines.

According to a first aspect of the present invention there is provided a set of genetic constructs comprising:

a) Construct (i) encoded by a nucleic acid molecule, which comprises at least the following components:

$$A1\text{-}A2\text{-}A3\text{-}A4\text{-}A5 \qquad (i)$$

wherein A1 is a first promoter; A2 is a first homologous portion; A3 is a meganuclease cleavage site; A4 is a first marker gene; A5 is a second homologous portion; and wherein construct (i) is configured to be stably integrated into the genome of at least one target cell;

b) Construct (ii) encoded by a nucleic acid molecule, which comprises at least the following components:

$$A2'\text{-}B1\text{-}B2\text{-}B3\text{-}B4\text{-}A5' \qquad (ii)$$

wherein A2' comprises a portion of said first homologous portion A2; B1 is a second marker gene different to said first marker gene; B2 is a second promoter; B3 is a multiple cloning site; B4 is a third promoter; A5' comprises a portion of said second homologous portion A5;

c) At least one construct selected from the group comprising, constructs (iii) or (iv) encoded by nucleic acid molecules, which comprise at least the following components:

$$C1\text{-}C2 \qquad (iii);$$

$$C3 \qquad (iv); \text{ or}$$

Construct (v) which is an isolated or recombinant protein which comprises at least the following component:

$$C4 \qquad (v);$$

wherein C1 is a fourth promoter; C2 is the open reading frame (ORF) of a meganuclease; C3 are messenger RNA (mRNA) versions of said meganuclease; C4 is an isolated or recombinant protein of said meganuclease; wherein said meganuclease from constructs (iii), (iv) or (v) recognize and cleave A3; and wherein constructs (iii), (iv) or (v) are configured to be co-transfected with construct (ii) into said at least one target cell.

This system of genetic constructs allows the integration and expression of a GOI in an engineered cell at a specific genomic location. Construct (ii) containing a GOI which can be cloned into portion B3 is integrated into the genome via Meganuclease induced Recombination at a specific site corresponding to the genomic integration position of construct (i). The insertion event occurs at a very high frequency and is very specific.

Each of the genetic constructs consists of the above essential components, A1 to A5, A2' and A5', B1 to B4 and C1 to C2, but between these other nucleotide sequences may be present so long as they do not affect the properties of the claimed components as defined herein.

In the present invention, a promoter is a nucleotide sequence which when placed in combination with a second nucleotide sequence encoding an open reading frame causes the transcription of the open reading frame. In addition in the case of a RNA molecule, a promoter can also refer to a non-coding sequence which acts to increase the levels of translation of the RNA molecule.

In the present invention, a homologous portion refers to a nucleotide sequence which shares nucleotide residues in common with another nucleotide sequence so as to lead to a homologous recombination between these sequences, more particularly having at least 95% identity, preferably 97% identity and more preferably 99% identity. The first and second homologous portions of construct (i) and the first and second homologous portions construct (ii) can be 100% identical or less as indicated.

In particular the overlap between the portions A2 and A5 from construct (i) and portions A2' and A5' from construct (ii) is at least 200 by and no more than 6000 bp. Preferably the overlap is between 1000 bp and 2000 bp.

In particular therefore components A2' and A5' from construct (ii), comprise at least 200 bp and no more than 6000 bp of components A2 and A5 from construct (i) respectively.

Most particularly components A2' and A5' from construct (ii), comprise at least 1000 bp and no more than 2000 bp of components A2 and A5 from construct (i) respectively.

The amounts of overlap necessary to allow efficient levels of homologous recombination are known in the art (49), starting from these known levels the inventors have identified the most efficient ranges of overlap for use with the set of constructs according to the present invention.

In the present invention, a meganuclease cleavage site is intended to mean a 22 to 24 by double-stranded palindromic, partially palindromic (pseudo-palindromic) or non-palindromic polynucleotide sequence that is recognized and cleaved by a LAGLIDADG homing endonuclease (SEQ ID NO: 69). These terms refer to a distinct DNA location, preferably a genomic location, at which a double stranded break (cleavage) is to be induced by the meganuclease.

The meganuclease cleavage site can be the DNA sequence recognized and cleaved by a wild type meganuclease such as I-CreI or I-DmoI. Alternatively the meganuclease cleavage site can be the DNA sequence recognized and cleaved by altered meganucleases which recognize and cleave different DNA target sequences.

The inventors and others have shown that meganucleases can be engineered so as to recognize different DNA targets. The I-CreI enzyme in particular has been studied extensively and different groups have used a semi-rational approach to locally alter the specificity of I-CreI (26-28).

In addition, hundreds of I-CreI derivatives with locally altered specificity were engineered by combining the semi-rational approach and High Throughput Screening:

Residues Q44, R68 and R70 or Q44, R68, D75 and I77 of I-CreI were mutagenized and a collection of variants with altered specificity at positions±3 to 5 of the DNA target (5NNN DNA target) were identified by screening (27, 28).

Residues K28, N30 and Q38 or N30, Y33, and Q38 or K28, Y33, Q38 and S40 of I-CreI were mutagenized and a collection of variants with altered specificity at positions±8 to 10 of the DNA target (10NNN DNA target) were identified by screening (29, 30).

All such variant meganucleases and the variant DNA targets which they recognize and cleave, are included in the present Patent Application and any combination of a particular meganuclease and its target can be used as the meganuclease target sequence represented by feature A3 from construct (i) and the meganuclease encoded variously by constructs (iii), (iv) and (v).

In the present invention a marker gene is a gene product which when expressed allows the differentiation of a cell or population of cells expressing the marker gene versus a cell or population of cells not expressing the marker gene.

In the present invention a multiple cloning site is a short segment of DNA which contains several restriction sites so as to allow the sub-cloning of a fragment of interest into the plasmid comprising the multiple cloning site.

In the present invention a meganuclease is intended to mean an endonuclease having a double-stranded DNA target sequence of 12 to 45 bp. This may be a wild type version of a meganuclease such as I-CreI or I-DmoI or an engineered version of one of these enzymes as described above or fusion proteins comprising portions of one or more meganuclease(s) (31-33).

The inventors have shown that this system can work with a number of diverse model mammalian cell lines for a number of GOIs.

Preferably component A5 comprises a marker gene or a portion thereof.

In accordance with this preferred embodiment of the present invention component A5 must encode a marker gene or a portion thereof such that following the homologous recombination event the detection of altered cells can be detected.

Alternatively a DNA sequence encoding a marker gene can be positioned after component A5, wherein this further portion encodes a marker gene and allows the detection of cells which have undergone homologous recombination.

Preferably component A5' comprises a 3' end deletion of said component A5.

Preferably the components of each of said constructs (i), (ii), (iii), (iv) and (v) are selected from the following groups:

| Component | Group |
|---|---|
| A1 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| A2 | EF1α intron 1 complete sequence, 5' homology (SEQ ID NO: 3) |
| A2' | EF1α intron 1 short sequence, 5' homology (SEQ ID NO: 29) |
| A3* | Meganuclease cleavage site (SEQ ID NO: 8) |
| A4 | Hygromycin resistance gene (SEQ ID NO: 2); Neomycin resistance gene (SEQ ID NO: 7); Puromycin resistance gene (SEQ ID NO: 21) |
| A5 | Neomycin resistance gene (SEQ ID NO: 7) |
| A5' | Inactive neomycin resistance gene deleted of its 3' end, 3' homology (SEQ ID NO: 13) |
| B1 | Hygromycin resistance gene (SEQ ID NO: 2); Neomycin resistance gene (SEQ ID NO: 7); Puromycin resistance gene (SEQ ID NO: 21) |
| B2 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| B3 | Multiple cloning site (SEQ ID NO: 23) |
| B4 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| C1 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| C2* | Meganuclease ORFs (SEQ ID NO: 14); (SEQ ID NO: 15) |
| C3* | Meganuclease ORFs (SEQ ID NO: 14); (SEQ ID NO: 15) and (SEQ ID NO 35) |
| C4* | Meganuclease peptide encoded by (SEQ ID NO: 14); (SEQ ID NO: 15) and (SEQ ID NO: 58) |

*The meganuclease cleavage site used in the set of constructs according to the present invention must be recognized and cleaved by the meganuclease also included in the set of constructs. As pointed out above the meganuclease cleavage site can be a wild type meganuclease target site, such as SEQ ID NO: 8 the wild type cleavage site of the wild type I-CreI meganuclease (provided herein in various forms as SEQ ID NO: 14, 15 and 58). If however component A3 is altered then the meganuclease of component C2, C3 or C4 will also be altered.

The above components are only examples and it is not intended that the present invention be limited to these specific sequences or combinations thereof. The characteristics of the claimed components are defined herein and the selection of other suitable components, such as resistance genes or promoter sequences is therefore encompassed by the present invention.

Preferred promoting sequences are pCMV promoter (SEQ ID NO: 25), pSV40 promoter (SEQ ID NO: 20), pEF1α (SEQ ID NO: 1) and Ubiquitin sub-unit c promoter (SEQ ID NO: 52).

Preferred marker genes are Neomycin resistance gene (SEQ ID NO: 7); Puromycin resistance gene (SEQ ID NO: 21), Hygromycin resistance gene (SEQ ID NO: 2); blasticidin resistance gene, zeocin resistance gene and phleomycin resistance gene. Many other selectable marker genes exist all these can be used in the present Patent Application Most preferably, the construct (i) comprises SEQ ID NO: 6, which consists of the Inventors preferred construct which was used to create cGPS (cellular Genome Positioning System) cell lines. In this construct, a specific Meganuclease target site has been inserted into the host cell genome at a unique locus. This site is the precise insertion locus of the gene(s) of interest. This site has been inserted at a single copy into the host cell line as part of a larger construct. In the final cGPS cell line, the Meganuclease target site is located near the hygromycin resistance gene and downstream the EF1α promoter. The cGPS cell line is then resistant to hygromycin. Furthermore, the neomycin resistance gene is located just downstream the hygromycin gene but lacks a promoter making the cGPS cell line G418 sensitive (see FIG. 1).

The important features of cGPS locus are listed in table 1 below.

TABLE 1

| Feature | Benefit |
| --- | --- |
| pEF1α (referred as A1) | Promoter from the human Elongation Factor I alpha gene driving the transcription of the puromycin resistance gene after HR in cGPS cells (SEQ ID NO: 1) |
| EF1α exon 1 | Exon 1 of the human Elongation Factor I alpha gene (SEQ ID NO: 11) |
| EF1α exon 2 | Exon 2 of the human Elongation Factor I alpha gene (SEQ ID NO: 12) |
| EF1α intron 1 (referred as A2, 5' homology) | Intron 1 of the human Elongation Factor I alpha gene, composed of a 1kb fragment (SEQ ID NO: 10) |
| Meganuclease cleavage site (referred as A3) | Meganuclease cleavage site for targeted insertion of the GOI |
| HygroR (referred as A4) | Hygromycin resistance gene |
| NeoR (referred as A5, 3' homology) | Neomycin resistance gene (inactive because lacking a promoting sequence to drive its transcription) |
| SV40 pA | Polyadenylation signal from SV40 virus (SEQ ID NO: 4, SEQ ID NO: 5), allowing efficient transcription termination and polyadenylation of hygromycin and neomycin resistance genes |

Most preferably, the construct (ii) comprises SEQ ID NO: 22, which consists of pTV-DS-MCS2 which is a 6932 bp vector that expresses a GOI under the control of the CMV promoter. It also contains two homology arms for efficient HR and insertion of the GOI at the cGPS locus (see FIG. 2).

The important features of pTV-DS-MCS2 are described in table 2 below. All features have been functionally tested.

TABLE 2

| Feature | Benefit |
| --- | --- |
| EF1α intron 1 (referred as A2', part of the 5' homology) | 0.8 kb fragment (SEQ ID NO: 28) for efficient homologous recombination at the cGPS site composed of the intron 1 of the human Elongation Factor I alpha gene; once reconstituted after HR at the cGPS site, it allows puromycin selection of stable cGPS expressing cell clones |

TABLE 2-continued

| Feature | Benefit |
| --- | --- |
| NeoR Del3' (referred as A5', part of the 3'homology) | 0.6 kb fragment (SEQ ID NO 26) for efficient homologous recombination at the cGPS site composed of an inactive neomycin resistance gene deleted of its 3' end; once reconstituted after HR at the cGPS site, it allows neomycin selection of stable expressing cell clones |
| PuroR | Puromycin resistance gene (inactive because lacking a promoting sequence to drive its transcription); once reconstituted after HR at the cGPS site, it allows puromycin selection of stable cell clones |
| pCMV | Human cytomegalovirus (CMV, SEQ ID NO: 25) immediate early promoter, driving high-level expression of the GOI |
| MCS2 | Multiple cloning site containing NheI, BmtI, Bsu36I, AscI, BglII, BsrGI, BstBI, EcoRV, PacI, NotI restriction sites for the molecular cloning of GOIs |
| SV40 pA | Polyadenylation signal from SV40 virus (SEQ ID NO: 19), allowing efficient transcription termination and polyadenylation of the puromycin resistance gene |
| BGH pA | Polyadenylation signal from bovine growth hormone gene (SEQ ID NO: 27), allowing efficient transcription termination and polyadenylation of the mRNA of interest |

TABLE 2-continued

| Feature | Benefit |
| --- | --- |
| pSV40 | SV40 promoter (SEQ ID NO: 20) driving high-level expression of the neomycin resistance gene only after HR |
| pMB1 ORI | Permits high-copy number replication and growth in E. coli bla promoter |
| AmpR | Ampicillin (bla) resistance gene (β-lactamase), for selection of transformants in E. coli |

Most preferably constructs (iii) comprise SEQ ID NO: 38 and SEQ ID NO: 39, which consist of pCLS1088 (FIG. 33) or pCLS2147 (FIG. 34), respectively. These 5647 bp vectors contain two different ORFs of the Meganuclease under the control of the CMV promoter.

The important features of pCLS1088 and pCLS2147 are described in table 3 below. All features have been functionally tested.

TABLE 3

| Feature | Benefit |
|---|---|
| pCMV | Human cytomegalovirus immediate early promoter; allowing high-level expression of your GOI (Andersson et al., 1989; Boshart et al., 1985; Nelson et al., 1987) |
| Meganuclease(s) | Meganuclease ORFs (SEQ ID NO: 14 or SEQ ID NO: 15), improving HR events at the cGPS locus |
| TK pA | Polyadenylation signal from herpes simplex virus thymidine kinase gene, allowing efficient transcription termination and polyadenylation of the meganuclease mRNA |
| pUC & f1 origins | Permits high-copy number replication and growth in *E. coli* |
| AmpR | Ampicillin resistance gene (β-lactamase) for selection of transformants in *E. coli* |

Most preferably constructs (iv) comprise ORFs of the Meganuclease (SEQ ID NO: 14 and SEQ ID NO: 15).

Wherein constructs (iv) consist of Meganuclease polyadenylated mRNAs (SEQ ID NO 34, SEQ ID NO 35), from which the ribosomal scanning is mediated either by 7-methylguanine capped sequence or by internal ribosome entry site (IRES). (see FIG. 3).

Wherein constructs (v) consist of a cell penetrating peptide fused to the N-terminal part of Meganuclease. An example of a meganuclease according to this aspect of the present invention is provided as SEQ ID NO: 58, this sequence encodes an I-CreI monomer with the cell-penetrating peptide DPV15b (SEQ ID NO: 56) fused to the N-terminal of the meganuclease and a 6x hisitidine tag (SEQ ID NO: 70) fused at the C-terminal of the meganuclease. The Inventors have also evaluated another cell-penetrating peptide DPV 1047 (SEQ ID NO: 57).

Cell penetrating peptides were initially developed following the observation that certain proteins, including the HIV-1 protein Tat, could cross the cell membrane (34). The HIV-1 transcriptional activator Tat is a multifunctional protein that, in addition to acting as a powerful inducer of viral gene expression, is transported in and out of the cells (35). This cell penetration property relies on the integrity of a highly basic arginine-rich sequence (amino acids 49-58).

Peptides containing this arginine-rich sequence have been developed, named Tat peptides, that after conjugation to a range of macromolecules can facilitate cellular entry of the conjugate. This method of intracellular delivery has been used successfully in vitro for a range of macromolecules including fluorochromes, enzymes, antibodies and liposomes (41, 42, 43, 45, 47, 48). The Tat peptide has also been shown to facilitate cellular entry of functional proteins such as β-galactosidase in vivo (46).

A number of other proteins and their peptide derivatives have been found to possess similar cell internalization properties including the herpes virus tegument protein VP22 (37), the homoeotic protein of *Drosophila melanogaster* antennapedia (Antp), (the internalizing peptide derived from full length Antp is called penetratin) (36), the protegrin 1 (PG-1) antimicrobial peptide SynB (40) and the basic fibroblast growth factor (39). The carrier peptides derived from these proteins show little sequence homology with each other, but are all highly cationic and arginine- or lysine-rich. Following on from this observation, synthetic polyarginine peptides have been shown to be internalized with a high level of efficiency (38, 44).

All such cell-penetrating peptides which can cause an increase in the rate of internalisation of a meganuclease linked thereto are incorporated in the present Patent Application.

According to a second aspect of the present invention there is provided a kit to introduce a sequence encoding a GOI into at least one cell, comprising the set of genetic constructs according to the first aspect of the present invention; and instructions for the generation of a transformed cell using said set of genetic constructs.

Preferably the kit, further comprising construct (vi) consisting of SEQ ID NO: 17 (Lac-Z) which consists of pTV-DS-LacZ.

pTV-DS-LacZ is a 9981 bp vector that expresses LacZ (as a positive control) in place of the GOI under the control of the CMV promoter as previously described (23). It also contains two homology arms for efficient homologous recombination and insertion of the GOI at the cGPS locus. FIG. 4 summarizes the features of the vector. Features of pTV-DS-LacZ are composed of the very same features as pTV-DS-MCS2 but this plasmid contains the LacZ gene encoding the β-galactosidase protein under the control of the CMV promoter. It can be used as a positive control for HR at the cGPS site.

Preferably, the kit further comprises at least one cell stably transformed with said construct (i).

Most preferably the at least one cell is selected from the group comprising: CHO-K1 cells (Sigma-Aldrich); HEK-293-derived cells (Invitrogen); Caco2 cells (Invitrotech); U2-OS cells (Invitrogen); NIH 3T3 cells (Invitrogen); NSO cells (Sigma-Aldrich); SP2 cells (Sigma-Aldrich); CHO-S cells (Invitrogen); DG44 cells (Invitrogen).

According to a third aspect of the present invention there is provided a method for transforming by HR at least one cell comprising the steps of:

A method for transforming by homologous recombination at least one cell comprising the steps of:

a) stably transforming at least one cell by inserting construct (i) as defined above into the genome of said at least one cell;

b) cloning a sequence coding for a gene of interest into position B3 of construct (ii) as defined above;

c) co-transfecting said cell of step a), with said construct (ii) of step b) and constructs (iii), (iv) or (v) as defined above;

d) following homologous recombination between said construct (ii) and said stably inserted construct (i), selecting at least one cell from step c) based upon: the absence of a first marker gene encoded by component A4 of said construct (i) and the activity of a second marker gene encoded by component B1 and the activity of a third marker gene encoded by component A5.

Most preferably, selection in step d) is carried out sequentially for each of said first marker, said second marker and said third marker.

For a better understanding of the invention and to show how the same may be carried into effect, there will now be shown by way of example only, specific embodiments, methods and processes according to the present invention with reference to the accompanying drawings in which:

FIG. 12 shows the production of double resistant lacz targeted clones in the cGPS NIH 3T3 system (FIG. 12A) and their molecular characterization (FIG. 12B).

FIG. 17 shows the results of radioligand saturation experiments performed on cGPS CHO-K1 hMT1-targeted clones. FIG. 17A shows the pKd values, while

FIG. 18 shows the results of radioligand saturation experiments performed on cGPS CHO-K1 hMT2-targeted clones. FIG. 18A shows the pKd values, while

FIG. 20 shows the stability of expression of β-galactosidase (mean value for 4 cGPS CHO-K1 lacz targeted clones) and luciferase (mean value for 4 cGPS CHO-K1 luciferase targeted clones) over a period of 23 weeks in the presence of the selecting agents and over a period of 15 weeks in the absence of selecting agents. FIG. 20A and FIG. 20B show the mean level of lacz expression for 4 cGPS CHO-K1 lacz targeted clones measured as a function of time in the presence or absence of selecting agents, respectively. FIG. 20C and FIG. 20D show the mean level of luciferase expression for 4 cGPS CHO-K1 luciferase targeted clones measured as a function of time in the presence or absence of selecting agents, respectively.

Figure 21A:
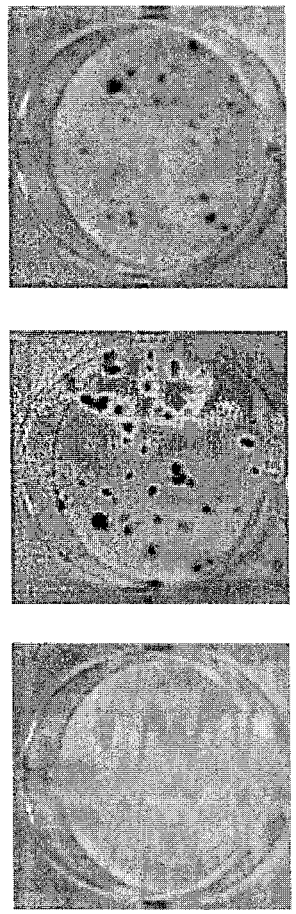
Figure 21B:
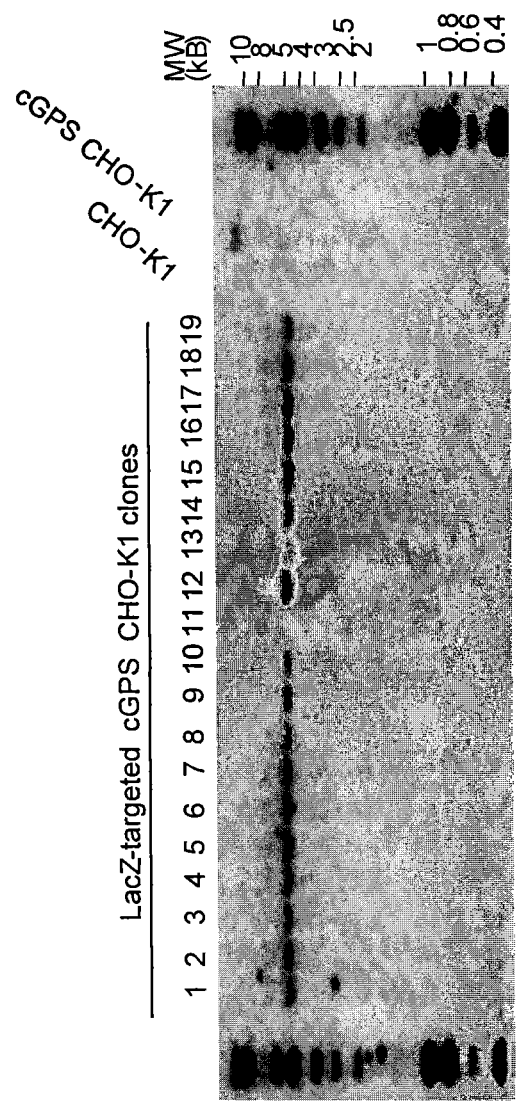

FIG. 21 shows the efficacy of gene targeting through the use of a I-CreI recombinant protein fused to a penetrating peptide (DPV15b/I-CreI N75/6xHis). FIG. 21A shows the generated colonies and FIG. 21B shows their molecular characterization.

Figure 22:
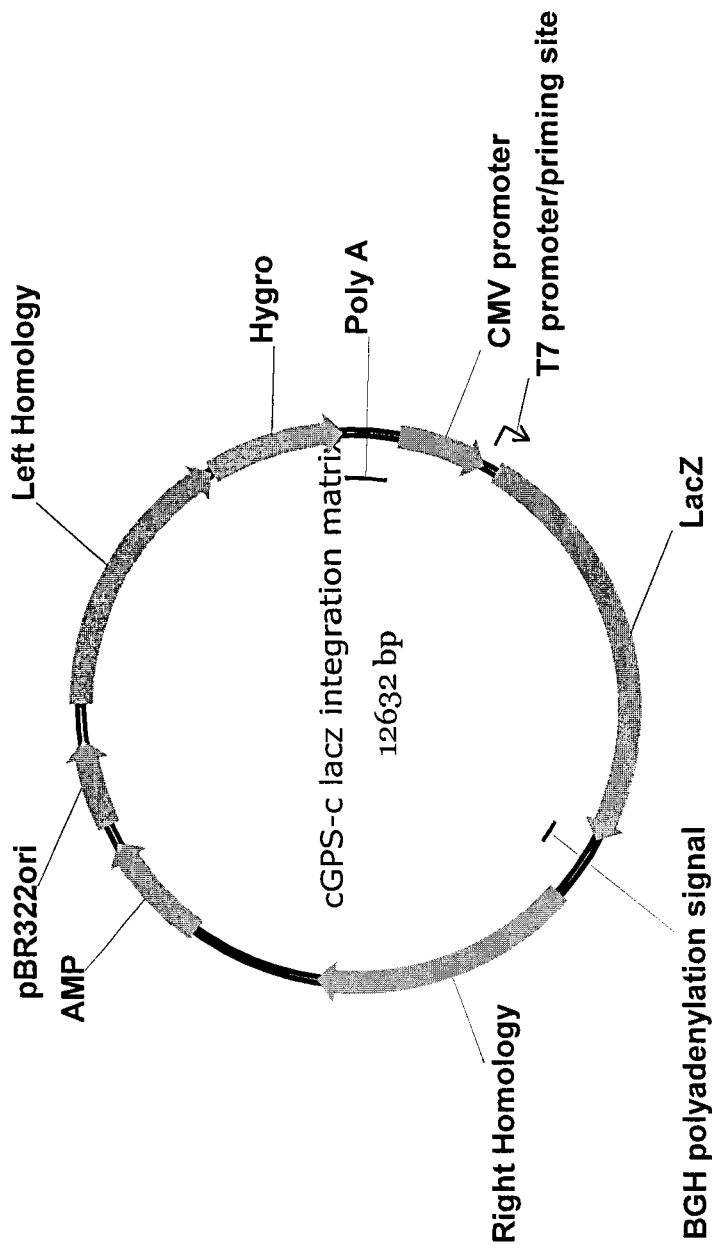

FIG. 22 shows a schematic representation of the cGPS custom CHO-K1 lacz integration matrix vector.

Figure 23:
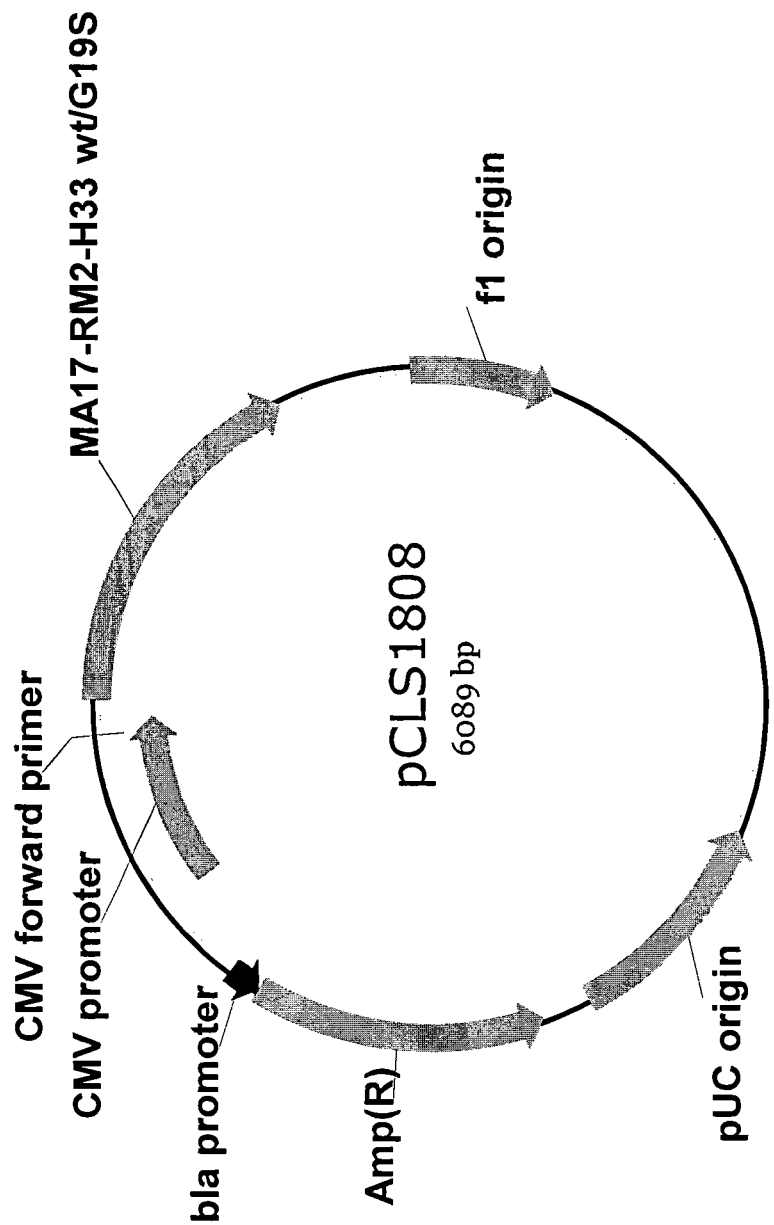

FIG. 23 shows a schematic representation of the Sc MA17-RM2-G19H33 meganuclease expression vector.

Figure 24A:
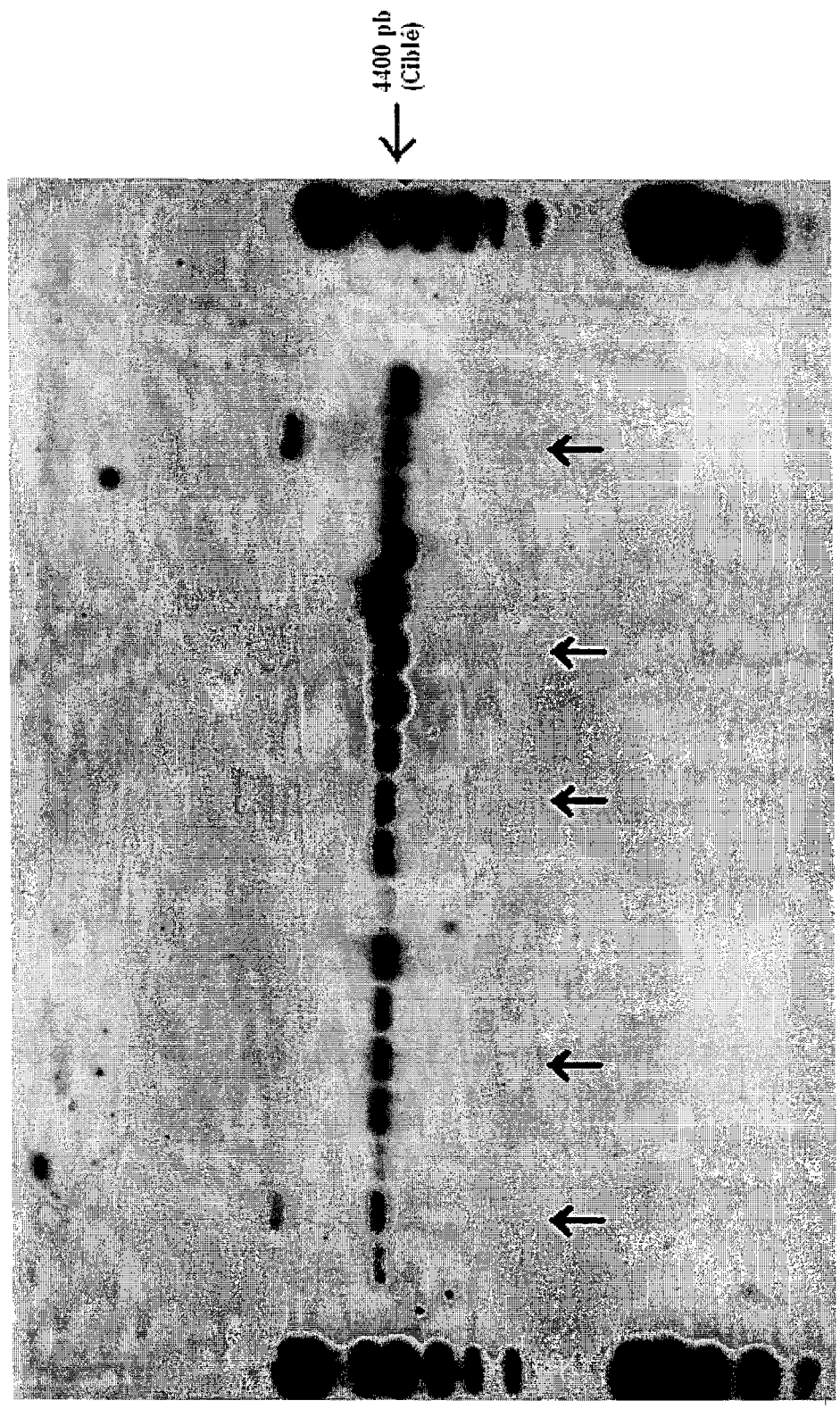
Figure 24B:
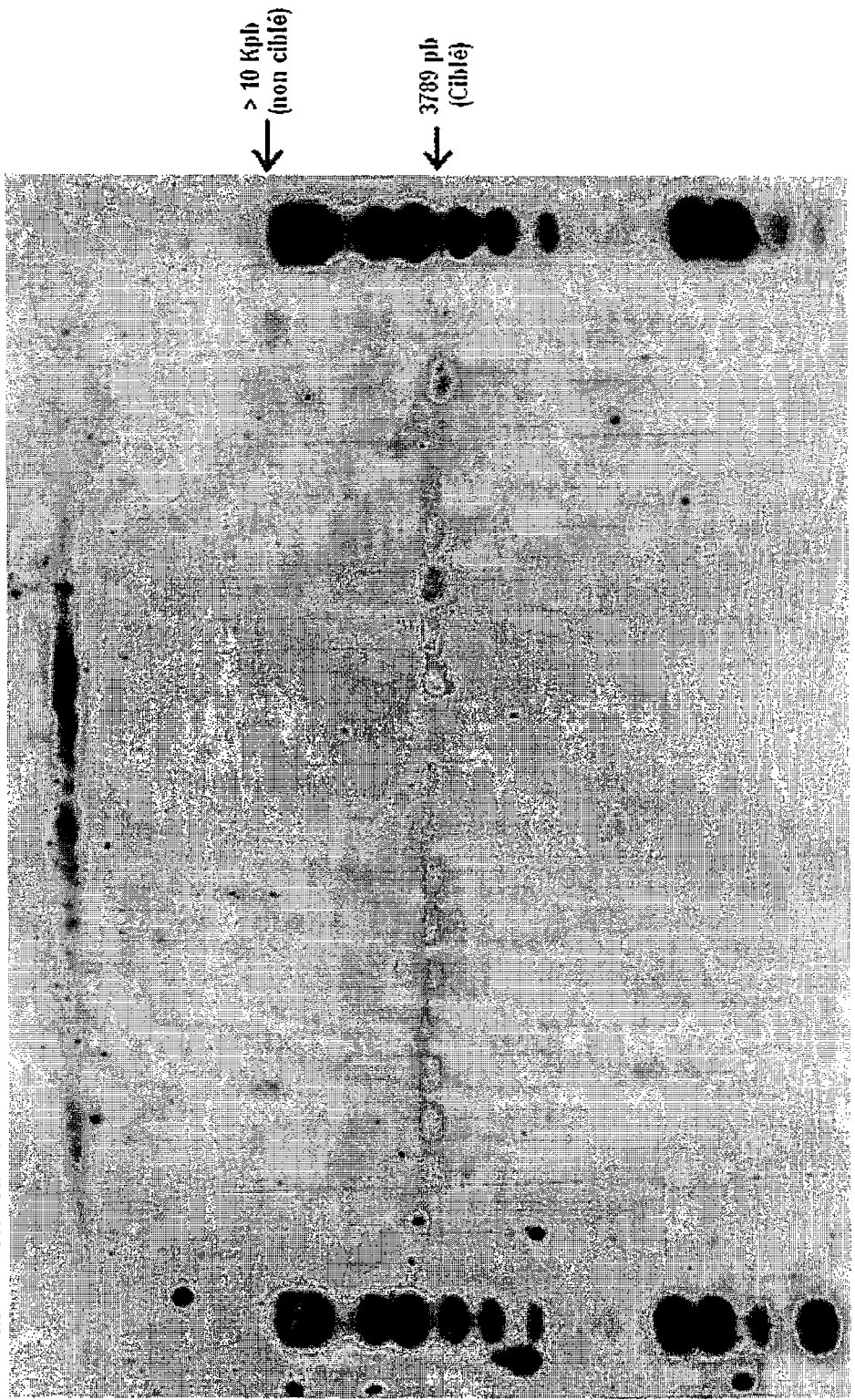

FIG. 24 shows a molecular characterization by southern blot of double targeted clones. FIG. 24A shows the analysis for correct insertion of the lacz gene in the Hprt gene. FIG. 24B shows verification that the cGPS CHO-K1 locus, site of the first targeted insertion is still modified.

Figure 25A:
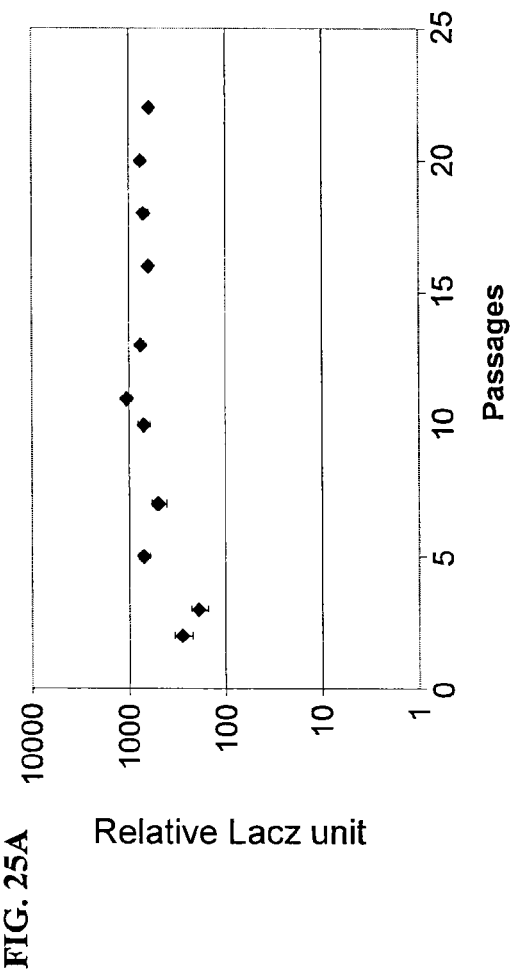
Figure 25B:
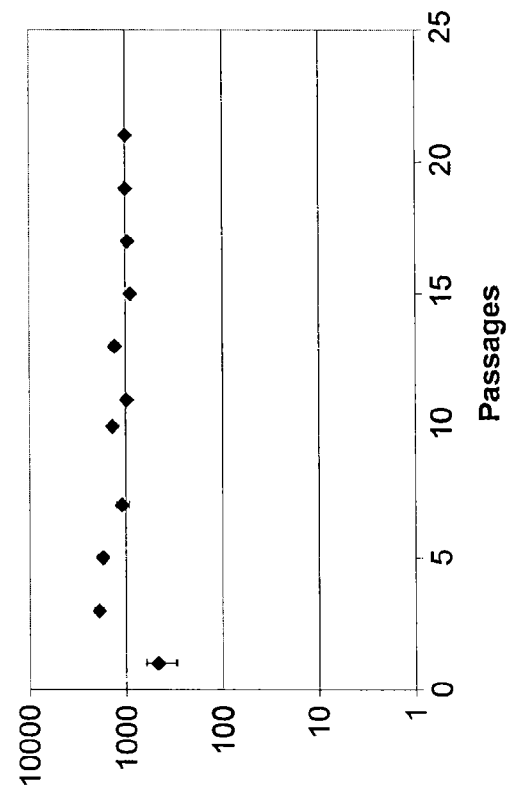

FIG. 25 shows the stability of expression of β-galactosidase (FIG. 25A) and luciferase (FIG. 25B) (mean value for 4 double targeted clones) over a period of 11 weeks.

Figure 26:
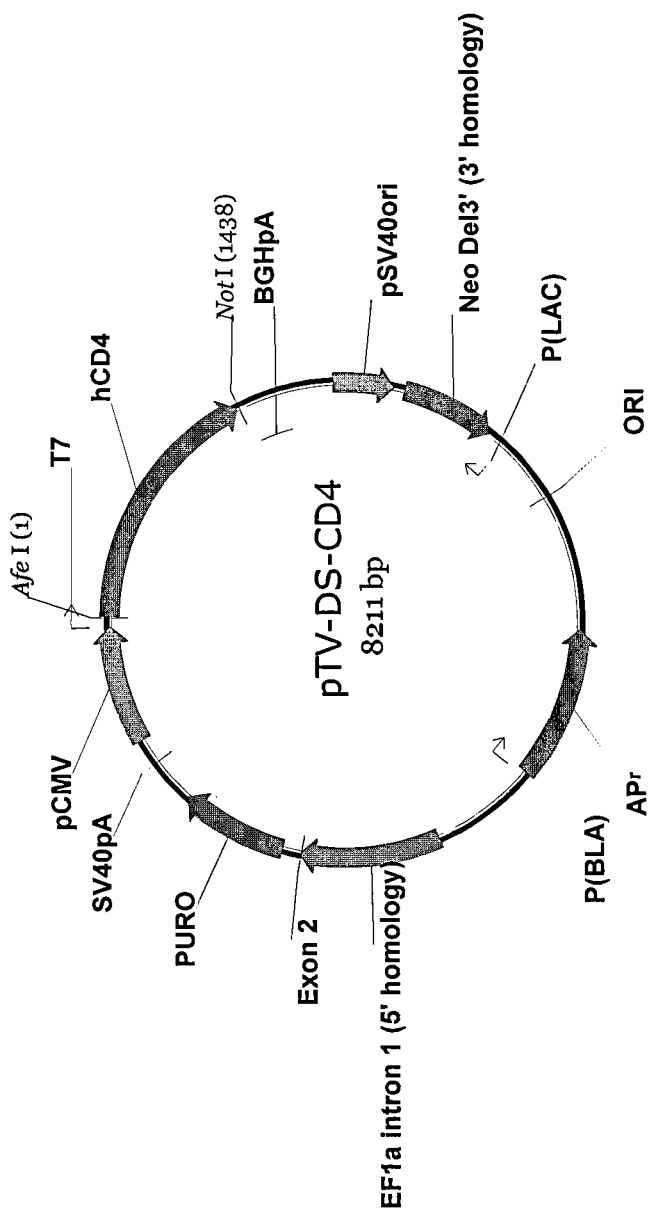

FIG. 26 shows a schematic representation of the pTV-DS-CD4 vector.

Figure 27:
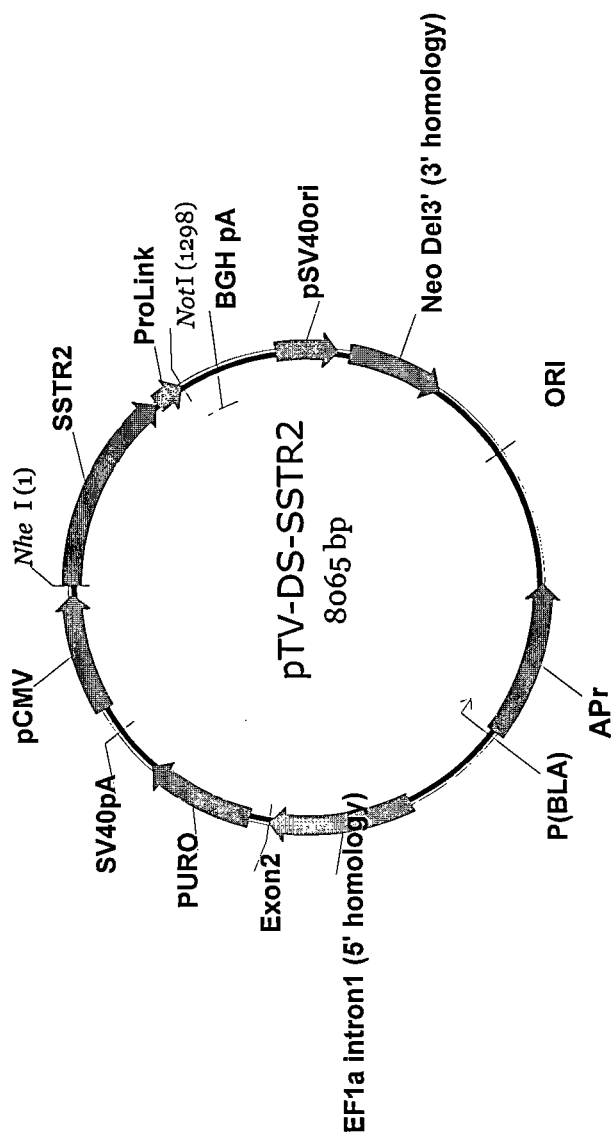

FIG. 27 shows a schematic representation of the pTV-DS-SSTR2 vector.

Figure 28:
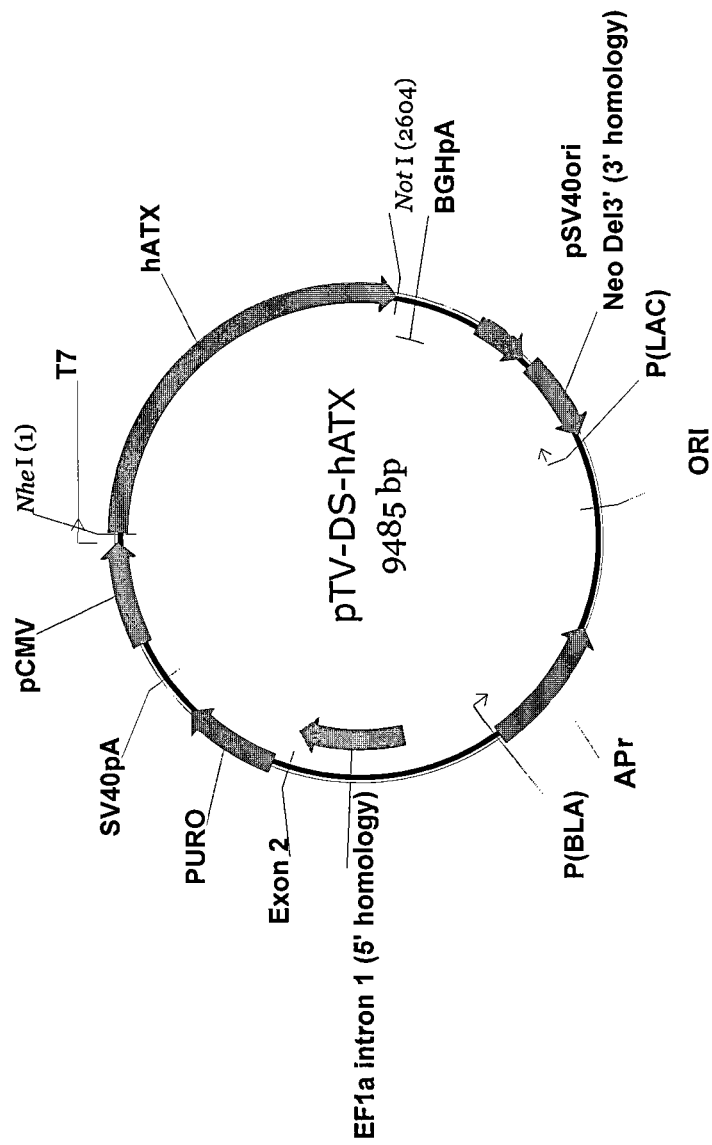

FIG. 28 shows a schematic representation of the pTV-DS-hATX vector.

Figure 29:
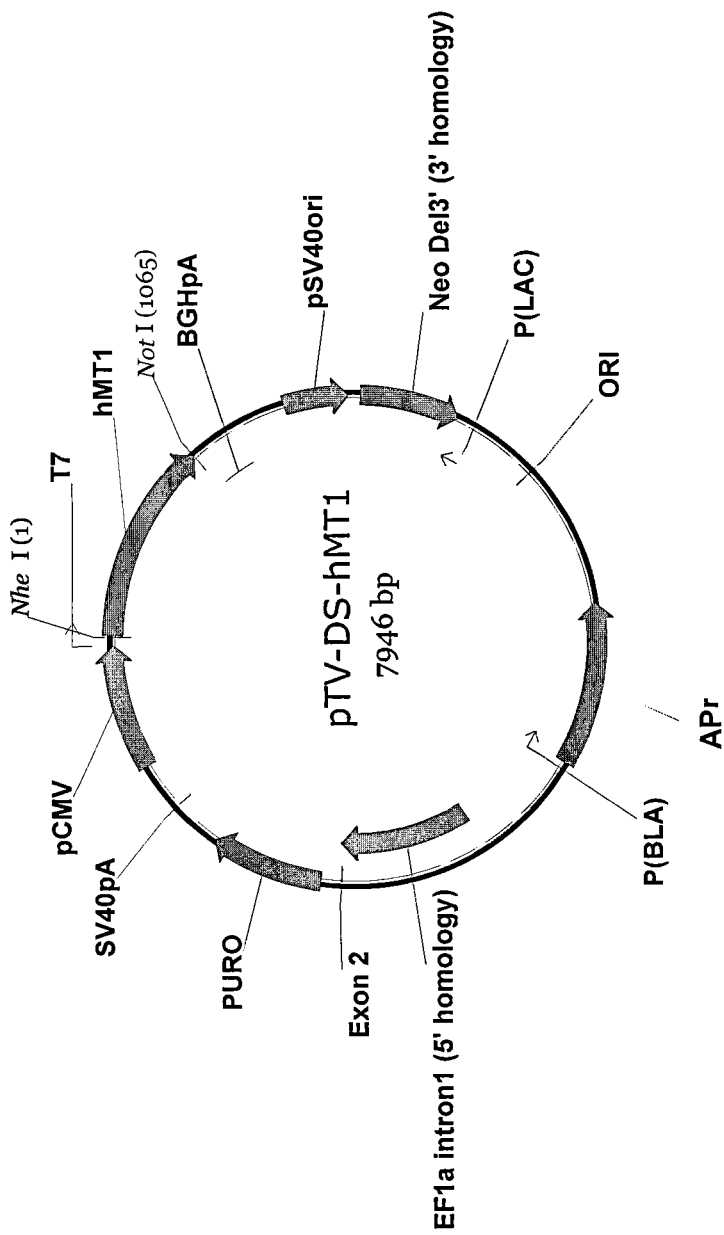

FIG. 29 shows a schematic representation of the pTV-DS-hMT1 vector.

Figure 30:
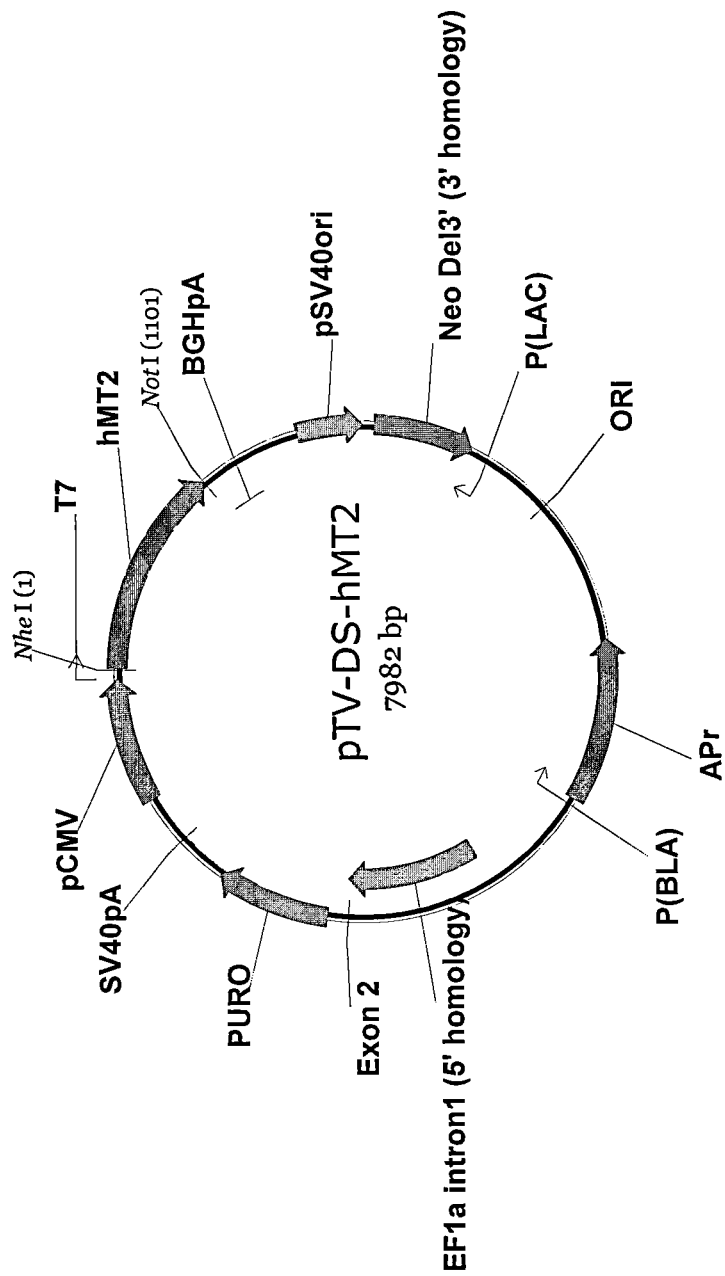

FIG. 30 shows a schematic representation of the pTV-DS-hMT2 vector.

Figure 31:
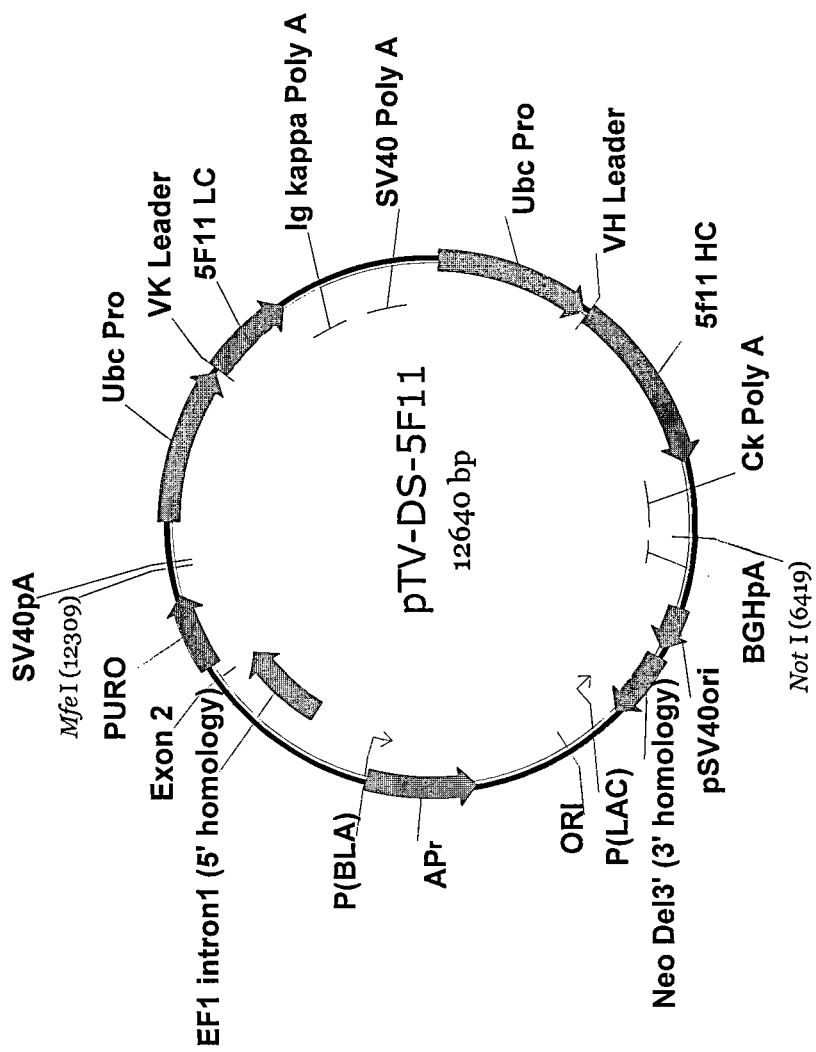

FIG. 31 shows a schematic representation of the pTV-DS-5F11 vector.

Figure 32:
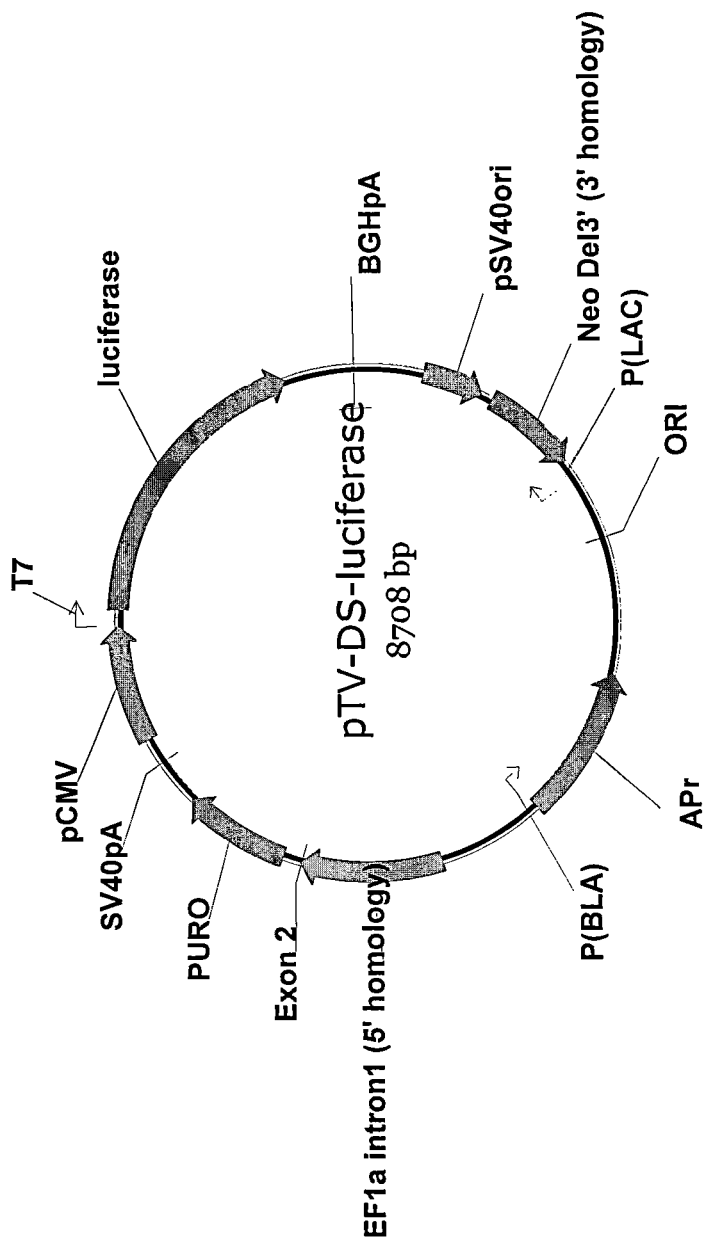

FIG. 32 shows a schematic representation of the pTV-DS-luciferase vector.

Figure 33:
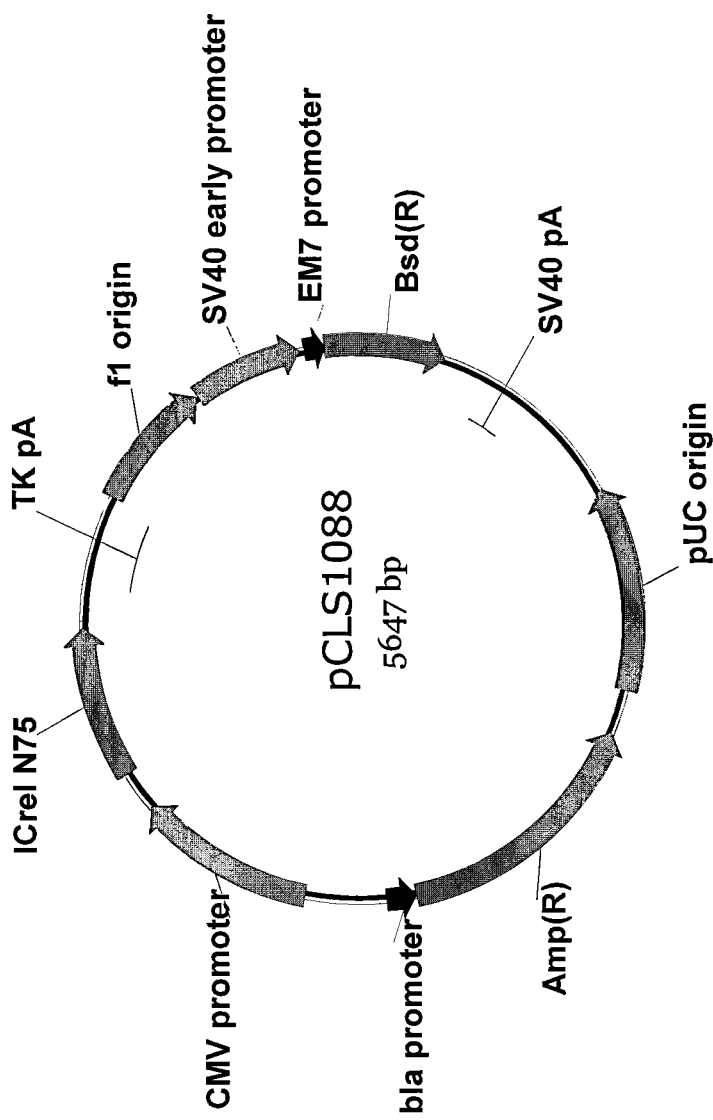

FIG. 33 shows a schematic representation of the I-CreI N75 meganuclease expression vector.

Figure 34:
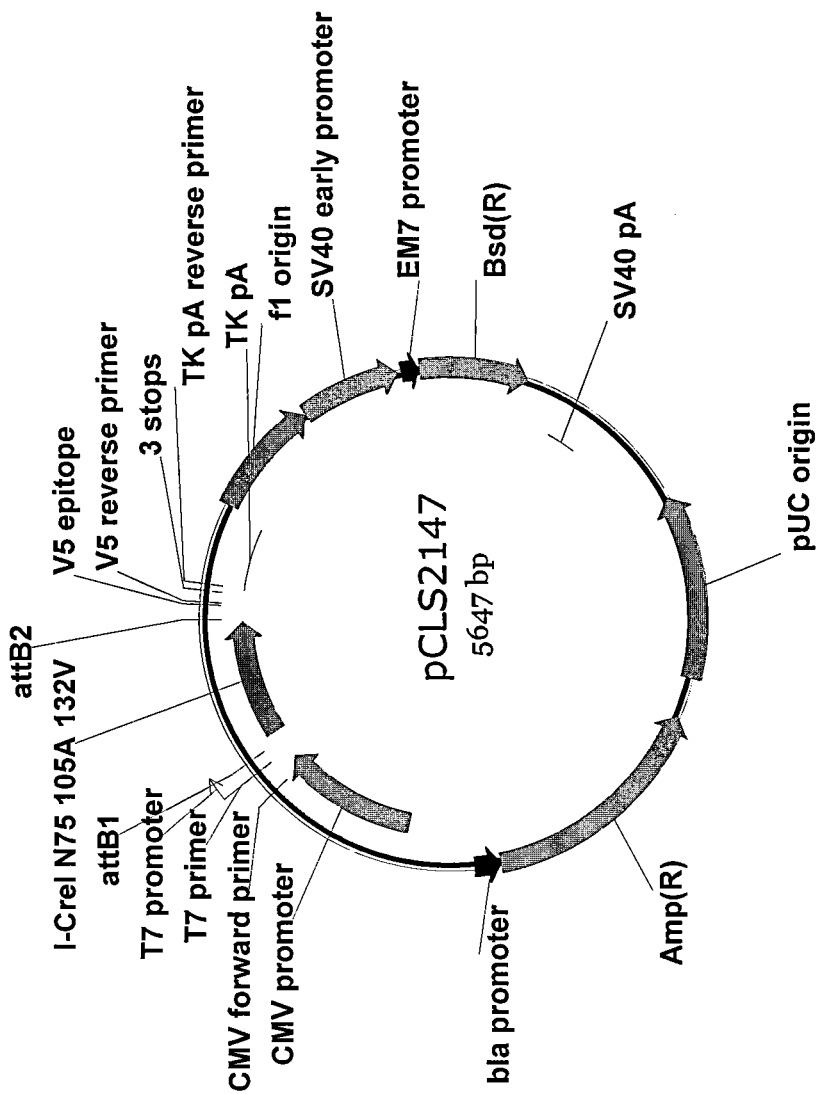

FIG. 34 shows a schematic representation of the I-CreI N75 105A 132V meganuclease expression vector.

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Definitions

Amino acid residues in a polypeptide sequence are designated herein according to the one-letter code, in which, for example, Q means Gln or Glutamine residue, R means Arg or Arginine residue and D means Asp or Aspartic acid residue.

hydrophobic amino acid refers to leucine (L), valine (V), isoleucine (I), alanine (A), methionine (M), phenylalanine (F), tryptophane (W) and tyrosine (Y).

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "meganuclease" is intended an endonuclease having a double-stranded DNA target sequence of 12 to 45 bp. Examples include I-Sce I, I-Chu I, I-Cre I-Csm I, PI-Sce I, PI-Tli I, PI-Mtu I, I-Ceu I, I-Sce II, I-Sce III, HO, PI-Civ I, PI-Ctr I, PI-Aae I, PI-Bsu 1, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, I-Msol.

by "parent LAGLIDADG homing endonuclease" (SEQ ID NO: 69) is intended a wild-type LAGLIDADG homing endonuclease (SEQ ID NO: 69) or a functional variant thereof. Said parent LAGLIDADG homing endonuclease (SEQ ID NO: 69) may be a monomer, a dimer (homodimer or heterodimer) comprising two LAGLIDADG homing endonuclease core domains (SEQ ID NO: 69) which are associated in a functional endonuclease able to cleave a double-stranded DNA target of 22 to 24 bp.

by "homodimeric LAGLIDADG homing endonuclease" (SEQ ID NO: 69) is intended a wild-type homodimeric LAGLIDADG homing endonuclease (SEQ ID NO: 69) having a single LAGLIDADG motif (SEQ ID NO: 69) and cleaving palindromic DNA target sequences, such as I-CreI or I-MsoI or a functional variant thereof.

by "LAGLIDADG homing endonuclease variant" (SEQ ID NO: 69) or "variant" is intended a protein obtained by replacing at least one amino acid of a LAGLIDADG homing endonuclease sequence(SEQ ID NO: 69), with a different amino acid.

by "functional variant" is intended a LAGLIDADG homing endonuclease variant (SEQ ID NO: 69) which is able to cleave a DNA target, preferably a new DNA target which is not cleaved by a wild type LAGLIDADG homing endonuclease (SEQ ID NO: 69). For example, such variants have amino acid variation at positions contacting the DNA target sequence or interacting directly or indirectly with said DNA target.

by "homing endonuclease variant with novel specificity" is intended a variant having a pattern of cleaved targets (cleavage profile) different from that of the parent homing endonuclease. The variants may cleave less targets (restricted profile) or more targets than the parent homing endonuclease. Preferably, the variant is able to cleave at least one target that is not cleaved by the parent homing endonuclease.

The terms "novel specificity", "modified specificity", "novel cleavage specificity", "novel substrate specificity" which are equivalent and used indifferently, refer to the specificity of the variant towards the nucleotides of the DNA target sequence.

by "I-CreI" is intended the wild-type I-CreI having the sequence SWISSPROT P05725 or pdb accession code 1g9y (SEQ ID NO: 36).

by "I-DmoI" is intended the wild-type I-DmoI having the sequence SWISSPROT number P21505 (SEQ ID NO: 37) or the structure PDB code 1b24 by "domain" or "core domain" is intended the "LAGLIDADG homing endonuclease core domain" (SEQ ID NO: 69) which is the characteristic αββαββα fold of the homing endonucleases of the LAGLIDADG (SEQ ID NO: 69) family, corresponding to a sequence of about one hundred amino acid residues. Said domain comprises four beta-strands folded in an antiparallel beta-sheet which interacts with one half of the DNA target. This domain is able to associate with another LAGLIDADG homing endonuclease core domain (SEQ ID NO: 69) which interacts with the other half of the DNA target to form a functional endonuclease able to cleave said DNA target. For example, in the case of the dimeric homing endonuclease I-CreI (163 amino acids), the LAGLIDADG homing endonuclease core domain (SEQ ID NO: 69) corresponds to the residues 6 to 94. In the case of monomeric homing endonucleases, two such domains are found in the sequence of the endonuclease; for example in I-DmoI (194 amino acids), the first domain (residues 7 to 99) and the second domain (residues 104 to 194) are separated by a short linker (residues 100 to 103).

by "subdomain" is intended the region of a LAGLIDADG homing endonuclease core domain (SEQ ID NO: 69) which interacts with a distinct part of a homing endonuclease DNA target half-site. Two different subdomains behave independently or partly independently, and the mutation in one subdomain does not alter the binding and cleavage properties of the other subdomain, or does not alter it in a number of cases. Therefore, two subdomains bind distinct part of a homing endonuclease DNA target half-site.

by "beta-hairpin" is intended two consecutive beta-strands of the antiparallel beta-sheet of a LAGLIDADG homing endonuclease core domain (SEQ ID NO: 69) which are connected by a loop or a turn, by "C1221" it is intended to refer to the first half of the I-CreI target site '12' repeated backwards so as to form a palindrome '21'.

by "cleavage activity" the cleavage activity of the variant of the invention may be measured by a direct repeat recombination assay, in yeast or mammalian cells, using a reporter vector, as described in the PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458. The reporter vector comprises two truncated, non-functional copies of a reporter gene (direct repeats) and a chimeric DNA target sequence within the intervening sequence, cloned in a yeast or a mammalian expression vector. The DNA target sequence is derived from the parent homing endonuclease cleavage site by replacement of at least one nucleotide by a different nucleotide. Preferably a panel of palindromic or non-palindromic DNA targets representing the different combinations of the 4 bases (g, a, c, t) at one or more positions of the DNA cleavage site is tested ($4^n$ palindromic targets for n mutated positions). Expression of the variant results in a functional endonuclease which is able to cleave the DNA target sequence. This cleavage induces homologous recombination between the direct repeats, resulting in a functional reporter gene, whose expression can be monitored by appropriate assay.

by "DNA target", "DNA target sequence", "target sequence", "target-site", "target", "site"; "recognition site", "recognition sequence", "homing recognition site", "homing site", "cleavage site" is intended a 22 to 24 by double-stranded palindromic, partially palindromic (pseudo-palindromic) or non-palindromic polynucleotide sequence that is recognized and cleaved by a LAGLIDADG homing endonuclease (SEQ ID NO: 69). These terms refer to a distinct DNA location, preferably a genomic location, at which a double stranded break (cleavage) is to be induced by the endonuclease. The DNA target is defined by the 5' to 3' sequence of one strand of the double-stranded polynucleotide. For example, the palindromic DNA target sequence cleaved by wild type I-CreI is defined by the sequence 5'- $t_{-12}c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}g_{+11}a_{+12}$ (SEQ ID NO:8) Cleavage of the DNA target occurs at the nucleotides in positions +2 and −2, respectively for the sense and the antisense strand. Unless otherwise indicated, the position at which cleavage of the DNA target by a meganuclease variant occurs, corresponds to the cleavage site on the sense strand of the DNA target.

by "DNA target half-site", "half cleavage site" or half-site" is intended the portion of the DNA target which is bound by each LAGLIDADG homing endonuclease core domain (SEQ ID NO: 69).

by "chimeric DNA target" or "hybrid DNA target" is intended the fusion of a different half of two parent meganuclease target sequences. In addition at least one half of said target may comprise the combination of nucleotides which are bound by separate subdomains (combined DNA target).

by "mutation" is intended the substitution, the deletion, and/or the addition of one or more nucleotides/amino acids in a nucleic acid/amino acid sequence.

by "homologous" is intended a sequence with enough identity to another one to lead to a homologous recombination between sequences, more particularly having at least 95% identity, preferably 97% identity and more preferably 99%.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

"individual" includes mammals, as well as other vertebrates (e.g., birds, fish and reptiles). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses).

"gene of interest" or "GOI" refers to any nucleotide sequence encoding a known or putative gene product.

"genetic disease" refers to any disease, partially or completely, directly or indirectly, due to an abnormality in one or several genes. Said abnormality can be a mutation, an insertion or a deletion. Said mutation can be a punctual mutation. Said abnormality can affect the coding sequence of the gene or its regulatory sequence. Said abnormality can affect the structure of the genomic sequence or the structure or stability of the encoded mRNA. This genetic disease can be recessive or dominant. Such genetic disease could be, but are not limited to, cystic fibrosis, Huntington's chorea, familial hypercholesterolemia (LDL receptor defect), hepatoblastoma, Wilson's disease, congenital hepatic porphyrias, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, Duchenne's muscular dystrophy, and Tay-Sachs disease.

"cGPS site" or "cGPS locus" refers to the genomic location at which the essential components of construct (i) have been introduced stably.

"cGPS cell line" refers to at least one cell in which the "cGPS site" or "cGPS locus" is present.

"cell-penetrating peptide" or "CPP" refers to peptides that facilitate cellular uptake of various molecular cargo in particular proteins and large macromolecules which would not normally be able to pass through the cell membrane at a rate sufficient for the cargo to have any effect upon the target cell.

"EF1α" refers to the human gene which encodes an isoform of the alpha subunit of the elongation factor-1 complex, which is responsible for the enzymatic delivery of aminoacyl tRNAs to the ribosome. The sequence of the human EF1α promoter, first and second exon and first intron is provided as SEQ ID NO: 9; the sequence of the human EF1α first intron is provided as SEQ ID NO: 10; the sequence of the human EF1α first exon is provided as SEQ ID NO: 11 and the sequence of the human EF1α second exon is provided as SEQ ID NO: 12.

"vectors": a vector which can be used in the present invention for instance as construct (ii) or (iii) as defined above includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picor-navirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracycline, rifampicin or ampicillin resistance in *E. coli*. These selectable markers can also be used as a part of the constructs (i) and (ii) according to the present invention.

Preferably said vectors are expression vectors, wherein a sequence encoding a polypeptide of the invention is placed under control of appropriate transcriptional and translational control elements to permit production or synthesis of said protein. Therefore, said polynucleotide is comprised in an expression cassette. More particularly, the vector comprises a replication origin, a promoter operatively linked to said encoding polynucleotide, a ribosome site, an RNA-splicing site (when genomic DNA is used), a polyadenylation site and a transcription termination site. It also can comprise enhancer or silencer elements. Selection of the promoter will depend upon the cell in which the polypeptide is expressed.

EXAMPLE 1

Generating Stable Eukaryotic Cell Lines Transfected with Construct (i)

Construct (i) can be stably transfected into cells using known techniques. There are various methods of introducing foreign DNA into a eukaryotic cell and many materials have been used as carriers for transfection, which can be divided into three kinds: (cationic) polymers, liposomes and nanoparticles. Other methods of transfection include nucleofection, electroporation, heat shock, magnetofection and proprietary transfection reagents such as Lipofectamine®, Dojindo Hilymax®, Fugene®, JetPEI®, Effectene®, DreamFect®, PolyFect®, Nucleofector®, Lyovec®, Attractene®, Transfast®, Optifect®.

1.1 CHO-K1

Figure 1:
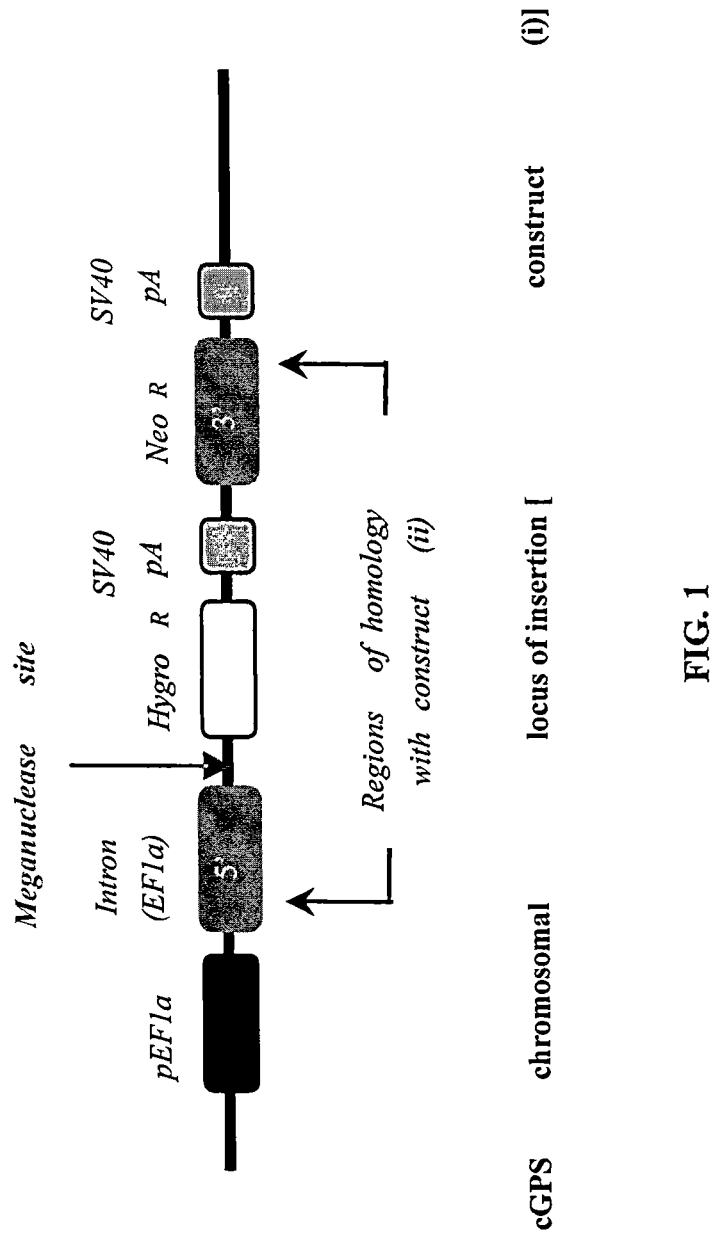
FIG. 1 shows a schematic representation of the cGPS locus.

In the present example construct (i), consists of SEQ ID NO: 6, which comprises a specific Meganuclease target site which has been inserted into the CHO-K1 genome at a unique locus. This site is the precise insertion locus of GOIs. This site has been inserted as a single copy into the CHO-K1 Cell line as part of a larger construct. In the final Cell Line, termed cGPS-CHO-K1, the Meganuclease target site is located near the hygromycin resistance gene and downstream the EF1 alpha promoter. The cGPS-CHO-K1 cell line is then resistant to hygromycin. Furthermore, the neomycin resistance gene is located just downstream the hygromycin gene but lacks a promoter making the cGPS-CHO-K1 cell line G418 sensitive (see FIG. 1).

1.2 NIH 3T3

In the present example construct (i) consists of SEQ ID NO: 6, which comprises a specific Meganuclease target site which has been inserted into the NIH 3T3 genome at a unique locus. This site is the precise insertion locus of GOIs. This site has been inserted as a single copy into the NIH 3T3 Cell line as part of a larger construct. In the final Cell Line, termed cGPSNIH 3T3, the Meganuclease target site is located near the hygromycin resistance gene and downstream the EF1 alpha promoter. The cGPSNIH 3T3 cell line is then resistant to hygromycin. Furthermore, the neomycin resistance gene is located just downstream the hygromycin gene but lacks a promoter making the cGPSNIH 3T3 cell line G418 sensitive (see FIG. 1).

1.3 HEK 293

In the present example construct (i), consists of SEQ ID NO: 6, which comprises a specific Meganuclease target site which has been inserted into the human HEK 293 genome at a unique locus. This site is the precise insertion locus of GOIs. This site has been inserted as a single copy into the HEK 293 Cell line as part of a larger construct. In the final Cell Line, termed cGPSHEK 293, the Meganuclease target site is located near the hygromycin resistance gene and downstream the EF1 alpha promoter. The cGPSHEK 293 cell line is then resistant to hygromycin. Furthermore, the neomycin resistance gene is located just downstream the hygromycin gene but lacks a promoter making the cGPSHEK 293 cell line G418 sensitive (see FIG. 1).

EXAMPLE 2

Highly Efficient Targeted Insertion of Gene of Interest (GOI) in cGPS Cell Line 2.1 Cloning of GOI into Construct (ii)

Figure 2:
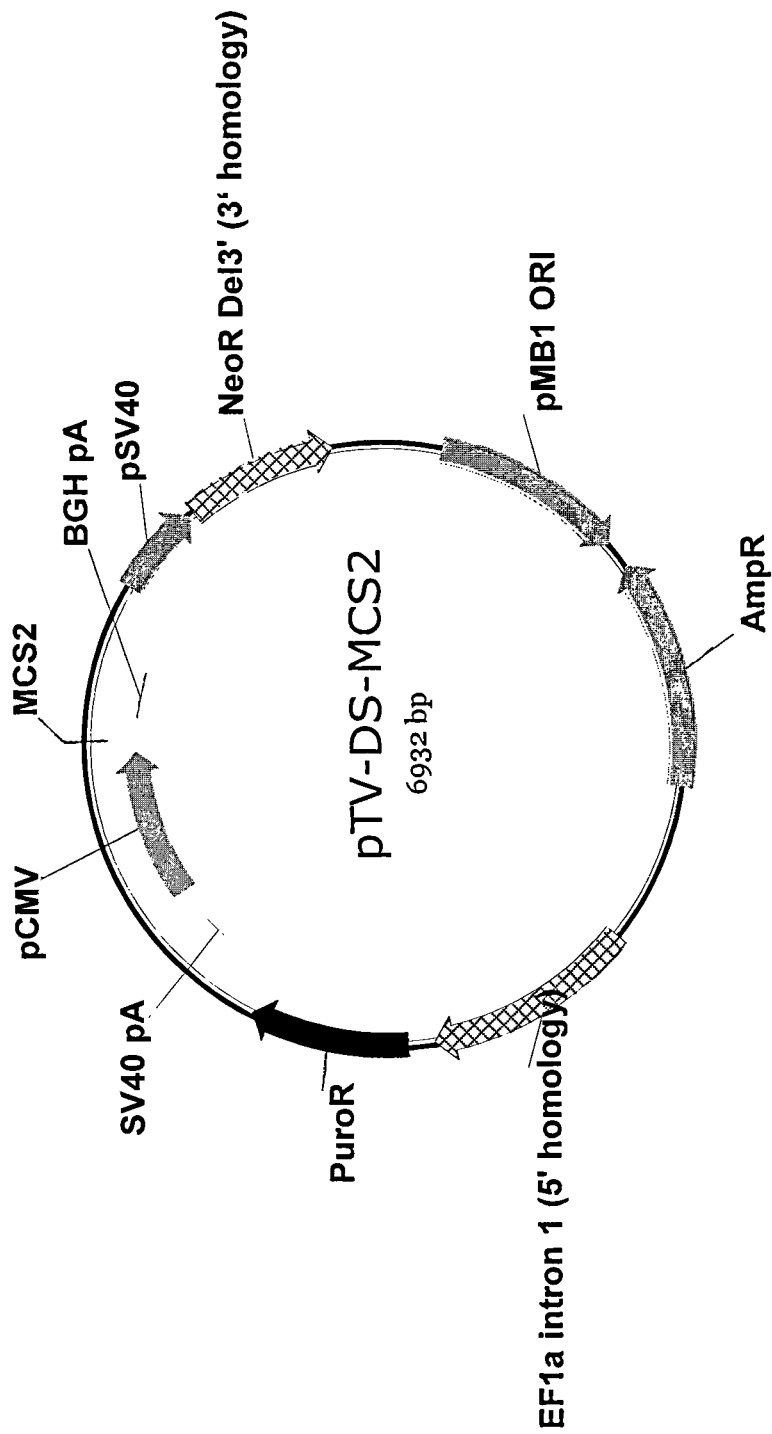
FIG. 2 shows a schematic representation of the pTV-DS-MCS2 vector.
Figure 3:
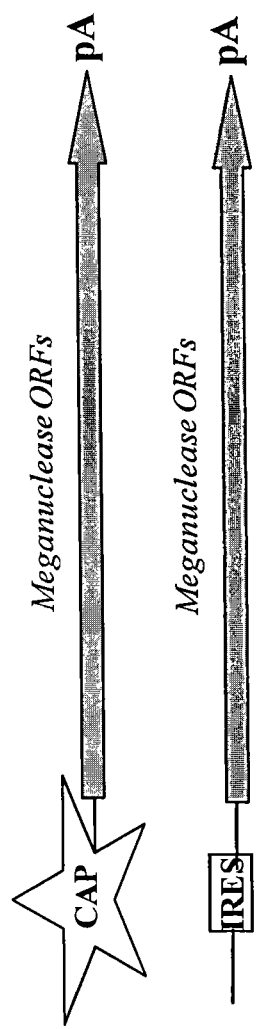
FIG. 3 shows a schematic representation of a Meganuclease capped polyadenylated mRNA.

The first step for generating a cell line expressing a GOI is to sub-clone the GOI into the pTV-DS-MCS2 vector (SEQ ID NO: 22; see FIG. 2). For this purpose a multiple cloning site has been introduced therein.

The expression of the gene of interest will be controlled by a CMV promoter and the bovine growth hormone (BGH) polyadenylation signal. The pTV-DS-MCS2 plasmid contains all the characteristics to favor a highly efficient HR event at the cGPS locus (SEQ ID NO: 6). A left homology arm (corresponding to portion A2 of construct (i) and A2' of construct (ii)) is composed of a 0.8 kb fragment homologous to the genomic 1 kb upstream the Meganuclease target site in the cGPS Cell Line. A right homology arm (corresponding to A5 of construct (i) and to A5' of construct (ii)) is composed of a 0.6 kb fragment homologous to the genomic 0.8 kb downstream the Meganuclease target site in the cGPS Cell Line.

Both homology arms are separated by (i) the puromycin resistance gene (which lacks a promoter on the plasmid), (ii) a CMV promoter for the expression of the GOI, (iii) a multiple cloning site for the insertion of the GOI, (iv) a polyadenylation signal controlling the stability of the mRNA for the GOI, and (v) a modified neomycin resistance gene. By itself, the pTV-DS-MCS2 plasmid cannot induce a puromycin and neomycin resistance phenotype.

Figure 4:
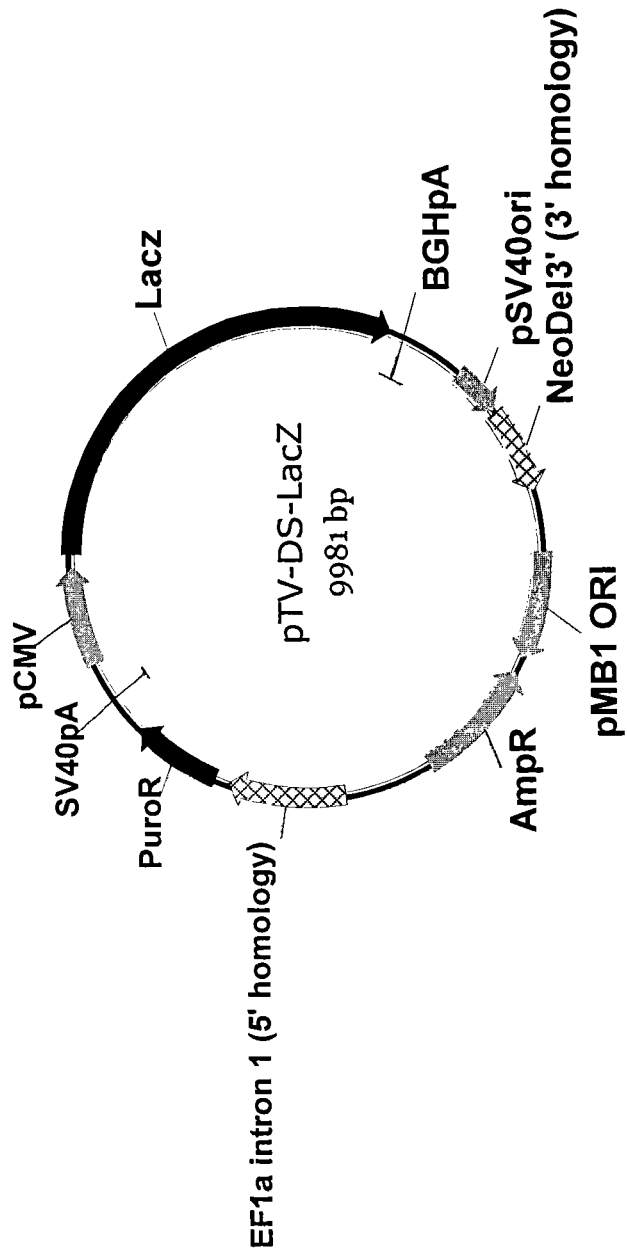
FIG. 4 shows a schematic representation of the pTV-DS-LacZ vector.

For example, the pTV-DS-LacZ plasmid (SEQ ID NO: 17; see FIG. 4) has been obtained by cloning the lacZ gene into the multiple cloning site of the pTV-DS-MCS2. The pTV-DS-LacZ plasmid (SEQ ID NO: 17) can be used as a positive control vector for mammalian cell transfection. It may be used to assay for expression levels in the cGPS cell lines. The sequence of the cGPS site following insertion of the lacZ gene is provided as SEQ ID NO: 18, the sequence of the cGPS site prior to insertion of the lacZ gene is provided as SEQ ID NO: 24.

Insertion of LacZ at the cGPS locus can be monitored as if it was the GOI.

2.2 cGPS CHO-K1 Cell Line 2.2.1 cGPSCHO-K1 Culture Conditions and Transfection cGPSCHO-K1 cells are sub-cultured in F-12K complete medium supplemented with 0.6 mg/ml of hygromycin. cGPSCHO-K1 cells are passed twice a week at 1:10-1:40 ratio.

Media and Supplements
　　Complete medium: F-12K medium (Invitrogen-Life Science) is supplemented with 2 mM L-glutamine, penicilline (100 UUm1), streptomycine (100 µg/ml), amphotericine B (Fongizone) (0.25 µg/ml) and 10% FBS.
　　PBS
　　Hygromycin B solution (Sigma).
　　Puromycin dichloride (Sigma).
　　G418 sulfate (Invitrogen-Life Science).
　　Trypsin-EDTA solution (Invitrogen-Life Science).
　　Freezing medium: F12K complete medium supplemented with 10% DMSO.
Transfection.

One day prior to transfection, the cGPSCHO-K1 cells are seeded in 10 cm tissue culture dishes ($2\times10^5$ cells per dish) in complete F-12K medium.

On D day, 2 µg of pTV plasmid versions (pTV-DS-MCS2 containing any GOI or pTV-DS-LacZ) and 1 µg of meganuclease constructs (pCLS1088 or pCLS2147 plasmid DNAs, or meganuclease-encoding mRNAs) are diluted in EC-R buffer. 6 µl of Enhancer Reagent is added (ratio nucleic acid (µg):enhancer (µl) should be 1:2).

Total volume DNA: enhancer EC-R buffer should be 1004 Vortex 10" and incubate 5' at room temperature.

Add 24 µl of TransMessenger™ (Qiagen) reagent (ratio nucleic acid (µg):TransMessenger™ (µl) should be 1:8) to the mix. Vortex 10" and incubate 10' at room temperature.

Meantime, replace culture medium with 9 ml of fresh medium.

Add 900 µl of serum- and antibiotic-free medium of the transfection mix and dispense over plated cells.

Incubate dish in a 37° C., 5% $CO_2$ humidified incubator.

Figure 5:
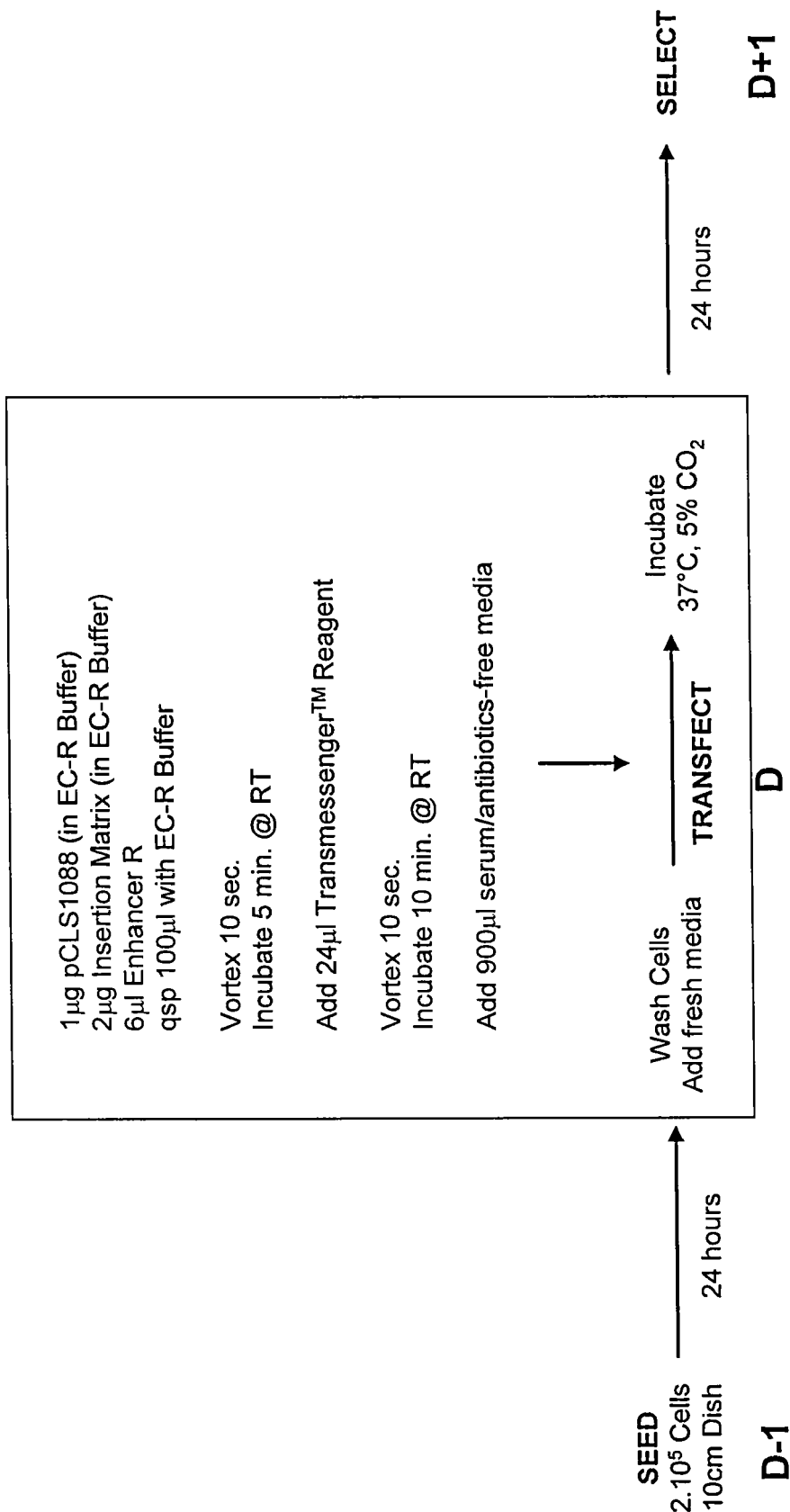
FIG. 5 shows a schematic representation of a transfection protocol for the cGPS CHO-K1 cell line according to the present invention.

A schematic representation of the transfection protocol is shown in FIG. 5.

Figure 6:
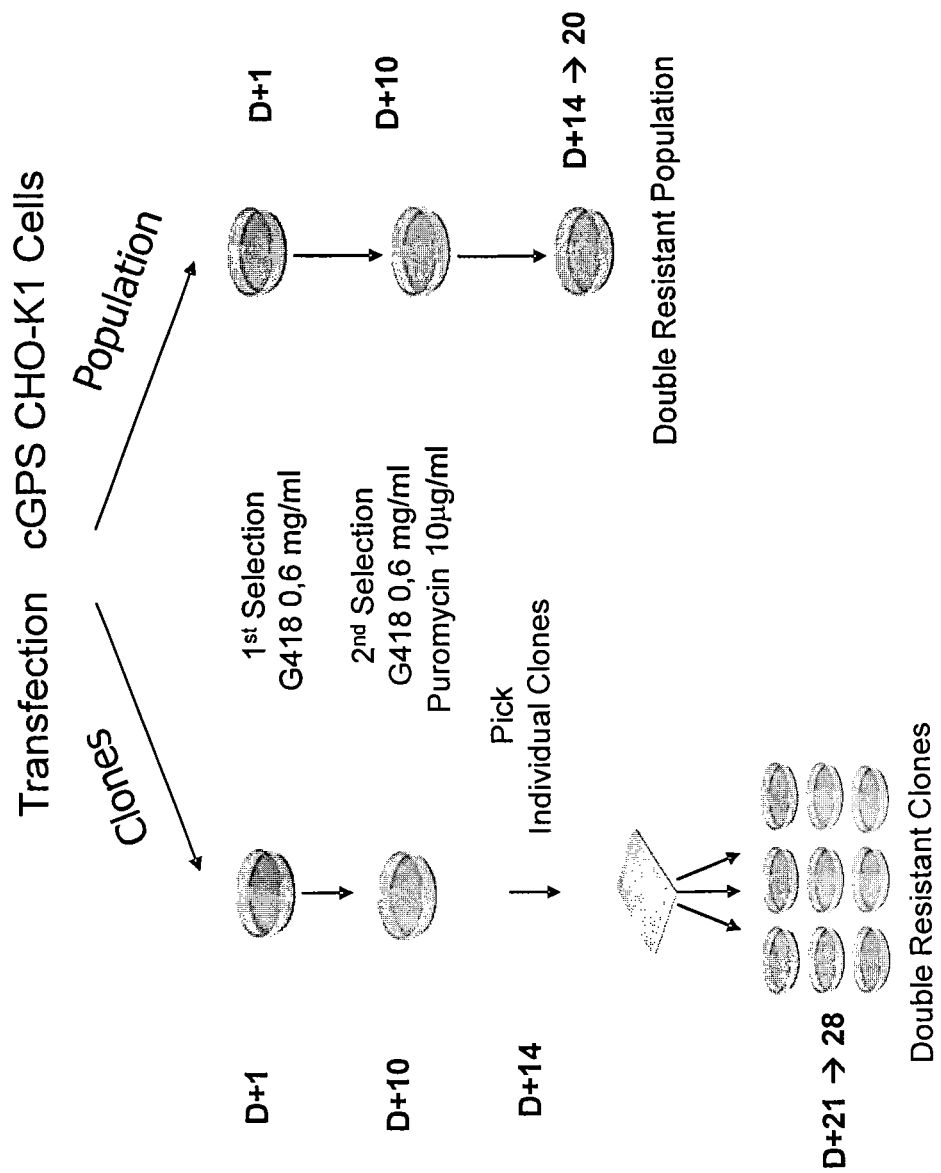
FIG. 6 shows a schematic representation of the clonal selection protocol (left column) and batch selection protocol (right column) for the cGPS CHO-K1 cell line.

2.2.2 cGPS CHO-K1 Targeted Clones Selection
2.2.2.1 cGPS CHO-K1 Clonal Selection Clonal selection is a longer but better protocol to select the proper cell line expressing the GOI. FIG. 6 shows a schematic representation of the clonal selection protocol (left column).

cGPS CHO-K1 cells are transfected with the protocol described above (2.2.1). 24 hours after transfection, the cells are washed and fresh medium supplemented with 0.6 mg/ml of G418 is added.

After 10 days of G418 selection, the culture medium is replaced with complete medium supplemented with G418 at 0.6 mg/ml and puromycin at 10 µg/ml.

3 to 4 days later, double resistant clones are picked up and seeded in a 96 well plate. Double resistant clones are amplified to reach confluence of a 10 cm culture dish 7 to 10 days later, double resistant clones can be characterized by analytical PCR and Southern blotting experiments. Positive control clones can be assayed for β-galactosidase activity, if pTV-DS-LacZ has been used as a positive control.

2.2.2.2 cGPS CHO-K1 Population Selection

In addition to the clonal selection described above, a population selection procedure can be used to retrieve the insertion clones. This procedure is faster and much easier to handle; however, the inventors believe that the clonal procedure is better to obtain pure single insertion clones.

For example, cGPS CHO-K1 cells are transfected with the protocol described above (2.2.1).

24 hours after transfection, wash the cells and add fresh medium supplemented with 0.6 mg/ml of G418.

10 days after G418 selection, wash the cells and add fresh medium supplemented with G418 at 0.6 mg/ml and puromycin at 10 µg/ml.

4 to 10 days later, double resistant population can be amplified in complete medium supplemented with the two selective agents.

FIG. 6 shows a schematic representation of the population selection protocol (right column).

Targeted insertion for different GOIs in the cGPS CHO-K1 are presented in examples 3, 4, 5, 6 and 7.

2.3 cGPS NIH 3T3 Cell Line
2.3.1 cGPS NIH 3T3 Culture Conditions and Transfection cGPS NIH 3T3 cells are sub-cultured in DMEM complete medium supplemented with 0.6 mg/ml of hygromycin. cGPS NIH 3T3 cells are passed twice a week at 1:3-1:10 ratio.

Media and Supplements
　　Complete medium: DMEM medium (Invitrogen-Life Science) is supplemented with 2 mM L-glutamine, penicilline (100 UI/ml), streptomycine (100 µg/ml), amphotericine B (Fongizone) (0.25 µg/ml) and 10% FBS.
　　PBS
　　Hygromycin B solution (Sigma).
　　Puromycin dichloride (Sigma).
　　G418 sulfate (Invitrogen-Life Science).
　　Trypsin-EDTA solution (Invitrogen-Life Science).
　　Freezing medium: DMEM complete medium supplemented with 10% DMSO.
Transfection.

One day prior to transfection, the cGPS NIH 3T3 cells are seeded in 10 cm tissue culture dishes ($2.5\times10^5$ cells per dish) in complete medium.

On D day, 1 µg of pTV plasmid versions (pTV-DS-MCS2 containing any GOI or pTV-DS-LacZ) and 1 µg of meganuclease constructs (pCLS1088 or pCLS2147 plasmid DNAs, or meganuclease-encoding mRNAs) are diluted in 300 µl of EC buffer. 16 µl of Enhancer Reagent is added (ratio nucleic acid (µg):enhancer (µl) should be 1:8).

Total volume DNA: EC buffer should be 3000. Vortex lightly and incubate 5' at room temperature.

Add 40 µl of Effectene™ (Qiagen) reagent (ratio nucleic acid (µg):Effectene™ (µl) should be 1:20) to the mix. Vortex 10" and incubate 10' at room temperature.

Meantime, replace culture medium with 9 ml of fresh medium.

Add 1 ml of complete medium of the transfection mix and dispense over plated cells.

Incubate dish in a 37° C., 5% $CO_2$ humidified incubator.

Figure 7:
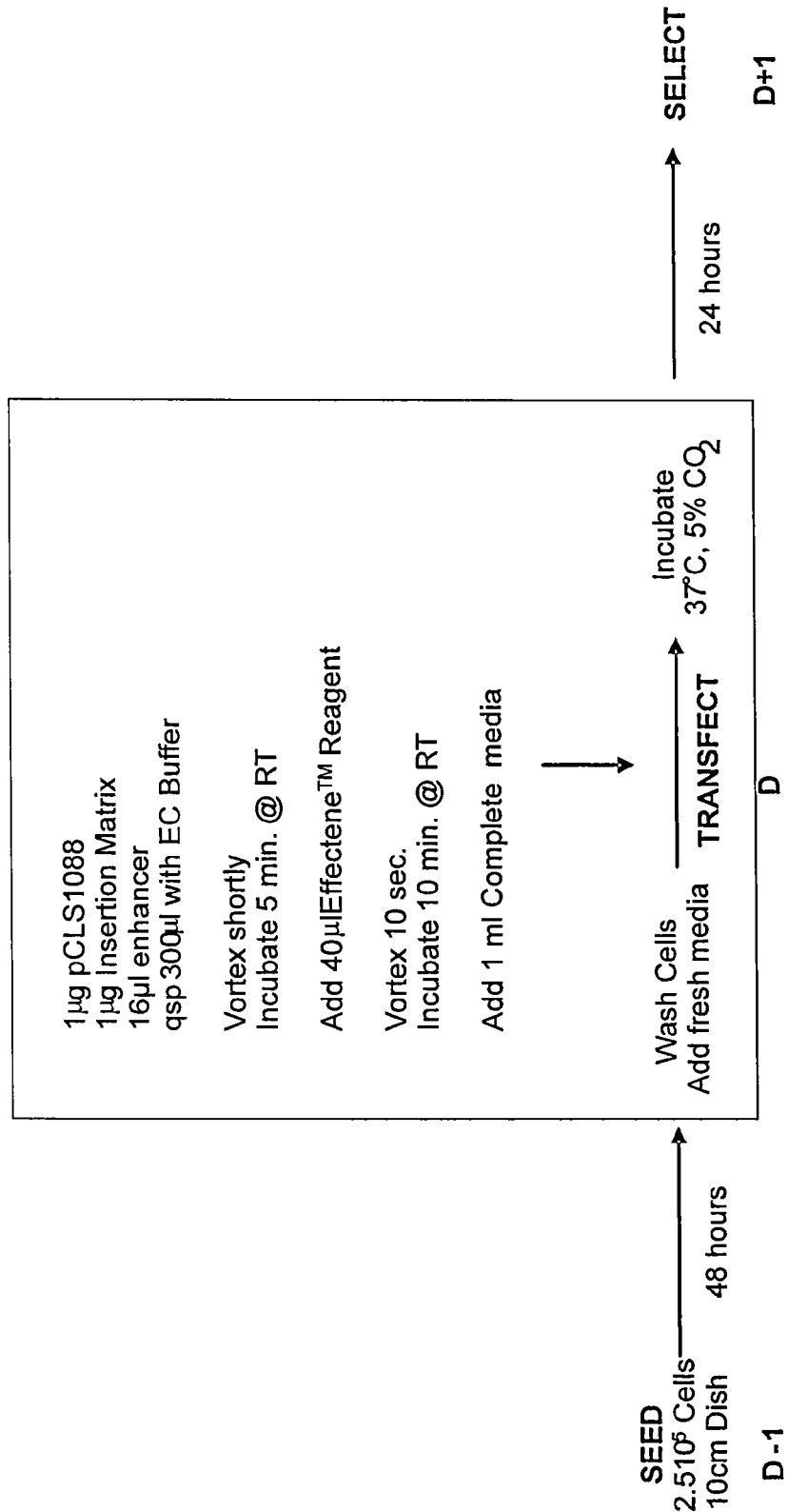
FIG. 7 shows a schematic representation of a transfection protocol for the cGPS NIH 3T3 cell line according to the present invention.

A schematic representation of the transfection protocol is shown in FIG. 7.

2.3.2 cGPS NIH 3T3 Targeted Clones Selection

Figure 8:
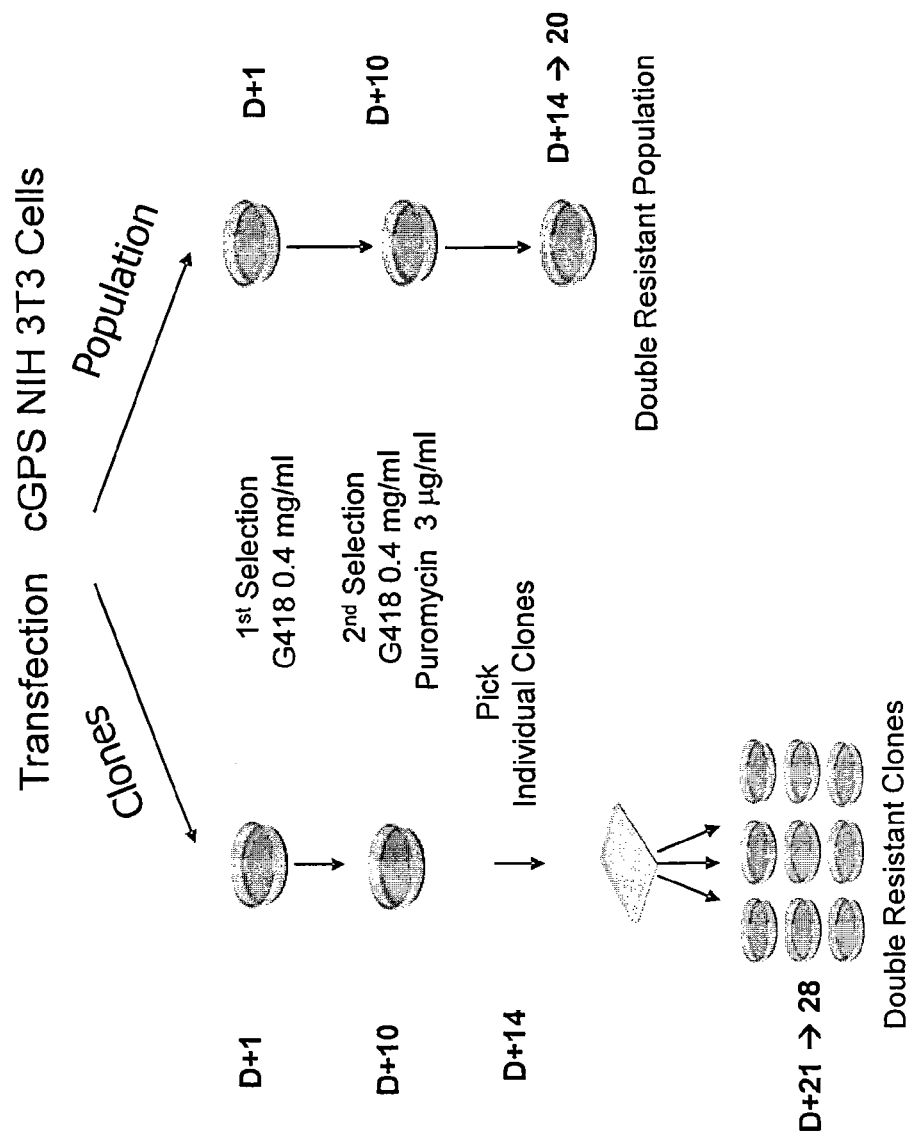
FIG. 8 shows a schematic representation of the clonal selection protocol (left column) and batch selection protocol (right column) for the cGPS NIH 3T3 cell line.

Clonal selection is a longer but better protocol to select the proper cell line expressing the GOI. FIG. 8 shows a schematic representation of the clonal selection protocol (left column).

cGPS NIH 3T3 cells are transfected with the protocol described above (2.3.1). 24 hours after transfection, the cells are washed and fresh medium supplemented with 0.4 mg/ml of G418 is added.

10 days after G418 selection, single colony clones are picked up and seeded in 96 well plates in complete medium supplemented with G418 at 0.4 mg/ml and puromycin at 3 µg/ml.

6 to 7 days later, double resistant clones can be amplified in complete medium supplemented with the two selective agents.

7 to 10 days later, double resistant clones can be characterized by analytical PCR and Southern blotting experiments. Positive control clones can be assayed for β-galactosidase activity, if pTV-DS-LacZ has been used as a positive control.

Figure 9A:
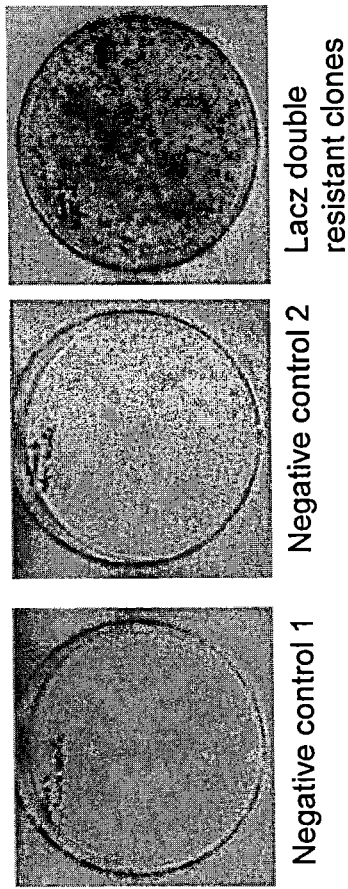
FIG. 9 shows the production of double resistant lacZ targeted clones in the cGPS NIH 3T3 system (FIG. 9A) and their molecular characterization (FIG. 9B).
Figure 9B:
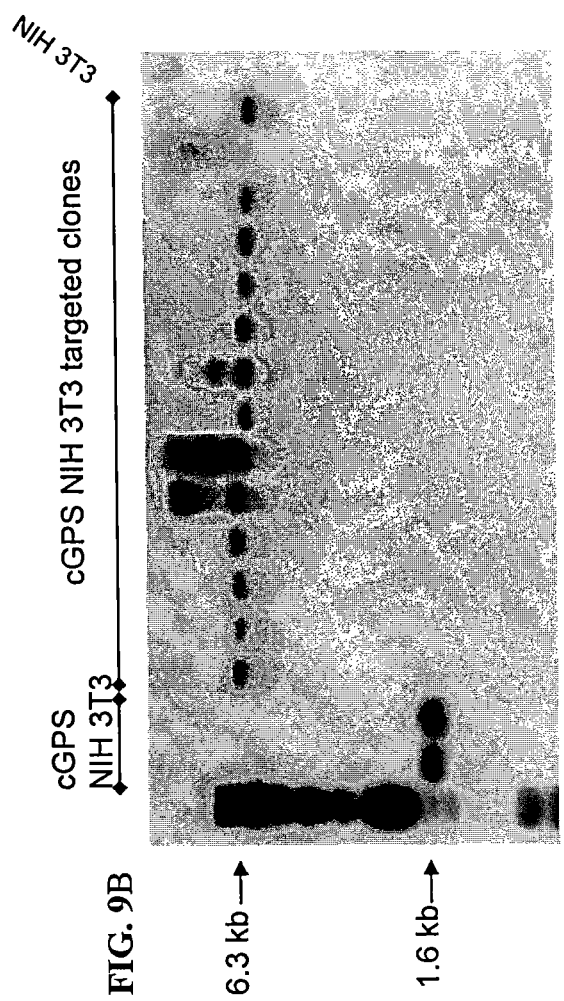

As shown on FIG. 9 panel A, double resistant clones are only present upon co-transfection with meganuclease expression vector and pTV-DS-Lacz. No double resistant clone is obtained in the controls (i.e. meganuclease expression vector transfected cells (negative control 1) or pTV-DS-lacZ (negative control 2) transfected cells). Furthermore, near all double resistant clones expressed the lacz gene as revealed by X-gal staining (see example 6 for materials and methods). Several double resistant clones are picked at random and amplified for molecular characterization by Southern blotting (see section 2.5). As shown on FIG. 9 panel B, genomic DNA from 14 double resistant clones is digested with the RsrII restriction enzyme, immobilized on nitrocellulose membrane and hybridized with a $^{32}$P-neomycine probe. A correct targeted insertion is characterized by the identification of a band at 6.3 kb. Such band is identified for all double resistant clones analyzed, while a band at 1.6 kb is shown for the parental cGPS NIH 3T3. In addition to the 6.3 kb band, others bands are present for 4/14 clones and is probably due to an additional random insertion. Hence, these results demonstrate that cGPS NIH 3T3 double resistant clones, obtained with the method described above, expressed the reported gene, present on the integration matrix, that is correctly targeted in the cGPS locus.

2.4 cGPS HEK 293 Cell Line 2.4.1 cGPS HEK 293 Culture Conditions and Transfection cGPS HEK 293 cells are sub-cultured in DMEM complete medium supplemented with 0.1 mg/ml of hygromycin. cGPS HEK 293 cells are passed twice a week at 1:3-1:10 ratio.

Media and Supplements

Complete medium: DMEM medium Glutamax (Invitrogen-Life Science) is supplemented with penicilline (100 UI/ml), streptomycine (100 µg/ml), amphotericine B (Fongizone) (0.25 µg/ml) and 10% FBS.

PBS

Hygromycin B solution (Sigma).

Puromycin dichloride (Sigma).

G418 sulfate (Invitrogen-Life Science).

Trypsin-EDTA solution (Invitrogen-Life Science).

Freezing medium: DMEM complete medium supplemented with 10% DMSO.

Transfection.

One day prior to transfection, the stable cGPSHEK 293 cells are seeded in 10 cm tissue culture dishes ($10^6$ cells per dish) in complete medium.

On D day, 3 µg of pTV plasmid versions (pTV-DS-MCS2 containing any GOI or pTV-DS-LacZ) and 2 µg of meganuclease constructs (pCLS1088 or pCLS2147 plasmid DNAs, or meganuclease-encoding mRNAs) are diluted in 300 µl of DMEM without serum. On the other hand, 10 µl of Lipofectamine 2000 (Invitrogen) are mixed with 290 µl of DMEM without serum.

The two mixes are incubated 5 min at room temperature. Then the DNA mix is added to the lipofectamine mix and incubated for 20 min. at room temperature.

Meantime, replace culture medium with 9 ml of fresh medium.

After the incubation period, add the total transfection mix (600 µl) over plated cells.

Incubate dish in a 37° C., 5% $CO_2$ humidified incubator.

Change medium 6 hours after transfection (optional)

Figure 10:
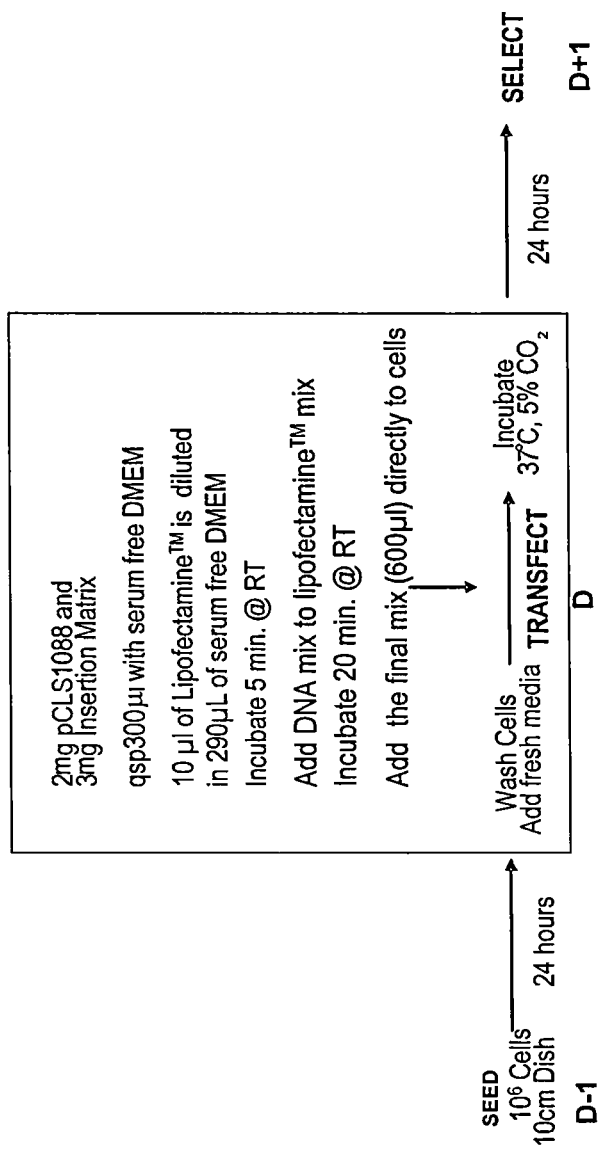
FIG. 10 shows a schematic representation of a transfection protocol for the cGPS HEK 293 cell line according to the present invention.

A schematic representation of the transfection protocol is shown in FIG. 10.

2.4.2 cGPS HEK 293 Targeted Clones Selection

Figure 11:
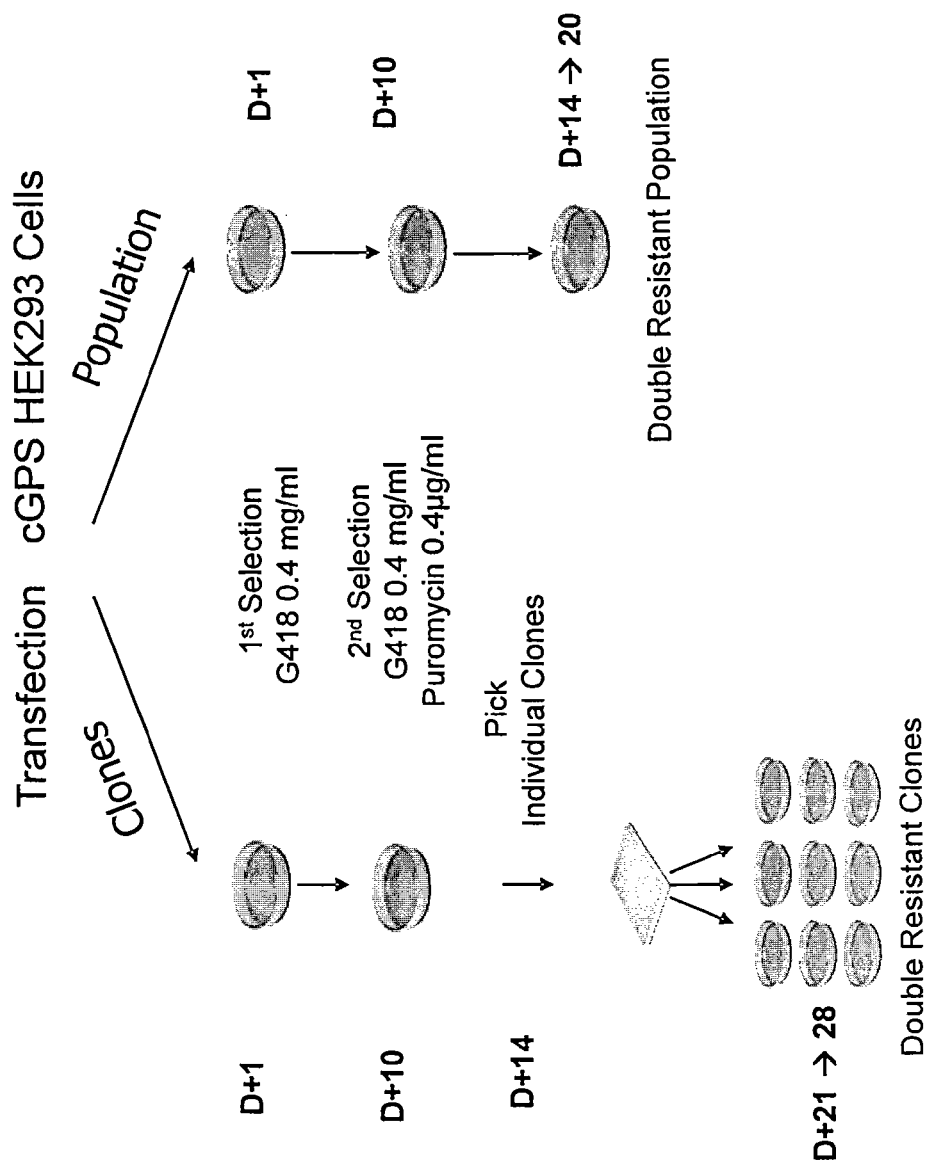
FIG. 11 shows a schematic representation of the clonal selection protocol (left column) and batch selection protocol (right column) for the cGPS HEK 293 cell line.

Clonal selection is a longer but better protocol to select the proper cell line expressing the GOI. FIG. 11 shows a schematic representation of the clonal selection protocol (left column).

cGPS HEK 293 cells are transfected with the protocol described above (2.4.1). 24 hours after transfection, culture medium is replaced with fresh medium supplemented with 0.4 mg/ml of G418.

After 12 days of G418 selection, the second selective agent (puromycin) is added at the concentration of 0.4 µg/ml.

After 7-9 days of double selection, single colony clones are picked up and seeded in 96 well plates in complete medium supplemented with G418 at 0.4 mg/ml and puromycin at 0.4 µg/ml.

10 days later, double resistant clones can be characterized by analytical PCR and Southern blotting experiments. Positive control clones can be assayed for β-galactosidase activity, if pTV-DS-LacZ has been used as a positive control.

As shown on FIG. 12 panel A, double resistant clones are obtained upon cotransfection with meganuclease expression vector and pTV-DS-lacZ. These double resistant clones expressed the lacz gene as revealed by X-gal staining (see example 6 for materials and methods). Several double resistant clones are picked at random and amplified for molecular characterization by Southern blotting (see section 2.5). As shown on FIG. 12 panel B, gDNA from 13 double resistant clones is digested with the RsrII restriction enzyme, immobilized on nitrocellulose membrane and hybridized with a $^{32}$P-neo probe. A correct targeted insertion is characterized by the identification of a band at 4.3 kb. Such band is identified for 11 double resistant clones out of 13 clones analyzed, while a band at 1.6 kb is shown for the parental cGPS HEK 293. In addition to the 4.3 kb band, a second band is present for 3 out of 11 clones and is probably due to an additional random insertion. Hence, these results demonstrate that cGPS HEK 293 double resistant clones, obtained with the method described above, expressed the reported gene, present on the integration matrix, that is correctly targeted in the cGPS locus.

2.5 Molecular Characterisation of Insertion Clones

Figure 13:
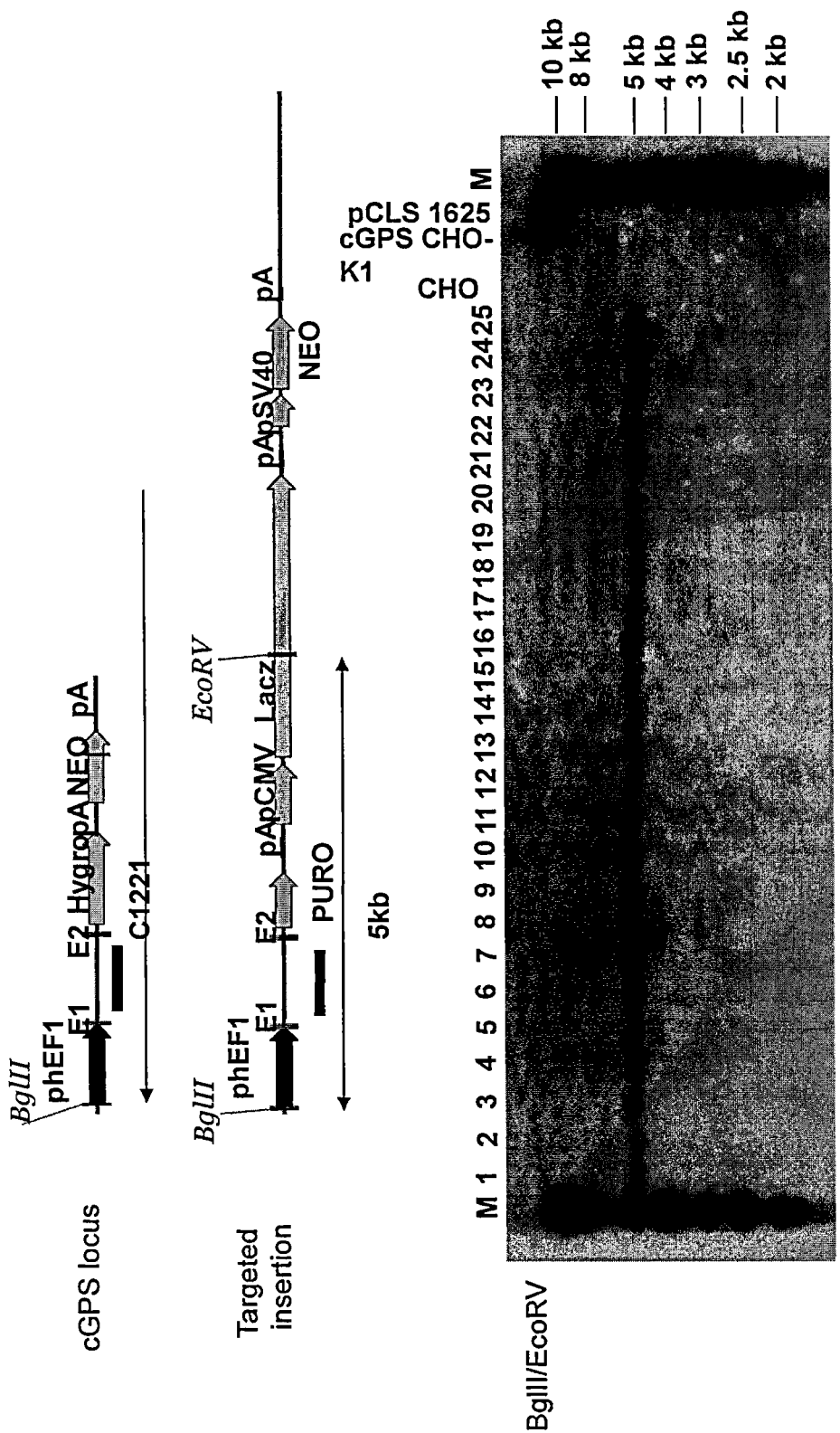
FIG. 13 shows a Southern blot analysis of 25 selected clones targeted with the pTV-DS-LacZ vector.

A correct targeted insertion in double resistant clones can be easily identified at the molecular level by Southern blot analysis (FIG. 13). Alternatively PCR primers can also be designed for a quicker characterization of targeted clones.

Materials and Methods

Genomic DNA (gDNA) from targeted clones was purified from $10^7$ cells (about a nearly confluent 10 cm dish) using the Blood and Cell culture DNA midi kit (Qiagen, 5 to 10 µg of gDNA are digested with a 10-fold excess of restriction enzyme by overnight incubation).

Digested gDNA was separated on a 0.8% agarose gel and transfer on nylon membrane.

Nylon membranes were then probed with a $^{32}$P DNA probe specific for the EF1α intron.

After appropriate washes, the specific hybridization of the probe is revealed by autoradiography.

To Check the Left Region of the Targeted Insertion:

```
Forward oligo (in the cGPS locus) F1_Prom:
                                  (SEQ ID NO: 30)
CCCCGACCGGAGCTGAGAGTAATT Reverse oligo (in the pTV-DS-MCS2 vector) B1_Pur:
                                  (SEQ ID NO: 31)
CAGGAGGCCTTCCATCTGTTG
```

The amplification product is 1794 base pairs (bp) long.

For Checking the Right Region of the Targeted Insertion:

```
Forward oligo (in the pTV-DS-MCS2 vector) SV40s:
                                  (SEQ ID NO: 32)
CTGTGGAATGTGTGTCAGT
```

```
                                -continued
Reverse oligo (in the cGPS locus) NEOr:
                                            (SEQ ID NO: 33)
CAACGCTATGTCCTGATAGCGGTC
```

The amplification product is 1073 bp long.

Results

For example (FIG. 13), the targeted insertion of LacZ is checked in the 5' side with a double digest BglII (1 site upstream of pEF1α promoter) and EcoRV (a unique site in the LacZ gene). The probe is located within the EF1α intron. Thus, the native locus when digested within BglII/EcoRV, gives a band higher than 10 kb. On the contrary, a targeted insertion will bring the EcoRV site from LacZ in the vicinity of the BglII site. Upon double digest, a 5 kb DNA fragment is generated that is identified with the intron probe. The same approach can be used for the 3' side of the insertion.

EXAMPLE 3

Expressing Gene of Interest in cGPS CHO-K1 Cell Line 3.1 CD4 Expression

The human CD4 ORF (SEQ ID NO: 40) has been cloned in the pTV-DS-MCS2. The resulting vector (pTV-DS-CD4, FIG. 26, SEQ ID NO: 41) has been transfected in cGPS CHO-K1 cells according to the protocol described in 2.2.1. The sequence of the cGPS site following insertion of the CD4 gene is provided as SEQ ID NO: 62. Targeted clones surviving the selection process (2.2.2) are isolated and the expression of the transmembrane CD4 protein is evaluated.

Materials and Methods

Cells from targeted clones are washed twice in PBS and incubated with 2 ml of Versene solution. After 5 min. incubation at 37° C., cells are collected in a 15 ml conical tube. The cells are counted.

$10^6$ cells are transferred in 5 ml tube (Falcon, 2058) and centrifuge at 300 g for 5 min. at 4° C. Cells are washed once with FACS buffer. Cell pellets are resuspended in 200 of Biotin conjugated anti-CD4 or Biotin-conjugated isotype control antibody. After 30 min. of incubation on ice, cells are washed once in FACS buffer. Cell pellets are then incubated with 20 ml of Streptavidin-conjugated PE for 30 min. on ice and protected from light. The cells are washed once in FACS buffer and finally re-suspended in 0.5 ml of FACS buffer.

Results

Figure 14:
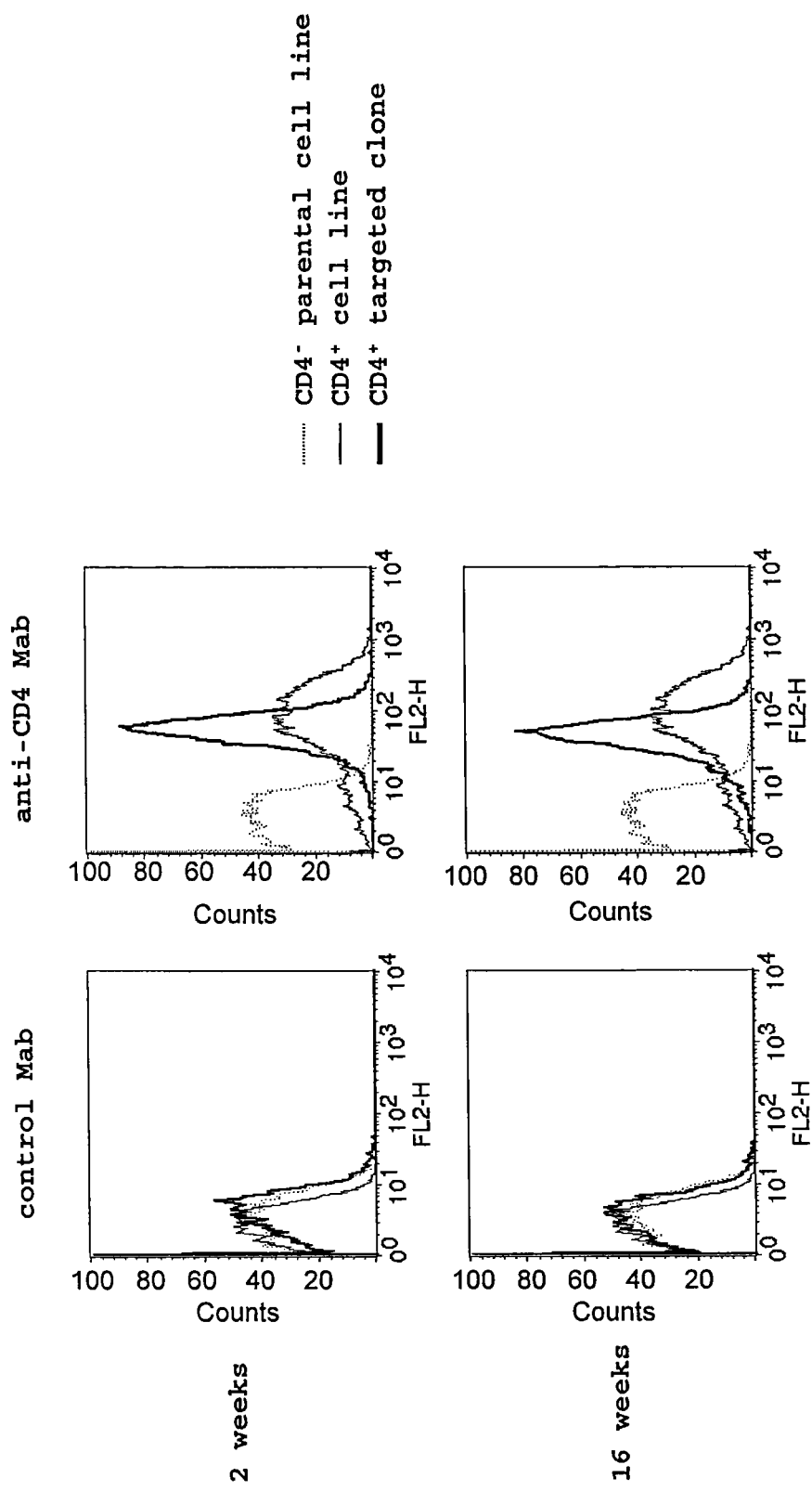
FIG. 14 shows the results of experiments to determine by FACS analysis the stability of human CD4 expression over time.

The cells sample are analyzed on a FACS vantage II (BD Bioscience) using a 488 nm Ion-Argon laser. The emitted fluorescence (emission wave length at approximately 580 nm) is collected in the fluorescence 2 channel (FIG. 14).

These experiments showed that the CD4 gene product could be reliably inserted into the cGPS locus and then be stably expressed over a prolonged period of time.

3.2 Somatostatin Receptor (GPCR SSTR2) Expression

The human GPCR SSTR2 ORF (SEQ ID NO: 42) has been cloned in the pTV-DS-MCS2. The resulting vector (pTV-DS-SSTR2, FIG. 27, SEQ ID NO: 43) has been transfected in cGPS CHO-K1 cells according to the protocol described in 2.2.1. The sequence of the cGPS site following insertion of the SSTR2 gene is provided as SEQ ID NO: 63. Targeted clones surviving the selection process (2.2.2) are isolated and the expression of the SSTR2 protein is evaluated.

Materials and Methods

Figure 15:
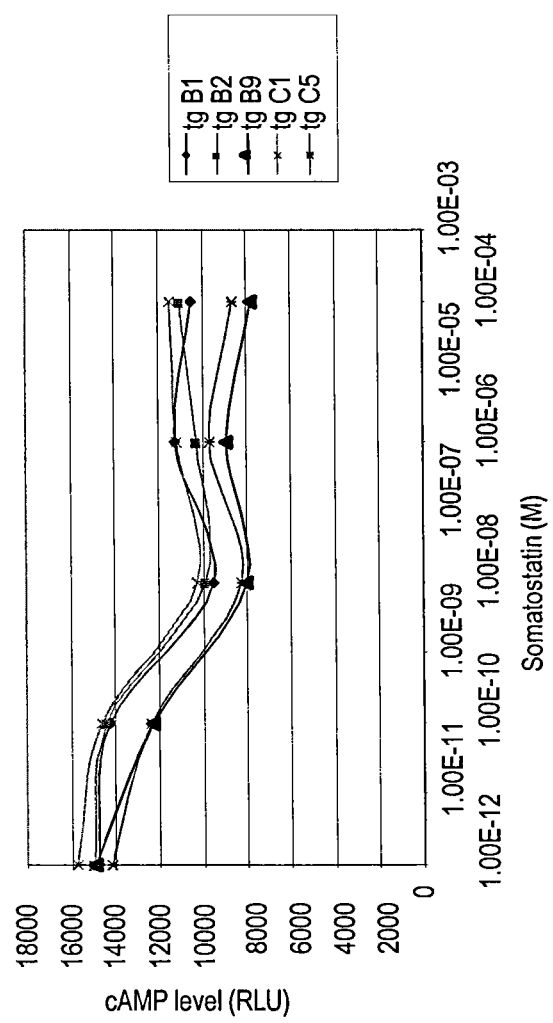
FIG. 15 shows the results of a functional assay for cAMP production inhibition performed upon clones targeted with the somatostatin receptor (GPCR-SSTR2) as GOI.

GPCR SSTR2 activity is accomplished by measuring the inhibition of cAMP production after proper agonist stimulation of the SSTR2 receptor. The inventors used the protocol and reagents provided by the HitHunter™ cAMP XS+ assay kit (DiscoverX). Briefly, cells from targeted clones are seeded in white 96 well plates at the density of $10^4$ cells per well. After co stimulation of cells with Forskolin (100 µM) and increasing concentrations of Somatostatin (from $10^{-12}$ M to $10^{-4}$ M), cells are lysed and cAMP level is measured using a microplate luminometer (Victor, Perkin Elmer) (FIG. 15).

Results

In these experiments individual clones were seen to show essentially the same cAMP production inhibition profile in response to different levels of somatostatin.

3.3 Human Autotaxin (hATX).

The human AUTOTAXIN ORF (SEQ ID NO: 44) has been cloned in the pTV-DS-MCS2. The resulting vector (pTV-DS-hATX, FIG. 28 SEQ ID NO: 45) has been transfected in cGPS CHO-K1 cells according to the protocol described in 2.2.1. The sequence of the cGPS site following insertion of the hATX gene is provided as SEQ ID NO: 64. Targeted clones surviving the selection process (2.2.2) are isolated and the expression of the hATX protein is evaluated by western blotting.

Materials and Methods

Preparation of ATX Conditioned Media cGPS CHO-K1 hATX targeted clones were washed twice with PBS first, 3 times with serum-free FK12 medium supplemented with 1% glutamin in order to remove serum (2 ml per well and per wash for a 6 wells plate), and then incubated with the same medium (1 ml per well) 6 hours at 37° C. in a humidified atmosphere containing 7% CO2. After incubation, conditioned-medium (CM) was separated from the cells, centrifuged to eliminate cell debris and then dialyzed overnight against 10 liters of 20 mM HEPES, pH 7.4, 6 mM D(+)-glucose, 1 mM $CaCl_2$, and 1.2 mM $MgSO_4$ using Spectra-Por 1.7 ml/cm tubing (Pierce Chemicals, Interchim, Montluçon, France). After dialysis CM are concentrated (about 15 fold) using an Amicon Ultra 10,000 (Millipore). Concentrated conditioned media (CCM) were aliquoted and stored at −20° C. before use.

SDS-PAGE Separation and Western Blotting

SDS-PAGE 4-12% was performed according to Laemmli (25) followed by Sypro Ruby staining and Western Blotting detection. After addition of sample buffer (Novex, Invitrogen) concentrated fractions of CM were boiled at 100° C. for 5 min. Electrophoretic separation of proteins was carried out on a 1 mm-thick 18×10-cm gel 4-12% acrylamide. An equivalent amount of total protein in sample buffer was loaded into a 4-mm well of the gel and separated at 40 mA. A total of 30 µg of standards (Mark12, or Magic Mark, Invitrogen) migrated in a neighboring lane. One of the gel was stained with Sypro Ruby and the other was transferred to nitrocellulose membranes and stained with chicken anti-autotaxin antibody followed by an HRP-conjugated anti-chicken antibody (Sigma Aldrich) before chemiluminescence detection of the immuno-complexes.

Results

Figure 16:
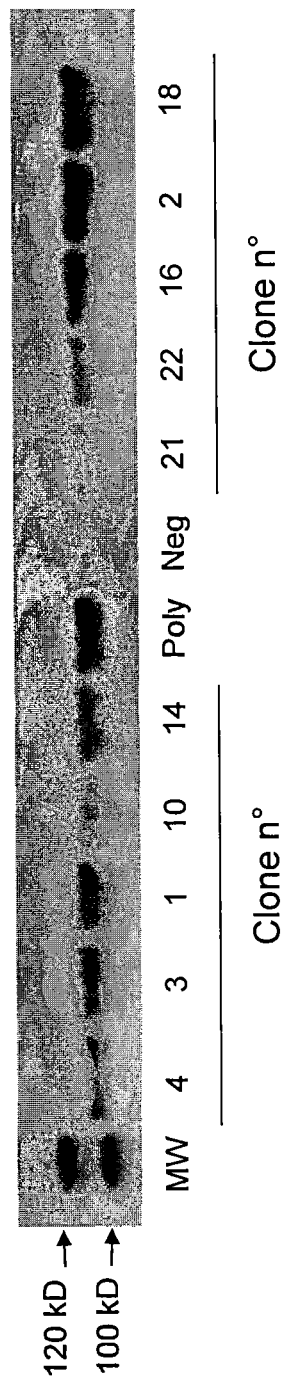
FIG. 16 shows the results of hATX expression from cGPS CHO-K1 hATX.

The detection of hATX in the supernatants of cGPS CHO-K1 hATX targeted clones is performed by western blot. FIG. 16 shows the identification of a band over 100 kD using a specific antibody for the human ATX, in conditioned media from 10 cGPS CHO-K1 hATX targeted clones supernatants or from a cGPS CHO-K1 hATX targeted cell population (poly). No band is detected in the supernatant from the negative control. These results indicate that this rather large secreted protein is expressed by all cGPS CHO-K1 hATX targeted clones.

3.4 Human Melatonin 1 Receptor (hMT1) and Human Melatonin 2 Receptor (hMT2)

The human GPCR MT1 ORF (SEQ ID NO: 46) has been cloned in the pTV-DS-MCS2. The resulting vector (pTV-DS-hMT1, FIG. 29, SEQ ID NO: 47) has been transfected in cGPS CHO-K1 cells according to the protocol described in 2.2.1. The sequence of the cGPS site following insertion of the hMT1 gene is provided as SEQ ID NO: 65. Targeted clones surviving the selection process (2.2.2) are isolated and the expression of the MT1 protein is evaluated.

The human GPCR MT2 ORF (SEQ ID NO: 48) has been cloned in the pTV-DS-MCS2. The resulting vector (pTV-DS-hMT2, FIG. 30, SEQ ID NO: 49) has been transfected in cGPS CHO-K1 cells according to the protocol described in 2.2.1. The sequence of the cGPS site following insertion of the hMT2 gene is provided as SEQ ID NO: 66. Targeted clones surviving the selection process (2.2.2) are isolated and the expression of the hMT2 protein is evaluated.

Materials and Methods
Radio-Ligand Saturations with Intact Cells cGPS CHO-K1 hMT1 targeted clones and cGPS CHO-K1 hMT2 targeted clones were resuspended in Tris/HCl 50 mM pH 7.4, EDTA 1 mM and MgCl2 5 mM and dispensed in 96-well polypropylene plates at 13,000 cells/well. [$^{125}$I]-2-Iodomelatonine 5 pM to 1.5 nM was added to determine the total binding signal, while control wells contained an additional 1 µM melatonin to determine non specific binding. The incubation was performed at 37° C. for 2 hrs in a total volume of 2504. Cells were then transferred to unifilter GF/B plates (Perkin Elmer) with a FilterMate cell harvester (Perkin Elmer) and washed 3 times with 1 ml of ice-cold Tris 50 mM. Microscint 20 (40 µl/well, Perkin Elmer) was added before sealing plates. The radioligand associated with filter plates was evaluated by scintillation counting using a TopCount (Perkin Elmer). Experiments were conducted in triplicates, and data are expressed as fmol radioligand specific binding sites (total minus non specific) per mg of total protein. Graphic representations and data analysis were generated using PRISM 4.03 (GraphPad).

Results

Figure 17A:
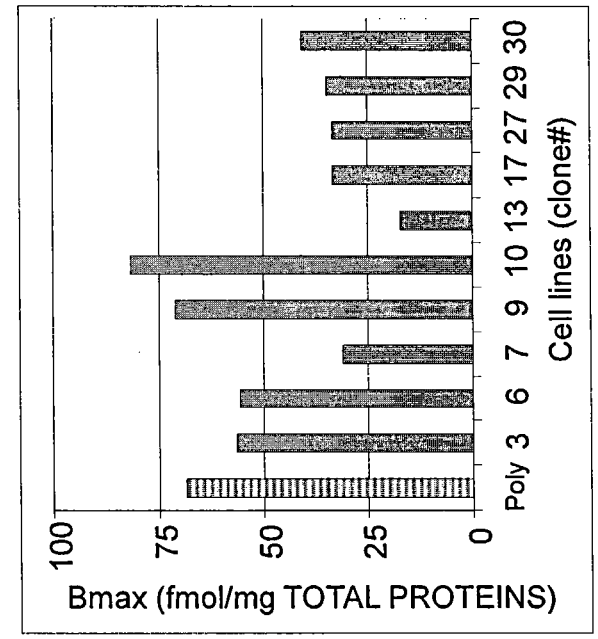
Figure 17B:
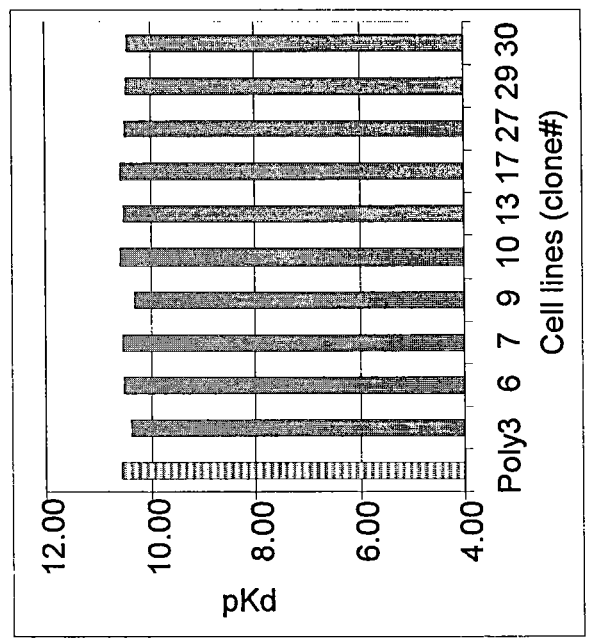
FIG. 17B shows the quantity (fmol) of specific binding sites per mg of total protein.
Figure 18B:
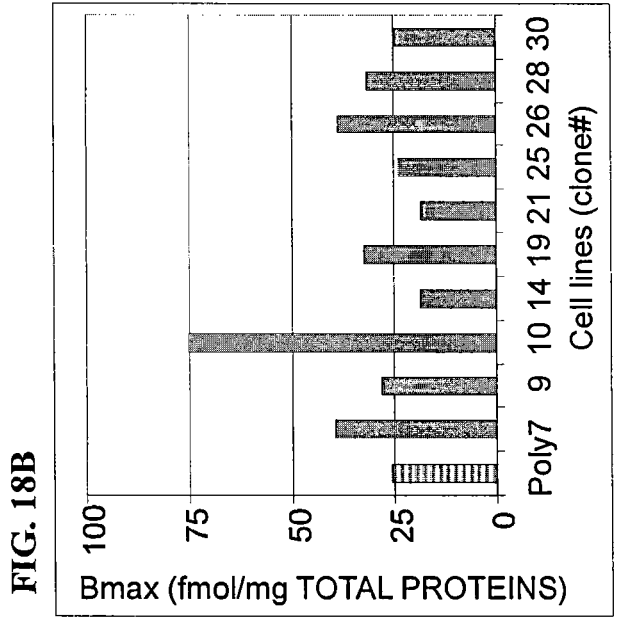
FIG. 18B shows the quantity (fmol) of specific binding sites per mg of total protein.
Figure 18A:
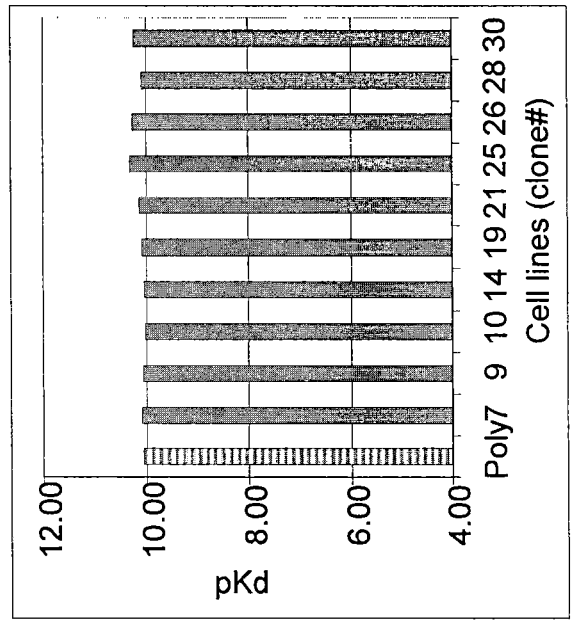

Ten cGPS CHO-K1 hMT1 targeted clones and 10 cGPS CHO-K1 hMT2 targeted clones were picked at random and functionally tested for radioligand saturations experiments using [$^{125}$I]-iodomelatonin. Results obtained for the hMT1 are presented on FIG. 17 and those for hMT2, on FIG. 18. From saturations curves, pKd values are obtained by Scatchard analysis (FIG. 17, panel A and FIG. 18, panel A). From the saturations curves, the quantity (fmol) of specific binding sites per mg of total protein (Bmax, FIG. 17 panel B and FIG. 18, panel A) is measured. Similar results are obtained with both receptors. The data indicate that pKd values from each clones are very closed to each other and to polyclonal cGPS CHO-K1 hMT1- or hMT2-targeted cell population. However, some variations of hMT1 and hMT2 receptors expression is observed from clones to clones. pKd and Bmax values for both receptors are consistent with previous published observations.

EXAMPLE 4

Expressing GOI Under the Control of Different Promoters

In this example, the heavy chain (SEQ ID NO: 50) and the light chain (SEQ ID NO: 51) of the 5F11 monoclonal antibody (Medarex Inc.) have been cloned in the pTV-DS-MCS2. Both chains are under the control of the Ubiquitin sub-unit c promoter (pUbc SEQ ID NO: 52). The resulting vector (pTV-DS-5F11, FIG. 31, SEQ ID NO: 53) has been transfected in cGPS CHO-K1 cells according to the protocol described in 2.2.1. The sequence of the cGPS site following insertion of the 5F11 gene is provided as SEQ ID NO: 67. Targeted clones surviving the selection process (2.2.2) are isolated and the expression of the 5F11 monoclonal antibody protein is evaluated.

Materials and Methods

Figure 19:
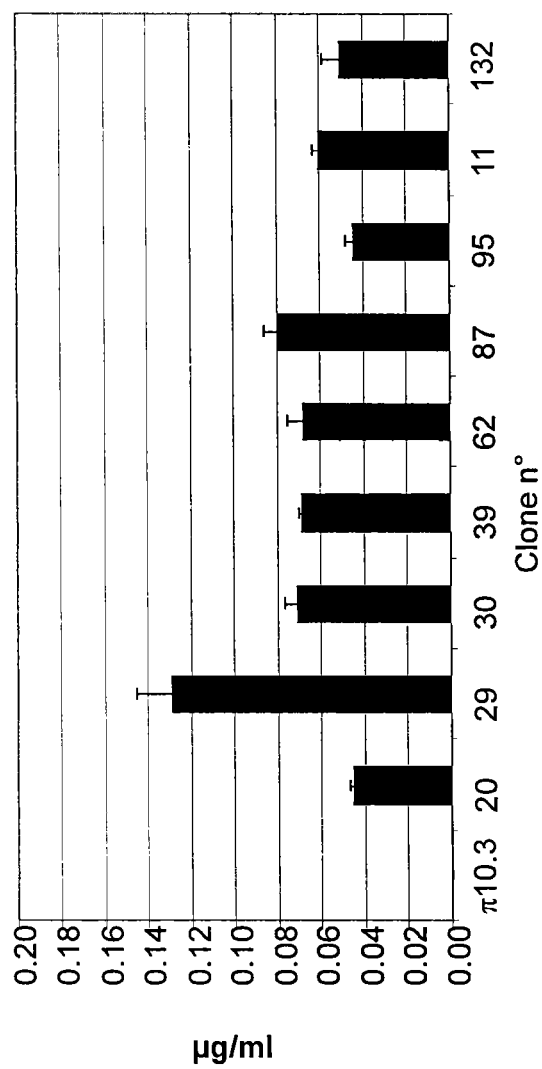
FIG. 19 shows the results of experiments to determine the homogeneity of expression levels of several clones expressing a monoclonal antibody that is controlled by the Ubiquitin sub unit c promoter (pUbc).

Cells from targeted clones are seeded in 96 well plates (Costar) at the density of $10^4$ cells per well. After 48 h of culture in complete medium, supernatants are collected and assayed for monoclonal antibody expression by ELISA. Briefly, 96 well plates are coated with a Goat-anti-Human kappa light chain (Southern Biotechnology Associates) in PBS overnight at 4° C. All washing steps are done in PBS, 0.1% Tween 20. After washing, plates are blocked in PBS, 1% BSA (PBA) for 90 min at 37° C. under shaking. After washing, 50 µl of diluted supernatant from samples are added and incubated for 90 min at 37° C. under shaking. After washing, a goat-anti-human IgG Fc coupled to Alkaline Phosphatase (Jackson ImmunoResearch) in PBA is added. After washing, the Developing buffer (Pierce) containing 1 mg/ml PNPP (Pierce) is added. Optical density (OD) is read at 405 nm using a microplate Reader (Model 550, BioRad) (FIG. 19).

Results

This study showed that the measured level of antibody expression was greater than 0.04 µg/ml in 48 hours for each of the generated clones and that expression levels were generally homogenous, although clone 29 showed higher expression levels in comparison to the other studied clones.

EXAMPLE 5

Long-Lasting Expression of GOI in the Presence or Absence of Selecting Drugs

In this example, the inventors monitored the level of expression of four cGPS CHO-K1 targeted clones expressing the lacZ gene and of four cGPS CHO-K1 targeted clones expressing the luciferase gene. The lacZ ORF (SEQ ID NO: 16) has been cloned in the pTV-DS-MCS2. The resulting vector (pTV-DS-lacz, FIG. 4, SEQ ID NO: 17) has been transfected in cGPS CHO-K1 cells according to the protocol described in 2.2.1. Targeted clones surviving the selection process (2.2.2) are isolated and characterized according to section 2.5. The luciferase ORF (SEQ ID NO: 54) has been cloned in the pTV-DS-MCS2. The resulting vector (pTV-DS-luciferase, FIG. 32, SEQ ID NO: 55) has been transfected in cGPS CHO-K1 cells according to the protocol described in 2.2.1. The sequence of the cGPS site following insertion of the luciferase gene is provided as SEQ ID NO: 68. Targeted clones surviving the selection process (2.2.2) are isolated and characterized according to section 2.5.

The 4 cGPS CHO-K1 lacz targeted clones and the 4 cGPS CHO-K1 luciferase targeted clones were maintained in culture over a period of 45 passages (two passages per week). Each clone was cultured in the presence of selecting drugs (Puro; 10 µg/ml and G418: 0.6 mg/ml). Furthermore, the inventors evaluated the expression of the two reporter gene for the same clones but without selecting drugs (i.e. in complete F12K medium) over a period of time corresponding to 30 passages.

Materials and Methods

Lacz Expression: Cells from targeted clones are washed twice in PBS then incubated with 5 ml of trypsin-EDTA solution. After 5 min. incubation at 37° C., cells are collected in a 15 ml conical tube and counted.

Cells are then resuspended in complete F-12K medium at the density of 50000 cells/ml. 100 µl (5000 cells) are aliquoted in triplicate in a white 96 well plate (Perkin-Elmer). 100 µl of beta-Glo reagent (Promega) is added per well and after a 30 min. incubation period, the plate can be read on a luminometer (Viktor, Perkin-Elmer).

Luciferase Expression: Cells from targeted clones are washed twice in PBS then incubated with 5 ml of trypsin-EDTA solution. After 5 min. incubation at 37° C., cells are collected in a 15 ml conical tube and counted.

Cells are then resuspended in complete F-12K medium at the density of 50000 cells/ml. 100 µl (5000 cells) are aliquoted in triplicate in a white 96 well plate (Perkin-Elmer). 100 µl of One-Glo reagent (Promega) is added per well and after a short incubation the plate can be read on a microplate luminometer (Viktor, Perkin-Elmer).

Results

The data are presented on FIG. 20. On panels A and B, the mean level of lacz expression for 4 cGPS CHO-K1 lacz targeted clones is measured as a function of time in the presence or absence of selecting agents, respectively. On panels C and D, the mean level of luciferase expression for 4 cGPS CHO-K1 luciferase targeted clones is shown as a function of time in the presence or absence of selecting agents, respectively. These data indicates that the expression of both reporters is remarkably stable even after a long period of culture. Furthermore the presence of the selecting agents is not necessary to ensure a long lasting expression of transgene since the stability of reporter expression is equivalent when the targeted clones are cultivated without selecting agents.

EXAMPLE 6

Generating Targeted Clones Using I-CreI Recombinant Protein

In this example, the inventors addressed the possibility to use I-CreI as a recombinant protein instead of I-CreI expression vector plasmid or mRNA to achieve efficient gene targeting in cGPS CHO-K1 system. Two different cell-penetrating peptides, also termed DPVs have been demonstrated to transport reporter proteins to the nucleus in a variety of mammalian cell lines including epithelial (HeLa, HCT116), myeloid (HL-60), erythroid (K562), lymphoid (Molt4), fibroblast (NIH-3T3) cells, as well as primary hepatocyte cultures (24). They have been shown to efficiently mediate the internalization of molecules as little as a few Daltons, and up to 200 kDa. These peptidic sequences, DPV15b (SEQ ID NO: 56) and DPV1047 (SEQ ID NO: 57) have been fused to the N-terminal part of the I-CreI N75 meganuclease protein (SEQ ID NO: 14) and resulting recombinant protein has been produced in E. coli and purified. In this example, the inventors used the purified recombinant protein termed DPV15b/I-CreI N75/6xHis (SEQ ID NO: 58).

Materials and Methods

Transfection: On D day, 0.5 µg of the pTV-DS-lacz (SEQ ID NO: 17) is transfected in cGPS CHO-K1 cells by using the PolyFect® reagent from Qiagen. One day after the transfection of the integration matrix (D+1), 1000 µg of the purified DPV15b/I-CreI N75/6xHis (SEQ ID NO: 58) meganuclease protein is directly added into transfected cGPS CHO-K1 cells.

Selection: cGPS CHO-K1 cells are transfected with the protocol described above. 24 hours after transfection, the cells are washed and fresh medium supplemented with 0.6 mg/ml of G418 is added. After 10 days of G418 selection, the culture medium is replaced with complete medium supplemented with G418 at 0.6 mg/ml and puromycin at 10 µg/ml. 3 to 4 days later, double resistant clones are visualized through an inverted microscope. At this step, double resistant clones are either stained for lacz expression monitoring or picked up for amplification and molecular characterization. (see section 2.5)

X-Gal Staining: Culture medium is removed and LacZ-targeted double resistant cGPS CHO-K1 adherent cells are washed once with PBS. 5 ml of fixing buffer (100 mM phosphate buffer, 1 mM $MgCl_2$, 0.5% (v/v) glutaraldehyde (Prolabo, 25% solution)) is added. After 10 min. of incubation on ice, fixing is replaced by 5 ml of washing buffer (100 mM phosphate buffer, 1 mM $MgCl_2$, 0.02% (v/v) NP40). Then, 5 ml of staining buffer (10 mM phosphate buffer, 1 mM $MgCl_2$, 33 mM KFerri [Potassium hexacyanoferrate (III)], 33 mM KFerro [Potassium hexacyanoferrate (II)], 0.1% (v/v) X-Gal) is added for incubation at 37° C. Blue cells should appear within 24 hours.

Results

As shown in FIG. 21 panel A, double resistant ($Neo^R$/$Puro^R$) cGPS CHO-K1 cell colonies are generated after the KI assay, from the moment that the I-CreI N75 meganuclease is expressed (pCLS1088) or added by fusion with a DPV cell penetrating peptide (DPV15b/I-CreI N75/6xHis (SEQ ID NO: 58)) in association with the transfection of a LacZ-encoding integration matrix (pCLS1625). By contrast, the sole transfection of the integration matrix does not generate any cell colony, highlighting the importance of I-CreI N75 meganuclease to mediate homologous recombination in the cGPS CHO-K1 KI model.

Although a fewer number of cell colonies have been generated by the delivery of DPV15b/I-CreI N75/6xHis (SEQ ID NO: 58) recombinant proteins (around 30, leading to a selection frequency of $3 \times 10^{-4}$) over those depicted from the transfection of I-CreI N75-encoding DNA plasmid (around 50, with a selection frequency of $5 \times 10^{-4}$), these results clearly indicates that the DPV15b/I-CreI N75/6xHis (SEQ ID NO: 58) recombinant protein triggers targeted integration of the lacz gene. Moreover, all these cGPS CHO-K1 lacZ targeted clones are blue after X-Gal staining for both DNA and protein conditions, probably suggesting that all cell clones have been positively targeted.

However, since the expression of the reporter LacZ gene could arise from a random chromosomal integration, a Southern blot analysis has been settled in order to check the correct cGPS genetic pattern of integration for different double resistant cGPS CHO-K1 cell clones. Genomic DNAs extracted from nineteen individual cGPS CHO-K1 lacz targeted clones, as well as from CHO-K1 and untargeted cGPS CHO-K1 cells have been submitted to the hybridization with a probe is specific to the cGPS chromosomal locus (i.e. the EF1α intron sequence).

As shown in FIG. 21 panel B, a vast majority of LacZ-targeted cGPS CHO-K1 cell clones (18 out of 19) contain the expected cGPS modified locus, with a band around 5 kb which demonstrates the targeted insertion of the LacZ gene. By contrast, the hybridization of genomic DNA extracts originating from the original untargeted cGPS CHO-K1 cell line reveals the presence of a higher band (10 kb), and no band is detected in the negative control, i.e. the CHO-K1 cell lineage that does not contain the EF1α intron sequence. The targeting at the cGPS locus is highly specific since no additional band is detected from LacZ-targeted cGPS CHO-K1 cell clones, therefore revealing the absence of any random integration elsewhere in the genome.

EXAMPLE 7

Generating Double Targeted Cell Line by Combining the Cgps Cho-K1 System with a Custom Meganuclease Gene Targeting System In this example, the inventors addressed the possibility to use the cGPS CHO-K1 system in combination with a custom meganuclease cGPS system, leading to the targeting of two genes of interest into two distinct loci of the CHO-K1 genome. The insertion of the two GOI is sequential. The first GOI is inserted in the cGPS locus as described in section 2.2. Once a cGPS CHO-K1 targeted clone is identified as described in section 2.5, a second GOI is inserted in the cGPS CHO-K1 targeted clone through a custom meganuclease, named Sc MA17-RM2-G19H33 (SEQ ID NO: 60), that has been engineered to cleave in the $3^{rd}$ exon of the CHO-K1 HPRT gene (WO2008/059382). The cGPS Custom CHO-K1 Integration Matrix containing the lacZ gene (FIG. 22; SEQ ID NO: 59), and Meganuclease Expression Vector (FIG. 23; SEQ ID NO: 61) are co-transfected into the cGPS CHO-K1 targeted clone. Upon co-transfection, the engineered meganuclease is expressed, recognizes its HPRT recognition site and induces a DNA double-strand break at this precise site. Homologous recombination occurs at the meganuclease recognition site. The gene of interest, cloned in the Integration Matrix in between the homology regions, is integrated at the meganuclease recognition site during this recombination event. Following meganuclease-induced homologous recombination, the hygromycin resistant gene is transcribed via the endogenous HPRT promoter and expressed as a fusion protein with the first exons of HPRT (exons 1, 2 and part of exon 3). In addition to the newly acquired hygromycin-resistance phenotype, targeting the mono-allelic HPRT gene locus leads to its inactivation, therefore allowing resistance to 6-thioguanine (6-TG) nucleotides. Thus, stable cGPS CHO-K1 targeted clone can be selected for the double hygromycin/6-TG resistance and expression of the recombinant protein of interest.

In the following example, the luciferase gene is chosen as the first GOI, to be inserted in the cGPS CHO-K1 locus, while the lacZ gene is the second GOI, to be inserted in the HPRT locus. After selection of double targeted clones, the expression of the two reporter genes is monitored over 20 passages (40 weeks) in order to evaluate their stability.

Materials and Methods

Transfection

One day prior to transfection, cGPS CHO-K1 targeted clone cells are seeded in a 10 cm tissue culture dish ($2\times10^5$ cells per dish). On transfection day, 1 µg of the Meganuclease Expression Vector and 2 µg of the Integration Matrix, containing the lacZ gene, are diluted in 275 µl of medium without serum. 25 µl of the PolyFect™ reagent is added to the diluted DNA and the transfection mix is vortexed for 10" and incubated 10' at room temperature.

In the meantime culture medium is replaced with 9 ml of fresh medium. Then 700 µl of complete medium is added to the transfection mix and the total volume is dispensed over plated cells.

Transfected cells are incubated in a 37° C., 5% $CO_2$ humidified incubator.

Selection 3 days after transfection, cells are washed and fresh medium, supplemented with 0.6 mg/ml of hygromycin B, is added.

After 7 days of hygromycin selection (Day+10), fresh medium, supplemented with 0.6 mg/ml of hygromycin B and 5 µg/ml of 6-thioguanine (Hybrimax, Sigma), is added.

After 5 or 8 days of double selection (Day+15 to Day+18), single colony clones are picked and seeded in 96 well plates in complete medium supplemented with 0.6 mg/ml of hygromycin B at and 5 µg/ml of 6-thioguanine.

Double resistant clones are amplified in complete medium supplemented with the two selective agents. For downstream experiments (i.e. molecular characterization, lacZ expression, etc. . . . ) the inventors strongly recommend to maintain both selective agents to maintain homogeneous expression.

Southern Blot

Genomic DNA (gDNA) is purified from $10^7$ cells (about a nearly confluent 10 cm dish). 5 to 10 µg of gDNA are digested with a 10-fold excess of EcoRV restriction enzyme by overnight incubation. Digested DNA is transferred on a nitrocellulose membrane and hybridization is performed with a $^{32}$P-labeled-lacz probe (see section 2.5 for details).

Results

The inventors have previously produced cGPS CHO-K1 targeted clones expressing the luciferase reporter gene (see example 4 and FIG. 20 panel C and D). One of these cGPS CHO-K1 luciferase targeted clone has been used to perform a second targeted insertion of the lacz gene into the Hprt locus. cGPS CHO-K1 luciferase targeted cells are co-transfected with the integration matrix containing the lacz gene and the meganuclease expression vector specific for the hamster Hprt gene. Upon selection, as described in the materials and methods section, hygromycin and 6-TG resistant clones are analyzed for correct insertion of the lacz gene in the Hprt gene. As shown on FIG. 24 panel A, 18 clones out of 18 are correctly targeted. 5 clones out of 18 present additional bands corresponding probably to the random insertion of the integration matrix. These data are in accordance with the data obtained when the experiment is done in CHO-K1. Furthermore, the inventors verified by southern blot that the cGPS CHO-K1 locus, site of the first targeted insertion is still modified. As shown on FIG. 24 panel B, the 18 analyzed clones present a hybridization pattern compatible with a modified cGPS CHO-K1 locus. All together, these data demonstrate that the first targeted insertion in the cGPS CHO-K1 locus has no impact on the efficiency of the second insertion, and the second targeted insertion is not prejudicial to the first, at least at the genomic level.

To verify whether the double insertion has an impact on the expression of the two reporter genes, four doubled targeted clones were maintained in culture over a period of 11 weeks (21 passages) and regularly checked for lacz and luciferase expression. As shown on FIG. 25 panel A, the expression of the lacz gene is stable allover the study period. Similarly, the luciferase expression is stable (FIG. 25 panel B) and comparable to those observed for single cGPS CHO-K1 targeted clones (FIG. 20 panel C and D).

REFERENCES

1. Hinnen, A., Hicks, J. B., and Fink, G. R. (1978) Transformation of yeast. *Proc Natl Acad Sci USA* 75, 1929-33.
2. Rothstein, R. J. (1983) One-step gene disruption in yeast. *Methods Enzymol* 101, 202-11.
3. Thomas, K. R., and Capecchi, M. R. (1987) Site-directed mutagenesis by gene targeting in mouse embryo-derived stem cells. *Cell* 51, 503-12.
4. Capecchi, M. R. (2001) Generating mice with targeted mutations. *Nat Med* 7, 1086-90.

5. Smithies, O. (2001) Forty years with homologous recombination. *Nat Med* 7, 1083-6.
6. Rouet, P., Smih, F., and Jasin, M. (1994) Introduction of double-strand breaks into the genome of mouse cells by expression of a rare-cutting endonuclease. *Mol Cell Biol* 14, 8096-106.
7. Choulika, A., Perrin, A., Dujon, B., and Nicolas, J. F. (1995) Induction of homologous recombination in mammalian chromosomes by using the I-SceI system of *Saccharomyces cerevisiae*. *Mol Cell Biol* 15, 1968-73.
8. Chevalier, B. S., and Stoddard, B. L. (2001) Homing endonucleases: structural and functional insight into the catalysts of intron/intein mobility. *Nucleic Acids Res* 29, 3757-74.
9. Dujon, B., Colleaux, L., Jacquier, A., Michel, F., and Monteilhet, C. (1986) Mitochondrial introns as mobile genetic elements: the role of intron-encoded proteins. *Basic Life Sci* 40, 5-27.
10. Haber, J. E. (1995) In vivo biochemistry: physical monitoring of recombination induced by site-specific endonucleases. *Bioessays* 17, 609-20.
11. Posfai, G., Kolisnychenko, V., Bereczki, Z., and Blattner, F. R. (1999) Markerless gene replacement in *Escherichia coli* stimulated by a double-strand break in the chromosome. *Nucleic Acids Res* 27, 4409-15.
12. Sargent, R. G., Brenneman, M. A., and Wilson, J. H. (1997) Repair of site-specific double-strand breaks in a mammalian chromosome by homologous and illegitimate recombination. *Mol Cell Biol* 17, 267-77.
13. Donoho, G., Jasin, M., and Berg, P. (1998) Analysis of gene targeting and intrachromosomal homologous recombination stimulated by genomic double-strand breaks in mouse embryonic stem cells. *Mol Cell Biol* 18, 4070-8.
14. Cohen-Tannoudji, M., Robine, S., Choulika, A., Pnto, D., El Marjou, F., Babinet, C., Louvard, D., and Jaisser, F. (1998) I-SceI-induced gene replacement at a natural locus in embryonic stem cells. *Mol Cell Biol* 18, 1444-8.
15. Gouble, A., Smith, J., Bruneau, S., Perez, C., Guyot, V., Cabaniols, J. P., Leduc, S., Fiette, L., Ave, P., Micheau, B., Duchateau, P., and Paques, F. (2006) Efficient in toto targeted recombination in mouse liver by meganuclease-induced double-strand break. *J Gene Med* 8, 616-22.
16. Siebert, R., and Puchta, H. (2002) Efficient Repair of Genomic Double-Strand Breaks by Homologous Recombination between Directly Repeated Sequences in the Plant Genome. *Plant Cell* 14, 1121-31.
17. Puchta, H., Dujon, B., and Hohn, B. (1996) Two different but related mechanisms are used in plants for the repair of genomic double-strand breaks by homologous recombination. *Proc Natl Acad Sci USA* 93, 5055-60.
18. Wurm, F. M. (2004) Production of recombinant protein therapeutics in cultivated mammalian cells. *Nat Biotechnol* 22, 1393-8.
19. Craig, N L. (1988) The mechanism of conservative site-specific recombination. *Annu Rev Genet* 22, 77-105.
20. Sauer, B. (1994) Site-specific recombination: developments and applications. *Curr Opin Biotechnol* 5, 521-7.
21. Sambrook, J., Fritsch, E. F., and Maniatis, T. (1989). Molecular Cloning: A Laboratory Manual, Second Edition (Plainview, N.Y.: Cold Spring Harbor Laboratory Press).
22. Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and Wiley-Interscience).
23. O'Gorman, S., Fox, D. T., and Wahl, G. M. (1991). Recombinase-Mediated Gene Activation and Site-Specific Integration in Mammalian Cells. *Science* 251, 1351-5.
24. de Coupade, C., Fittipaldi, A., Chagnas, V., Michel, M., Carlier, S., Tasciotti, E., Darmon, A., Ravel, D., Kearsley, J., Giacca, J. and Cailler, F. (2005) Novel human-derived cell-penetrating peptides for specific subcellular delivery of therapeutic biomolecules. *Biochem. J.* 390, 407-418.
25. Laemmli, U. (1970) Cleavage of structural proteins during the assembly of the head of bacteriophage T4. *Nature* 227, 680-685.
26. Seligman et al., Genetics, 1997, 147, 1653-1664; Sussman et al., J. Mol. Biol., 2004, 342, 31-41.
27. International PCT Applications WO 2006/097784 and WO 2006/097853.
28. Arnould et al., J. Mol. Biol., 2006, 355, 443-458; Rosen et al., Nucleic Acids Res., 2006, 34, 4791-4800; Smith et al., Nucleic Acids Res., 2006, 34, e149.
29. Smith et al., Nucleic Acids Res., 2006, 34, e149;
30. International PCT Applications WO 2007/060495 and WO 2007/049156
31. Chevalier et al., Mol. Cell., 2002, 10, 895-905.
32. Epinat et al., Nucleic Acids Res, 2003, 31, 2952-62.
33. International PCT Applications WO 03/078619 and WO 2004/031346.
34. Ruben, S., Perkins, A., Purcell, R., Joung, K., Sia, R., Burghoff, R., Haseltine, W. A. and Rosen, C. A. (1989) Structural and functional characterization of human immunodeficiency virus tat protein. *J. Virol.* 63, 1-8
35. Tyagi, M., Rusnati, M., Presta, M. and Giacca, M. (2001) Internalization of HIV-1 tat requires cell surface heparan sulfate proteoglycans. *J. Biol. Chem.* 276, 3254-3261
36. Derossi, D., Calvet, S., Trembleau, A., Brunissen, A., Chassaing, G. and Prochiantz, A. (1996) Cell internalization of the third helix of the Antennapedia homeodomain is receptor-independent. *J. Biol. Chem.* 271, 18188-18193 *Res,* 566, 131-67.
37. Elliott, G. and O'Hare, P. (1997) Intercellular trafficking and protein delivery by a herpesvirus structural protein. *Cell (Cambridge, Mass.)* 88, 223-233
38. Futaki, S., Goto, S, and Sugiura, Y. (2003) Membrane permeability commonly shared among arginine-rich peptides. *J. Mol. Recognit.* 16, 260-264
39. Jans, D. A. (1994) Nuclear signaling pathways for polypeptide ligands and their membrane receptors FASEB J. 8, 841-847
40. Kokryakov, V. N., Harwig, S. S., Panyutich, E. A., Shevchenko, A. A., Aleshina, G. M., Shamova, O. V., Korneva, H. A. and Lehrer, R. I. (1993) Protegrins: leukocyte antimicrobial peptides that combine features of corticostatic defensins and tachyplesins. *FEBS Lett.* 327, 231-236
41. Mie, M., Takahashi, F., Funabashi, H., Yanagida, Y., Aizawa, M. and Kobatake, E. (2003) Intracellular delivery of antibodies using TAT fusion protein A. *Biochem. Biophys. Res. Commun.* 310, 730-734
42. Silhol, M., Tyagi, M., Giacca, M., Lebleu, B. and Vives, E. (2002) Different mechanisms for cellular internalization of the HIV-1 Tat-derived cell penetrating peptide and recombinant proteins fused to Tat. *Eur. J. Biochem.* 269, 494-501
43. Stein, S., Weiss, A., Adermann, K., Lazarovici, P., Hochman, J. and Wellhoner, H. (1999) A disulfide conjugate between anti-tetanus antibodies and HIV (37-72) Tat neutralizes tetanus toxin inside chromaffin cells. *FEBS Lett.* 458, 383-386
44. Suzuki, T., Futaki, S., Niwa, M., Tanaka, S., Ueda, K. and Sugiura, Y. (2001) Possible existence of common internalization mechanisms among arginine-rich peptides. *J. Biol. Chem.* 277, 2437-2443

45. Torchilin, V. P., Rammohan, R., Weissig, V. and Levchenko, T. S. (2001) TAT peptide on the surface of liposomes affords their efficient intracellular delivery even at low temperature and in the presence of metabolic inhibitors. Proc. Natl. Acad. Sci. U.S.A. 98, 8786-8791
46. Schwarze, S. R., Ho, A., Vocero-Akbani, A. and Dowdy, S. F. (1999) In vivo protein transduction: delivery of a biologically active protein into the mouse. Science 285, 1569-1572
47. Tasciotti, E., Zoppe, M. and Giacca, M. (2003) Transcellular transfer of active HSV-1 thymidine kinase mediated by an 11-amino-acid peptide from HIV-1 Tat. Cancer Gene Ther. 10, 64-74
48. Vives, E., Brodin, P. and Lebleu, B. (1997) A truncated HIV-1 Tat protein basic domain rapidly translocates through the plasma membrane and accumulates in the cell nucleus. J. Biol. Chem. 272, 16010-16017
49. PEREZ C, GUYOT V, CABANIOLS J, GOUBLE A, MICHEAUX B, SMITH J, LEDUC S, PAQUES F, DUCHATEAU P, (2005) BioTechniques vol. 39, no 1, pp. 109-115

The invention claimed is:

1. A method for transforming by homologous recombination at least one cell in vitro, comprising:
   (a) stably transforming at least one cell by inserting construct (i), which is encoded by a nucleic acid molecule, which comprises:

A1-A2-A3-A4-A5    (i), wherein A1 is a first promoter, A2 is a first homologous portion, A3 is a meganuclease cleavage site, A4 is a first marker gene, A5 consists of the neomycin resistance gene of SEQ ID NO:7, and wherein construct (i) is configured to be stably integrated into the genome of at least one target cell, into the genome of said at least one cell;
   (b) cloning a sequence coding for a gene of interest into position B3 of construct (ii), which is encoded by a nucleic acid molecule, which comprises at least the following components:

A2'-B1-B2-B3-B4-A5'    (ii), wherein A2' comprises a portion of said first homologous portion A2, B1 is a second marker gene different from said first marker gene, B2 is a second promoter, B3 is a multiple cloning site, B4 is a third promoter, A5' consists of the inactive neomycin resistance gene of SEQ ID NO:13;
   (c) co-transfecting said cell of (a) with said construct (ii) of (b) and construct (iii), (iv), or (v), which are encoded by nucleic acid molecules, which comprise components:

C1-C2    (iii),

C3    (iv), or an isolated or recombinant protein which comprises component:

C4    (v), wherein C1 is a fourth promoter, C2 is the open reading frame (ORF) of a meganuclease, C3 is a messenger RNA (mRNA) encoding said meganuclease, and C4 is an isolated or recombinant protein of said meganuclease, wherein a meganuclease from construct (iii), (iv), or (v) recognizes and cleaves A3, and construct (iii), (iv), or (v) are configured to be co-transfected with construct (ii) into said at least one target cell;
   (d) following homologous recombination between said construct (ii) and said stably inserted construct (i), selecting at least one cell from (c) based upon: the absence of a first marker gene encoded by component A4 of said construct (i) and the activity of a second marker gene encoded by component B1 and neomycin resistance activity.

2. The method of claim 1, wherein A1 is a promoter selected from an EF1α promoter, an SV40 promoter, a CMV promoter, and a Ubiqitin subunit c promoter.

3. The method of claim 1, wherein A2 consists of the EF1α intron 1 sequence of SEQ ID NO:3.

4. The method of claim 1, wherein A3 consists of the meganuclease cleavage site of SEQ ID NO:8.

5. The method of claim 1, wherein A4 is a hygromycin gene.

6. The method of claim 1, wherein A4 is a puromycin gene.

7. The method of claim 1, wherein A2' consists of the EF1α intron 1 sequence of SEQ ID NO:29.

8. The method of claim 1, wherein B1 is a hygromycin gene.

9. The method of claim 1, wherein B1 is a puromycin gene.

10. The method of claim 1, wherein B2 is a promoter selected from an EF1α promoter, an SV40 promoter, a CMV promoter, and a Ubiqitin subunit c promoter.

11. The method of claim 1, wherein B3 consists of the multiple cloning site of SEQ ID NO:23.

12. The method of claim 1, wherein B4 is a promoter selected from an EF1α promoter, an SV40 promoter, a CMV promoter, and a Ubiqitin subunit c promoter.

13. The method of claim 1, wherein C1 is a promoter selected from an EF1α promoter, an SV40 promoter, a CMV promoter, and a Ubiqitin subunit c promoter.

14. The method of claim 1, wherein C2 consists of the meganuclease ORF of SEQ ID NO:14.

15. The method of claim 1, wherein C2 consists of the meganuclease ORF of SEQ ID NO:15.

16. The method of claim 1, wherein C3 is an mRNA equivalent of the sequence of SEQ ID NO:14, SEQ ID NO:15, or SEQ ID NO:35.

17. The method of claim 1, wherein C4 is a meganuclease protein encoded by SEQ ID NO:14.

18. The method of claim 1, wherein C4 is a meganuclease protein encoded by SEQ ID NO:15.

19. The method of claim 1, wherein C4 is the meganuclease protein of SEQ ID NO:58.

* * * * *

SEQUENCE LISTING

```
<160> NUMBER OF SEQ ID NOS: 70

<210> SEQ ID NO 1
<211> LENGTH: 883
<212> TYPE: DNA
<213> ORGANISM: Homo sapiens

<400> SEQUENCE: 1
gatctaaagc taactgtagg actgagtcta ttctaaactg aaagcctgga catctggagt      60
accaggggga gatgacgtgt tacgggcttc cataaaagca gctggctttg aatggaagga    120
gccaagaggc cagcacagga gcggattcgt cgctttcacg gccatcgagc cgaacctctc    180
gcaagtccgt gagccgttaa ggaggccccc agtcccgacc cttcgcccca agcccctcgg    240
ggtccccggg cctggtactc cttgccacac gggaggggcg cggaagccgg ggcggaggag    300
gagccaaccc cgggctgggc tgagacccgc agaggaagac gctctaggga tttgtcccgg    360
actagcgaga tggcaaggct gaggacggga ggctgattga gaggcgaagg tacaccctaa    420
tctcaataca acctttggag ctaagccagc aatggtagag ggaagattct gcacgtccct    480
tccaggcggc ctccccgtca ccaccccccc caacccgccc cgaccggagc tgagagtaat    540
tcatacaaaa ggactcgccc ctgccttggg gaatcccagg gaccgtcgtt aaactcccac    600
taacgtagaa cccagagatc gctgcgttcc cgccccctca cccgcccgct ctcgtcatca    660
ctgaggtgga gaagagcatg cgtgaggctc cggtgcccgt cagtgggcag agcgcacatc    720
gcccacagtc cccgagaagt tgggggggagg ggtcggcaat tgaaccggtg cctagagaag    780
gtggcgcggg gtaaactggg aaagtgatgt cgtgtactgg ctccgccttt ttcccgaggg    840
tgggggagaa ccgtatataa gtgcagtagt cgccgtgaac gtt                       883

<210> SEQ ID NO 2
<211> LENGTH: 1026
<212> TYPE: DNA
<213> ORGANISM: Artificial Sequence
<220> FEATURE:
<223> OTHER INFORMATION: Description of Artificial Sequence: Synthetic
      Hygromycin resistance gene

<400> SEQUENCE: 2
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
```

```
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

```
<210> SEQ ID NO 3
<211> LENGTH: 946
<212> TYPE: DNA
<213> ORGANISM: Artificial Sequence
<220> FEATURE:
<223> OTHER INFORMATION: Description of Artificial Sequence: Synthetic
      first homologous portion

<400> SEQUENCE: 3
taagtgccgt gtgtggttcc cgcgggcctg gcctctttac gggttatggc ccttgcgtgc     60
cttgaattac ttccacgccc ctggctgcag tacgtgattc ttgatcccga gcttcgggtt    120
ggaagtgggt gggagagttc gaggccttgc gcttaaggag ccccttcgcc tcgtgcttga    180
gttgaggcct ggcttgggcg ctggggccgc gcgtgcgaa tctggtggca ccttcgcgcc     240
tgtctcgctg ctttcgataa gtctctagcc atttaaaatt tttgatgacc tgctgcgacg    300 cttttttttct ggcaagatag tcttgtaaat gcgggccaag atcgatctgc acactggtat   360
ttcggttttt ggggccgcgg gcggcgacgg ggcccgtgcg tcccagcgca catgttcggc    420 gaggcgggc ctgcgagcgc ggccaccgag aatcggacgg gggtagtctc aagctggccg    480
gcctgctctg gtgcctggcc tcgcgccgcc gtgtatcgcc ccgccctggg cggcaaggct    540
ggcccggtcg gcaccagttg cgtgagcgga aagatggccg cttcccggcc tgctgcagg     600 gagctcaaaa tggaggacgc ggcgctcggg agagcgggcg ggtgagtcac ccacacaaag    660
gaaaagggcc tttccgtcct cagccgtcgc ttcatgtgac tccacggagt accgggcgcc    720
gtccaggcac ctcgattagt tctcgagctt ttggagtacg tcgtctttag gttgggggga    780
ggggttttat gcgatggagt ttccccacac tgagtgggtg gagactgaag ttaggccagc    840
ttggcacttg atgtaattct ccttggaatt tgccctttt gagtttggat cttggttcat     900
tctcaagcct cagacagtgg ttcaaagttt ttttcttcca tttcag                   946
```

```
<210> SEQ ID NO 4
<211> LENGTH: 265
<212> TYPE: DNA
<213> ORGANISM: Artificial Sequence
<220> FEATURE:
<223> OTHER INFORMATION: Description of Artificial Sequence: Synthetic
      SV40 polyA (for hygro) polynucleotide

<400> SEQUENCE: 4
gagatttcga ttccaccgcc gccttctatg aaaggttggg cttcggaatc gttttccggg    60
```

```
acgccggctg gatgatcctc cagcgcgggg atctcatgct ggagttcttc gcccacccca    120
acttgtttat tgcagcttat aatggttaca aataaagcaa tagcatcaca aatttcacaa    180
ataaagcatt ttttcactg cattctagtt gtggtttgtc caaactcatc aatgtatctt    240
atcatgtctg tataccgtcg acctc                                          265
```

```
<210> SEQ ID NO 5
<211> LENGTH: 250
<212> TYPE: DNA
<213> ORGANISM: Artificial Sequence
<220> FEATURE:
<223> OTHER INFORMATION: Description of Artificial Sequence: Synthetic
      SV40 polyA (for Neo) polynucleotide

<400> SEQUENCE: 5
gagatttcga ttccaccgcc gccttctatg aaaggttggg cttcggaatc gttttccggg     60
acgccggctg gatgatcctc cagcgcgggg atctcatgct ggagttcttc gcccacccca    120
acttgtttat tgcagcttat aatggttaca aataaagcaa tagcatcaca aatttcacaa    180
ataaagcatt ttttcactg cattctagtt gtggtttgtc caaactcatc aatgtatctt    240
atcatgtctg                                                           250
```

```
<210> SEQ ID NO 6
<211> LENGTH: 4424
<212> TYPE: DNA
<213> ORGANISM: Artificial Sequence
<220> FEATURE:
<223> OTHER INFORMATION: Description of Artificial Sequence: Synthetic
      cGPS insert

<400> SEQUENCE: 6
cgacggatcg ggagatctaa agctaactgt aggactgagt ctattctaaa ctgaaagcct     60
ggacatctgg agtaccaggg ggagatgacg tgttacgggc ttccataaaa gcagctggct    120
ttgaatggaa ggagccaaga ggccagcaca ggagcggatt cgtcgctttc acggccatcg    180
agccgaacct ctcgcaagtc cgtgagccgt taaggaggcc cccagtcccg acccttcgcc    240
ccaagcccct cggggtcccc gggcctggta ctccttgcca cacggagggg cgcggaagc     300 cggggcggag gaggagccaa ccccgggctg ggctgagacc cgcagaggaa gacgctctag    360 ggattttgtcc cggactagcg agatggcaag gctgaggacg ggaggctgat tgagaggcga    420
aggtacaccc taatctcaat acaaccttg gagctaagcc agcaatggta gagggaagat    480
tctgcacgtc ccttccaggc ggcctccccg tcaccacccc cccaacccg ccccgaccgg    540 agctgagagt aattcataca aaaggactcg ccctgccttt ggggaatccc agggaccgtc    600
gttaaactcc cactaacgta gaacccgagag atcgctgcgt tcccgccccc tcacccgccc    660
gctctcgtca tcactgaggt ggagaagagc atgcgtgagg ctccggtgcc cgtcagtggg    720
cagagcgcac atcgcccaca gtccccgaga agttgggggg aggggtcggc aattgaaccg    780
gtgcctagag aaggtggcgc ggggtaaact gggaaagtga tgtcgtgtac tggctccgcc    840 ttttcccga gggtggggga gaaccgtata taagtgcagt agtcgccgtg aacgttcttt    900
ttcgcaacgg gtttgccgcc agaacacagg taagtgccgt gtgtggttcc cgcgggcctg    960 gcctcttac gggttatggc ccttgcgtgc cttgaattac ttccacgccc ctggctgcag    1020
tacgtgattc ttgatcccga gctcgggtt ggaagtgggt gggagagttc gaggccttgc    1080
gcttaaggag ccccttcgcc tcgtgcttga gttgaggcct ggcttgggcg ctggggccgc    1140
cgcgtgcgaa tctggtggca ccttcgcgcc tgtctcgctg ctttcgataa gtctctagcc    1200
```

```
atttaaaatt tttgatgacc tgctgcgacg cttttttttct ggcaagatag tcttgtaaat    1260
gcgggccaag atcgatctgc acactggtat ttcggttttt ggggccgcgg gcggcgacgg    1320
ggcccgtgcg tcccagcgca catgttcggc gaggcgggc ctgcgagcgc ggccaccgag     1380
aatcggacgg gggtagtctc aagctggccg gcctgctctg gtgcctggcc tcgcgccgcc    1440
gtgtatcgcc ccgccctggg cggcaaggct ggcccggtcg caccagttg cgtgagcgga     1500
aagatggccg cttcccggcc ctgctgcagg gagctcaaaa tggaggacgc ggcgctcggg    1560
agagcgggcg ggtgagtcac ccacacaaag gaaaagggcc tttccgtcct cagccgtcgc    1620
ttcatgtgac tccacggagt accggcgcc gtccaggcac ctcgattagt tctcgagctt     1680
ttggagtacg tcgtctttag gttgggggga ggggttttat gcgatggagt ttccccacac    1740
tgagtgggtg gagactgaag ttaggccagc ttggcacttg atgtaattct ccttggaatt    1800
tgccctttt gagtttggat cttggttcat tctcaagcct cagacagtgg ttcaaagttt     1860
ttttcttcca tttcaggtgt cgtggaatca aaacgtcgta cgacgttttg agggatccag    1920
cgccaccatg aaaaagcctg aactcaccgc gacgtctgtc gagaagtttc tgatcgaaaa    1980
gttcgacagc gtctccgacc tgatgcagct ctcggagggc gaagaatctc gtgctttcag    2040
cttcgatgta ggagggcgtg gatatgtcct gcgggtaaat agctgcgccg atggtttcta    2100
caaagatcgt tatgtttatc ggcactttgc atcggccgcg ctcccgattc cggaagtgct    2160
tgacattggg gaattcagcg agagcctgac ctattgcatc tcccgccgtg cacagggtgt    2220
cacgttgcaa gacctgcctg aaaccgaact gcccgctgtt ctgcagccgg tcgcggaggc    2280
catggatgcg atcgctgcgg ccgatcttag ccagacgagc gggttcggcc cattcggacc    2340
gcaaggaatc ggtcaataca ctacatggcg tgatttcata tgcgcgattg ctgatcccca    2400
tgtgtatcac tggcaaactg tgatggacga caccgtcagt gcgtccgtcg cgcaggctct    2460
cgatgagctg atgctttggg ccgaggactg ccccgaagtc cggcacctcg tgcacgcgga    2520
tttcggctcc aacaatgtcc tgacggacaa tggccgcata acagcggtca ttgactggag    2580
cgaggcgatg ttcggggatt cccaatacga ggtcgccaac atcttcttct ggaggccgtg    2640
gttggcttgt atggagcagc agacgcgcta cttcgagcgg aggcatccgg agcttgcagg    2700
atcgccgcgg ctccgggcgt atatgctccg cattggtctt gaccaactct atcagagctt    2760
ggttgacggc aatttcgatg atgcagcttg gcgcagggt cgatgcgacg caatcgtccg     2820
atccggagcc gggactgtcg ggcgtacaca atcgcccgc agaagcgcgg ccgtctggac     2880
cgatggctgt gtagaagtac tcgccgatag tggaaaccga cgcccagca ctcgtccgag     2940
ggcaaaggaa tagcacgtgc tacgagattt cgattccacc gccgccttct atgaaaggtt    3000
gggcttcgga atcgttttcc gggacgccgg ctggatgatc ctccagcgcg gggatctcat    3060
gctggagttc ttcgcccacc ccaacttgtt tattgcagct tataatggtt acaaataaag    3120
caatagcatc acaaatttca caaataaagc attttttca ctgcattcta gttgtggttt     3180
gtccaaactc atcaatgtat cttatcatgt ctgtataccg tcgacctcta gctagagctt    3240
ggctaggctt ttgcaaaaag ctcccgggag cttgtatatc catttcgga tctgatcaag     3300
agacaggatg aggatcgttt cgcatgattg aacaagatgg attgcacgca ggttctccgg    3360
ccgcttgggt ggagaggcta ttcggctatg actgggcaca acagacaatc ggctgctctg    3420
atgccgccgt gttccggctg tcagcgcagg ggcgcccggt tctttttgtc aagaccgacc    3480
tgtccggtgc cctgaatgaa ctgcaggacg aggcagcgcg gctatcgtgg ctggccacga    3540
```

```
cgggcgttcc ttgcgcagct gtgctcgacg ttgtcactga agcgggaagg gactggctgc    3600
tattgggcga agtgccgggg caggatctcc tgtcatctca ccttgctcct gccgagaaag    3660
tatccatcat ggctgatgca atgcggcggc tgcatacgct tgatccggct acctgcccat    3720
tcgaccacca agcgaaacat cgcatcgagc gagcacgtac tcggatggaa gccggtcttg    3780
tcgatcagga tgatctggac gaagagcatc aggggctcgc gccagccgaa ctgttcgcca    3840
ggctcaaggc gcgcatgccc gacggcgagg atctcgtcgt gacccatggc gatgcctgct    3900
tgccgaatat catggtggaa aatggccgct tttctggatt catcgactgt ggccggctgg    3960
gtgtggcgga ccgctatcag gacatagcgt tggctacccg tgatattgct gaagagcttg    4020
gcggcgaatg ggctgaccgc ttcctcgtgc tttacggtat cgccgctccc gattcgcagc    4080
gcatcgcctt ctatcgcctt cttgacgagt tcttctgagc gggactctgg ggttcgaaat    4140
gaccgaccaa gcgacgccca acctgccatc acgagatttc gattccaccg ccgccttcta    4200
tgaaaggttg ggcttcggaa tcgttttccg ggacgccggc tggatgatcc tccagcgcgg    4260
ggatctcatg ctggagttct cgcccaccc caacttgttt attgcagctt ataatggtta    4320
caaataaagc aatagcatca caaatttcac aaataaagca ttttttttcac tgcattctag    4380 ttgtggtttg tccaaactca tcaatgtatc ttatcatgtc tgta                      4424

<210> SEQ ID NO 7
<211> LENGTH: 795
<212> TYPE: DNA
<213> ORGANISM: Artificial Sequence
<220> FEATURE:
<223> OTHER INFORMATION: Description of Artificial Sequence: Synthetic
      Neomycin polynucleotide w/o promoter

<400> SEQUENCE: 7
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795

<210> SEQ ID NO 8
<211> LENGTH: 24
<212> TYPE: DNA
<213> ORGANISM: Chlamydomonas reinhardtii

<400> SEQUENCE: 8
tcaaaacgtc gtacgacgtt ttga                                             24
```

<210> SEQ ID NO 9
<211> LENGTH: 1872
<212> TYPE: DNA
<213> ORGANISM: Homo sapiens

<400> SEQUENCE: 9

```
gatctaaagc taactgtagg actgagtcta ttctaaactg aaagcctgga catctggagt      60
accaggggga gatgacgtgt tacgggcttc cataaaagca gctggctttg aatggaagga     120
gccaagaggc cagcacagga gcggattcgt cgctttcacg gccatcgagc cgaacctctc     180
gcaagtccgt gagccgttaa ggaggccccc agtcccgacc cttcgcccca agcccctcgg     240
ggtccccggg cctggtactc cttgccacac gggaggggcg cggaagccgg ggcggaggag     300
gagccaaccc cgggctgggc tgagacccgc agaggaagac gctctaggga tttgtcccgg     360
actagcgaga tggcaaggct gaggacggga ggctgattga gaggcgaagg tacaccctaa     420
tctcaataca acctttggag ctaagccagc aatggtagag ggaagattct gcacgtccct     480
tccaggcggc ctcccgtca ccaccccccc caacccgccc cgaccggagc tgagagtaat     540
tcatacaaaa ggactcgccc ctgccttggg gaatcccagg gaccgtcgtt aaactcccac     600
taacgtagaa cccagagatc gctgcgttcc cgccccctca cccgcccgct ctcgtcatca     660
ctgaggtgga aagagcatg cgtgaggctc cggtgcccgt cagtgggcag agcgcacatc     720
gcccacagtc cccgagaagt tgggggagg gtcggcaat tgaacggtg cctagagaag       780
gtggcgcggg gtaaactggg aaagtgatgt cgtgtactgg ctccgccttt ttcccgaggg     840
tgggggagaa ccgtatataa gtgcagtagt cgccgtgaac gttcttttc gcaacgggtt     900
tgccgccaga acacaggtaa gtgccgtgtg tggttcccgc gggcctggcc tctttacggg     960
ttatggcct tgcgtgcctt gaattacttc cacgccctg gctgcagtac gtgattcttg     1020
atcccgagct tcgggttgga agtgggtggg agagttcgag gccttgcgct taaggagccc    1080
cttcgcctcg tgcttgagtt gaggcctggc ttgggcgctg gggccgccgc gtgcgaatct    1140
ggtggcacct tcgcgcctgt ctcgctgctt tcgataagtc tctagccatt taaaattttt    1200
gatgacctgc tgcgacgctt tttttctggc aagatagtct tgtaaatgcg ggccaagatc    1260
gatctgcaca ctggtatttc ggttttttggg gccgcgggcg gcgacggggc ccgtgcgtcc    1320
cagcgcacat gttcggcgag gcggggcctg cgagcgcggc caccgagaat cggacggggg    1380
tagtctcaag ctggccggcc tgctctggtg cctggcctcg cgccgccgtg tatcgccccg    1440
ccctgggcgg caaggctggc ccggtcggca ccagttgcgt gagcggaaag atggccgctt    1500
cccggccctg ctgcagggag ctcaaaatgg aggacgcggc gctcgggaga gcgggcgggt    1560
gagtcaccca cacaaaggaa aagggccttt ccgtcctcag ccgtcgcttc atgtgactcc    1620
acggagtacc gggcgccgtc caggcacctc gattagttct cgagcttttg gagtacgtcg    1680
tctttaggtt gggggaggg gttttatgcg atggagtttc cccacactga gtgggtggag    1740
actgaagtta ggccagcttg gcacttgatg taattctcct tggaatttgc ccttttttgag    1800
tttggatctt ggttcattct caagcctcag acagtggttc aaagtttttt tcttccattt    1860
caggtgtcgt gg                                                        1872
```

<210> SEQ ID NO 10
<211> LENGTH: 946
<212> TYPE: DNA
<213> ORGANISM: Homo sapiens

<400> SEQUENCE: 10

```
taagtgccgt gtgtggttcc cgcgggcctg gcctctttac gggttatggc ccttgcgtgc    60
cttgaattac ttccacgccc ctggctgcag tacgtgattc ttgatcccga gcttcgggtt   120
ggaagtgggt gggagagttc gaggccttgc gcttaaggag ccccttcgcc tcgtgcttga   180
gttgaggcct ggcttgggcg ctgggccgc cgcgtgcgaa tctggtggca ccttcgcgcc    240
tgtctcgctg ctttcgataa gtctctagcc atttaaaatt tttgatgacc tgctgcgacg   300
ctttttttct ggcaagatag tcttgtaaat gcgggccaag atcgatctgc acactggtat   360
ttcggttttt ggggccgcgg gcggcgacgg ggcccgtgcg tcccagcgca catgttcggc   420 gaggcgggc ctgcgagcgc ggccaccgag aatcggacgg gggtagtctc aagctggccg    480
gcctgctctg gtgcctggcc tcgcgccgcc gtgtatcgcc ccgccctggg cggcaaggct   540
ggcccggtcg gcaccagttg cgtgagcgga aagatggccg cttcccggcc tgctgcagg    600 gagctcaaaa tggaggacgc ggcgctcggg agagcgggcg ggtgagtcac ccacacaaag   660
gaaaagggcc tttccgtcct cagccgtcgc ttcatgtgac tccacggagt accgggcgcc   720
gtccaggcac ctcgattagt tctcgagctt ttggagtacg tcgtctttag gttggggga    780 ggggttttat gcgatggagt ttccccacac tgagtgggtg gagactgaag ttaggccagc   840
ttggcacttg atgtaattct ccttggaatt tgcccttttt gagtttggat cttggttcat   900
tctcaagcct cagacagtgg ttcaaagttt ttttcttcca tttcag                  946

<210> SEQ ID NO 11
<211> LENGTH: 34
<212> TYPE: DNA
<213> ORGANISM: Homo sapiens

<400> SEQUENCE: 11 cttttttcgca acgggtttgc cgccagaaca cagg                               34

<210> SEQ ID NO 12
<211> LENGTH: 9
<212> TYPE: DNA
<213> ORGANISM: Homo sapiens

<400> SEQUENCE: 12 gtgtcgtgg                                                             9

<210> SEQ ID NO 13
<211> LENGTH: 530
<212> TYPE: DNA
<213> ORGANISM: Artificial Sequence
<220> FEATURE:
<223> OTHER INFORMATION: Description of Artificial Sequence: Synthetic
      5' homology region/2nd homologous portion

<400> SEQUENCE: 13
atgattgaac aagatggatt gcacgcaggt tctccggccg cttgggtgga gaggctattc    60
ggctatgact gggcacaaca gacaatcggc tgctctgatg ccgccgtgtt ccggctgtca   120 gcgcagggc gcccggttct ttttgtcaag accgacctgt ccggtgccct gaatgaactg    180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
```

```
gagcatcagg ggctcgcgcc agccgaactg ttcgccaggc tcaaggcgcg        530
```

<210> SEQ ID NO 14
<211> LENGTH: 504
<212> TYPE: DNA
<213> ORGANISM: Artificial Sequence
<220> FEATURE:
<223> OTHER INFORMATION: Description of Artificial Sequence: Synthetic
    I-CreI N75 polynucleotide

<400> SEQUENCE: 14

```
atggccaata ccaaatataa caaagagttc ctgctgtacc tggccggctt tgtggacggt     60
gacggtagca tcatcgctca gattaaacca aaccagtctt ataagtttaa acatcagcta    120
agcttgacct ttcaggtgac tcaaaagacc cagcgccgtt ggtttctgga caaactagtg    180
gatgaaattg gcgttggtta cgtacgtgat cgcggatccg tttccaacta catcttaagc    240
gaaatcaagc cgctgcacaa cttcctgact caactgcagc cgtttctgaa actgaaacag    300
aaacaggcaa acctggttct gaaaattatc gaacagctgc cgtctgcaaa agaatccccg    360
gacaaattcc tggaagtttg tacctgggtg gatcagattg cagctctgaa cgattctaag    420
acgcgtaaaa ccacttctga aaccgttcgt gctgtgctgg acagcctgag cgagaagaag    480
aaatcctccc cggcggccga ctaa                                           504
```

<210> SEQ ID NO 15
<211> LENGTH: 504
<212> TYPE: DNA
<213> ORGANISM: Artificial Sequence
<220> FEATURE:
<223> OTHER INFORMATION: Description of Artificial Sequence: Synthetic
    I-CreI 75N 105A 132V polynucleotide

<400> SEQUENCE: 15

```
atggccaata ccaaatataa caaagagttc ctgctgtacc tggccggctt tgtggacggt     60
gacggtagca tcatcgctca gattaaacca aaccagtctt ataagtttaa acatcagcta    120
agcttgacct ttcaggtgac tcaaaagacc cagcgccgtt ggtttctgga caaactagtg    180
gatgaaattg gcgttggtta cgtacgtgat cgcggatccg tttccaacta catcttaagc    240
gaaatcaagc cgctgcacaa cttcctgact caactgcagc cgtttctgaa actgaaacag    300
aaacaggcaa acctggctct gaaaattatc gaacagctgc cgtctgcaaa agaatccccg    360
gacaaattcc tggaagtttg tacctgggtg gatcaggttg cagctctgaa cgattctaag    420
acgcgtaaaa ccacttctga aaccgttcgt gctgtgctgg acagcctgag cgagaagaag    480
aaatcctccc cggcggccga ctaa                                           504
```

<210> SEQ ID NO 16
<211> LENGTH: 3075
<212> TYPE: DNA
<213> ORGANISM: Artificial Sequence
<220> FEATURE:
<223> OTHER INFORMATION: Description of Artificial Sequence: Synthetic
    LacZ gene

<400> SEQUENCE: 16

```
atgatagatc ccgtcgtttt acaacgtcgt gactgggaaa accctggcgt tacccaactt     60
aatcgccttg cagcacatcc ccctttcgcc agctggcgta atagcgaaga ggcccgcacc    120
gatcgccctt cccaacagtt gcgcagcctg aatggcgaat ggcgctttgc ctggtttccg    180
gtaccagaag cggtgccgga aagctggctg gagtgcgatc ttcctgaggc cgatactgtc    240
```

```
gtcgtcccct caaactggca gatgcacggt tacgatgcgc ccatctacac caacgtaacc    300
tatcccatta cggtcaatcc gccgtttgtt cccacggaga atccgacggg ttgttactcg    360
ctcacattta atgttgatga aagctggcta caggaaggcc agacgcgaat tattttgat     420 ggcgttaact cggcgtttca tctgtggtgc aacgggcgct gggtcggtta cggccaggac    480
agtcgtttgc cgtctgaatt tgacctgagc gcatttttac gcgccggaga aaaccgcctc    540
gcggtgatgg tgctgcgttg gagtgacggc agttatctgg aagatcagga tatgtggcgg    600
atgagcggca ttttccgtga cgtctcgttg ctgcataaac cgactacaca aatcagcgat    660
ttccatgttg ccactcgctt taatgatgat ttcagccgcg ctgtactgga ggctgaagtt    720
cagatgtgcg gcgagttgcg tgactaccta cgggtaacag tttctttatg gcagggtgaa    780
acgcaggtcg ccagcggcac cgcgcctttc ggcggtgaaa ttatcgatga gcgtggtggt    840
tatgccgatc gcgtcacact acgtctgaac gtcgaaaacc cgaaactgtg gagcgccgaa    900
atcccgaatc tctatcgtgc ggtggttgaa ctgcacaccg ccgacggcac gctgattgaa    960
gcagaagcct gcgatgtcgg tttccgcgag gtgcggattg aaaatggtct gctgctgctg   1020
aacggcaagc cgttgctgat tcgaggcgtt aaccgtcacg agcatcatcc tctgcatggt   1080
caggtcatgg atgagcagac gatggtgcag gatatcctgc tgatgaagca gaacaacttt   1140
aacgccgtgc gctgttcgca ttatccgaac catccgctgt ggtacacgct gtgcgaccgc   1200
tacggcctgt atgtggtgga tgaagccaat attgaaaccc acggcatggt gccaatgaat   1260
cgtctgaccg atgatccgcg ctggctaccg gcgatgagcg aacgcgtaac gcgaatggtg   1320
cagcgcgatc gtaatcaccc gagtgtgatc atctggtcgc tggggaatga atcaggccac   1380
ggcgctaatc acgacgcgct gtatcgctgg atcaaatctg tcgatccttc ccgcccggtg   1440
cagtatgaag gcggcggagc cgacaccacg gccaccgata ttatttgccc gatgtacgcg   1500
cgcgtggatg aagaccagcc cttcccggct gtgccgaaat ggtccatcaa aaaatggctt   1560
tcgctacctg gagagacgcg cccgctgatc ctttgcgaat acgcccacgc gatgggtaac   1620
agtcttggcg gtttcgctaa atactggcag gcgtttcgtc agtatccccg tttacagggc   1680
ggcttcgtct gggactgggt ggatcagtcg ctgattaaat atgatgaaaa cggcaacccg   1740
tggtcggctt acggcggtga ttttggcgat acgccgaacg atcgccagtt ctgtatgaac   1800
ggtctggtct tgccgaccg cacgccgcat ccagcgctga cggaagcaaa acaccagcag   1860 cagttttttcc agttccgttt atccgggcaa accatcgaag tgaccagcga atacctgttc   1920
cgtcatagcg ataacgagct cctgcactgg atggtggcgc tggatggtaa gccgctggca   1980
agcggtgaag tgcctctgga tgtcgctcca caaggtaaac agttgattga actgcctgaa   2040
ctaccgcagc cggagagcgc cgggcaactc tggctcacag tacgcgtagt gcaaccgaac   2100
gcgaccgcat ggtcagaagc cgggcacatc agcgcctggc agcagtggcg tctggcggaa   2160
aacctcagtg tgacgctccc cgccgcgtcc cacgccatcc gcatctgac caccagcgaa   2220 atggattttt gcatcgagct gggtaataag cgttggcaat taaccgcca gtcaggcttt   2280 ctttcacaga tgtggattgg cgataaaaaa caactgctga cgccgctgcg cgatcagttc   2340
acccgtgcac cgctggataa cgacattggc gtaagtgaag cgaccgcat tgaccctaac   2400 gcctgggtcg aacgctggaa ggcggcgggc cattaccagg ccgaagcagc gttgttgcag   2460
tgcacggcag atacacttgc tgatgcgtg ctgattacga ccgctcacgc gtggcagcat   2520
caggggaaaa cctatttat cagccggaaa acctaccgga ttgatggtag tggtcaaatg   2580
```

```
gcgattaccg ttgatgttga agtggcgagc gatacaccgc atccggcgcg gattggcctg    2640
aactgccagc tggcgcaggt agcagagcgg gtaaactggc tcggattagg gccgcaagaa    2700
aactatcccg accgccttac tgccgcctgt tttgaccgct gggatctgcc attgtcagac    2760
atgtataccc cgtacgtctt cccgagcgaa aacggtctgc gctgcgggac gcgcgaattg    2820
aattatggcc cacaccagtg gcgcggcgac ttccagttca acatcagccg ctacagtcaa    2880
cagcaactga tggaaaccag ccatcgccat ctgctgcacg cggaagaagg cacatggctg    2940
aatatcgacg gtttccatat ggggattggt ggcgacgact cctggagccc gtcagtatcg    3000
gcggaattcc agctgagcgc cggtcgctac cattaccagt tggtctggtg tcaaaaagcg    3060
gccgctcgag tctag                                                     3075

<210> SEQ ID NO 17
<211> LENGTH: 9981
<212> TYPE: DNA
<213> ORGANISM: Artificial Sequence
<220> FEATURE:
<223> OTHER INFORMATION: Description of Artificial Sequence: Synthetic
      pTV_DS_LacZ polynucleotide

<400> SEQUENCE: 17
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ttaaggagcc ccttcgcctc     420
gtgcttgagt tgaggcctgg cttgggcgct ggggccgccg cgtgcgaatc tggtggcacc     480
ttcgcgcctg tctcgctgct ttcgataagt ctctagccat ttaaaatttt tgatgacctg     540
ctgcgacgct ttttttctgg caagatagtc ttgtaaatgc gggccaagat cgatctgcac     600
actggtattt cggtttttgg ggccgcgggc ggcgacgggg cccgtgcgtc ccagcgcaca     660
tgttcggcga ggcggggcct gcgagcgcgg ccaccgagaa tcggacgggg gtagtctcaa     720
gctggccggc ctgctctggt gcctggcctc gcgccgccgt gtatcgcccc gccctgggcg     780
gcaaggctgg cccggtcggc accagttgcg tgagcggaaa gatggccgct tcccggccct     840
gctgcaggga gctcaaaatg gaggacgcgg cgctcgggag agcgggcggg tgagtcaccc     900
acacaaagga aaagggcctt tccgtcctca gccgtcgctt catgtgactc cacggagtac     960
cgggcgccgt ccaggcacct cgattagttc tcgagctttt ggagtacgtc gtctttaggt    1020
tggggggagg ggttttatgc gatggagttt ccccacactg agtgggtgga gactgaagtt    1080
aggccagctt ggcacttgat gtaattctcc ttggaatttg ccctttttga gtttggatct    1140
tggttcattc tcaagcctca gacagtggtt caaagttttt ttcttccatt tcaggtgtcg    1200
tggaattggc tagagcttgc atgcctgcag gtcggccgcc acgaccggtg ccgccaccat    1260
cccctgaccc acgcccctga cccctcacaa ggagacgacc ttcatgacc gagtacaagc    1320 ccacggtgcg cctcgccacc cgcgacgacg tccccgggc cgtacgcacc ctcgccgccg    1380
cgttcgccga ctaccccgcc acgcgccaca ccgtcgaccc ggaccgccac atcgagcggg    1440
tcaccgagct gcaagaactc ttcctcacgc gcgtcgggct cgacatcggc aaggtgtggg    1500
```

-continued

```
tcgcggacga cggcgccgcg gtggcggtct ggaccacgcc ggagagcgtc gaagcggggg    1560
cggtgttcgc cgagatcggc ccgcgcatgg ccgagttgag cggttcccgg ctggccgcgc    1620
agcaacagat ggaaggcctc ctggcgccgc accggcccaa ggagcccgcg tggttcctgg    1680
ccaccgtcgg cgtctcgccc gaccaccagg gcaagggtct gggcagcgcc gtcgtgctcc    1740
ccggagtgga ggcggccgag cgcgccgggg tgcccgcctt cctggagacc tccgcgcccc    1800
gcaacctccc cttctacgag cggctcggct tcaccgtcac cgccgacgtc gaggtgcccg    1860
aaggaccgcg cacctggtgc atgacccgca agcccggtgc ctgacgcccg ccccacgacc    1920
cgcagcgccc gaccgaaagg agcgcacgac cccatggctc cgaccgaagc cgacccgggc    1980
ggccccgccg accccgcacc cgcccccgag gcccaccgac tctagaggat cataatcagc    2040
cataccacat ttgtagaggt tttacttgct ttaaaaaacc tcccacacct cccctgaac     2100 ctgaaacata aaatgaatgc aattgttgtt gttaacttgt ttattgcagc ttataatggt    2160
tacaaataaa gcaatagcat cacaaatttc acaaataaag cattttttc actgcattct     2220 agttgtggtt tgtccaaact catcaatgta tcttatcatg tctggatcct agcgtttaaa    2280
cttaagcttg gtaccgagct cggatccact agtaatggtt acaaataaag caatagcatc    2340
acaaatttca caaataaagc attttttca ctgcattcta gttgtggttt gtccaaactc     2400
atcaatgtat cttatcatgt ctgtacgatg tacgggccag atatacgcgt tgacattgat    2460
tattgactag ttattaatag taatcaatta cggggtcatt agttcatagc ccatatatgg    2520
agttccgcgt tacataactt acggtaaatg gcccgcctgg ctgaccgccc aacgacccc     2580 gcccattgac gtcaataatg acgtatgttc ccatagtaac gccaataggg actttccatt    2640
gacgtcaatg ggtggagtat ttacggtaaa ctgcccactt ggcagtacat caagtgtatc    2700
atatgccaag tacgccccct attgacgtca atgacggtaa atggcccgcc tggcattatg    2760
cccagtacat gaccttatgg gactttccta cttggcagta catctacgta ttagtcatcg    2820
ctattaccat ggtgatgcgg ttttggcagt acatcaatgg gcgtggatag cggtttgact    2880
cacggggatt tccaagtctc cacccccattg acgtcaatgg gagtttgttt tggcaccaaa    2940
atcaacggga ctttccaaaa tgtcgtaaca actccgcccc attgacgcaa atgggcggta    3000
ggcgtgtacg gtgggaggtc tatataagca gagctctctg gctaactaga gaacccactg    3060
cttactggct tatcgaaatt aatacgactc actataggga cccaagctgg ctagctag     3120 tccagtgtgg tggaattctg cagatcgaaa cgatgataga tcccgtcgtt ttacaacgtc    3180
gtgactggga aaaccctggc gttacccaac ttaatcgcct tgcagcacat ccccctttcg    3240
ccagctggcg taatagcgaa gaggcccgca ccgatcgccc ttcccaacag ttgcgcagcc    3300
tgaatggcga atggcgcttt gcctggtttc cggtaccaga agcggtgccg gaaagctggc    3360
tggagtgcga tcttcctgag gccgatactg tcgtcgtccc ctcaaactgg cagatgcacg    3420
gttacgatgc gcccatctac accaacgtaa cctatcccat tacggtcaat ccgccgtttg    3480
ttcccacgga gaatccgacg ggttgttact cgctcacatt taatgttgat gaaagctggc    3540
tacaggaagg ccagacgcga attatttttg atggcgttaa ctcggcgttt catctgtggt    3600
gcaacgggct gggtcggt tacgccagg acagtcgttt gccgtctgaa tttgacctga      3660
gcgcattttt acgcgccgga gaaaaccgcc tcgcggtgat ggtgctgcgt tggagtgacg    3720
gcagttatct ggaagatcag gatatgtggc ggatgagcgg cattttccgt gacgtctcgt    3780
tgctgcataa accgactaca caaatcagcg atttccatgt tgccactcgc tttaatgatg    3840
atttcagccg cgctgtactg gaggctgaag ttcagatgtg cggcgagttg cgtgactacc    3900
```

```
tacgggtaac agtttcttta tggcagggtg aaacgcaggt cgccagcggc accgcgcctt   3960
tcggcggtga aattatcgat gagcgtggtg gttatgccga tcgcgtcaca ctacgtctga   4020
acgtcgaaaa cccgaaactg tggagcgccg aaatcccgaa tctctatcgt gcggtggttg   4080
aactgcacac cgccgacggc acgctgattg aagcagaagc ctgcgatgtc ggtttccgcg   4140
aggtgcggat tgaaaatggt ctgctgctgc tgaacggcaa gccgttgctg attcgaggcg   4200
ttaaccgtca cgagcatcat cctctgcatg gtcaggtcat ggatgagcag acgatggtgc   4260
aggatatcct gctgatgaag cagaacaact ttaacgccgt gcgctgttcg cattatccga   4320
accatccgct gtggtacacg ctgtgcgacc gctacgcct tatgtggtg gatgaagcca     4380
atattgaaac ccacggcatg gtgccaatga atcgtctgac cgatgatccg cgctggctac   4440
cggcgatgag cgaacgcgta acgcgaatgg tgcagcgcga tcgtaatcac ccgagtgtga   4500
tcatctggtc gctggggaat gaatcaggcc acggcgctaa tcacgacgcg ctgtatcgct   4560
ggatcaaatc tgtcgatcct tcccgcccgg tgcagtatga aggcggcgga gccgacacca   4620
cggccaccga tattatttgc ccgatgtacg cgcgcgtgga tgaagaccag cccttcccgg   4680
ctgtgccgaa atggtccatc aaaaaatggc tttcgctacc tggagagacg cgcccgctga   4740
tcctttgcga atacgcccac gcgatgggta acagtcttgg cggtttcgct aaatactggc   4800
aggcgtttcg tcagtatccc cgtttacagg gcggcttcgt ctgggactgg gtggatcagt   4860
cgctgattaa atatgatgaa aacggcaacc cgtggtcggc ttacggcggt gattttggcg   4920
atacgccgaa cgatcgccag ttctgtatga acggtctggt cttttgccgac cgcacgccgc   4980
atccagcgct gacggaagca aaacaccagc agcagttttt ccagttccgt ttatccgggc   5040
aaaccatcga agtgaccagc gaatacctgt tccgtcatag cgataacgag ctcctgcact   5100
ggatggtggc gctggatggt aagccgctgg caagcggtga agtgcctctg gatgtcgctc   5160
cacaaggtaa acagttgatt gaactgcctg aactaccgca gccggagagc gccgggcaac   5220
tctggctcac agtacgcgta gtgcaaccga acgcgaccgc atggtcagaa gccgggcaca   5280
tcagcgcctg gcagcagtgg cgtctggcgg aaaacctcag tgtgacgctc cccgccgcgt   5340
cccacgccat cccgcatctg accaccagcg aaatggattt ttgcatcgag ctgggtaata   5400
agcgttggca atttaaccgc cagtcaggct ttctttcaca gatgtggatt ggcgataaaa   5460
aacaactgct gacgccgctg cgcgatcagt tcacccgtgc accgctggat aacgacattg   5520
gcgtaagtga agcgacccgc attgacccta cgcctgggt cgaacgctgg aaggcggcgg    5580
gccattacca ggccgaagca gcgttgttgc agtgcacggc agatacactt gctgatgcgg   5640
tgctgattac gaccgctcac gcgtggcagc atcagggaa aaccttattt atcagccgga    5700
aaacctaccg gattgatggt agtggtcaaa tggcgattac cgttgatgtt gaagtggcga   5760
gcgatacacc gcatccggcg cggattggcc tgaactgcca gctggcgcag gtagcagagc   5820
gggtaaactg gctcggatta gggccgcaag aaaactatcc cgaccgcctt actgccgcct   5880
gttttgaccg ctgggatctg ccattgtcag acatgtatac cccgtacgtc ttcccgagcg   5940
aaaacggtct gcgctgcggg acgcgcgaat tgaattatgg cccacaccag tggcgcggcg   6000
acttccagtt caacatcagc cgctacagtc aacagcaact gatggaaacc agccatcgcc   6060
atctgctgca cgcggaagaa ggcacatggc tgaatatcga cggttccat atggggattg    6120
gtggcgacga ctcctggagc ccgtcagtat cggcggaatt ccagctgagc gccggtcgct   6180
accattacca gttggtctgg tgtcaaaaag cggccgctcg agtctagagg gcccgtttaa   6240
```

```
acccgctgat cagcctcgac tgtgccttct agttgccagc catctgttgt ttgcccctcc   6300
cccgtgcctt ccttgaccct ggaaggtgcc actcccactg tcctttccta ataaaatgag   6360
gaaattgcat cgcattgtct gagtaggtgt cattctattc tggggggtgg ggtggggcag   6420
gacagcaagg gggaggattg ggaagacaat agcaggcatg ctgggatgc ggtgggctct    6480 atggcttctg aggcggaaag aaccagctgg ggctctaggg ggtatcccca cgcgccctgt   6540
agcggcgcat taagcgcggc gggtgtggtg gttacgcgca gcgtgaccgc tacacttgcc   6600
agcgccctag cgcccgctcc tttcgctttc ttcccttcct ttctcgccac gttcgcctac   6660
cgtcgaatca ccggtaacct tataaggat ttttgccgatt tcggcctatt ggttaaaaaa    6720
tgagctgatt taacaaaaat ttaacgcgaa ttaattctgt ggaatgtgtg tcagttaggg   6780
tgtggaaagt ccccaggctc cccagcaggc agaagtatgc aaagcatgca tctcaattag   6840
tcagcaacca ggtgtggaaa gtccccaggc tccccagcag gcagaagtat gcaaagcatg   6900
catctcaatt agtcagcaac catagtcccg cccctaactc cgcccatccc gcccctaact   6960
ccgcccagtt ccgcccattc tccgcccat ggctgactaa ttttttttat ttatgcagag     7020
gccgaggccg cctctgcctc tgagctattc cagaagtagt gaggaggctt ttttggaggc   7080
ctaggctttt gcaaaaagct cccggggagct tgtatatcca ttttcggatc tgatcaagag   7140
acaggatgag gatcgtttcg catgattgaa caagatggat tgcacgcagg ttctccggcc   7200
gcttgggtgg agaggctatt cggctatgac tgggcacaac agacaatcgg ctgctctgat   7260
gccgccgtgt tccggctgtc agcgcagggg cgcccggttc ttttgtcaa gaccgacctg    7320 tccggtgccc tgaatgaact gcaggacgag gcagcgcggc tatcgtggct ggccacgacg   7380
ggcgttcctt gcgcagctgt gctcgacgtt gtcactgaag cgggaaggga ctggctgcta   7440
ttgggcgaag tgccggggca ggatctcctg tcatctcacc ttgctcctgc cgagaaagta   7500
tccatcatgg ctgatgcaat gcggcggctg catacgcttg atccggctac ctgcccattc   7560
gaccaccaag cgaaacatcg catcgagcga gcacgtactc ggatggaagc cggtcttgtc   7620
gatcaggatg atctggacga agagcatcag gggctcgcgc cagccgaact gttcgccagg   7680
ctcaaggcgc gaattcgagc tcggtacccg gggatcctct agagtcgacc tgcaggcatg   7740
caagcttggc gtaatcatgg tcatagctgt ttcctgtgtg aaattgttat ccgctcacaa   7800
ttccacacaa catacgagcc ggaagcataa agtgtaaagc ctggggtgcc taatgagtga   7860
gctaactcac attaattgcg ttgcgctcac tgcccgcttt ccagtcggga aacctgtcgt   7920
gccagctgca ttaatgaatc ggccaacgcg cggggagagg cggtttgcgt attgggcgct   7980
cttccgcttc ctcgctcact gactcgctgc gctcggtcgt tcggctgcgg cgagcggtat   8040
cagctcactc aaaggcggta atacggttat ccacagaatc aggggataac gcaggaaaga   8100
acatgtgagc aaaaggccag caaaaggcca ggaaccgtaa aaaggccgcg ttgctggcgt   8160
ttttccatag gctccgcccc cctgacgagc atcacaaaaa tcgacgctca agtcagaggt   8220
ggcgaaaccc gacaggacta taaagatacc aggcgtttcc ccctggaagc tccctcgtgc   8280
gctctcctgt tccgaccctg ccgcttaccg gatacctgtc cgcctttctc ccttcgggaa   8340
gcgtggcgct ttctcatagc tcacgctgta ggtatctcag ttcggtgtag tcgttcgct    8400 ccaagctggg ctgtgtgcac gaaccccccg ttcagcccga ccgctgcgcc ttatccggta   8460
actatcgtct tgagtccaac ccggtaagac acgacttatc gccactggca gcagccactg   8520
gtaacaggat tagcagagcg aggtatgtag gcggtgctac agagttcttg aagtggtggc   8580
ctaactacgg ctacactaga aggacagtat ttggtatctg cgctctgctg aagccagtta   8640
```

```
ccttcggaaa aagagttggt agctcttgat ccggcaaaca aaccaccgct ggtagcggtg    8700
gtttttttgt ttgcaagcag cagattacgc gcagaaaaaa aggatctcaa gaagatcctt    8760
tgatcttttc tacggggtct gacgctcagt ggaacgaaaa ctcacgttaa gggattttgg    8820
tcatgagatt atcaaaaagg atcttcacct agatcctttt aaattaaaaa tgaagtttta    8880
aatcaatcta agtatatat gagtaaactt ggtctgacag ttaccaatgc ttaatcagtg    8940
aggcacctat ctcagcgatc tgtctatttc gttcatccat agttgcctga ctccccgtcg    9000
tgtagataac tacgatacgg gagggcttac catctggccc cagtgctgca atgataccgc    9060
gagacccacg ctcaccggct ccagatttat cagcaataaa ccagccagcc ggaagggccg    9120
agcgcagaag tggtcctgca actttatccg cctccatcca gtctattaat tgttgccggg    9180
aagctagagt aagtagttcg ccagttaata gtttgcgcaa cgttgttgcc attgctacag    9240
gcatcgtggt gtcacgctcg tcgtttggta tggcttcatt cagctccggt tcccaacgat    9300
caaggcgagt tacatgatcc cccatgttgt gcaaaaaagc ggttagctcc ttcggtcctc    9360
cgatcgttgt cagaagtaag ttggccgcag tgttatcact catggttatg gcagcactgc    9420
ataattctct tactgtcatg ccatccgtaa gatgcttttc tgtgactggt gagtactcaa    9480
ccaagtcatt ctgagaatag tgtatgcggc gaccgagttg ctcttgcccg gcgtcaatac    9540
gggataatac cgcgccacat agcagaactt taaaagtgct catcattgga aaacgttctt    9600
cggggcgaaa actctcaagg atcttaccgc tgttgagatc cagttcgatg taacccactc    9660
gtgcacccaa ctgatcttca gcatctttta ctttcaccag cgtttctggg tgagcaaaaa    9720
caggaaggca aaatgccgca aaaaagggaa taagggcgac acggaaatgt tgaatactca    9780
tactcttcct ttttcaatat tattgaagca tttatcaggg ttattgtctc atgagcggat    9840
acatatttga atgtatttag aaaaataaac aaataggggt tccgcgcaca tttccccgaa    9900
aagtgccacc tgacgtctaa gaaaccatta ttatcatgac attaacctat aaaaataggc    9960
gtatcacgag gccctttcgt c                                              9981
```

<210> SEQ ID NO 18
<211> LENGTH: 7291
<212> TYPE: DNA
<213> ORGANISM: Artificial Sequence
<220> FEATURE:
<223> OTHER INFORMATION: Description of Artificial Sequence: Synthetic
      KI-construct-LacZ control polynucleotide

<400> SEQUENCE: 18

```
ttaaggagcc ccttcgcctc gtgcttgagt tgaggcctgg cttgggcgct ggggccgccg      60
cgtgcgaatc tggtggcacc ttcgcgcctg tctcgctgct ttcgataagt ctctagccat     120
ttaaaatttt tgatgacctg ctgcgacgct ttttttctgg caagatagtc ttgtaaatgc     180
gggccaagat cgatctgcac actggtattt cggttttgg ggccgcgggc ggcgacgggg      240
cccgtgcgtc ccagcgcaca tgttcggcga ggcggggcct gcgagcgcgg ccaccgagaa     300
tcggacgggg gtagtctcaa gctggccggc ctgctctggt gcctggcctc gcgccgccgt     360
gtatcgcccc gccctgggcg gcaaggctgg cccgtcggc accagttgcg tgagcggaaa      420
gatggccgct tccggccct gctgcaggga gctcaaaatg gaggacgcgg cgctcgggag      480
agcgggcggg tgagtcaccc acacaaagga aagggccttt ccgtcctca gccgtcgctt      540
catgtgactc cacggagtac cgggcgccgt ccaggcacct cgattagttc tcgagctttt    600
ggagtacgtc gtctttaggt tggggggagg ggttttatgc gatggagttt ccccacactg     660
```

```
agtgggtgga gactgaagtt aggccagctt ggcacttgat gtaattctcc ttggaatttg    720
ccctttttga gtttggatct tggttcattc tcaagcctca gacagtggtt caaagttttt    780
ttcttccatt tcaggtgtcg tggaattggc tagagcttgc atgcctgcag gtcggccgcc    840
acgaccggtg ccgccaccat ccctgaccc acgcccctga ccctcacaa ggagacgacc    900 ttccatgacc gagtacaagc ccacggtgcg cctcgccacc cgcgacgacg tccccgggc    960 cgtacgcacc ctcgccgccg cgttcgccga ctaccccgcc acgcgccaca ccgtcgaccc    1020
ggaccgccac atcgagcggg tcaccgagct gcaagaactc ttcctcacgc gcgtcgggct    1080
cgacatcggc aaggtgtggg tcgcggacga cggcgccgcg gtggcggtct ggaccacgcc    1140
ggagagcgtc gaagcggggg cggtgttcgc cgagatcggc ccgcgcatgg ccgagttgag    1200
cggttcccgg ctggccgcgc agcaacagat ggaaggcctc ctggcgccgc accgcccaa    1260 ggagcccgcg tggttcctgg ccaccgtcgg cgtctcgccc gaccaccagg gcaagggtct    1320
gggcagcgcg gtcgtgctcc ccggagtgga ggcggccgag cgcgccgggg tgcccgcctt    1380
cctggagacc tccgcgcccc gcaacctccc cttctacgag cggctcggct tcaccgtcac    1440
cgccgacgtc gaggtgcccg aaggaccgcg cacctggtgc atgacccgca agccggtgc    1500 ctgacgcccg ccccacgacc cgcagcgccc gaccgaaagg agcgcacgac cccatggctc    1560
cgaccgaagc cgaccgggc ggccccgccg accccgcacc cgccccgag gcccaccgac    1620 tctagaggat cataatcagc ataccacat ttgtagaggt tttacttgct ttaaaaaacc    1680
tcccacacct ccccctgaac ctgaaacata aatgaatgc aattgttgtt gttaacttgt    1740
ttattgcagc ttataatggt tacaaataaa gcaatagcat cacaaatttc acaaataaag    1800
catttttttc actgcattct agttgtggtt tgtccaaact catcaatgta tcttatcatg    1860
tctggatcct agcgtttaaa cttaagcttg gtaccgagct cggatccact agtaatggtt    1920
acaaataaag caatagcatc acaaatttca caaataaagc atttttttca ctgcattcta    1980
gttgtggttt gtccaaactc atcaatgtat cttatcatgt ctgtacgatg tacgggccag    2040
atatacgcgt tgacattgat tattgactag ttattaatag taatcaatta cggggtcatt    2100
agttcatagc ccatatatgg agttccgcgt tacataactt acggtaaatg gcccgcctgg    2160
ctgaccgccc aacgacccc gcccattgac gtcaataatg acgtatgttc ccatagtaac    2220 gccaatagg actttccatt gacgtcaatg ggtggagtat ttacggtaaa ctgcccactt    2280
ggcagtacat caagtgtatc atatgccaag tacgccccct attgacgtca atgacggtaa    2340
atggcccgcc tggcattatg cccagtacat gaccttatgg gactttccta cttggcagta    2400
catctacgta ttagtcatcg ctattaccat ggtgatgcgg ttttggcagt acatcaatgg    2460
gcgtggatag cggtttgact cacggggatt tccaagtctc cacccattg acgtcaatgg    2520 gagtttgttt tggcaccaaa atcaacggga ctttccaaa tgtcgtaaca actccgcccc    2580
attgacgcaa atgggcggta ggcgtgtacg gtgggaggtc tatataagca gagctctctg    2640
gctaactaga gaacccactg cttactggct tatcgaaatt aatacgactc actataggga    2700
gacccaagct ggctagctag tccagtgtgg tggaattctg cagatcgaaa cgatgataga    2760
tcccgtcgtt ttacaacgtc gtgactggga aaaccctggc gttacccaac ttaatcgcct    2820
tgcagcacat ccccctttcg ccagctggcg taatagcgaa gaggcccgca ccgatcgccc    2880
ttcccaacag ttgcgcagcc tgaatggcga atggcgcttt gcctggtttc cggtaccaga    2940
agcggtgccg gaaagctggc tggagtgcga tcttcctgag gccgatactg tcgtcgtccc    3000
```

```
ctcaaactgg cagatgcacg gttacgatgc gcccatctac accaacgtaa cctatcccat   3060
tacggtcaat ccgccgtttg ttcccacgga gaatccgacg ggttgttact cgctcacatt   3120
taatgttgat gaaagctggc tacaggaagg ccagacgcga attattttg atggcgttaa    3180
ctcggcgttt catctgtggt gcaacgggcg ctgggtcggt tacggccagg acagtcgttt   3240
gccgtctgaa tttgacctga gcgcatttt acgcgccgga gaaaaccgcc tcgcggtgat    3300
ggtgctgcgt tggagtgacg gcagttatct ggaagatcag gatatgtggc ggatgagcgg   3360
cattttccgt gacgtctcgt tgctgcataa accgactaca caaatcagcg atttccatgt   3420
tgccactcgc tttaatgatg atttcagccg cgctgtactg gaggctgaag ttcagatgtg   3480
cggcgagttg cgtgactacc tacgggtaac agtttcttta tggcagggtg aaacgcaggt   3540
cgccagcggc accgcgcctt cggcggtga  aattatcgat gagcgtggtg ttatgccga    3600
tcgcgtcaca ctacgtctga acgtcgaaaa cccgaaactg tggagcgccg aaatcccgaa   3660
tctctatcgt gcggtggttg aactgcacac cgccgacggc acgctgattg aagcagaagc   3720
ctgcgatgtc ggtttccgcg aggtgcggat tgaaaatggt ctgctgctgc tgaacggcaa   3780
gccgttgctg attcgaggcg ttaaccgtca cgagcatcat cctctgcatg gtcaggtcat   3840
ggatgagcag acgatggtgc aggatatcct gctgatgaag cagaacaact ttaacgccgt   3900
gcgctgttcg cattatccga accatccgct gtggtacacg ctgtgcgacc gctacggcct   3960
gtatgtggtg gatgaagcca atattgaaac ccacggcatg gtgccaatga atcgtctgac   4020
cgatgatccg cgctggctac cggcgatgag cgaacgcgta acgcgaatgg tgcagcgcga   4080
tcgtaatcac ccgagtgtga tcatctggtc gctggggaat gaatcaggcc acggcgctaa   4140
tcacgacgcg ctgtatcgct ggatcaaatc tgtcgatcct tcccgcccgg tgcagtatga   4200
aggcggcgga gccgacacca cggccaccga tattatttgc ccgatgtacg cgcgcgtgga   4260
tgaagaccag cccttcccgg ctgtgccgaa atggtccatc aaaaaatggc tttcgctacc   4320
tggagagacg cgcccgctga tcctttgcga atacgcccac gcgatgggta acagtcttgg   4380
cggtttcgct aaatactggc aggcgtttcg tcagtatccc cgtttacagg gcggcttcgt   4440
ctgggactgg gtggatcagt cgctgattaa atatgatgaa acggcaacc  cgtggtcggc    4500
ttacggcggt gattttggcg atacgccgaa cgatcgccag ttctgtatga cggtctggt    4560
ctttgccgac cgcacgccgc atccagcgct gacggaagca aaacaccagc agcagttttt   4620
ccagttccgt ttatccgggc aaaccatcga agtgaccagc gaatacctgt ccgtcatag    4680
cgataacgag ctcctgcact ggatggtggc gctggatggt aagccgctgg caagcggtga   4740
agtgcctctg gatgtcgctc cacaaggtaa acagttgatt gaactgcctg aactaccgca   4800
gccggagagc gccgggcaac tctggctcac agtacgcgta gtgcaaccga acgcgaccgc   4860
atggtcagaa gccgggcaca tcagcgcctg gcagcagtgg cgtctggcgg aaaacctcag   4920
tgtgacgctc cccgccgcgt cccacgccat cccgcatctg accaccagcg aaatggattt   4980
ttgcatcgag ctgggtaata gcgttggca  atttaaccgc cagtcaggct ttctttcaca   5040
gatgtggatt ggcgataaaa acaactgct  gacgccgctg cgcgatcagt tcacccgtgc   5100
accgctggat aacgacattg gcgtaagtga agcgacccgc attgaccta  acgcctgggt   5160
cgaacgctgg aaggcggcgg gccattacca ggccgaagca gcgttgttgc agtgcacggc   5220
agatacactt gctgatgcgg tgctgattac gaccgctcac gcgtggcagc atcaggggaa   5280
aaccttattt atcagccgga aaacctaccg gattgatggt agtggtcaaa tggcgattac   5340
cgttgatgtt gaagtggcga gcgatacacc gcatccggcg cggattggcc tgaactgcca   5400
```

```
gctggcgcag gtagcagagc gggtaaactg gctcggatta gggccgcaag aaaactatcc      5460
cgaccgcctt actgccgcct gttttgaccg ctgggatctg ccattgtcag acatgtatac      5520
cccgtacgtc ttcccgagcg aaaacggtct gcgctgcggg acgcgcgaat tgaattatgg      5580
cccacaccag tggcgcggcg acttccagtt caacatcagc cgctacagtc aacagcaact      5640
gatggaaacc agccatcgcc atctgctgca cgcggaagaa ggcacatggc tgaatatcga      5700
cggtttccat atggggattg gtggcgacga ctcctggagc ccgtcagtat cggcggaatt      5760
ccagctgagc gccggtcgct accattacca gttggtctgg tgtcaaaaag cggccgctcg      5820
agtctagagg gcccgtttaa acccgctgat cagcctcgac tgtgccttct agttgccagc      5880
catctgttgt ttgcccctcc cccgtgcctt ccttgaccct ggaaggtgcc actcccactg      5940
tcctttccta ataaaatgag gaaattgcat cgcattgtct gagtaggtgt cattctattc      6000
tggggggtgg ggtggggcag gacagcaagg gggaggattg ggaagacaat agcaggcatg      6060
ctggggatgc ggtgggctct atggcttctg aggcggaaag aaccagctgg ggctctaggg      6120
ggtatcccca cgcgccctgt agcggcgcat taagcgcggc gggtgtggtg gttacgcgca      6180
gcgtgaccgc tacacttgcc agcgccctag cgcccgctcc tttcgctttc ttcccttcct      6240
ttctcgccac gttcgcctac cgtcgaatca ccggtaacct tataagggat tttgccgatt      6300
tcggcctatt ggttaaaaaa tgagctgatt taacaaaaat ttaacgcgaa ttaattctgt      6360
ggaatgtgtg tcagttaggg tgtggaaagt ccccaggctc cccagcaggc agaagtatgc      6420
aaagcatgca tctcaattag tcagcaacca ggtgtggaaa gtcccaggc tccccagcag      6480 gcagaagtat gcaaagcatg catctcaatt agtcagcaac catagtcccg cccctaactc      6540
cgcccatccc gcccctaact ccgcccagtt ccgcccattc tccgccccat ggctgactaa      6600
ttttttttat ttatgcagag gccgaggccg cctctgcctc tgagctattc cagaagtagt      6660
gaggaggctt ttttggaggc ctaggctttt gcaaaaagct cccgggagct tgtatatcca      6720
ttttcggatc tgatcaagag acaggatgag gatcgtttcg catgattgaa caagatggat      6780
tgcacgcagg ttctccggcc gcttgggtgg agaggctatt cggctatgac tgggcacaac      6840
agacaatcgg ctgctctgat gccgccgtgt tccggctgtc agcgcagggg cgcccggttc      6900
tttttgtcaa gaccgacctg tccggtgccc tgaatgaact gcaggacgag gcagcgcggc      6960
tatcgtggct ggccacgacg ggcgttcctt gcgcagctgt gctcgacgtt gtcactgaag      7020
cgggaaggga ctggctgcta ttgggcgaag tgccggggca ggatctcctg tcatctcacc      7080
ttgctcctgc cgagaaagta tccatcatgg ctgatgcaat gcggcggctg catacgcttg      7140
atccggctac ctgcccattc gaccaccaag cgaaacatcg catcgagcga cacgtactc      7200 ggatggaagc cggtcttgtc gatcaggatg atctggacga agagcatcag gggctcgcgc      7260
cagccgaact gttcgccagg ctcaaggcgc g                                    7291
```

<210> SEQ ID NO 19
<211> LENGTH: 131
<212> TYPE: DNA
<213> ORGANISM: Artificial Sequence
<220> FEATURE:
<223> OTHER INFORMATION: Description of Artificial Sequence: Synthetic
      SV40pA (for puro) polynucleotide

<400> SEQUENCE: 19

```
aacttgttta ttgcagctta taatggttac aaataaagca atagcatcac aaatttcaca       60
aataaagcat ttttttcact gcattctagt tgtggtttgt ccaaactcat caatgtatct      120
```

```
tatcatgtct g                                                         131

<210> SEQ ID NO 20
<211> LENGTH: 344
<212> TYPE: DNA
<213> ORGANISM: Artificial Sequence
<220> FEATURE:
<223> OTHER INFORMATION: Description of Artificial Sequence: Synthetic
      SV40 promoter polynucleotide

<400> SEQUENCE: 20
ctgtggaatg tgtgtcagtt agggtgtgga aagtccccag gctccccagc aggcagaagt    60
atgcaaagca tgcatctcaa ttagtcagca accaggtgtg gaaagtcccc aggctcccca   120
gcaggcagaa gtatgcaaag catgcatctc aattagtcag caaccatagt cccgccccta   180
actccgccca tcccgcccct aactccgccc agttccgccc attctccgcc ccatggctga   240 ctaattttttt ttatttatgc agaggccgag gccgcctctg cctctgagct attccagaag   300
tagtgaggag gcttttttgg aggcctaggc ttttgcaaaa agct                    344

<210> SEQ ID NO 21
<211> LENGTH: 600
<212> TYPE: DNA
<213> ORGANISM: Artificial Sequence
<220> FEATURE:
<223> OTHER INFORMATION: Description of Artificial Sequence: Synthetic
      puromycin resistance gene

<400> SEQUENCE: 21
atgaccgagt acaagcccac ggtgcgcctc gccacccgcg acgacgtccc ccgggccgta    60
cgcaccctcg ccgccgcgtt cgccgactac cccgccacgc gccacaccgt cgacccggac   120
cgccacatcg agcgggtcac cgagctgcaa gaactcttcc tcacgcgcgt cggcctcgac   180
atcggcaagg tgtgggtcgc ggacgacggc gccgcggtgg cggtctggac cacgccggag   240
agcgtcgaag cgggggcggt gttcgccgag atcggcccgc gcatggccga gttgagcggt   300
tcccggctgg ccgcgcagca acagatggaa ggcctcctgg cgccgcaccg gcccaaggag   360
cccgcgtggt tcctggccac cgtcggcgtc tcgcccgacc accagggcaa gggtctgggc   420
agcgccgtcg tgctccccgg agtggaggcg gccgagcgcg ccggggtgcc cgccttcctg   480
gagacctccg cgccccgcaa cctccccttc tacgagcggc tcggcttcac cgtcaccgcc   540
gacgtcgagg tgcccgaagg accgcgcacc tggtgcatga cccgcaagcc cggtgcctga   600

<210> SEQ ID NO 22
<211> LENGTH: 6932
<212> TYPE: DNA
<213> ORGANISM: Artificial Sequence
<220> FEATURE:
<223> OTHER INFORMATION: Description of Artificial Sequence: Synthetic
      pTV_DS_MCS polynucleotide

<400> SEQUENCE: 22
ctagccttag gcgcgccaga tctgtacatt cgaagatatc ttaattaagc ggccgctcga    60
gtctagaggg cccgtttaaa cccgctgatc agcctcgact gtgccttcta gttgccagcc   120
atctgttgtt tgcccctccc ccgtgccttc cttgaccctg gaaggtgcca ctcccactgt   180
cctttcctaa taaaatgagg aaattgcatc gcattgtctg agtaggtgtc attctattct   240
ggggggtggg gtggggcagg acagcaaggg ggaggattgg gaagacaata gcaggcatgc   300
tggggatgcg gtgggctcta tggcttctga ggcggaaaga accagctggg gctctagggg   360
```

```
gtatccccac gcgccctgta gcggcgcatt aagcgcggcg ggtgtggtgg ttacgcgcag    420
cgtgaccgct acacttgcca gcgccctagc gcccgctcct ttcgctttct tcccttcctt    480
tctcgccacg ttcgcctacc gtcgaatcac cggtaacctt ataagggatt ttgccgattt    540
cggcctattg gttaaaaaat gagctgattt aacaaaaatt taacgcgaat taattctgtg    600
gaatgtgtgt cagttagggt gtggaaagtc cccaggctcc ccagcaggca gaagtatgca    660
aagcatgcat ctcaattagt cagcaaccag gtgtggaaag tccccaggct ccccagcagg    720
cagaagtatg caaagcatgc atctcaatta gtcagcaacc atagtcccgc ccctaactcc    780
gcccatcccg cccctaactc cgcccagttc cgcccattct ccgcccccatg gctgactaat    840 ttttttttatt tatgcagagg ccgaggccgc ctctgcctct gagctattcc agaagtagtg    900
aggaggcttt tttggaggcc taggcttttg caaaaagctc ccgggagctt gtatatccat    960
tttcggatct gatcaagaga caggatgagg atcgtttcgc atgattgaac aagatggatt   1020
gcacgcaggt tctccggccg cttgggtgga gaggctattc ggctatgact gggcacaaca   1080
gacaatcggc tgctctgatg ccgccgtgtt ccggctgtca gcgcaggggc gcccggttct   1140
ttttgtcaag accgacctgt ccggtgccct gaatgaactg caggacgagg cagcgcggct   1200
atcgtggctg gccacgacgg gcgttccttg cgcagctgtg ctcgacgttg tcactgaagc   1260
gggaagggac tggctgctat tgggcgaagt gccggggcag gatctcctgt catctcacct   1320
tgctcctgcc gagaaagtat ccatcatggc tgatgcaatg cggcggctgc atacgcttga   1380
tccggctacc tgcccattcg accaccaagc gaaacatcgc atcgagcgag cacgtactcg   1440
gatggaagcc ggtcttgtcg atcaggatga tctggacgaa gagcatcagg ggctcgcgcc   1500
agccgaactg ttcgccaggc tcaaggcgcg aattcgagct cggtaccgg ggatcctcta   1560 gagtcgacct gcaggcatgc aagcttggcg taatcatggt catagctgtt tcctgtgtga   1620
aattgttatc cgctcacaat tccacacaac atacgagccg gaagcataaa gtgtaaagcc   1680
tggggtgcct aatgagtgag ctaactcaca ttaattgcgt tgcgctcact gcccgctttc   1740
cagtcgggaa acctgtcgtg ccagctgcat taatgaatcg gccaacgcgc ggggagaggc   1800
ggtttgcgta ttgggcgctc ttccgcttcc tcgctcactg actcgctgcg ctcggtcgtt   1860
cggctgcggc gagcggtatc agctcactca aaggcggtaa tacggttatc cacagaatca   1920
ggggataacg caggaaagaa catgtgagca aaaggccagc aaaaggccag gaaccgtaaa   1980
aaggccgcgt tgctggcgtt tttccatagg ctccgccccc ctgacgagca tcacaaaaat   2040
cgacgctcaa gtcagaggtg gcgaaacccg acaggactat aaagatacca ggcgtttccc   2100
cctggaagct ccctcgtgcg ctctcctgtt ccgaccctgc cgcttaccgg atacctgtcc   2160
gcctttctcc cttcgggaag cgtggcgctt tctcatagct cacgctgtag gtatctcagt   2220
tcggtgtagg tcgttcgctc caagctgggc tgtgtgcacg aaccccccgt tcagcccgac   2280
cgctgcgcct tatccggtaa ctatcgtctt gagtccaacc cggtaagaca cgacttatcg   2340
ccactggcag cagccactgg taacaggatt agcagagcga ggtatgtagg cggtgctaca   2400
gagttcttga agtggtggcc taactacggc tacactagaa ggacagtatt tggtatctgc   2460
gctctgctga agccagttac cttcggaaaa agagttggta gctcttgatc cggcaaacaa   2520
accaccgctg gtagcggtgg tttttttgtt tgcaagcagc agattacgcg cagaaaaaaa   2580
ggatctcaag aagatccttt gatcttttct acggggtctg acgctcagtg gaacgaaaac   2640
tcacgttaag ggattttggt catgagatta tcaaaaagga tcttcaccta gatccttta   2700
```

```
aattaaaaat gaagttttaa atcaatctaa agtatatatg agtaaacttg gtctgacagt    2760
taccaatgct taatcagtga ggcacctatc tcagcgatct gtctatttcg ttcatccata    2820
gttgcctgac tccccgtcgt gtagataact acgatacggg agggcttacc atctggcccc    2880
agtgctgcaa tgataccgcg agacccacgc tcaccggctc cagatttatc agcaataaac    2940
cagccagccg gaagggccga gcgcagaagt ggtcctgcaa ctttatccgc ctccatccag    3000
tctattaatt gttgccggga agctagagta agtagttcgc cagttaatag tttgcgcaac    3060
gttgttgcca ttgctacagg catcgtggtg tcacgctcgt cgtttggtat ggcttcattc    3120
agctccggtt cccaacgatc aaggcgagtt acatgatccc ccatgttgtg caaaaaagcg    3180
gttagctcct tcggtcctcc gatcgttgtc agaagtaagt tggccgcagt gttatcactc    3240
atggttatgg cagcactgca taattctctt actgtcatgc catccgtaag atgcttttct    3300
gtgactggtg agtactcaac caagtcattc tgagaatagt gtatgcggcg accgagttgc    3360
tcttgcccgg cgtcaatacg ggataatacc gcgccacata gcagaacttt aaaagtgctc    3420
atcattggaa aacgttcttc ggggcgaaaa ctctcaagga tcttaccgct gttgagatcc    3480
agttcgatgt aacccactcg tgcacccaac tgatcttcag catctttac  tttcaccagc    3540
gtttctgggt gagcaaaaac aggaaggcaa atgccgcaa  aaaagggaat aagggcgaca    3600
cggaaatgtt gaatactcat actcttcctt tttcaatatt attgaagcat ttatcagggt    3660
tattgtctca tgagcggata catatttgaa tgtatttaga aaaataaaca aatagggggtt   3720
ccgcgcacat ttccccgaaa agtgccacct gacgtctaag aaaccattat tatcatgaca    3780
ttaacctata aaaataggcg tatcacgagg ccctttcgtc tcgcgcgttt cggtgatgac    3840
ggtgaaaacc tctgacacat gcagctcccg gagacggtca gcttgtct  gtaagcggat    3900
gccgggagca gacaagcccg tcagggcgcg tcagcgggtg ttggcgggtg tcggggctgg    3960
cttaactatg cggcatcaga gcagattgta ctgagagtgc accatatgcg gtgtgaaata    4020
ccgcacagat gcgtaaggag aaaataccgc atcaggcgcc attcgccatt caggctgcgc    4080
aactgttggg aagggcgatc ggtgcgggcc tcttcgctat tacgccagct ggcgaaaggg    4140
ggatgtgctg caaggcgatt aagttgggta acgccagggt tttcccagtc acgacgttgt    4200
aaaacgacgg ccagtgaatt ttaaggagcc ccttcgcctc gtgcttgagt tgaggcctgg    4260
cttgggcgct ggggccgccg cgtgcgaatc tggtggcacc ttcgcgcctg tctcgctgct    4320
ttcgataagt ctctagccat ttaaaatttt tgatgacctg ctgcgacgct ttttttctgg    4380
caagatagtc ttgtaaatgc gggccaagat cgatctgcac actggtattt cggttttttgg   4440
ggccgcgggc ggcgacgggg cccgtgcgtc ccagcgcaca tgttcggcga ggcggggcct    4500
gcgagcgcgg ccaccgagaa tcggacgggg gtagtctcaa gctggccggc ctgctctggt    4560
gcctggcctc gcgccgccgt gtatcgcccc gccctgggcg gcaaggctgg cccggtcggc    4620
accagttgcg tgagcggaaa gatggccgct tcccggccct gctgcaggga gctcaaaatg    4680
gaggacgcgg cgctcgggag agcgggcggg tgagtcaccc acacaaagga aaagggcctt    4740
tccgtcctca gccgtcgctt catgtgactc cacggagtac cggcgccgt  ccaggcacct    4800
cgattagttc tcgagctttt ggagtacgtc gtctttaggt tggggggagg ggttttatgc    4860
gatggagttt cccacactg  agtgggtgga gactgaagtt aggccagctt ggcacttgat    4920
gtaattctcc ttggaatttg ccctttttga gtttggatct tggttcattc tcaagcctca    4980
gacagtggtt caaagttttt ttcttccatt tcagtgtcg  tggaattggc tagagcttgc    5040
atgcctgcag gtcggccgcc acgaccggtg ccgccaccat ccctgaccc  acgcccctga    5100
```

```
cccctcacaa ggagacgacc ttccatgacc gagtacaagc ccacggtgcg cctcgccacc    5160
cgcgacgacg tccccgggc cgtacgcacc ctcgccgccg cgttcgccga ctaccccgcc     5220
acgcgccaca ccgtcgaccc ggaccgccac atcgagcggg tcaccgagct gcaagaactc    5280
ttcctcacgc gcgtcgggct cgacatcggc aaggtgtggg tcgcggacga cggcgccgcg    5340
gtggcggtct ggaccacgcc ggagagcgtc gaagcggggg cggtgttcgc cgagatcggc    5400
ccgcgcatgg ccgagttgag cggttccgg ctggccgcgc agcaacagat ggaaggcctc     5460
ctggcgccgc accggcccaa ggagcccgcg tggttcctgg ccaccgtcgg cgtctcgccc    5520
gaccaccagg gcaagggtct gggcagcgcc gtcgtgctcc ccggagtgga ggcggccgag    5580
cgcgccgggg tgcccgcctt cctggagacc tccgcgcccc gcaacctccc cttctacgag    5640
cggctcggct tcaccgtcac cgccgacgtc gaggtgcccg aaggaccgcg cacctggtgc    5700
atgacccgca agcccggtgc ctgacgcccg ccccacgacc cgcagcgccc gaccgaaagg    5760
agcgcacgac cccatggctc cgaccgaagc cgacccgggc ggccccgccg accccgcacc    5820
cgcccccgag gcccaccgac tctagaggat cataatcagc cataccacat ttgtagaggt    5880
tttacttgct ttaaaaaacc tcccacacct cccctgaaac tgaaacata aatgaatgc     5940 aattgttgtt gttaacttgt ttattgcagc ttataatggt tacaaataaa gcaatagcat    6000
cacaaatttc acaaataaag cattttttc actgcattct agttgtggtt tgtccaaact     6060
catcaatgta tcttatcatg tctggatcct agcgtttaaa cttaagcttg gtaccgagct    6120
cggatccact agtaatggtt acaaataaag caatagcatc acaaatttca caaataaagc    6180
atttttttca ctgcattcta gttgtggttt gtccaaactc atcaatgtat cttatcatgt    6240
ctgtacgatg tacgggccag atatacgcgt tgacattgat tattgactag ttattaatag    6300
taatcaatta cggggtcatt agttcatagc ccatatatgg agttccgcgt tacataactt    6360
acggtaaatg gcccgcctgg ctgaccgccc aacgacccc gcccattgac gtcaataatg     6420
acgtatgttc ccatagtaac gccaataggg actttccatt gacgtcaatg ggtggagtat    6480
ttacggtaaa ctgcccactt ggcagtacat caagtgtatc atatgccaag tacgccccct    6540
attgacgtca atgacggtaa atggcccgcc tggcattatg cccagtacat gaccttatgg    6600
gactttccta cttggcagta catctacgta ttagtcatcg ctattaccat ggtgatgcgg    6660
ttttggcagt acatcaatgg gcgtggatag cggtttgact cacggggatt tccaagtctc    6720
caccccattg acgtcaatgg gagtttgttt tggcaccaaa atcaacggga ctttccaaaa    6780
tgtcgtaaca actccgcccc attgacgcaa atgggcggta ggcgtgtacg gtgggaggtc    6840
tatataagca gagctctctg gctaactaga gaacccactg cttactggct tatcgaaatt    6900
aatacgactc actataggga gacccaagct gg                                  6932
```

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      MCS/Multiple Cloning Site oligonucleotide

<400> SEQUENCE: 23

```
ctagccttag gcgcgccaga tctgtacatt cgaagatatc ttaattaagc g             51
```

<210> SEQ ID NO 24
<211> LENGTH: 4216

<212> TYPE: DNA
<213> ORGANISM: Artificial Sequence
<220> FEATURE:
<223> OTHER INFORMATION: Description of Artificial Sequence: Synthetic KI-construct

<400> SEQUENCE: 24

```
ttaaggagcc ccttcgcctc gtgcttgagt tgaggcctgg cttgggcgct ggggccgccg      60
cgtgcgaatc tggtggcacc ttcgcgcctg tctcgctgct ttcgataagt ctctagccat     120
ttaaaatttt tgatgacctg ctgcgacgct ttttttctgg caagatagtc ttgtaaatgc     180
gggccaagat cgatctgcac actggtattt cggttttttgg ggccgcgggc ggcgacgggg    240
cccgtgcgtc ccagcgcaca tgttcggcga ggcggggcct gcgagcgcgg ccaccgagaa     300
tcggacgggg gtagtctcaa gctggccggc ctgctctggt gcctggcctc cgccgccgt      360
gtatcgcccc gccctgggcg gcaaggctgg cccggtcggc accagttgcg tgagcggaaa     420
gatggccgct tcccggccct gctgcaggga gctcaaaatg gaggacgcgg cgctcgggag     480
agcgggcggg tgagtcaccc acacaaagga aagggccttt tccgtcctca gccgtcgctt     540
catgtgactc cacggagtac cgggcgccgt ccaggcacct cgattagttc tcgagctttt     600
ggagtacgtc gtctttaggt tgggggggagg ggttttatgc gatggagttt ccccacactg    660
agtgggtgga gactgaagtt aggccagctt ggcacttgat gtaattctcc ttggaatttg     720
cccttttttga gtttggatct tggttcattc tcaagcctca gacagtggtt caaagttttt    780
ttcttccatt tcaggtgtcg tggaattggc tagagcttgc atgcctgcag gtcggccgcc    840
acgaccggtg ccgccaccat ccctgaccc acgcccctga ccctcacaa ggagacgacc      900
ttccatgacc gagtacaagc ccacggtgcg cctcgccacc cgcgacgacg tccccgggc     960
cgtacgcacc ctcgccgccg cgttcgccga ctaccccgcc acgcgccaca ccgtcgaccc   1020
ggaccgccac atcgagcggg tcaccgagct gcaagaactc ttcctcacgc gcgtcgggct  1080
cgacatcggc aaggtgtggg tcgcggacga cggcgccgcg gtggcggtct ggaccacgcc  1140
ggagagcgtc gaagcggggg cggtgttcgc cgagatcggc ccgcgcatgg ccgagttgag  1200
cggttcccgg ctggccgcgc agcaacagat ggaaggcctc ctggcgccgc accggcccaa  1260
ggagcccgcg tggttcctgg ccaccgtcgg cgtctcgccc gaccaccagg gcaagggtct  1320
gggcagcgcc gtcgtgctcc ccggagtgga ggcggccgag cgcgccgggg tgcccgcctt  1380
cctggagacc tccgcgcccc gcaacctccc cttctacgag cggctcggct tcaccgtcac  1440
cgccgacgtc gaggtgcccg aaggaccgcg cacctggtgc atgacccgca agcccggtgc  1500
ctgacgcccg cccacgacc cgcagcgccc gaccgaaagg agcgcacgac cccatggctc   1560
cgaccgaagc cgacccgggc ggccccgccg acccgcacc cgcccccgag gccaccgac    1620
tctagaggat cataatcagc cataccacat ttgtagaggt tttacttgct ttaaaaaacc  1680
tcccacacct cccctgaac ctgaaacata aatgaatgc aattgttgtt gttaacttgt    1740
ttattgcagc ttataatggt tacaaataaa gcaatagcat cacaaatttc acaaataaag  1800
catttttttc actgcattct agttgtggtt tgtccaaact catcaatgta tcttatcatg  1860
tctggatcct agcgtttaaa cttaagcttg gtaccgagct cggatccact agtaatggtt  1920
acaaataaag caatagcatc acaaatttca caaataaagc attttttca ctgcattcta    1980
gttgtggttt gtccaaactc atcaatgtat cttatcatgt ctgtacgatg tacgggccag  2040
atatacgcgt tgacattgat tattgactag ttattaatag taatcaatta cggggtcatt  2100
agttcatagc ccatatatgg agttccgcgt tacataactt acggtaaatg gcccgcctgg  2160
```

```
ctgaccgccc aacgaccccc gcccattgac gtcaataatg acgtatgttc ccatagtaac    2220
gccaataggg actttccatt gacgtcaatg ggtggagtat ttacggtaaa ctgcccactt    2280
ggcagtacat caagtgtatc atatgccaag tacgccccct attgacgtca atgacggtaa    2340
atggcccgcc tggcattatg cccagtacat gaccttatgg gactttccta cttggcagta    2400
catctacgta ttagtcatcg ctattaccat ggtgatgcgg ttttggcagt acatcaatgg    2460
gcgtggatag cggtttgact cacggggatt tccaagtctc cacccccattg acgtcaatgg    2520 gagtttgttt tggcaccaaa atcaacggga ctttccaaaa tgtcgtaaca actccgcccc    2580
attgacgcaa atgggcggta ggcgtgtacg gtgggaggtc tatataagca gagctctctg    2640
gctaactaga acccactg cttactggct tatcgaaatt aatacgactc actataggga    2700
gacccaagct ggctagcgct gatatcgatc gcgagcggcc gctcgagtct agagggcccg    2760
tttaaacccg ctgatcagcc tcgactgtgc cttctagttg ccagccatct gttgtttgcc    2820
cctcccccgt gccttccttg accctggaag gtgccactcc cactgtcctt tcctaataaa    2880
atgaggaaat tgcatcgcat tgtctgagta ggtgtcattc tattctgggg ggtggggtgg    2940
ggcaggacag caaggggag gattgggaag acaatagcag gcatgctggg gatgcggtgg    3000
gctctatggc ttctgaggcg gaaagaacca gctgggctc taggggtat ccccacgcgc    3060 cctgtagcgg cgcattaagc gcggcgggtg tggtggttac gcgcagcgtg accgctacac    3120
ttgccagcgc cctagcgccc gctccttcg ctttcttccc ttcctttctc gccacgttcg    3180
cctaccgtcg aatcaccggt aaccttataa gggatttttgc cgatttcggc ctattggtta    3240
aaaaatgagc tgatttaaca aaaatttaac gcgaattaat tctgtggaat gtgtgtcagt    3300
tagggtgtgg aaagtcccca ggctccccag caggcagaag tatgcaaagc atgcatctca    3360
attagtcagc aaccaggtgt ggaaagtccc caggctcccc agcaggcaga agtatgcaaa    3420
gcatgcatct caattagtca gcaaccatag tcccgcccct aactccgccc atcccgcccc    3480
taactccgcc cagttccgcc cattctccgc cccatggctg actaattttt tttatttatg    3540
cagaggccga ggccgcctct gcctctgagc tattccagaa gtagtgagga ggcttttttg    3600
gaggcctagg cttttgcaaa aagctcccgg gagcttgtat atccattttc ggatctgatc    3660
aagagacagg atgaggatcg tttcgcatga ttgaacaaga tggattgcac gcaggttctc    3720
cggccgcttg ggtggagagg ctattcggct atgactgggc acaacagaca atcggctgct    3780
ctgatgccgc cgtgttccgg ctgtcagcgc aggggcgccc ggttcttttt gtcaagaccg    3840
acctgtccgg tgccctgaat gaactgcagg acgaggcagc gcggctatcg tggctggcca    3900
cgacgggcgt tccttgcgca gctgtgctcg acgttgtcac tgaagcggga agggactggc    3960
tgctattggg cgaagtgccg gggcaggatc tcctgtcatc tcaccttgct cctgccgaga    4020
aagtatccat catggctgat gcaatgcggc ggctgcatac gcttgatccg gctacctgcc    4080
cattcgacca ccaagcgaaa catcgcatcg agcgagcacg tactcggatg gaagccggtc    4140
ttgtcgatca ggatgatctg gacgaagagc atcaggggct cgcgccagcc gaactgttcg    4200
ccaggctcaa ggcgcg                                                    4216
```

<210> SEQ ID NO 25
<211> LENGTH: 655
<212> TYPE: DNA
<213> ORGANISM: Artificial Sequence
<220> FEATURE:
<223> OTHER INFORMATION: Description of Artificial Sequence: Synthetic hCMV promoter polynucleotide

<400> SEQUENCE: 25

```
cgatgtacgg gccagatata cgcgttgaca ttgattattg actagttatt aatagtaatc    60
aattacgggg tcattagttc atagcccata tatggagttc cgcgttacat aacttacggt   120
aaatggcccg cctggctgac cgcccaacga cccccgccca ttgacgtcaa taatgacgta   180
tgttcccata gtaacgccaa tagggacttt ccattgacgt caatgggtgg agtatttacg   240
gtaaactgcc cacttggcag tacatcaagt gtatcatatg ccaagtacgc ccccattga   300
cgtcaatgac ggtaaatggc ccgcctggca ttatgcccag tacatgacct tatgggactt   360
tcctacttgg cagtacatct acgtattagt catcgctatt accatggtga tgcggttttg   420
gcagtacatc aatgggcgtg atagcggtt tgactcacgg ggatttccaa gtctccaccc   480
cattgacgtc aatgggagtt gttttggca ccaaaatcaa cgggactttc caaaatgtcg   540
taacaactcc gccccattga cgcaaatggg cggtaggcgt gtacggtggg aggtctatat   600
aagcagagct ctctggctaa ctagagaacc cactgcttac tggcttatcg aaatt       655
```

<210> SEQ ID NO 26
<211> LENGTH: 530
<212> TYPE: DNA
<213> ORGANISM: Artificial Sequence
<220> FEATURE:
<223> OTHER INFORMATION: Description of Artificial Sequence: Synthetic
    delta Neomycin gene

<400> SEQUENCE: 26

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg               530
```

<210> SEQ ID NO 27
<211> LENGTH: 215
<212> TYPE: DNA
<213> ORGANISM: Artificial Sequence
<220> FEATURE:
<223> OTHER INFORMATION: Description of Artificial Sequence: Synthetic
    bovine growth hormone polyA polynucleotide

<400> SEQUENCE: 27

```
gcctcgactg tgccttctag ttgccagcca tctgttgttt gcccctcccc cgtgccttcc    60
ttgaccctgg aaggtgccac tcccactgtc ctttcctaat aaaatgagga aattgcatcg   120
cattgtctga gtaggtgtca ttctattctg ggggtgggg tggggcagga cagcaagggg   180
gaggattggg aagacaatag caggcatgct gggga                              215
```

<210> SEQ ID NO 28
<211> LENGTH: 806
<212> TYPE: DNA
<213> ORGANISM: Artificial Sequence
<220> FEATURE:

<223> OTHER INFORMATION: Description of Artificial Sequence: Synthetic
      5' homologous portion in vector

<400> SEQUENCE: 28

| | | |
|---|---|---|
| ttaaggagcc ccttcgcctc gtgcttgagt tgaggcctgg cttgggcgct ggggccgccg | 60 |
| cgtgcgaatc tggtggcacc ttcgcgcctg tctcgctgct ttcgataagt ctctagccat | 120 |
| ttaaaatttt tgatgacctg ctgcgacgct ttttttctgg caagatagtc ttgtaaatgc | 180 |
| gggccaagat cgatctgcac actggtattt cggttttttgg ggccgcgggc ggcgacgggg | 240 |
| cccgtgcgtc ccagcgcaca tgttcggcga ggcggggcct gcgagcgcgg ccaccgagaa | 300 |
| tcggacgggg gtagtctcaa gctggccggc ctgctctggt gcctggcctc cgccgccgt | 360 |
| gtatcgcccc gccctgggcg gcaaggctgg cccggtcggc accagttgcg tgagcggaaa | 420 |
| gatggccgct tcccggccct gctgcaggga gctcaaaatg gaggacgcgg cgctcggag | 480 |
| agcgggcggg tgagtcaccc acacaaagga aagggccttt ccgtcctca gccgtcgctt | 540 |
| catgtgactc cacggagtac cgggcgccgt ccaggcacct cgattagttc tcgagcttt | 600 |
| ggagtacgtc gtctttaggt tgggggagg ggttttatgc gatggagttt ccccacactg | 660 |
| agtgggtgga gactgaagtt aggccagctt ggcacttgat gtaattctcc ttggaatttg | 720 |
| ccctttttga gtttggatct tggttcattc tcaagcctca gacagtggtt caaagttttt | 780 |
| ttcttccatt tcaggtgtcg tggaat | 806 |

<210> SEQ ID NO 29
<211> LENGTH: 801
<212> TYPE: DNA
<213> ORGANISM: Artificial Sequence
<220> FEATURE:
<223> OTHER INFORMATION: Description of Artificial Sequence: Synthetic
      3' homologous portion in vector

<400> SEQUENCE: 29

| | | |
|---|---|---|
| agccccttcg cctcgtgctt gagttgaggc ctggcttggg cgctgggggcc gccgcgtgcg | 60 |
| aatctggtgg caccttcgcg cctgtctcgc tgctttcgat aagtctctag ccatttaaaa | 120 |
| ttttttgatga cctgctgcga cgcttttttt ctggcaagat agtcttgtaa atgcgggcca | 180 |
| agatcgatct gcacactggt atttcggttt ttggggccgc gggcggcgac ggggcccgtg | 240 |
| cgtcccagcg cacatgttcg gcgaggcggg gcctgcgagc gcggccaccg agaatcggac | 300 |
| gggggtagtc tcaagctggc cggcctgctc tggtgcctgg cctcgcgccg ccgtgtatcg | 360 |
| ccccgccctg gcggcaagg ctggcccggt cggcaccagt tgcgtgagcg gaaagatggc | 420 |
| cgcttcccgg ccctgctgca gggagctcaa aatggaggac gcggcgctcg ggagagcggg | 480 |
| cgggtgagtc acccacacaa aggaaaaggg cctttccgtc ctcagccgtc gcttcatgtg | 540 |
| actccacgga gtaccgggcg ccgtccaggc acctcgatta gttctcgagc ttttggagta | 600 |
| cgtcgtcttt aggttggggg gaggggttt atgcgatgga gtttccccac actgagtggg | 660 |
| tggagactga agttaggcca gcttggcact tgatgtaatt ctccttggaa tttgcccttt | 720 |
| ttgagtttgg atcttggttc attctcaagc tcagacagt ggttcaaagt ttttttcttc | 780 |
| catttcaggt gtcgtggaat t | 801 |

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic

```
                              F1_Prom oligonucleotide

<400> SEQUENCE: 30
ccccgaccgg agctgagagt aatt                                              24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      B1_Pur oligonucleotide

<400> SEQUENCE: 31
caggaggcct tccatctgtt g                                                 21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      CLS_P4_Fwd2 oligonucleotide

<400> SEQUENCE: 32
ctgtggaatg tgtgtcagt                                                    19

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      CLS_P4_Rev1 oligonucleotide

<400> SEQUENCE: 33
caacgctatg tcctgatagc ggtc                                              24

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      Capped polyA oligonucleotide

<400> SEQUENCE: 34
aaaaaaaaaa aaaaaaaaaa aaaaaaaaaa                                        30

<210> SEQ ID NO 35
<211> LENGTH: 642
<212> TYPE: DNA
<213> ORGANISM: Artificial Sequence
<220> FEATURE:
<223> OTHER INFORMATION: Description of Artificial Sequence: Synthetic
      Capped polyA meganuclease polynucleotide

<400> SEQUENCE: 35
aaaaaaaaaa aaaaaaaaaa aaaaaaaaaa tggctaatac taaatataat aaagaatttc       60
ttctttatct tgctggtttt gttgatggtg atggttctat tattgctcaa attaaaccta      120
atcaatctta taatttaaa catcaacttt ctcttacttt tcaagttact caaaaaactc       180
aacgtcgttg gtttcttgat aaacttgttg atgaaattgg tgttggttat gttcgtgatc      240
gtggttctgt ttctaattat attctttctg aaattaaacc tcttcataat tttcttactc      300
```

-continued

```
aacttcaacc tttcttaaa cttaaacaaa acaagctaa tcttgttctt aaaattattg    360
aacaacttcc ttctgctaaa gaatctcctg ataaatttct tgaagtttgt acttgggttg   420
atcaaattgc tgctcttaat gattctaaaa ctcgtaaaac tacttctgaa actgttcgtg   480
ctgttcttga ttctctttct gaaaaaaaaa aatcttctcc tgctgctgat aaaaaaaaaa   540
aaaaaaaaaa aaaaaaaaaa aaaaaaaaaa aaaaaaaaaa aaaaaaaaaa aaaaaaaaaa   600
aaaaaaaaaa aaaaaaaaaa aaaaaaaaaa aaaaaaaaaa aa                     642
```

<210> SEQ ID NO 36
<211> LENGTH: 163
<212> TYPE: PRT
<213> ORGANISM: Chlamydomonas reinhardtii

<400> SEQUENCE: 36

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro
```

<210> SEQ ID NO 37
<211> LENGTH: 194
<212> TYPE: PRT
<213> ORGANISM: Desulfurococcus mobilis

<400> SEQUENCE: 37

```
Met His Asn Asn Glu Asn Val Ser Gly Ile Ser Ala Tyr Leu Leu Gly
1               5                   10                  15

Leu Ile Ile Gly Asp Gly Gly Leu Tyr Lys Leu Lys Tyr Lys Gly Asn
            20                  25                  30

Arg Ser Glu Tyr Arg Val Val Ile Thr Gln Lys Ser Glu Asn Leu Ile
        35                  40                  45

Lys Gln His Ile Ala Pro Leu Met Gln Phe Leu Ile Asp Glu Leu Asn
    50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Tyr Phe Ala Asn Met Leu Glu
                85                  90                  95

Arg Ile Arg Leu Phe Asn Met Arg Glu Gln Ile Ala Phe Ile Lys Gly
```

```
                 100                 105                 110
Leu Tyr Val Ala Glu Gly Asp Lys Thr Leu Lys Arg Leu Arg Ile Trp
            115                 120                 125

Asn Lys Asn Lys Ala Leu Leu Glu Ile Val Ser Arg Trp Leu Asn Asn
        130                 135                 140

Leu Gly Val Arg Asn Thr Ile His Leu Asp Asp His Arg His Gly Val
145                 150                 155                 160

Tyr Val Leu Asn Ile Ser Leu Arg Asp Arg Ile Lys Phe Val His Thr
                165                 170                 175

Ile Leu Ser Ser His Leu Asn Pro Leu Pro Pro Glu Arg Ala Gly Gly
                180                 185                 190

Tyr Thr

<210> SEQ ID NO 38
<211> LENGTH: 5647
<212> TYPE: DNA
<213> ORGANISM: Artificial Sequence
<220> FEATURE:
<223> OTHER INFORMATION: Description of Artificial Sequence: Synthetic
      pCLS1088 polynucleotide

<400> SEQUENCE: 38
cttgtacaaa gtggttgatc tagagggccc gcggttcgaa ggtaagccta tccctaaccc      60
tctcctcggt ctcgattcta cgcgtaccgg ttagtaatga gtttaaacgg gggaggctaa     120
ctgaaacacg gaaggagaca ataccggaag gaacccgcgc tatgacggca ataaaaagac     180
agaataaaac gcacgggtgt tgggtcgttt gttcataaac gcggggttcg gtcccagggc     240
tggcactctg tcgataccc accgagaccc cattggggcc aatacgcccg cgtttcttcc     300
ttttccccac cccacccccc aagttcgggt gaaggcccag ggctcgcagc caacgtcggg     360
gcggcaggcc ctgccatagc agatctgcgc agctgggct ctaggggta tccccacgcg     420 ccctgtagcg gcgcattaag cgcggcgggt gtggtggtta cgcgcagcgt gaccgctaca     480
cttgccagcg ccctagcgcc cgctcctttc gctttcttcc cttcctttct cgccacgttc     540
gccggctttc cccgtcaagc tctaaatcgg ggcatccctt tagggttccg atttagtgct     600
ttacggcacc tcgaccccaa aaaacttgat tagggtgatg gttcacgtag tgggccatcg     660
ccctgataga cggttttttcg ccctttgacg ttggagtcca cgttctttaa tagtggactc     720
ttgttccaaa ctggaacaac actcaaccct atctcggtct attcttttga tttataaggg     780
attttgggga tttcggccta ttggttaaaa aatgagctga tttaacaaaa atttaacgcg     840
aattaattct gtggaatgtg tgtcagttag ggtgtggaaa gtccccaggc tccccagcag     900
gcagaagtat gcaaagcatg catctcaatt agtcagcaac caggtgtgga agtcccccag     960
gctccccagc aggcagaagt atgcaaagca tgcatctcaa ttagtcagca accatagtcc    1020
cgcccctaac tccgcccatc ccgccctaa ctccgcccag ttccgcccat tctccgcccc    1080
atggctgact aatttttttt atttatgcag aggccgaggc cgcctctgcc tctgagctat    1140
tccagaagta gtgaggaggc ttttttggag gcctaggctt ttgcaaaaag ctcccgggag    1200
cttgtatatc cattttcgga tctgatcagc acgtgttgac aattaatcat cggcatagta    1260
tatcggcata gtataatacg acaaggtgag gaactaaacc atggccaagc ctttgtctca    1320
agaagaatcc accctcattg aaagagcaac ggctacaatc aacagcatcc ccatctctga    1380
agactacagc gtcgccagcg cagctctctc tagcgacggc cgcatcttca ctggtgtcaa    1440
tgtatatcat tttactgggg gaccttgtgc agaactcgtg gtgctgggca ctgctgctgc    1500
```

```
tgcggcagct ggcaacctga cttgtatcgt cgcgatcgga aatgagaaca ggggcatctt    1560
gagcccctgc ggacggtgcc gacaggtgct tctcgatctg catcctggga tcaaagccat    1620
agtgaaggac agtgatggac agccgacggc agttgggatt cgtgaattgc tgccctctgg    1680
ttatgtgtgg gagggctaag cacttcgtgg ccgaggagca ggactgacac gtgctacgag    1740
atttcgattc caccgccgcc ttctatgaaa ggttgggctt cggaatcgtt ttccgggacg    1800
ccggctggat gatcctccag cgcgggatc tcatgctgga gttcttcgcc cacccccaact   1860 tgtttattgc agcttataat ggttacaaat aaagcaatag catcacaaat ttcacaaata    1920
aagcattttt ttcactgcat tctagttgtg gtttgtccaa actcatcaat gtatcttatc    1980
atgtctgtat accgtcgacc tctagctaga gcttggcgta atcatggtca tagctgtttc    2040
ctgtgtgaaa ttgttatccg ctcacaattc cacacaacat acgagccgga agcataaagt    2100
gtaaagcctg gggtgcctaa tgagtgagct aactcacatt aattgcgttg cgctcactgc    2160
ccgctttcca gtcgggaaac ctgtcgtgcc agctgcatta atgaatcggc caacgcgcgg    2220
ggagaggcgg tttgcgtatt gggcgctctt ccgcttcctc gctcactgac tcgctgcgct    2280
cggtcgttcg gctgcggcga gcggtatcag ctcactcaaa ggcggtaata cggttatcca    2340
cagaatcagg ggataacgca ggaaagaaca tgtgagcaaa aggccagcaa aaggccagga    2400
accgtaaaaa ggccgcgttg ctggcgtttt tccataggct ccgcccccct gacgagcatc    2460
acaaaaatcg acgctcaagt cagaggtggc gaaacccgac aggactataa agataccagg    2520
cgtttccccc tggaagctcc ctcgtgcgct ctcctgttcc gaccctgccg cttaccggat    2580
acctgtccgc ctttctccct tcgggaagcg tggcgctttc tcatagctca cgctgtaggt    2640
atctcagttc ggtgtaggtc gttcgctcca agctgggctg tgtgcacgaa ccccccgttc    2700
agcccgaccg ctgcgcctta tccggtaact atcgtcttga gtccaacccg gtaagacacg    2760
acttatcgcc actggcagca gccactggta acaggattag cagagcgagg tatgtaggcg    2820
gtgctacaga gttcttgaag tggtggccta actacggcta cactagaaga acagtatttg    2880
gtatctgcgc tctgctgaag ccagttacct tcggaaaaag agttggtagc tcttgatccg    2940
gcaaacaaac caccgctggt agcggttttt ttgtttgcaa gcagcagatt acgcgcagaa    3000
aaaaaggatc tcaagaagat cctttgatct tttctacggg gtctgacgct cagtggaacg    3060
aaaactcacg ttaagggatt ttggtcatga gattatcaaa aaggatcttc acctagatcc    3120
ttttaaatta aaaatgaagt tttaaatcaa tctaaagtat atatgagtaa acttggtctg    3180
acagttacca atgcttaatc agtgaggcac ctatctcagc gatctgtcta tttcgttcat    3240
ccatagttgc ctgactcccc gtcgtgtaga taactacgat acgggagggc ttaccatctg    3300
gccccagtgc tgcaatgata ccgcgagacc cacgctcacc ggctccagat ttatcagcaa    3360
taaaccagcc agccggaagg gccgagcgca gaagtggtcc tgcaacttta tccgcctcca    3420
tccagtctat taattgttgc cgggaagcta gagtaagtag ttcgccagtt aatagtttgc    3480
gcaacgttgt tgccattgct acaggcatcg tggtgtcacg ctcgtcgttt ggtatggctt    3540
cattcagctc cggttcccaa cgatcaaggc gagttacatg atcccccatg ttgtgcaaaa    3600
aagcggttag ctccttcggt cctccgatcg ttgtcagaag taagttggcc gcagtgttat    3660
cactcatggt tatggcagca ctgcataatt ctcttactgt catgccatcc gtaagatgct    3720
tttctgtgac tggtgagtac tcaaccaagt cattctgaga atagtgtatg cggcgaccga    3780
gttgctcttg cccggcgtca atacgggata ataccgcgcc acatagcaga actttaaaag    3840
```

```
tgctcatcat tggaaaacgt tcttcggggc gaaaactctc aaggatctta ccgctgttga    3900
gatccagttc gatgtaaccc actcgtgcac ccaactgatc ttcagcatct tttactttca    3960
ccagcgtttc tgggtgagca aaaacaggaa ggcaaaatgc cgcaaaaaag ggaataaggg    4020
cgacacggaa atgttgaata ctcatactct cctttttca atattattga agcatttatc     4080
agggttattg tctcatgagc ggatacatat ttgaatgtat ttagaaaaat aaacaaatag    4140
gggttccgcg cacatttccc cgaaaagtgc cacctgacgt cgacggatcg ggagatctcc    4200 cgatcccta tggtgcactc tcagtacaat ctgctctgat gccgcatagt taagccagta    4260
tctgctccct gcttgtgtgt tggaggtcgc tgagtagtgc gcgagcaaaa tttaagctac    4320
aacaaggcaa ggcttgaccg acaattgcat gaagaatctg cttagggtta ggcgttttgc    4380
gctgcttcgc gatgtacggg ccagatatac gcgttgacat tgattattga ctagttatta    4440
atagtaatca attacggggt cattagttca tagcccatat atggagttcc gcgttacata    4500
acttacggta aatggcccgc ctggctgacc gcccaacgac ccccgcccat tgacgtcaat    4560
aatgacgtat gttcccatag taacgccaat agggactttc cattgacgtc aatgggtgga    4620
gtatttacgg taaactgccc acttggcagt acatcaagtg tatcatatgc caagtacgcc    4680
ccctattgac gtcaatgacg gtaaatggcc cgcctggcat tatgcccagt acatgacctt    4740
atgggacttt cctacttggc agtacatcta cgtattagtc atcgctatta ccatggtgat    4800
gcggttttgg cagtacatca atgggcgtgg atagcggttt gactcacggg gatttccaag    4860
tctccacccc attgacgtca atgggagttt gttttggcac caaaatcaac gggactttcc    4920
aaaatgtcgt aacaactccg ccccattgac gcaaatgggc ggtaggcgtg tacggtggga    4980
ggtctatata agcagagctc tctggctaac tagagaaccc actgcttact ggcttatcga    5040
aattaatacg actcactata gggagaccca agctggctag ttaagctatc aacaagtttg    5100
tacaaaaaag caggcttcga aggagataga accatggcca ataccaaata taacaaagag    5160
ttcctgctgt acctggccgg ctttgtggac ggtgacggta gcatcatcgc tcagattaaa    5220
ccaaaccagt cttataagtt aaacatcag ctaagcttga cctttcaggt gactcaaaag    5280
acccagcgcc gttggtttct ggacaaacta gtggatgaaa ttggcgttgg ttacgtacgt    5340
gatcgcggat ccgtttccaa ctacatctta agcgaaatca agccgctgca caacttcctg    5400
actcaactgc agccgtttct gaaactgaaa cagaaacagg caaacctggt tctgaaaatt    5460
atcgaacagc tgccgtctgc aaaagaatcc ccggacaaat tcctggaagt tgtacctgg    5520 gtggatcaga ttgcagctct gaacgattct aagacgcgta aaaccacttc tgaaaccgtt    5580
cgtgctgtgc tggacagcct gagcgagaag aagaaatcct ccccggcggc cgactaaacc    5640
cagcttt                                                             5647
```

<210> SEQ ID NO 39
<211> LENGTH: 5647
<212> TYPE: DNA
<213> ORGANISM: Artificial Sequence
<220> FEATURE:
<223> OTHER INFORMATION: Description of Artificial Sequence: Synthetic
      pCLS2147 polynucleotide

<400> SEQUENCE: 39

```
cttgtacaaa gtggttgatc tagagggccc gcggttcgaa ggtaagccta tccctaaccc      60
tctcctcggt ctcgattcta cgcgtaccgg ttagtaatga gtttaaacgg gggaggctaa     120
ctgaaacacg gaaggagaca ataccggaag gaacccgcgc tatgacggca ataaaaagac     180
```

```
agaataaaac gcacgggtgt tgggtcgttt gttcataaac gcggggttcg gtcccagggc    240
tggcactctg tcgataccc accgagaccc cattggggcc aatacgcccg cgtttcttcc     300
ttttccccac cccaccccc aagttcgggt gaaggcccag ggctcgcagc caacgtcggg     360
gcggcaggcc ctgccatagc agatctgcgc agctggggct ctaggggta tccccacgcg     420 ccctgtagcg gcgcattaag cgcggcgggt gtggtggtta cgcgcagcgt gaccgctaca    480
cttgccagcg ccctagcgcc cgctcctttc gctttcttcc cttcctttct cgccacgttc    540
gccggctttc cccgtcaagc tctaaatcgg ggcatcccctt tagggttccg atttagtgct   600
ttacggcacc tcgaccccaa aaaacttgat tagggtgatg gttcacgtag tgggccatcg    660
ccctgataga cggttttttcg cccttttgacg ttggagtcca cgttctttaa tagtggactc  720
ttgttccaaa ctggaacaac actcaaccct atctcggtct attctttga tttataaggg     780 attttgggga tttcggccta ttggttaaaa aatgagctga tttaacaaaa atttaacgcg    840
aattaattct gtggaatgtg tgtcagttag ggtgtggaaa gtcccaggc tccccagcag     900 gcagaagtat gcaaagcatg catctcaatt agtcagcaac caggtgtgga aagtccccag    960 gctcccagc aggcagaagt atgcaaagca tgcatctcaa ttagtcagca accatagtcc    1020
cgcccctaac tccgcccatc ccgccccctaa ctccgcccag ttccgcccat tctccgcccc   1080
atggctgact aatttttttt atttatgcag aggccgaggc cgcctctgcc tctgagctat    1140
tccagaagta gtgaggaggc ttttttggag gcctaggctt ttgcaaaaag ctcccgggag   1200
cttgtatatc cattttcgga tctgatcagc acgtgttgac aattaatcat cggcatagta    1260
tatcggcata gtataatacg acaaggtgag gaactaaacc atggccaagc ctttgtctca    1320
agaagaatcc accctcattg aaagagcaac ggctacaatc aacagcatcc ccatctctga    1380
agactacagc gtcgccagcg cagctctctc tagcgacggc cgcatcttca ctggtgtcaa    1440
tgtatatcat tttactgggg gaccttgtgc agaactcgtg gtgctgggca ctgctgctgc    1500
tgcggcagct ggcaacctga cttgtatcgt cgcgatcgga aatgagaaca ggggcatctt   1560 gagccccctgc ggacggtgcc gacaggtgct tctcgatctg catcctggga tcaaagccat  1620
agtgaaggac agtgatggac agccgacggc agttgggatt cgtgaattgc tgccctctgg   1680
ttatgtgtgg gagggctaag cacttcgtgg ccgaggagca ggactgacac gtgctacgag   1740
atttcgattc caccgccgcc ttctatgaaa ggttgggctt cggaatcgtt ttccgggacg    1800
ccggctggat gatcctccag cgcggggatc tcatgctgga gttcttcgcc caccccaact    1860
tgtttattgc agcttataat ggttacaaat aaagcaatag catcacaaat ttcacaaata    1920
aagcattttt ttcactgcat tctagttgtg gtttgtccaa actcatcaat gtatcttatc    1980
atgtctgtat accgtcgacc tctagctaga gcttggcgta atcatggtca tagctgtttc    2040
ctgtgtgaaa ttgttatccg ctcacaattc cacacaacat acgagccgga agcataaagt    2100
gtaaagcctg gggtgcctaa tgagtgagct aactcacatt aattgcgttg cgctcactgc    2160
ccgctttcca gtcgggaaac ctgtcgtgcc agctgcatta atgaatcggc caacgcgcgg    2220
ggagaggcgg tttgcgtatt gggcgctctt ccgcttcctc gctcactgac tcgctgcgct    2280
cggtcgttcg gctgcggcga gcggtatcag ctcactcaaa ggcggtaata cggttatcca    2340
cagaatcagg ggataacgca ggaaagaaca tgtgagcaaa aggccagcaa aaggccagga    2400
accgtaaaaa ggccgcgttg ctggcgtttt tccataggct ccgcccccct gacgagcatc    2460
acaaaaatcg acgctcaagt cagaggtggc gaaacccgac aggactataa agataccagg    2520
cgtttccccc tggaagctcc ctcgtgcgct ctcctgttcc gaccctgccg cttaccggat    2580
```

```
acctgtccgc ctttctccct tcgggaagcg tggcgctttc tcatagctca cgctgtaggt   2640
atctcagttc ggtgtaggtc gttcgctcca agctgggctg tgtgcacgaa ccccccgttc   2700
agcccgaccg ctgcgcctta tccggtaact atcgtcttga gtccaacccg gtaagacacg   2760
acttatcgcc actggcagca gccactggta acaggattag cagagcgagg tatgtaggcg   2820
gtgctacaga gttcttgaag tggtggccta actacggcta cactagaaga acagtatttg   2880
gtatctgcgc tctgctgaag ccagttacct tcggaaaaag agttggtagc tcttgatccg   2940
gcaaacaaac caccgctggt agcggttttt ttgtttgcaa gcagcagatt acgcgcagaa   3000
aaaaaggatc tcaagaagat cctttgatct tttctacggg gtctgacgct cagtggaacg   3060
aaaactcacg ttaagggatt ttggtcatga gattatcaaa aaggatcttc acctagatcc   3120
ttttaaatta aaaatgaagt tttaaatcaa tctaaagtat atatgagtaa acttggtctg   3180
acagttacca atgcttaatc agtgaggcac ctatctcagc gatctgtcta tttcgttcat   3240
ccatagttgc ctgactcccc gtcgtgtaga taactacgat acgggagggc ttaccatctg   3300
gccccagtgc tgcaatgata ccgcgagacc cacgctcacc ggctccagat ttatcagcaa   3360
taaaccagcc agccggaagg gccgagcgca gaagtggtcc tgcaacttta tccgcctcca   3420
tccagtctat taattgttgc cgggaagcta gagtaagtag ttcgccagtt aatagtttgc   3480
gcaacgttgt tgccattgct acaggcatcg tggtgtcacg ctcgtcgttt ggtatggctt   3540
cattcagctc cggttcccaa cgatcaaggc gagttacatg atccccccatg ttgtgcaaaa   3600
aagcggttag ctccttcggt cctccgatcg ttgtcagaag taagttggcc gcagtgttat   3660
cactcatggt tatggcagca ctgcataatt ctcttactgt catgccatcc gtaagatgct   3720
tttctgtgac tggtgagtac tcaaccaagt cattctgaga atagtgtatg cggcgaccga   3780
gttgctcttg cccggcgtca atacgggata ataccgcgcc acatagcaga actttaaaag   3840
tgctcatcat tggaaaacgt tcttcggggc gaaaactctc aaggatctta ccgctgttga   3900
gatccagttc gatgtaaccc actcgtgcac ccaactgatc ttcagcatct tttactttca   3960
ccagcgtttc tgggtgagca aaaacaggaa ggcaaaatgc cgcaaaaaag gaataagggc   4020
gacacggaaa tgttgaataa ctcatactct tccttttttca atattattga gcatttatc   4080
agggttattg tctcatgagc ggatacatat ttgaatgtat ttagaaaaat aaacaaatag   4140
gggttccgcg cacatttccc cgaaaagtgc cacctgacgt cgacgatcg ggagatctcc   4200
cgatccccta tggtgcactc tcagtacaat ctgctctgat gccgcatagt taagccagta   4260
tctgctccct gcttgtgtgt tggaggtcgc tgagtagtgc gcgagcaaaa tttaagctac   4320
aacaaggcaa ggcttgaccg acaattgcat gaagaatctg cttagggtta ggcgttttgc   4380
gctgcttcgc gatgtacggg ccagatatac gcgttgacat tgattattga ctagttatta   4440
atagtaatca attacggggt cattagttca tagcccatat atggagttcc gcgttacata   4500
acttacggta aatggcccgc ctggctgacc gcccaacgac ccccgcccat tgacgtcaat   4560
aatgacgtat gttcccatag taacgccaat agggactttc cattgacgtc aatgggtgga   4620
gtatttacgg taaactgccc acttggcagt acatcaagtg tatcatatgc caagtacgcc   4680
ccctattgac gtcaatgacg gtaaatggcc cgcctggcat tatgcccagt acatgacctt   4740
atgggacttt cctacttggc agtacatcta cgtattagtc atcgctatta ccatggtgat   4800
gcggttttgg cagtacatca atgggcgtgg atagcggttt gactcacggg gatttccaag   4860
tctccacccc attgacgtca atgggagttt gttttggcac caaaatcaac gggactttcc   4920
```

| | |
|---|---|
| aaaatgtcgt aacaactccg ccccattgac gcaaatgggc ggtaggcgtg tacggtggga | 4980 |
| ggtctatata agcagagctc tctggctaac tagagaaccc actgcttact ggcttatcga | 5040 |
| aattaatacg actcactata gggagaccca agctggctag ttaagctatc aacaagtttg | 5100 |
| tacaaaaaag caggcttcga aggagataga accatggcca ataccaaata taacaaagag | 5160 |
| ttcctgctgt acctggccgg cttttgtggac ggtgacggta gcatcatcgc tcagattaaa | 5220 |
| ccaaaccagt cttataagtt taaacatcag ctaagcttga cctttcaggt gactcaaaag | 5280 |
| acccagcgcc gttggtttct ggacaaacta gtggatgaaa ttggcgttgg ttacgtacgt | 5340 |
| gatcgcggat ccgtttccaa ctacatctta agcgaaatca agccgctgca aacttcctg | 5400 |
| actcaactgc agccgtttct gaaactgaaa cagaaacagg caaacctggc tctgaaaatt | 5460 |
| atcgaacagc tgccgtctgc aaaagaatcc ccggacaaat tcctggaagt ttgtacctgg | 5520 |
| gtggatcagg ttgcagctct gaacgattct aagacgcgta aaaccacttc tgaaaccgtt | 5580 |
| cgtgctgtgc tggacagcct gagcgagaag aagaaatcct ccccggcggc cgactaaacc | 5640 |
| cagcttt | 5647 |

<210> SEQ ID NO 40
<211> LENGTH: 1428
<212> TYPE: DNA
<213> ORGANISM: Homo sapiens

<400> SEQUENCE: 40

| | |
|---|---|
| atggcgtact accatcacca tcaccatcac tctagatcag aaggagttcg aaccaaccgg | 60 |
| ggagtcccctt ttaggcactt gcttctggtg ctgcaactgg cgctcctccc agcagccact | 120 |
| cagggaaaga agtggtgct gggcaaaaaa ggggatacag tggaactgac ctgtacagct | 180 |
| tcccagaaga gagcatcaa attccactgg aaaaactcca accagataaa gattctggga | 240 |
| aatcagggct ccttcttaac taaaggtcca tccaagctga atgatcgcgc tgactcaaga | 300 |
| agaagccttt gggaccaagg aaacttcccc ctgatcatca agaatcttaa gatagaagac | 360 |
| tcagatactt acatctgtga agtggaggac cagaaggagg aggtgcaatt gctagtgttc | 420 |
| ggattgactg ccaactctga caccacctg cttcaggggc agagcctgac cctgacctg | 480 |
| gagagccccc ctggtagtag cccctcagtg caatgtagga gtccaagggg taaaaacata | 540 |
| caggggggga agaccctctc cgtgtctcag ctggagctcc aggatagtgg cacctggaca | 600 |
| tgcactgtct tgcagaacca gaagaaggtg gagttcaaaa tagacatcgt ggtgctagct | 660 |
| ttccagaagg cctccagcat agtctataag aaagaggggg aacaggtgga gttctccttc | 720 |
| ccactcgcct ttacagttga aaagctgacg ggcagtggcg agctgtggtg gcaggcggag | 780 |
| agggcttcct cctccaagtc ttggatcacc tttgacctga aaaacaagga agtgtctgta | 840 |
| aaacgggtta cccaggaccc taagctccag atgggcaaga agctcccgct ccacctcacc | 900 |
| ctgccccagg ccttgcctca gtatgctggc tctggaaacc tcaccctggc ccttgaagcg | 960 |
| aaaacaggaa agttgcatca ggaagtgaac ctggtggtga tgagagccac tcagctccag | 1020 |
| aaaaatttga cctgtgaggt gtggggaccc acctcccccta agctgatgct gagcttgaaa | 1080 |
| ctggagaaca aggaggcaaa ggtctcgaag cgggagaagg cggtgtgggt gctgaaccct | 1140 |
| gaggcgggga tgtggcagtg tctgctgagt gactcgggac aggtcctgct ggaatccaac | 1200 |
| atcaaggttc tgcccacatg gtccacccg gtgcagccaa tggccctgat tgtgctgggg | 1260 |
| ggcgtcgccg gcctcctgct tttcattggg ctaggcatct tcttctgtgt caggtgccgg | 1320 |
| caccgaaggc gccaagcaga gcggatgtct cagatcaaga gactcctcag tgagaagaag | 1380 | acctgccagt gccctcaccg gtttcagaag acatgtagcc ccatttag        1428

<210> SEQ ID NO 41
<211> LENGTH: 8211
<212> TYPE: DNA
<213> ORGANISM: Artificial Sequence
<220> FEATURE:
<223> OTHER INFORMATION: Description of Artificial Sequence: Synthetic
      pTV-DS-CD4 polynucleotide

<400> SEQUENCE: 41

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt ttaaggagcc ccttcgcctc   420
gtgcttgagt tgaggcctgg cttgggcgct ggggccgccg cgtgcgaatc tggtggcacc   480
ttcgcgcctg tctcgctgct ttcgataagt ctctagccat ttaaaatttt tgatgacctg   540
ctgcgacgct ttttttctgg caagatagtc ttgtaaatgc gggccaagat cgatctgcac   600
actggtattt cggttttttgg ggccgcgggc ggcgacgggg cccgtgcgtc ccagcgcaca   660
tgttcggcga ggcggggcct gcgagcgcgg ccaccgagaa tcggacgggg gtagtctcaa   720
gctggccggc ctgctctggt gcctggcctc gcgccgccgt gtatcgcccc gccctgggcg   780
gcaaggctgg cccggtcggc accagttgcg tgagcggaaa gatggccgct tcccggccct   840
gctgcaggga gctcaaaatg gaggacgcgg cgctcgggag agcgggcggg tgagtcaccc   900
acacaaagga aaagggcctt tccgtcctca gccgtcgctt catgtgactc cacgagtac    960
cgggcgccgt ccaggcacct cgattagttc tcgagctttt ggagtacgtc gtctttaggt  1020
tgggggggagg ggttttatgc gatggagttt ccccacactg agtgggtgga gactgaagtt  1080
aggccagctt ggcacttgat gtaattctcc ttggaatttg ccctttttga gtttggatct  1140
tggttcattc tcaagcctca gacagtggtt caaagttttt tcttccatt tcaggtgtcg   1200
tggaattggc tagagcttgc atgcctgcag gtcggccgcc acgaccggtg ccgccaccat  1260
cccctgaccc acgcccctga cccctcacaa ggagacgacc ttccatgacc gagtacaagc  1320
ccacggtgcg cctcgccacc cgcgacgacg tccccgggc cgtacgcacc ctcgccgccg  1380
cgttcgccga ctaccccgcc acgcgccaca ccgtcgaccc ggaccgccac atcgagcggg  1440
tcaccgagct gcaagaactc ttcctcacgc gcgtcgggct cgacatcggc aaggtgtggg  1500
tcgcggacga cggcgccgcg gtggcggtct ggaccacgcc ggagagcgtc gaagcggggg  1560
cggtgttcgc cgagatcggc ccgcgcatgg ccgagttgag cggttcccgg ctggccgcgc  1620
agcaacagat ggaaggcctc ctggcgccgc accggcccaa ggagcccgcg tggttcctgg  1680
ccaccgtcgg cgtctcgccc gaccaccagg gcaaggtct gggcagcgcc gtcgtgctcc  1740
ccggagtgga ggcggccgag cgcgccgggg tgcccgcctt cctggagacc tccgcgcccc  1800
gcaacctccc cttctacgag cggctcggct tcaccgtcac cgccgacgtc gaggtgcccg  1860
aaggaccgcg cacctggtgc atgacccgca agcccgtgc ctgacgcccg ccccacgacc  1920
cgcagcgccc gaccgaaagg agcgcacgac cccatggctc cgaccgaagc cgacccgggc  1980
```

```
ggccccgccg accccgcacc cgcccccgag gcccaccgac tctagaggat cataatcagc    2040
cataccacat ttgtagaggt tttacttgct ttaaaaaacc tcccacacct cccccctgaac   2100 ctgaaacata aaatgaatgc aattgttgtt gttaacttgt ttattgcagc ttataatggt    2160
tacaaataaa gcaatagcat cacaaatttc acaaataaag cattttttc actgcattct     2220 agttgtggtt tgtccaaact catcaatgta tcttatcatg tctggatcct agcgtttaaa    2280
cttaagcttg gtaccgagct cggatccact agcgatgtac gggccagata tacgcgttga    2340
cattgattat tgactagtta ttaatagtaa tcaattacgg ggtcattagt tcatagccca    2400
tatatggagt tccgcgttac ataacttacg gtaaatggcc cgcctggctg accgcccaac    2460
gacccccgcc cattgacgtc aataatgacg tatgttccca tagtaacgcc aatagggact    2520
ttccattgac gtcaatgggt ggagtattta cggtaaactg cccacttggc agtacatcaa    2580
gtgtatcata tgccaagtac gccccctatt gacgtcaatg acggtaaatg gcccgcctgg    2640
cattatgccc agtacatgac cttatgggac tttcctactt ggcagtacat ctacgtatta    2700
gtcatcgcta ttaccatggt gatgcggttt tggcagtaca tcaatgggcg tggatagcgg    2760
tttgactcac ggggatttcc aagtctccac cccattgacg tcaatgggag tttgttttgg    2820
caccaaaatc aacgggactt tccaaaatgt cgtaacaact ccgccccatt gacgcaaatg    2880
ggcggtaggc gtgtacggtg ggaggtctat ataagcagag ctctctggct aactagagaa    2940
cccactgctt actggcttat cgaaattaat acgactcact atagggagac ccaagctggc    3000
tagcgctgat atggcgtact accatcacca tcaccatcac tctagatcag aaggagttcg    3060
aaccaaccgg ggagtccctt ttaggcactt gcttctggtg ctgcaactgg cgctcctccc    3120
agcagccact cagggaaaga aagtggtgct gggcaaaaaa ggggatacag tggaactgac    3180
ctgtacagct tcccagaaga agagcataca attccactgg aaaaactcca accagataaa    3240
gattctggga aatcagggct ccttcttaac taaaggtcca tccaagctga atgatcgcgc    3300
tgactcaaga agaagccttt gggaccaagg aaacttcccc ctgatcatca agaatcttaa    3360
gatagaagac tcagatactt acatctgtga agtggaggac cagaaggagg aggtgcaatt    3420
gctagtgttc ggattgactg ccaactctga cacccacctg cttcagggc agagcctgac     3480 cctgaccttg gagagccccc ctggtagtag ccctcagtg caatgtagga gtccaagggg     3540
taaaaacata caggggggga agaccctctc cgtgtctcag ctggagctcc aggatagtgg    3600
cacctggaca tgcactgtct tgcagaacca gaagaaggtg gagttcaaaa tagacatcgt    3660
ggtgctagct ttccagaagg cctccagcat agtctataag aaagaggggg aacaggtgga    3720
gttctccttc ccactcgcct ttacagttga aaagctgacg ggcagtggcg agctgtggtg    3780
gcaggcggag agggcttcct cctccaagtc ttggatcacc tttgacctga aacaagga     3840 agtgtctgta aacggggtta cccaggaccc taagctccag atgggcaaga agctcccgct    3900
ccacctcacc ctgcccgcagg ccttgcctca gtatgctggc tctggaaacc tcaccctggc   3960
ccttgaagcg aaaacaggaa agttgcatca ggaagtgaac ctggtggtga tgagagccac    4020
tcagctccag aaaaatttga cctgtgaggt gtggggaccc acctccccta agctgatgct    4080
gagcttgaaa ctggagaaca aggaggcaaa ggtctcgaag cgggagaagg cggtgtgggt    4140
gctgaaccct gaggcgggga tgtggcagtg tctgctgagt gactcgggac aggtcctgct    4200
ggaatccaac atcaaggttc tgcccacatg gtccaccccg gtgcagccaa tggccctgat    4260
tgtgctgggg ggcgtcgccg gcctcctgct tttcattggg ctaggcatct tcttctgtgt    4320
```

```
caggtgccgg caccgaaggc gccaagcaga gcggatgtct cagatcaaga gactcctcag    4380
tgagaagaag acctgccagt gccctcaccg gtttcagaag acatgtagat cgatcgcgag    4440
cggccgctcg agtctagagg gcccgtttaa acccgctgat cagcctcgac tgtgccttct    4500
agttgccagc catctgttgt ttgcccctcc cccgtgcctt ccttgaccct ggaaggtgcc    4560
actcccactg tcctttccta ataaaatgag gaaattgcat cgcattgtct gagtaggtgt    4620
cattctattc tggggggtgg ggtggggcag gacagcaagg gggaggattg gaagacaat    4680
agcaggcatg ctggggatgc ggtgggctct atggcttctg aggcggaaag aaccagctgg    4740
ggctctaggg ggtatcccca cgcgccctgt agcggcgcat taagcgcggc gggtgtggtg    4800
gttacgcgca gcgtgaccgc tacacttgcc agcgccctag cgcccgctcc tttcgctttc    4860
ttcccttcct ttctcgccac gttcgccggc cgtcgaatca ccgtaaccct tataagggat    4920
tttgccgatt tcggcctatt ggttaaaaaa tgagctgatt taacaaaaat ttaacgcgaa    4980
ttaattctgt ggaatgtgtg tcagttaggg tgtggaaagt ccccaggctc ccagcaggc    5040
agaagtatgc aaagcatgca tctcaattag tcagcaacca ggtgtggaaa gtccccaggc    5100
tccccagcag gcagaagtat gcaaagcatg catctcaatt agtcagcaac catagtcccg    5160
cccctaactc cgcccatccc gcccctaact ccgcccagtt ccgcccattc tccgccccat    5220
ggctgactaa ttttttttat ttatgcagag gccgaggccg cctctgcctc tgagctattc    5280
cagaagtagt gaggaggctt ttttggaggc ctaggctttt gcaaaaagct cccgggagct    5340
tgtatatcca ttttcggatc tgatcaagag acaggatgag gatcgtttcg catgattgaa    5400
caagatggat tgcacgcagg ttctccggcc gcttgggtgg agaggctatt cggctatgac    5460
tgggcacaac agacaatcgg ctgctctgat gccgccgtgt tccggctgtc agcgcagggg    5520
cgcccggttc tttttgtcaa gaccgacctg tccggtgccc tgaatgaact gcaggacgag    5580
gcagcgcggc tatcgtggct ggccacgacg ggcgttcctt gcgcagctgt gctcgacgtt    5640
gtcactgaag cgggaaggga ctggctgcta ttgggcgaag tgccggggca ggatctcctg    5700
tcatctcacc ttgctcctgc cgagaaagta tccatcatgg ctgatgcaat gcggcggctg    5760
catacgcttg atccggctac ctgcccattc gaccaccaag cgaaacatcg catcgagcga    5820
gcacgtactc ggatggaagc cggtcttgtc gatcaggatg atctggacga agagcatcag    5880
gggctcgcgc cagccgaact gttgccaggc tcaaggcgc gaattcgagc tcggtacccg    5940
gggatcctct agagtcgacc tgcaggcatg caagcttggc gtaatcatgg tcatagctgt    6000
ttcctgtgtg aaattgttat ccgctcacaa ttccacacaa catacgagcc ggaagcataa    6060
agtgtaaagc ctggggtgcc taatgagtga gctaactcac attaattgcg ttgcgctcac    6120
tgcccgcttt ccagtcggga aacctgtcgt gccagctgca ttaatgaatc ggccaacgcg    6180
cggggagagg cggtttgcgt attgggcgct cttccgcttc ctcgctcact gactcgctgc    6240
gctcggtcgt tcggctgcgg cgagcggtat cagctcactc aaaggcggta atacggttat    6300
ccacagaatc aggggataac gcaggaaaga acatgtgagc aaaaggccag caaaaggcca    6360
ggaaccgtaa aaaggccgcg ttgctggcgt ttttccatag gctccgcccc cctgacgagc    6420
atcacaaaaa tcgacgctca agtcagaggt ggcgaaaccc gacaggacta taaagatacc    6480
aggcgtttcc ccctggaagc tccctcgtgc gctctcctgt tccgaccctg ccgcttaccg    6540
gatacctgtc cgcctttctc ccttcgggaa gcgtggcgct ttctcatagc tcacgctgta    6600
ggtatctcag ttcggtgtag gtcgttcgct ccaagctggg ctgtgtgcac gaacccccg    6660
ttcagcccga ccgctgcgcc ttatccggta actatcgtct tgagtccaac ccggtaagac    6720
```

```
acgacttatc gccactggca gcagccactg gtaacaggat tagcagagcg aggtatgtag    6780
gcggtgctac agagttcttg aagtggtggc ctaactacgg ctacactaga aggacagtat    6840
ttggtatctg cgctctgctg aagccagtta ccttcggaaa aagagttggt agctcttgat    6900
ccggcaaaca aaccaccgct ggtagcggtg gttttttttgt ttgcaagcag cagattacgc    6960
gcagaaaaaa aggatctcaa gaagatcctt tgatcttttc tacggggtct gacgctcagt    7020
ggaacgaaaa ctcacgttaa gggattttgg tcatgagatt atcaaaaagg atcttcacct    7080
agatcctttt aaattaaaaa tgaagtttta aatcaatcta agtatatat gagtaaactt    7140 ggtctgacag ttaccaatgc ttaatcagtg aggcacctat ctcagcgatc tgtctatttc    7200
gttcatccat agttgcctga ctccccgtcg tgtagataac tacgatacgg gagggcttac    7260
catctggccc cagtgctgca atgataccgc gagacccacg ctcaccggct ccagatttat    7320
cagcaataaa ccagccagcc ggaagggccg agcgcagaag tggtcctgca actttatccg    7380
cctccatcca gtctattaat tgttgccggg aagctagagt aagtagttcg ccagttaata    7440
gtttgcgcaa cgttgttgcc attgctacag gcatcgtggt gtcacgctcg tcgtttggta    7500
tggcttcatt cagctccggt tcccaacgat caaggcgagt tacatgatcc cccatgttgt    7560
gcaaaaaagc ggttagctcc ttcggtcctc cgatcgttgt cagaagtaag ttggccgcag    7620
tgttatcact catggttatg gcagcactgc ataattctct tactgtcatg ccatccgtaa    7680
gatgcttttc tgtgactggt gagtactcaa ccaagtcatt ctgagaatag tgtatgcggc    7740
gaccgagttg ctcttgcccg gcgtcaatac gggataatac cgcgccacat agcagaactt    7800
taaaagtgct catcattgga aaacgttctt cggggcgaaa actctcaagg atcttaccgc    7860
tgttgagatc cagttcgatg taacccactc gtgcacccaa ctgatcttca gcatctttta    7920
ctttcaccag cgtttctggg tgagcaaaaa caggaaggca aaatgccgca aaaaagggaa    7980
taagggcgac acggaaatgt tgaatactca tactcttcct ttttcaatat tattgaagca    8040
tttatcaggg ttattgtctc atgagcggat acatatttga atgtatttag aaaaataaac    8100
aaataggggt tccgcgcaca tttccccgaa aagtgccacc tgacgtctaa gaaaccatta    8160
ttatcatgac attaacctat aaaaataggc gtatcacgag gccctttcgt c            8211

<210> SEQ ID NO 42
<211> LENGTH: 1109
<212> TYPE: DNA
<213> ORGANISM: Homo sapiens

<400> SEQUENCE: 42
atggacatgg cggatgagcc actcaatgga agccacacat ggctatccat tccatttgac      60
ctcaatggct ctgtggtgtc aaccaacacc tcaaaccaga cagagccgta ctatgacctg     120
acaagcaatg cagtcctcac attcatctat tttgtggtct gcatcattgg gttgtgtggc     180
aacacacttg tcatttatgt catcctccgc tatgccaaga tgaagaccat caccaacatt     240
tacatcctca acctggccat cgcagatgag ctcttcatgc tgggtctgcc tttcttggct     300
atgcaggtgg ctctggtcca ctggcccttt ggcaaggcca tttgccgggt ggtcatgact     360
gtggatggca tcaatcagtt caccagcatc ttctgcctga cagtcatgag catcgaccga     420
tacctggctg tggtccaccc catcaagtcg gccaagtgga ggagaccccg gacggccaag     480
atgatcacca tggctgtgtg gggagtctct ctgctggtca tcttgccat catgatatat     540 gctgggctcc ggagcaacca gtgggggaga agcagctgca ccatcaactg gccaggtgaa     600
```

| | |
|---|---|
| tctggggctt ggtacacagg gttcatcatc tacactttca ttctggggtt cctggtaccc | 660 |
| ctcaccatca tctgtctttg ctacctgttc attatcatca aggtgaagtc ctctggaatc | 720 |
| cgagtgggct cctctaagag aagaagtct gagaagaagg tcacccgaat ggtgtccatc | 780 |
| gtggtggctg tcttcatctt ctgctggctt cccttctaca tattcaacgt ttcttccgtc | 840 |
| tccatggcca tcagccccac cccagccctt aaaggcatgt ttgactttgt ggtggtcctc | 900 |
| acctatgcta acagctgtgc caaccctatc ctatatgcct tcttgtctga caacttcaag | 960 |
| aagagcttcc agaatgtcct ctgcttggtc aaggtgagcg gcacagatga tggggagcgg | 1020 |
| agtgacagta agcaggacaa atcccggctg aatgagacca cggagaccca gaggaccctc | 1080 |
| ctcaatggag acctccaaac cagtatctc | 1109 |

<210> SEQ ID NO 43
<211> LENGTH: 8065
<212> TYPE: DNA
<213> ORGANISM: Artificial Sequence
<220> FEATURE:
<223> OTHER INFORMATION: Description of Artificial Sequence: Synthetic
    pTV-DS-SSTR2 polynucleotide

<400> SEQUENCE: 43

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt taaggagccc cttcgcctcg | 420 |
| tgcttgagtt gaggcctggc ctgggcgctg gggccgccgc gtgcgaatct ggtggcacct | 480 |
| tcgcgcctgt ctcgctgctt tcgataagtc tctagccatt taaaatttt gatgacctgc | 540 |
| tgcgacgctt ttttctggc aagatagtct tgtaaatgcg ggccaagatc gatctgcaca | 600 |
| ctggtatttc ggttttggg gccgcgggcg gcgacgggc ccgtgcgtcc cagcgcacat | 660 |
| gttcggcgag gcggggcctg cgagcgcggc caccgagaat cggacggggg tagtctcaag | 720 |
| ctggccggcc tgctctggtg cctggcctcg cgccgccgtg tatcgccccg ccctgggcgg | 780 |
| caaggctggc ccggtcggca ccagttgcgt gagcggaaag atggccgctt cccggccctg | 840 |
| ctgcagggag ctcaaaatgg aggacgcggc gctcgggaga gcgggcgggt gagtcaccca | 900 |
| cacaaaggaa aagggccttt ccgtcctcag ccgtcgcttc atgtgactcc acggagtacc | 960 |
| gggcgccgtc caggcacctc gattagttct cgagctttg gagtacgtcg tctttaggtt | 1020 |
| gggggagg gttttatgcg atggagtttc cccacactga gtgggtggag actgaagtta | 1080 |
| ggccagcttg gcacttgatg taattctcct tggaatttgc ccttttttgag tttggatctt | 1140 |
| ggttcattct caagcctcag acagtggttc aaagtttttt tcttccattt caggtgtcgt | 1200 |
| gaggaattgg ctaagcttgc atgcctgcag gtcggccgcc acgaccggtg ccgccaccat | 1260 |
| cccctgaccc acgcccctga ccccctcacaa ggagacgacc ttccatgacc gagtacaagc | 1320 |
| ccacggtgcg cctcgccacc cgcgacgacg tccccgggc cgtacgcacc ctcgccgccg | 1380 |
| cgttcgccga ctaccccgcc acgcgccaca ccgtcgaccc ggaccgccac atcgagcggg | 1440 |
| tcaccgagct gcaagaactc ttcctcacgc gcgtcgggct cgacatcggc aaggtgtggg | 1500 |

```
tcgcggacga cggcgccgcg gtggcggtct ggaccacgcc ggagagcgtc gaagcggggg    1560
cggtgttcgc cgagatcggc ccgcgcatgg ccgagttgag cggttcccgg ctggccgcgc    1620
agcaacagat ggaaggcctc ctggcgccgc accggcccaa ggagcccgcg tggttcctgg    1680
ccaccgtcgg cgtctcgccc gaccaccagg gcaagggtct gggcagcgcc gtcgtgctcc    1740
ccggagtgga ggcggccgag cgcgccgggg tgcccgcctt cctggagacc tccgcgcccc    1800
gcaacctccc cttctacgag cggctcggct tcaccgtcac cgccgacgtc gaggtgcccg    1860
aaggaccgcg cacctggtgc atgacccgca agcccggtgc ctgacgcccg ccccacgacc    1920
cgcagcgccc gaccgaaagg agcgcacgac cccatggctc cgaccgaagc cacccggggc    1980
ggccccgccg accccgcacc cgccccgag gcccaccgac tctagaggat cataatcagc    2040
cataccacat ttgtagaggt tttacttgct ttaaaaaacc tcccacacct ccccctgaac    2100
ctgaaacata aaatgaatgc aattgttgtt gttaacttgt ttattgcagc ttataatggt    2160
tacaaataaa gcaatagcat cacaaatttc acaaataaag cattttttc actgcattct    2220
agttgtggtt tgtccaaact catcaatgta tcttatcatg tctggatcta gcgtttaaac    2280
ttaagcttgg taccgagctc ggatccacta gcgatgtacg ggccagatat acgcgttgac    2340
attgattatt gactagttat taatagtaat caattacggg gtcattagtt catagcccat    2400
atatggagtt ccgcgttaca taacttacgg taaatggccc gcctggctga ccgcccaacg    2460
acccccgccc attgacgtca ataatgacgt atgttcccat agtaacgcca atagggactt    2520
tccattgacg tcaatgggtg gagtatttac ggtaaactgc ccacttggca gtacatcaag    2580
tgtatcatat gccaagtacg ccccctattg acgtcaatga cggtaaatgg cccgcctggc    2640
attatgccca gtacatgacc ttatgggact ttcctacttg gcagtacatc tacgtattag    2700
tcatcgctat taccatggtg atgcggtttt ggcagtacat caatgggcgt ggatagcggt    2760
ttgactcacg gggatttcca agtctccacc ccattgacgt caatgggagt ttgttttggc    2820
accaaaatca acgggacttt ccaaaatgtc gtaacaactc cgccccattg acgcaaatgg    2880
gcggtaggcg tgtacggtgg gaggtctata taagcagagc tctctggcta actagagaac    2940
ccactgctta ctggcttatc gaaattaata cgactcacta gggagaccc aagctggct    3000
agcaccatgg acatggcgga tgagccactc aatggaagcc acacatggct atccattcca    3060
tttgacctca atggctctgt ggtgtcaacc aacacctcaa accagacaga gccgtactat    3120
gacctgacaa gcaatgcagt cctcacattc atctattttg tggtctgcat cattgggttg    3180
tgtggcaaca cacttgtcat ttatgtcatc ctccgctatg ccaagatgaa gaccatcacc    3240
aacatttaca tcctcaacct ggccatcgca gatgagctct tcatgctggg tctgcctttc    3300
ttggctatgc aggtggctct ggtccactgg cccttggca aggccatttg ccgggtggtc    3360
atgactgtgg atggcatcaa tcagttcacc agcatcttct gcctgacagt catgagcatc    3420
gaccgatacc tggctgtggt ccaccccatc aagtcggcca gtggaggag accccggacg    3480
gccaagatga tcaccatggc tgtgtgggga gtctctctgc tggtcatctt gcccatcatg    3540
atatatgctg ggctccggag caaccagtgg gggagaagca gctgcaccat caactggcca    3600
ggtgaatctg ggcttggta cacagggttc atcatctaca ctttcattct ggggttcctg    3660
gtaccctca ccatcatctg tctttgctac ctgttcatta tcatcaaggt gaagtcctct    3720
ggaatccgag tgggctcctc taagaggaag aagtctgaga agaaggtcac ccgaatggtg    3780
tccatcgtgt tggctgtctt catcttctgc tggcttccct tctacatatt caacgtttct    3840
tccgtctcca tggccatcag ccccaccca gcccttaaag gcatgtttga ctttgtggtg    3900
```

```
gtcctcacct atgctaacag ctgtgccaac cctatcctat atgccttctt gtctgacaac   3960
ttcaagaaga gcttccagaa tgtcctctgc ttggtcaagg tgagcggcac agatgatggg   4020
gagcggagtg acagtaagca ggacaaatcc cggctgaatg agaccacgga gacccagagg   4080
accctcctca atggagacct ccaaaccagt atctcaagct tcgaattggg aggtggcggt   4140
agcggaggtg gcgtagcct cgaggattca ctggccgtcg ttttacaacg tcgtgactgg   4200
gaaaaccctg gcgttaccca acttaatcgc cttgcagcac gtccccettt cgccagctgg   4260
cgtaatagcg aagaggcccg caccgatcgc tgagcggccg ctcgagtcta gagggcccgt   4320
ttaaacccgc tgatcagcct cgactgtgcc ttctagttgc cagccatctg ttgtttgccc   4380
ctccccgtg ccttccttga ccctggaagg tgccactccc actgtccttt cctaataaaa   4440
tgaggaaatt gcatcgcatt gtctgagtag gtgtcattct attctggggg gtggggtggg   4500
gcaggacagc aaggggagg attgggaaga caatagcagg catgctgggg atgcggtggg   4560
ctctatggct tctgaggcgg aaagaaccag ctggggctct aggggggtatc cccacgcgcc   4620
ctgtagcggc gcattaagcg cggcgggtgt ggtggttacg cgcagcgtga ccgctacact   4680
tgccagcgcc ctagcgcccg ctcctttcgc tttcttccct tcctttctcg ccacgttcgc   4740
ctaccgtcga atcaccggta accttataag ggattttgcc gatttcggcc tattggttaa   4800
aaaatgagct gatttaacaa aaatttaacg cgaattaatt ctgtggaatg tgtgtcagtt   4860
agggtgtgga agtccccag gctccccagc aggcagaagt atgcaaagca tgcatctcaa   4920
ttagtcagca accaggtgtg gaaagtcccc aggctcccca gcaggcagaa gtatgcaaag   4980
catgcatctc aattagtcag caaccatagt cccgccccta actccgccca tcccgcccct   5040
aactccgccc agttccgccc attctccgcc ccatggctga ctaatttttt ttatttatgc   5100
agaggccgag gccgcctctg cctctgagct attccagaag tagtgaggag gctttttgg   5160
aggcctaggc ttttgcaaaa agctcccggg agcttgtata tccattttcg gatctgatca   5220
agagacagga tgaggatcgt ttcgcatgat tgaacaagat ggattgcacg caggttctcc   5280
ggccgcttgg gtggagaggc tattcggcta tgactgggca caacagacaa tcggctgctc   5340
tgatgccgcc gtgttccggc tgtcagcgca ggggcgcccg gttcttttg tcaagaccga   5400
cctgtccggt gccctgaatg aactgcagga cgaggcagcg cggctatcgt ggctggccac   5460
gacgggcgtt ccttgcgcag ctgtgctcga cgttgtcact gaagcgggaa gggactggct   5520
gctattgggc gaagtgccgg ggcaggatct cctgtcatct caccttgctc ctgccgagaa   5580
agtatccatc atggctgatg caatgcggcg gctgcatacg cttgatccgg ctacctgccc   5640
attcgaccac caagcgaaac atcgcatcga gcgagcacgt actcggatgg aagccggtct   5700
tgtcgatcag gatgatctgg acgaagagca tcagggctc gcgccagccg aactgttcgc   5760
caggctcaag gcgcgaattc gagctcggta cccggggatc ctctagagtc gacctgcagg   5820
catgcaagct tggcgtaatc atggtcatag ctgtttcctg tgtgaaattg ttatccgctc   5880
acaattccac acaacatacg agccggaagc ataaagtgta aagcctgggg tgcctaatga   5940
gtgagctaac tcacattaat tgcgttgcgc tcactgcccg ctttccagtc gggaaacctg   6000
tcgtgccagc tgcattaatg aatcggccaa cgcgcgggga gaggcggttt gcgtattggg   6060
cgctcttccg cttcctcgct cactgactcg ctgcgctcgg tcgttcggct gcggcgagcg   6120
gtatcagctc actcaaaggc ggtaatacgg ttatccacag aatcagggga taacgcagga   6180
aagaacatgt gagcaaaagg ccagcaaaag gccaggaacc gtaaaaaggc cgcgttgctg   6240
```

```
gcgttttttcc ataggctccg ccccCctgac gagcatcaca aaaatcgacg ctcaagtcag    6300
aggtggcgaa acccgacagg actataaaga taccaggcgt ttcccctgg aagctccctc     6360 gtgcgctctc ctgttccgac cctgccgctt accggatacc tgtccgcctt tctcccttcg    6420
ggaagcgtgg cgcttctca tagctcacgc tgtaggtatc tcagttcggt gtaggtcgtt     6480
cgctccaagc tgggctgtgt gcacgaaccc cccgttcagc ccgaccgctg cgccttatcc    6540
ggtaactatc gtcttgagtc caacccggta agacacgact tatcgccact ggcagcagcc    6600
actggtaaca ggattagcag agcgaggtat gtaggcggtg ctacagagtt cttgaagtgg    6660
tggcctaact acggctacac tagaagaaca gtatttggta tctgcgctct gctgaagcca    6720
gttaccttcg gaaaaagagt tggtagctct tgatccggca acaaaccac cgctggtagc     6780 ggtggttttt ttgtttgcaa gcagcagatt acgcgcagaa aaaaggatc tcaagaagat     6840 cctttgatct tttctacggg gtctgacgct cagtggaacg aaaactcacg ttaagggatt    6900
ttggtcatga gattatcaaa aaggatcttc acctagatcc ttttaaatta aaaatgaagt    6960
tttaaatcaa tctaaagtat atatgagtaa acttggtctg acagttacca atgcttaatc    7020
agtgaggcac ctatctcagc gatctgtcta tttcgttcat ccatagttgc ctgactcccc    7080
gtcgtgtaga taactacgat acgggagggc ttaccatctg gccccagtgc tgcaatgata    7140
ccgcgagacc cacgctcacc ggctccagat ttatcagcaa taaaccagcc agccggaagg    7200
gccgagcgca gaagtggtcc tgcaacttta tccgcctcca tccagtctat taattgttgc    7260
cgggaagcta gagtaagtag ttcgccagtt aatagtttgc gcaacgttgt tgccattgct    7320
acaggcatcg tggtgtcacg ctcgtcgttt ggtatggctt cattcagctc cggttcccaa    7380
cgatcaaggc gagttacatg atccccatg ttgtgcaaaa aagcggttag ctccttcggt     7440
cctccgatcg ttgtcagaag taagttggcc gcagtgttat cactcatggt tatggcagca    7500
ctgcataatt ctcttactgt catgccatcc gtaagatgct tttctgtgac tggtgagtac    7560
tcaaccaagt cattctgaga atagtgtatg cggcgaccga gttgctcttg cccggcgtca    7620
atacgggata taccgcgcc acatagcaga actttaaaag tgctcatcat ggaaaacgt      7680 tcttcggggc gaaaactctc aaggatctta ccgctgttga tccagttc gatgtaaccc      7740 actcgtgcac ccaactgatc ttcagcatct tttactttca ccagcgtttc tgggtgagca    7800
aaaacaggaa ggcaaaatgc cgcaaaaaag gaataaggg cgacacggaa atgttgaata    7860
ctcatactct tcctttttca atattattga agcatttatc agggttattg tctcatgagc    7920
ggatacatat ttgaatgtat ttagaaaaat aaacaaatag gggttccgcg cacatttccc    7980
cgaaaagtgc cacctgacgt ctaagaaacc attattatca tgacattaac ctataaaaat    8040
aggcgtatca cgaggccctt tcgtc                                          8065

<210> SEQ ID NO 44
<211> LENGTH: 2589
<212> TYPE: DNA
<213> ORGANISM: Homo sapiens

<400> SEQUENCE: 44
atggcaagga ggagctcgtt ccagtcgtgt cagataatat ccctgttcac ttttgccgtt      60
ggagtcaata tctgcttagg attcactgca catcgaatta agagagcaga aggatgggag    120
gaaggtcctc ctacagtgct atcagactcc ccctggacca catctccgg atcttgcaag     180 ggcaggtgct ttgaacttca agaggctgga cctcctgatt gtcgctgtga caacttgtgt    240
aagagctata ccagttgctg ccatgacttt gatgagctgt gtttgaagac agcccgtggc    300
```

```
tgggagtgta ctaaggacag atgtggagaa gtcagaaatg aagaaaatgc ctgtcactgc    360
tcagaggact gcttggccag gggagactgc tgtaccaatt accaagtggt ttgcaaagga    420
gagtcgcatt gggttgatga tgactgtgag gaaataaagg ccgcagaatg ccctgcaggg    480
tttgttcgcc ctccattaat catcttctcc gtggatggct tccgtgcatc atacatgaag    540
aaaggcagca aagtcatgcc taatattgaa aaactaaggt cttgtggcac acactctccc    600
tacatgaggc cggtgtaccc aactaaaacc tttcctaact tatacacttt ggccactggg    660
ctatatccag aatcacatgg aattgttggc aattcaatgt atgatcctgt atttgatgcc    720
acttttcatc tgcgagggcg agagaaattt aatcatagat ggtggggagg tcaaccgcta    780
tggattacag ccaccaagca agggtgaaa  gctggaacat tcttttggtc tgttgtcatc    840
cctcacgagc ggagaatatt aaccatattg cagtggctca ccctgccaga tcatgagagg    900
ccttcggtct atgccttcta ttctgagcaa cctgatttct ctggacacaa atatggccct    960
ttcggccctg agatgacaaa tcctctgagg gaaatcgaca aaattgtggg gcaattaatg    1020
gatggactga acaactaaa  actgcatcgg tgtgtcaacg tcatctttgt cggagaccat   1080
ggaatggaag atgtcacatg tgatagaact gagttcttga gtaattacct aactaatgtg   1140
gatgatatta ctttagtgcc tggaactcta ggaagaattc gatccaaatt tagcaacaat   1200
gctaaatatg accccaaagc cattattgcc aatctcacgt gtaaaaaacc agatcagcac   1260
tttaagcctt acttgaaaca gcaccttccc aaacgtttgc actatgccaa caacagaaga   1320
attgaggata tccatttatt ggtggaacgc agatggcatg ttgcaaggaa acctttggat   1380
gtttataaga aaccatcagg aaaatgcttt ttccagggag accacggatt tgataacaag   1440
gtcaacagca tgcagactgt ttttgtaggt tatggcccaa catttaagta caagactaaa   1500
gtgcctccat ttgaaaacat tgaactttac aatgttatgt gtgatctcct gggattgaag   1560
ccagctccta ataatgggac ccatggaagt ttgaatcatc tcctgcgcac taataccttc   1620
aggccaacca tgccagagga agttaccaga cccaattatc cagggattat gtaccttcag   1680
tctgattttg acctgggctg cacttgtgat gataaggtag agccaaagaa caagttggat   1740
gaactcaaca aacggcttca tacaaaaggg tctacagaag agagacacct cctctatggg   1800
cgacctgcag tgctttatcg gactagatat gatatcttat atcacactga ctttgaaagt   1860
ggttatagtg aaatattcct aatgccactc tggacatcat atactgtttc caaacaggct   1920
gaggtttcca gcgttcctga ccatctgacc agttgcgtcc ggcctgatgt ccgtgtttct   1980
ccgagtttca gtcagaactg tttggcctac aaaaatgata gcagatgtc  ctacggattc   2040
ctctttcctc cttatctgag ctcttcacca gaggctaaat atgatgcatt ccttgtaacc   2100
aatatggttc caatgtatcc tgctttcaaa cgggtctgga ttatttcca  aagggtattg   2160
gtgaagaaat atgcttcgga aagaaatgga gttaacgtga taagtggacc aatcttcgac   2220
tatgactatg atggcttaca tgacacagaa gacaaaataa aacagtacgt ggaaggcagt   2280
tccattcctg ttccaactca ctactacagc atcatcacca gctgtctgga tttcactcag   2340
cctgccgaca gtgtgacgg  cccctctctct gtgtcctcct tcatcctgcc tcaccggcct   2400
gacaacgagg agagctgcaa tagctcagag gacgaatcaa aatgggtaga agaactcatg   2460
aagatgcaca cagctagggt gcgtgacatt gaacatctca ccagcctgga cttcttccga   2520
aagaccagcc gcagctaccc agaaatcctg acactcaaga cataccctgca tacatatgag   2580
agcgagatt                                                            2589
```

<210> SEQ ID NO 45
<211> LENGTH: 9485
<212> TYPE: DNA
<213> ORGANISM: Artificial Sequence
<220> FEATURE:
<223> OTHER INFORMATION: Description of Artificial Sequence: Synthetic pTV-DS-hATX polynucleotide

<400> SEQUENCE: 45

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | ttaaggagcc | cttcgcctc | 420 |
| gtgcttgagt | tgaggcctgg | cttgggcgct | ggggccgccg | cgtgcgaatc | tggtggcacc | 480 |
| ttcgcgcctg | tctcgctgct | ttcgataagt | ctctagccat | ttaaaatttt | tgatgacctg | 540 |
| ctgcgacgct | ttttttctgg | caagatagtc | ttgtaaatgc | gggccaagat | cgatctgcac | 600 |
| actggtattt | cggtttttgg | ggccgcgggc | ggcgacgggg | cccgtgcgtc | cagcgcaca | 660 |
| tgttcggcga | ggcggggcct | gcgagcgcgg | ccaccgagaa | tcggacgggg | gtagtctcaa | 720 |
| gctggccggc | ctgctctggt | gcctggcctc | gcgccgccgt | gtatcgcccc | gccctgggcg | 780 |
| gcaaggctgg | cccggtcggc | accagttgcg | tgagcggaaa | gatggccgct | tcccggccct | 840 |
| gctgcaggga | gctcaaaatg | gaggacgcgg | cgctcgggag | agcgggcggg | tgagtcaccc | 900 |
| acacaaagga | aaagggcctt | tccgtcctca | gccgtcgctt | catgtgactc | cacggagtac | 960 |
| cgggcgccgt | ccaggcacct | cgattagttc | tcgagctttt | ggagtacgtc | gtctttaggt | 1020 |
| tggggggagg | ggttttatgc | gatggagttt | ccccacactg | agtgggtgga | gactgaagtt | 1080 |
| aggccagctt | ggcacttgat | gtaattctcc | ttggaatttg | ccctttttga | gtttggatct | 1140 |
| tggttcattc | tcaagcctca | gacagtggtt | caaagttttt | ttcttccatt | tcaggtgtcg | 1200 |
| tggaattggc | tagagcttgc | atgcctgcag | gtcggccgcc | acgaccggtg | ccgccaccat | 1260 |
| cccctgaccc | acgcccctga | cccctcacaa | ggagacgacc | ttccatgacc | gagtacaagc | 1320 |
| ccacggtgcg | cctcgccacc | cgcgacgacg | tccccgggc | cgtacgcacc | ctcgccgccg | 1380 |
| cgttcgccga | ctaccccgcc | acgcgccaca | ccgtcgaccc | ggaccgccac | atcgagcggg | 1440 |
| tcaccgagct | gcaagaactc | ttcctcacgc | gcgtcgggct | cgacatcggc | aaggtgtggg | 1500 |
| tcgcggacga | cggcgccgcg | gtggcggtct | ggaccacgcc | ggagagcgtc | gaagcggggg | 1560 |
| cggtgttcgc | cgagatcggc | ccgcgcatgg | ccgagttgag | cggttcccgg | ctggccgcgc | 1620 |
| agcaacagat | ggaaggcctc | ctggcgccgc | accggcccaa | ggagcccgcg | tggttcctgg | 1680 |
| ccaccgtcgg | cgtctcgccc | gaccaccagg | gcaagggtct | gggcagcgcc | gtcgtgctcc | 1740 |
| ccggagtgga | ggcggccgag | cgcgccgggg | tgcccgcctt | cctggagacc | tccgcgcccc | 1800 |
| gcaacctccc | cttctacgag | cggctcggct | tcaccgtcac | cgccgacgtc | gaggtgcccg | 1860 |
| aaggaccgcg | cacctggtgc | atgacccgca | agcccggtgc | ctgacgcccg | cccacgacc | 1920 |
| cgcagcgccc | gaccgaaagg | agcgcacgac | cccatggctc | cgaccgaagc | cgacccgggc | 1980 |
| ggccccgccg | accccgcacc | cgcccccgag | gcccaccgac | tctagaggat | cataatcagc | 2040 |

```
cataccacat tgtagaggt tttacttgct ttaaaaaacc tcccacacct cccctgaac     2100 ctgaaacata aaatgaatgc aattgttgtt gttaacttgt ttattgcagc ttataatggt   2160
tacaaataaa gcaatagcat cacaaatttc acaaataaag cattttttc actgcattct    2220 agttgtggtt tgtccaaact catcaatgta tcttatcatg tctggatcct agcgtttaaa   2280
cttaagcttg gtaccgagct cggatccact agtaatggtt acaaataaag caatagcatc   2340
acaaatttca caaataaagc attttttca ctgcattcta gttgtggttt gtccaaactc    2400
atcaatgtat cttatcatgt ctgtacgatg tacgggccag atatacgcgt tgacattgat   2460
tattgactag ttattaatag taatcaatta cggggtcatt agttcatagc ccatatatgg   2520
agttccgcgt tacataactt acggtaaatg gcccgcctgg ctgaccgccc aacgacccc    2580 gcccattgac gtcaataatg acgtatgttc ccatagtaac gccaataggg actttccatt   2640
gacgtcaatg ggtggagtat ttacggtaaa ctgcccactt ggcagtacat caagtgtatc   2700
atatgccaag tacgccccct attgacgtca atgacggtaa atggcccgcc tggcattatg   2760
cccagtacat gaccttatgg gactttccta cttggcagta catctacgta ttagtcatcg   2820
ctattaccat ggtgatgcgg ttttggcagt acatcaatgg gcgtggatag cggtttgact   2880
cacggggatt tccaagtctc cacccattg acgtcaatgg gagtttgttt tggcaccaaa    2940
atcaacggga ctttccaaaa tgtcgtaaca actccgcccc attgacgcaa atgggcggta   3000
ggcgtgtacg gtgggaggtc tatataagca gagctctctg gctaactaga acccactg     3060 cttactggct tatcgaaatt aatacgactc actatagga gacccaagct ggctagccac     3120
catggcaagg aggagctcgt tccagtcgtg tcagataata tcctgttca cttttgccgt    3180 tggagtcaat atctgcttag gattcactgc acatcgaatt aagagagcag aaggatggga   3240
ggaaggtcct cctacagtgc tatcagactc cccctggacc aacatctccg gatcttgcaa   3300
gggcaggtgc tttgaacttc aagaggctgg acctcctgat tgtcgctgtg caacttgtg    3360 taagagctat accagttgct gccatgactt tgatgagctg tgttgaaga cagcccgtgg    3420 ctgggagtgt actaaggaca gatgtggaga agtcagaaat gaagaaaatg cctgtcactg   3480
ctcagaggac tgcttggcca ggggagactg ctgtaccaat taccaagtgg tttgcaaagg   3540
agagtcgcat tgggttgatg atgactgtga ggaaataaag gccgcagaat gccctgcagg   3600
gtttgttcgc cctccattaa tcatcttctc cgtggatggc ttccgtgcat catacatgaa   3660
gaaaggcagc aaagtcatgc ctaatattga aaaactaagg tcttgtggca cacactctcc   3720
ctacatgagg ccggtgtacc caactaaaac ctttcctaac ttatacactt tggccactgg   3780
gctatatcca gaatcacatg gaattgttgg caattcaatg tatgatcctg tatttgatgc   3840 cactttctcat ctgcgagggc gagagaaatt taatcataga tggtggggag gtcaaccgct   3900
atggattaca gccaccaagc aagggtgaa agctggaaca ttcttttggt ctgttgtcat    3960
ccctcacgag cggagaatat taaccatatt gcagtggctc accctgccag atcatgagag   4020
gccttcggtc tatgccttct attctgagca acctgatttc tctggacaca aatatggccc   4080
tttcggccct gagatgacaa atcctctgag ggaaatcgac aaaattgtgg ggcaattaat   4140
ggatggactg aaacaactaa aactgcatcg gtgtgtcaac gtcatctttg tcggagacca   4200
tggaatggaa gatgtcacat gtgatagaac tgagttcttg agtaattacc taactaatgt   4260
ggatgatatt actttagtgc ctggaactct aggaagaatt cgatccaaat ttagcaacaa   4320 tgctaaaatat gaccccaaag ccattattgc caatctcacg tgtaaaaaac cagatcagca   4380 cttttaagcct tacttgaaac agcaccttcc caaacgtttg cactatgcca acaacagaag   4440
```

```
aattgaggat atccatttat tggtggaacg cagatggcat gttgcaagga aacctttgga    4500
tgtttataag aaaccatcag gaaaatgctt tttccaggga gaccacggat ttgataacaa    4560
ggtcaacagc atgcagactg tttttgtagg ttatggccca acatttaagt acaagactaa    4620
agtgcctcca tttgaaaaca ttgaacttta caatgttatg tgtgatctcc tgggattgaa    4680
gccagctcct aataatggga cccatggaag tttgaatcat ctcctgcgca ctaataccttt   4740 caggccaacc atgccagagg aagttaccag acccaattat ccagggatta tgtaccttca    4800
gtctgatttt gacctgggct gcacttgtga tgataaggta gagccaaaga acaagttgga    4860
tgaactcaac aaacggcttc atacaaaagg gtctacagaa gagagacacc tcctctatgg    4920
gcgacctgca gtgctttatc ggactagata tgatatctta tatcacactg actttgaaag    4980
tggttatagt gaaatattcc taatgccact ctggacatca tatactgttt ccaaacaggc    5040
tgaggtttcc agcgttcctg accatctgac cagttgcgtc cggcctgatg tccgtgtttc    5100
tccgagtttc agtcagaact gtttggccta caaaaatgat aagcagatgt cctacggatt    5160
cctctttcct ccttatctga gctcttcacc agaggctaaa tatgatgcat tccttgtaac    5220
caatatggtt ccaatgtatc ctgctttcaa acgggtctgg aattatttcc aaagggtatt    5280
ggtgaagaaa tatgcttcgg aaagaaatgg agttaacgtg ataagtggac caatcttcga    5340
ctatgactat gatggcttac atgacacaga agacaaaata aaacagtacg tggaaggcag    5400
ttccattcct gttccaactc actactacag catcatcacc agctgtctgg atttcactca    5460
gcctgccgac aagtgtgacg gccctctctc tgtgtcctcc ttcatcctgc ctcaccggcc    5520
tgacaacgag gagagctgca atagctcaga ggacgaatca aaatgggtag aagaactcat    5580
gaagatgcac acagctaggg tgcgtgacat tgaacatctc accagcctgg acttcttccg    5640
aaagaccagc cgcagctacc cagaaatcct gacactcaag acatacctgc atacatatga    5700
gagcgagatt taagcggccg ctcgagtcta gagggcccgt ttaaacccgc tgatcagcct    5760
cgactgtgcc ttctagttgc cagccatctg ttgtttgccc ctcccccgtg ccttccttga    5820
ccctggaagg tgccactccc actgtccttt cctaataaaa tgaggaaatt gcatcgcatt    5880
gtctgagtag gtgtcattct attctggggg gtggggtggg gcaggacagc aaggggagg    5940 attgggaaga caatagcagg catgctgggg atgcggtggg ctctatggct tctgaggcgg    6000
aaagaaccag ctggggctct aggggtatc cccacgcgcc ctgtagcggc gcattaagcg    6060
cggcgggtgt ggtggttacg cgcagcgtga ccgctacact tgccagcgcc ctagcgcccg    6120
ctcctttcgc tttcttccct cctttctcg ccacgttcgc ctaccgtcga tcaccggta    6180 accttataag ggattttgcc gatttcggcc tattggttaa aaaatgagct gatttaacaa    6240
aaatttaacg cgaattaatt ctgtggaatg tgtgtcagtt agggtgtgga aagtcccag    6300 gctccccagc aggcagaagt atgcaaagca tgcatctcaa ttagtcagca accaggtgtg    6360
gaaagtcccc aggctcccca gcaggcagaa gtatgcaaag catgcatctc aattagtcag    6420
caaccatagt cccgccccta actccgccca tcccgcccct aactccgccc agttccgccc    6480
attctccgcc ccatggctga ctaattttt ttatttatgc agaggccgag gccgcctctg    6540
cctctgagct attccagaag tagtgaggag gcttttttgg aggcctaggc ttttgcaaaa    6600
agctcccggg agcttgtata tccattttcg gatctgatca agagacagga tgaggatcgt    6660
ttcgcatgat tgaacaagat ggattgcacg caggttctcc ggccgcttgg gtggagaggc    6720
tattcggcta tgactgggca acacagacaa tcggctgctc tgatgccgcc gtgttccggc    6780
```

```
tgtcagcgca ggggcgcccg gttcttttg tcaagaccga cctgtccggt gccctgaatg   6840
aactgcagga cgaggcagcg cggctatcgt ggctggccac gacgggcgtt ccttgcgcag   6900
ctgtgctcga cgttgtcact gaagcgggaa gggactggct gctattgggc gaagtgccgg   6960
ggcaggatct cctgtcatct caccttgctc ctgccgagaa agtatccatc atggctgatg   7020
caatgcggcg gctgcatacg cttgatccgg ctacctgccc attcgaccac caagcgaaac   7080
atcgcatcga gcgagcacgt actcggatgg aagccggtct tgtcgatcag gatgatctgg   7140
acgaagagca tcagggctc gcgccagccg aactgttcgc caggctcaag gcgcgaattc   7200
gagctcggta cccggggatc ctctagagtc gacctgcagg catgcaagct tggcgtaatc   7260
atggtcatag ctgtttcctg tgtgaaattg ttatccgctc acaattccac acaacatacg   7320
agccggaagc ataaagtgta aagcctgggg tgcctaatga gtgagctaac tcacattaat   7380
tgcgttgcgc tcactgcccg ctttccagtc gggaaacctg tcgtgccagc tgcattaatg   7440
aatcggccaa cgcgcgggga gaggcggttt gcgtattggg cgctcttccg cttcctcgct   7500
cactgactcg ctgcgctcgg tcgttcggct gcggcgagcg gtatcagctc actcaaaggc   7560
ggtaatacgg ttatccacag aatcagggga taacgcagga agaacatgt gagcaaaagg   7620 ccagcaaaag gccaggaacc gtaaaaaggc cgcgttgctg gcgtttttcc ataggctccg   7680
cccccctgac gagcatcaca aaatcgacg ctcaagtcag aggtggcgaa acccgacagg   7740
actataaaga taccaggcgt ttccccctgg aagctccctc gtgcgctctc ctgttccgac   7800
cctgccgctt accggatacc tgtccgcctt tctcccttcg ggaagcgtgg cgctttctca   7860
tagctcacgc tgtaggtatc tcagttcggt gtaggtcgtt cgctccaagc tgggctgtgt   7920
gcacgaaccc cccgttcagc ccgaccgctg cgccttatcc ggtaactatc gtcttgagtc   7980
caacccggta agacacgact tatcgccact ggcagcagcc actggtaaca ggattagcag   8040
agcgaggtat gtaggcggtg ctacagagtt cttgaagtgg tggcctaact acggctacac   8100
tagaaggaca gtatttggta tctgcgctct gctgaagcca gttaccttcg gaaaaagagt   8160
tggtagctct tgatccggca acaaaccac cgctggtagc ggtggttttt tgtttgcaa   8220 gcagcagatt acgcgcagaa aaaaggatc tcaagaagat cctttgatct tttctacggg   8280
gtctgacgct cagtggaacg aaaactcacg ttaagggatt ttggtcatga gattatcaaa   8340
aaggatcttc acctagatcc ttttaaatta aaaatgaagt tttaaatcaa tctaaagtat   8400
atatgagtaa acttggtctg acagttacca atgcttaatc agtgaggcac ctatctcagc   8460
gatctgtcta tttcgttcat ccatagttgc ctgactcccc gtcgtgtaga taactacgat   8520
acgggagggc ttaccatctg gccccagtgc tgcaatgata ccgcgagacc cacgctcacc   8580
ggctccagat ttatcagcaa taaaccagcc agccggaagg gccgagcgca gaagtggtcc   8640 tgcaactta tccgcctcca tccagtctat taattgttgc cgggaagcta gagtaagtag   8700
ttcgccagtt aatagtttgc gcaacgttgt tgccattgct acaggcatcg tggtgtcacg   8760
ctcgtcgttt ggtatggctt cattcagctc cggttcccaa cgatcaaggc gagttacatg   8820
atcccccatg ttgtgcaaaa aagcggttag ctccttcggt cctccgatcg ttgtcagaag   8880
taagttggcc gcagtgttat cactcatggt tatggcagca ctgcataatt ctcttactgt   8940
catgccatcc gtaagatgct tttctgtgac tggtgagtac tcaaccaagt cattctgaga   9000
atagtgtatg cggcgaccga gttgctcttg cccggcgtca atacgggata ataccgcgcc   9060
acatagcaga actttaaaag tgctcatcat tggaaaacgt tcttcgggc gaaaactctc   9120 aaggatctta ccgctgttga gatccagttc gatgtaaccc actcgtgcac ccaactgatc   9180
```

```
ttcagcatct tttactttca ccagcgtttc tgggtgagca aaaacaggaa ggcaaaatgc    9240
cgcaaaaaag ggaataaggg cgacacggaa atgttgaata ctcatactct tccttttca    9300 atattattga agcatttatc agggttattg tctcatgagc ggatacatat ttgaatgtat    9360
ttagaaaaat aaacaaatag gggttccgcg cacatttccc cgaaaagtgc cacctgacgt    9420
ctaagaaacc attattatca tgacattaac ctataaaaat aggcgtatca cgaggccctt    9480
tcgtc                                                                9485

<210> SEQ ID NO 46
<211> LENGTH: 1053
<212> TYPE: DNA
<213> ORGANISM: Homo sapiens

<400> SEQUENCE: 46 atgcaggggca acggcagcgc gctgcccaac gcctcccagc ccgtgctccg cggggacggc     60
gcgcggccct cgtggctggc gtccgccctg gcctgcgtcc tcatcttcac catcgtggtg    120
gacatcctgg gcaacctcct ggtcatcctg tcggtgtatc ggaacaagaa gctcaggaac    180
gccggcaaca tctttgtggt gagcttagcg gtggcagacc tggtggtggc cattatccg    240 tacccgttgg tgctgatgtc gatatttaac aacgggtgga acctgggcta tctgcactgc    300
caagtcagtg ggttcctgat gggcctgagc gtcatcggct ccatattcaa catcaccggc    360
atcgccatca accgctactg ctacatctgc cacagtctca gtacgacaa actgtacagc    420 agcaagaact ccctctgcta cgtgctcctc atatggctcc tgacgctggc ggccgtcctg    480
cccaacctcc gtgcagggac tctccagtac gacccgagga tctactcgtg caccttcgcc    540
cagtccgtca gctccgccta caccatcgcc gtggtggttt tccactcct cgtccccatg    600 atcatagtca tcttctgtta cctgagaata tggatcctgg ttctccaggt cagacagagg    660
gtgaaacctg accgcaaacc caaactgaaa ccacaggact tcaggaattt tgtcaccatg    720
tttgtggttt ttgtcctttt tgccatttgc tgggctcctc tgaacttcat tggcctggcc    780
gtggcctctg accccgccag catggtgcct aggatcccag agtggctgtt tgtggccagt    840
tactacatgg cgtatttcaa cagctgcctc aatgccatta tatacgggct actgaaccaa    900
aatttcagga aggaatacag gagaattata gtctcgctct gtacagccag ggtgttcttt    960
gtggacagct ctaacgacgt ggccgatagg gttaaatgga aaccgtctcc actgatgacc   1020
aacaataatg tagtaaaggt ggactccgtt taa                                 1053

<210> SEQ ID NO 47
<211> LENGTH: 7946
<212> TYPE: DNA
<213> ORGANISM: Artificial Sequence
<220> FEATURE:
<223> OTHER INFORMATION: Description of Artificial Sequence: Synthetic
      pTV-DS-hMT1 polynucleotide

<400> SEQUENCE: 47
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
```

```
tttcccagtc acgacgttgt aaaacgacgg ccagtgaatt ttaaggagcc ccttcgcctc    420
gtgcttgagt tgaggcctgg cttgggcgct ggggccgccg cgtgcgaatc tggtggcacc    480
ttcgcgcctg tctcgctgct ttcgataagt ctctagccat ttaaaatttt tgatgacctg    540
ctgcgacgct ttttttctgg caagatagtc ttgtaaatgc gggccaagat cgatctgcac    600
actggtattt cggttttttgg ggccgcgggc ggcgacgggg cccgtgcgtc ccagcgcaca    660
tgttcggcga ggcggggcct gcgagcgcgg ccaccgagaa tcggacgggg gtagtctcaa    720
gctggccggc ctgctctggt gcctggcctc gcgccgccgt gtatcgcccc gccctgggcg    780
gcaaggctgg cccggtcggc accagttgcg tgagcggaaa gatggccgct ccccggccct    840
gctgcaggga gctcaaaatg gaggacgcgg cgctcgggag agcgggcggg tgagtcaccc    900
acacaaagga aaagggcctt tccgtcctca gccgtcgctt catgtgactc cacgagtac     960
cgggcgccgt ccaggcacct cgattagttc tcgagctttt ggagtacgtc gtctttaggt   1020
tgggggagg ggttttatgc gatggagttt ccccacactg agtgggtgga gactgaagtt    1080
aggccagctt ggcacttgat gtaattctcc ttggaatttg cccttttga gtttggatct     1140
tggttcattc tcaagcctca gacagtggtt caaagttttt ttcttccatt tcaggtgtcg   1200
tggaattggc tagagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgg cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
aaggaccgcg cacctggtgc atgacccgca agcccggtgc ctgacgcccg ccccacgacc   1920
cgcagcgccc gaccgaaagg agcgcacgac cccatggctc cgaccgaagc cgacccgggc   1980
ggccccgccg accccgcacc cgccccgag gcccaccgac tctagaggat cataatcagc     2040
cataccacat ttgtagaggt tttacttgct ttaaaaaacc tcccacacct cccctgaac    2100
ctgaaacata aaatgaatgc aattgttgtt gttaacttgt ttattgcagc ttataatggt   2160
tacaaataaa gcaatagcat cacaaatttc acaaataaag cattttttc actgcattct    2220
agttgtggtt tgtccaaact catcaatgta tcttatcatg tctggatcct agcgtttaaa   2280
cttaagcttg gtaccgagct cggatccact agtaatggtt acaaataaag caatagcatc   2340
acaaatttca caaataaagc attttttttca ctgcattcta gttgtggttt gtccaaactc   2400
atcaatgtat cttatcatgt ctgtacgatg tacgggccag atatacgcgt tgacattgat   2460
tattgactag ttattaatag taatcaatta cggggtcatt agttcatagc ccatatatgg   2520
agttccgcgt tacataactt acggtaaatg gcccgcctgg ctgaccgccc aacgaccccc   2580
gcccattgac gtcaataatg acgtatgttc ccatagtaac gccaataggg actttccatt   2640
gacgtcaatg ggtggagtat ttacggtaaa ctgcccactt ggcagtacat caagtgtatc   2700
```

```
atatgccaag tacgcccct attgacgtca atgacggtaa atggcccgcc tggcattatg    2760
cccagtacat gaccttatgg gactttccta cttggcagta catctacgta ttagtcatcg    2820
ctattaccat ggtgatgcgg ttttggcagt acatcaatgg gcgtggatag cggtttgact    2880
cacggggatt tccaagtctc cacccattg acgtcaatgg gagtttgttt tggcaccaaa     2940
atcaacggga ctttccaaaa tgtcgtaaca actccgcccc attgacgcaa atgggcggta    3000
ggcgtgtacg gtgggaggtc tatataagca gagctctctg gctaactaga acccactg     3060 cttactggct tatcgaaatt aatacgactc actatagggA gacccaagct ggctagccac    3120
catgcagggc aacggcagcg cgctgcccaa cgcctcccag cccgtgctcc gcggggacgg    3180
cgcgcggccc tcgtggctgg cgtccgccct ggcctgcgtc ctcatcttca ccatcgtggt    3240
ggacatcctg gcaacctcc tggtcatcct gtcggtgtat cggaacaaga agctcaggaa     3300
cgccggcaac atctttgtgg tgagcttagc ggtggcagac ctggtggtgg ccatttatcc    3360
gtacccgttg gtgctgatgt cgatatttaa caacgggtgg aacctgggct atctgcactg    3420
ccaagtcagt gggttcctga tgggcctgag cgtcatcggc tccatattca acatcaccgg    3480
catcgccatc aaccgctact gctacatctg ccacagtctc aagtacgaca aactgtacag    3540
cagcaagaac tccctctgct acgtgctcct catatggctc ctgacgctgg cggccgtcct    3600
gcccaacctc cgtgcaggga ctctccagta cgacccgagg atctactcgt gcaccttcgc    3660
ccagtccgtc agctccgcct acaccatcgc cgtggtggtt ttccacttcc tcgtccccat    3720
gatcatagtc atcttctgtt acctgagaat atggatcctg gttctccagg tcagacagag    3780
ggtgaaacct gaccgcaaac ccaaactgaa accacaggac ttcaggaatt ttgtcaccat    3840
gtttgtggtt tttgtccttt ttgccatttg ctgggctcct ctgaacttca ttggcctggc    3900
cgtggcctct gaccccgcca gcatggtgcc taggatccca gagtggctgt ttgtgggcag    3960
ttactacatg gcgtatttca acagctgcct caatgccatt atatacgggc tactgaacca    4020
aaatttcagg aaggaataca ggagaattat agtctcgctc tgtacagcca gggtgttctt    4080
tgtggacagc tctaacgacg tggccgatag ggttaaatgg aaaccgtctc cactgatgac    4140
caacaataat gtagtaaagg tggactccgt ttaagcggcc gctcgagtct agagggcccg    4200
tttaaacccg ctgatcagcc tcgactgtgc cttctagttg ccagccatct gttgtttgcc    4260 cctccccgt gccttccttg acctggaag gtgccactcc cactgtcctt tcctaataaa      4320
atgaggaaat tgcatcgcat tgtctgagta ggtgtcattc tattctgggg ggtggggtgg    4380
ggcaggacag caaggggag gattgggaag acaatagcag gcatgctggg gatgcggtgg    4440
gctctatggc ttctgaggcg gaaagaacca gctgggctc taggggtat ccccacgcgc     4500 cctgtagcgg cgcattaagc gcggcgggtg tggtggttac gcgcagcgtg accgctacac    4560
ttgccagcgc cctagcgccc gctcctttcg ctttcttccc ttcctttctc gccacgttcg    4620
cctaccgtcg aatcaccggt aaccttataa gggattttgc cgatttcggc ctattggtta    4680
aaaaatgagc tgatttaaca aaaatttaac gcgaattaat tctgtggaat gtgtgtcagt    4740
tagggtgtgg aaagtcccca ggctcccag caggcagaag tatgcaaagc atgcatctca     4800
attagtcagc aaccaggtgt ggaaagtccc caggctcccc agcaggcaga agtatgcaaa    4860
gcatgcatct caattagtca gcaaccatag tcccgcccct aactccgccc atcccgcccc    4920
taactccgcc cagttccgcc cattctccgc cccatggctg actaatttt tttatttatg     4980 cagaggccga ggccgcctct gcctctgagc tattccagaa gtagtgagga ggcttttttg    5040
gaggcctagg cttttgcaaa aagctcccgg gagcttgtat atccattttc ggatctgatc    5100
```

```
aagagacagg atgaggatcg tttcgcatga ttgaacaaga tggattgcac gcaggttctc   5160
cggccgcttg ggtggagagg ctattcggct atgactgggc acaacagaca atcggctgct   5220
ctgatgccgc cgtgttccgg ctgtcagcgc aggggcgccc ggttctttt gtcaagaccg    5280
acctgtccgg tgccctgaat gaactgcagg acgaggcagc cgcgctatcg tggctggcca   5340
cgacgggcgt tccttgcgca gctgtgctcg acgttgtcac tgaagcggga agggactggc   5400
tgctattggg cgaagtgccg gggcaggatc tcctgtcatc tcaccttgct cctgccgaga   5460
aagtatccat catggctgat gcaatgcggc ggctgcatac gcttgatccg gctacctgcc   5520
cattcgacca ccaagcgaaa catcgcatcg agcgagcacg tactcggatg gaagccggtc   5580
ttgtcgatca ggatgatctg gacgaagagc atcaggggct cgcgccagcc gaactgttcg   5640
ccaggctcaa ggcgcgaatt cgagctcggt acccggggat cctctagagt cgacctgcag   5700
gcatgcaagc ttggcgtaat catggtcata gctgtttcct gtgtgaaatt gttatccgct   5760
cacaattcca cacaacatac gagccggaag cataaagtgt aaagcctggg gtgcctaatg   5820
agtgagctaa ctcacattaa ttgcgttgcg ctcactgccc gctttccagt cgggaaacct   5880
gtcgtgccag ctgcattaat gaatcggcca acgcgcgggg agaggcggtt tgcgtattgg   5940
gcgctcttcc gcttcctcgc tcactgactc gctgcgctcg gtcgttcggc tgcggcgagc   6000
ggtatcagct cactcaaagg cggtaatacg gttatccaca gaatcagggg ataacgcagg   6060
aaagaacatg tgagcaaaag gccagcaaaa ggccaggaac cgtaaaaagg ccgcgttgct   6120
ggcgtttttc cataggctcc gcccccctga cgagcatcac aaaaatcgac gctcaagtca   6180
gaggtggcga aacccgacag gactataaag ataccaggcg tttccccctg gaagctccct   6240
cgtgcgctct cctgttccga ccctgccgct taccggatac ctgtccgcct ttctcccttc   6300
gggaagcgtg gcgctttctc atagctcacg ctgtaggtat ctcagttcgg tgtaggtcgt   6360
tcgctccaag ctgggctgtg tgcacgaacc ccccgttcag cccgaccgct gcgccttatc   6420
cggtaactat cgtcttgagt ccaacccggt aagacacgac ttatcgccac tggcagcagc   6480
cactggtaac aggattagca gagcgaggta tgtaggcggt gctacagagt tcttgaagtg   6540
gtggcctaac tacggctaca ctagaaggac agtatttggt atctgcgctc tgctgaagcc   6600
agttaccttc ggaaaaagag ttggtagctc ttgatccggc aaacaaacca ccgctggtag   6660
cggtggtttt tttgtttgca agcagcagat tacgcgcaga aaaaaggat ctcaagaaga    6720
tcctttgatc ttttctacgg ggtctgacgc tcagtggaac gaaaactcac gttaagggat   6780
tttggtcatg agattatcaa aaaggatctt cacctagatc cttttaaatt aaaaatgaag   6840
ttttaaatca atctaaagta tatatgagta aacttggtct gacagttacc aatgcttaat   6900
cagtgaggca cctatctcag cgatctgtct atttcgttca tccatagttg cctgactccc   6960
cgtcgtgtag ataactacga tacgggaggg cttaccatct ggccccagtg ctgcaatgat   7020
accgcgagac ccacgctcac cggctccaga tttatcagca ataaaccagc cagccggaag   7080
ggccgagcgc agaagtggtc ctgcaacttt atccgcctcc atccagtcta ttaattgttg   7140
ccgggaagct agagtaagta gttcgccagt taatagtttg cgcaacgttg ttgccattgc   7200
tacaggcatc gtggtgtcac gctcgtcgtt tggtatggct tcattcagct ccggttccca   7260
acgatcaagg cgagttacat gatcccccat gttgtgcaaa aaagcggtta gctccttcgg   7320
tcctccgatc gttgtcagaa gtaagttggc cgcagtgtta tcactcatgg ttatggcagc   7380
actgcataat tctcttactg tcatgccatc cgtaagatgc ttttctgtga ctggtgagta   7440
```

```
ctcaaccaag tcattctgag aatagtgtat gcggcgaccg agttgctctt gcccggcgtc    7500
aatacgggat aataccgcgc cacatagcag aactttaaaa gtgctcatca ttggaaaacg    7560
ttcttcgggg cgaaaactct caaggatctt accgctgttg agatccagtt cgatgtaacc    7620
cactcgtgca cccaactgat cttcagcatc ttttactttc accagcgttt ctgggtgagc    7680
aaaaacagga aggcaaaatg ccgcaaaaaa gggaataagg gcgacacgga aatgttgaat    7740
actcatactc ttcctttttc aatattattg aagcatttat cagggttatt gtctcatgag    7800
cggatacata tttgaatgta tttagaaaaa taaacaaata ggggttccgc gcacatttcc    7860
ccgaaaagtg ccacctgacg tctaagaaac cattattatc atgacattaa cctataaaaa    7920
taggcgtatc acgaggccct ttcgtc                                         7946
```

<210> SEQ ID NO 48
<211> LENGTH: 1089
<212> TYPE: DNA
<213> ORGANISM: Homo sapiens

<400> SEQUENCE: 48

```
atgtcagaga acggctcctt cgccaactgc tgcgaggcgg gcgggtgggc agtgcgcccg      60
ggctggtcgg gggctggcag cgcgcggccc tccaggaccc ctcgacctcc ctgggtggct     120
ccagcgctgt ccgcggtgct catcgtcacc accgccgtgg acgtcgtggg caacctcctg     180
gtgatcctct ccgtgctcag gaaccgcaag ctccggaacg caggtaattt gttcttggtg     240
agtctggcat tggctgacct ggtggtggcc ttctacccct acccgctaat cctcgtggcc     300
atcttctatg acggctgggc cctggggag gagcactgca aggccagcgc ctttgtgatg     360
ggcctgagcg tcatcggctc tgtcttcaat atcactgcca tcgccattaa ccgctactgc     420
tacatctgcc acagcatggc ctaccaccga atctaccggc gctggcacac ccctctgcac     480
atctgcctca tctggctcct caccgtggtg gccttgctgc ccaacttctt tgtggggtcc     540
ctggagtacg acccacgcat ctattcctgc accttcatcc agaccgccag cacccagtac     600
acggcggcag tggtggtcat ccacttcctc ctccctatcg ctgtcgtgtc cttctgctac     660
ctgcgcatct gggtgctggt gcttcaggcc cgcaggaaag ccaagccaga gagcaggctg     720
tgcctgaagc ccagcgactt gcggagcttt ctaaccatgt ttgtggtgtt tgtgatcttt     780
gccatctgct gggctccact taactgcatc ggcctcgctg tggccatcaa cccccaagaa     840
atggctcccc agatccctga ggggctattt gtcactagct acttactggc ttatttcaac     900
agctgcctga atgccattgt ctatgggctc ttgaaccaaa acttccgcag ggaatacaag     960
aggatcctct tggccctttg gaacccacgg cactgcattc aagatgcttc caagggcagc    1020
cacgcggagg ggctgcagag cccagctcca cccatcattg gtgtgcagca ccaggcagat    1080
gctctctag                                                          1089
```

<210> SEQ ID NO 49
<211> LENGTH: 7982
<212> TYPE: DNA
<213> ORGANISM: Artificial Sequence
<220> FEATURE:
<223> OTHER INFORMATION: Description of Artificial Sequence: Synthetic
      pTV-DS-hMT2 polynucleotide

<400> SEQUENCE: 49

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

```
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ttaaggagcc ccttcgcctc    420
gtgcttgagt tgaggcctgg cttgggcgct ggggccgccg cgtgcgaatc tggtggcacc    480
ttcgcgcctg tctcgctgct ttcgataagt ctctagccat ttaaaatttt tgatgacctg    540
ctgcgacgct ttttttctgg caagatagtc ttgtaaatgc gggccaagat cgatctgcac    600
actggtattt cggttttttgg ggccgcgggc ggcgacgggg cccgtgcgtc ccagcgcaca    660
tgttcggcga ggcggggcct gcgagcgcgg ccaccgagaa tcggacgggg gtagtctcaa    720
gctggccggc ctgctctggt gcctggcctc gcgccgccgt gtatcgcccc gccctgggcg    780
gcaaggctgg cccggtcggc accagttgcg tgagcgaaaa gatggccgct tcccggccct    840
gctgcaggga gctcaaaatg gaggacgcgg cgctcgggag agcgggcggg tgagtcaccc    900
acacaaagga aagggccttt tccgtcctca gccgtcgctt catgtgactc cacggagtac    960
cgggcgccgt ccaggcacct cgattagttc tcgagctttt ggagtacgtc gtctttaggt   1020
tggggggagg ggttttatgc gatggagttt ccccacactg agtgggtgga gactgaagtt   1080
aggccagctt ggcacttgat gtaattctcc ttggaatttg ccctttttga gtttggatct   1140
tggttcattc tcaagcctca gacagtggtt caaagttttt ttcttccatt tcaggtgtcg   1200
tggaattggc tagagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgc cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
aaggaccgcg cacctggtgc atgacccgca agcccggtgc ctgacgcccg ccccacgacc   1920
cgcagcgccc gaccgaaagg agcgcacgac cccatggctc cgaccgaagc cgacccgggc   1980
ggccccgccg acccgcacc cgcccccgag gcccaccgac tctagaggat cataatcagc   2040
cataccacat ttgtagaggt tttacttgct taaaaaaacc tcccacacct ccccctgaac   2100
ctgaaacata aaatgaatgc aattgttgtt gttaacttgt ttattgcagc ttataatggt   2160
tacaaataaa gcaatagcat cacaaatttc acaaataaag catttttttc actgcattct   2220
agttgtggtt tgtccaaact catcaatgta tcttatcatg tctggatcct agcgtttaaa   2280
cttaagcttg gtaccgagct cggatccact agtaatggtt acaaataaag caatagcatc   2340
acaaatttca caaataaagc attttttttca ctgcattcta gttgtggttt gtccaaactc   2400
atcaatgtat cttatcatgt ctgtacgatg tacgggccag atatacgcgt tgacattgat   2460
tattgactag ttattaatag taatcaatta cggggtcatt agttcatagc ccatatatgg   2520
```

```
agttccgcgt tacataactt acggtaaatg gcccgcctgg ctgaccgccc aacgaccccc    2580
gcccattgac gtcaataatg acgtatgttc ccatagtaac gccaataggg actttccatt    2640
gacgtcaatg ggtggagtat ttacggtaaa ctgcccactt ggcagtacat caagtgtatc    2700
atatgccaag tacgccccct attgacgtca atgacggtaa atggcccgcc tggcattatg    2760
cccagtacat gaccttatgg gactttccta cttggcagta catctacgta ttagtcatcg    2820
ctattaccat ggtgatgcgg ttttggcagt acatcaatgg gcgtggatag cggtttgact    2880
cacggggatt tccaagtctc cacccccattg acgtcaatgg gagtttgttt tggcaccaaa    2940
atcaacggga ctttccaaaa tgtcgtaaca actccgcccc attgacgcaa atgggcggta    3000
ggcgtgtacg gtgggaggtc tatataagca gagctctctg gctaactaga acccactg     3060 cttactggct tatcgaaatt aatacgactc actataggga gacccaagct ggctagccac    3120
catgtcagag aacggctcct tcgccaactg ctgcgaggcg ggcgggtggg cagtgcgccc    3180
gggctggtcg gggctggca gcgcgcggcc ctccaggacc cctcgacctc cctgggtggc    3240
tccagcgctg tccgcggtgc tcatcgtcac caccgccgtg gacgtcgtgg caacctcct    3300 ggtgatcctc tccgtgctca ggaaccgcaa gctccggaac gcaggtaatt tgttcttggt    3360
gagtctggca ttggctgacc tggtggtggc cttctacccc tacccgctaa tcctcgtggc    3420
catcttctat gacggctggg ccctggggga ggagcactgc aaggccagcg cctttgtgat    3480
gggcctgagc gtcatcggct ctgtcttcaa tatcactgcc atcgccatta accgctactg    3540
ctacatctgc cacagcatgg cctaccaccg aatctaccgg cgctggcaca cccctctgca    3600
catctgcctc atctggctcc tcaccgtggt ggccttgctg cccaacttct tgtggggtc     3660 cctggagtac gacccacgca tctattcctg caccttcatc cagaccgcca gcacccagta    3720
cacggcggca gtggtggtca tccacttcct cctccctatc gctgtcgtgt ccttctgcta    3780
cctgcgcatc tgggtgctgg tgcttcaggc ccgcaggaaa gccaagcagg agagcaggct    3840
gtgcctgaag cccagcgact gcggagcttt tctaaccatg tttgtggtgt ttgtgatctt    3900
tgccatctgc tgggctccac ttaactgcat cggcctcgct gtggccatca acccccaaga    3960
aatggctccc cagatccctg aggggctatt tgtcactagc tacttactgg cttatttcaa    4020
cagctgcctg aatgccattg tctatgggct cttgaaccaa aacttccgca gggaatacaa    4080
gaggatcctc ttgccctttt ggaacccacg cactgcatt caagatgctt ccaagggcag    4140
ccacgcggag ggctgcaga gcccagctcc acccatcatt ggtgtgcagc accaggcaga    4200
tgctctctag gcggccgctc gagtctagag gcccgttta aacccgctga tcagcctcga    4260
ctgtgccttc tagttgccag ccatctgttg tttgcccctc cccgtgcct tccttgaccc    4320 tggaaggtgc cactcccact gtcctttcct aataaaatga ggaaattgca tcgcattgtc    4380
tgagtaggtg tcattctatt ctggggggtg gggtggggca ggacagcaag ggggaggatt    4440
gggaagacaa tagcaggcat gctggggatg cggtgggctc tatggcttct gaggcggaaa    4500
gaaccagctg gggctctagg gggtatcccc acgcgccctg tagcggcgca ttaagcgcgg    4560
cgggtgtggt ggttacgcgc agcgtgaccg ctacacttgc cagcgcccta gcgcccgctc    4620
ctttcgcttt cttcccttcc tttctcgcca cgttcgccta ccgtcgaatc accgtaacc     4680 ttataaggga ttttgccgat ttcggcctat tggttaaaaa atgagctgat ttaacaaaaa    4740
tttaacgcga attaattctg tggaatgtgt gtcagttagg gtgtgaaag tcccaggct      4800 ccccagcagg cagaagtatg caaagcatgc atctcaatta gtcagcaacc aggtgtggaa    4860
```

```
agtccccagg ctccccagca ggcagaagta tgcaaagcat gcatctcaat tagtcagcaa    4920
ccatagtccc gccoctaact ccgcccatcc cgccoctaac tccgcccagt tccgcccatt    4980
ctccgcccca tggctgacta attttttta  tttatgcaga ggccgaggcc gcctctgcct    5040
ctgagctatt ccagaagtag tgaggaggct tttttggagg cctaggcttt tgcaaaaagc    5100
tcccgggagc ttgtatatcc attttcggat ctgatcaaga gacaggatga ggatcgtttc    5160
gcatgattga acaagatgga ttgcacgcag gttctccggc cgcttgggtg gagaggctat    5220
tcggctatga ctgggcacaa cagacaatcg gctgctctga tgccgccgtg ttccggctgt    5280
cagcgcaggg cgcccggtt  cttttgtca  gaccgacct  gtccggtgcc ctgaatgaac    5340
tgcaggacga ggcagcgcgg ctatcgtggc tggccacgac gggcgttcct tgcgcagctg    5400
tgctcgacgt tgtcactgaa gcgggaaggg actggctgct attgggcgaa gtgccggggc    5460
aggatctcct gtcatctcac cttgctcctg ccgagaaagt atccatcatg gctgatgcaa    5520
tgcggcggct gcatacgctt gatccggcta cctgcccatt cgaccaccaa gcgaaacatc    5580
gcatcgagcg agcacgtact cggatggaag ccggtcttgt cgatcaggat gatctggacg    5640
aagagcatca ggggctcgcg ccagccgaac tgttcgccag gctcaaggcg cgaattcgag    5700
ctcggtaccc ggggatcctc tagagtcgac ctgcaggcat gcaagcttgg cgtaatcatg    5760
gtcatagctg tttcctgtgt gaaattgtta tccgctcaca attccacaca acatacgagc    5820
cggaagcata aagtgtaaag cctggggtgc ctaatgagtg agctaactca cattaattgc    5880
gttgcgctca ctgcccgctt tccagtcggg aaacctgtcg tgccagctgc attaatgaat    5940
cggccaacgc gcggggagag gcggtttgcg tattgggcgc tcttccgctt cctcgctcac    6000
tgactcgctg cgctcggtcg ttcggctgcg gcgagcggta tcagctcact caaaggcggt    6060
aatacggtta tccacagaat caggggataa cgcaggaaag aacatgtgag caaaaggcca    6120
gcaaaaggcc aggaaccgta aaaaggccgc gttgctggcg tttttccata ggctccgccc    6180
ccctgacgag catcacaaaa atcgacgctc aagtcagagg tggcgaaacc cgacaggact    6240
ataaagatac caggcgtttc ccoctggaag ctccctcgtg cgctctcctg ttccgaccct    6300
gccgcttacc ggatacctgt ccgcctttct cccttcggga agcgtggcgc tttctcatag    6360
ctcacgctgt aggtatctca gttcggtgta ggtcgttcgc tccaagctgg gctgtgtgca    6420 cgaaccccc  gttcagcccg accgctgcgc cttatccggt aactatcgtc ttgagtccaa    6480
cccggtaaga cacgacttat cgccactggc agcagccact ggtaacagga ttagcagagc    6540
gaggtatgta ggcggtgcta cagagttctt gaagtggtgg cctaactacg gctacactag    6600
aaggacagta tttggtatct gcgctctgct gaagccagtt accttcggaa aaagagttgg    6660
tagctcttga tccggcaaac aaaccaccgc tggtagcggt ggtttttttg tttgcaagca    6720
gcagattacg cgcagaaaaa aaggatctca agaagatcct ttgatctttt ctacggggtc    6780
tgacgctcag tggaacgaaa actcacgtta agggattttg gtcatgagat tatcaaaaag    6840
gatcttcacc tagatccttt taaattaaaa atgaagtttt aaatcaatct aaagtatata    6900
tgagtaaact tggtctgaca gttaccaatg cttaatcagt gaggcaccta tctcagcgat    6960
ctgtctattt cgttcatcca tagttgcctg actccccgtc gtgtagataa ctacgatacg    7020
ggagggctta ccatctggcc ccagtgctgc aatgataccg cgagacccac gctcaccggc    7080
tccagattta tcagcaataa accagccagc cggaagggcc gagcgcagaa gtggtcctgc    7140
aactttatcc gcctccatcc agtctattaa ttgttgccgg gaagctagag taagtagttc    7200
gccagttaat agtttgcgca acgttgttgc cattgctaca ggcatcgtgg tgtcacgctc    7260
```

```
gtcgtttggt atggcttcat tcagctccgg ttcccaacga tcaaggcgag ttacatgatc    7320
ccccatgttg tgcaaaaaag cggttagctc cttcggtcct ccgatcgttg tcagaagtaa    7380
gttggccgca gtgttatcac tcatggttat ggcagcactg cataattctc ttactgtcat    7440
gccatccgta agatgctttt ctgtgactgg tgagtactca accaagtcat tctgagaata    7500
gtgtatgcgg cgaccgagtt gctcttgccc ggcgtcaata cgggataata ccgcgccaca    7560
tagcagaact ttaaaagtgc tcatcattgg aaaacgttct cggggcgaaa actctcaag     7620 gatcttaccg ctgttgagat ccagttcgat gtaacccact cgtgcaccca actgatcttc    7680
agcatctttt actttcacca gcgtttctgg gtgagcaaaa acaggaaggc aaaatgccgc    7740
aaaaaaggga ataagggcga cacggaaatg ttgaatactc atactcttcc tttttcaata    7800
ttattgaagc atttatcagg gttattgtct catgagcgga tacatatttg aatgtattta    7860
gaaaaataaa caaataggg ttccgcgcac atttccccga aaagtgccac ctgacgtcta     7920
agaaaccatt attatcatga cattaaccta taaaaatagg cgtatcacga ggccctttcg    7980
tc                                                                    7982

<210> SEQ ID NO 50
<211> LENGTH: 1386
<212> TYPE: DNA
<213> ORGANISM: Homo sapiens

<400> SEQUENCE: 50
atgggatgga gctgtatcat cctgttcctc gtggccacag caaccggtgt ccacagccag      60
gtgcagctac agcagtgggg cgcaggactg ttgaagcctt cggagaccct gtccctcacc     120
tgcgctgtct atggtgggtc cttcagtgct tactactgga gctggatccg ccagccccca     180 gggaagggc tggagtggat tggggacatc aatcatggtg gaggcaccaa ctacaacccg      240
tccctcaaga gtcgagtcac catatcagta gacacgtcca agaaccagtt ctccctgaag     300
ctgaactctg taaccgccgc ggacacggct gtgtattact gtgcgagcct aactgcctac     360
tggggccagg gaagcctggt caccgtctcc tcagctagca ccaagggccc atcggtcttc     420
cccctggcac cctcctccaa gagcacctct ggggggcacag cggccctggg ctgcctggtc     480
aaggactact ccccgaacc ggtgacggtg tcgtggaact caggcgccct gaccagcggc     540
gtgcacacct tccggccgt cctacagtcc tcaggactct actccctcag cagcgtggtg     600
accgtgccct ccagcagctt gggcacccag acctacatct gcaacgtgaa tcacaagccc     660
agcaacacca aggtggacaa gagagttgag cccaaatctt gtgacaaaac tcacacatgc     720
ccaccgtgcc cagcacctga actcctgggg ggaccgtcag tcttcctctt ccccccaaaa    780
cccaaggaca cctcatgat ctcccggacc cctgaggtca catgcgtggt ggtggacgtg     840
agccacgaag accctgaggt caagttcaac tggtacgtgg acggcgtgga ggtgcataat     900
gccaagacaa agccgcggga ggagcagtac aacagcacgt accgtgtggt cagcgtcctc     960
accgtcctgc accaggactg gctgaatggc aaggagtaca agtgcaaggt ctccaacaaa    1020
gccctcccag cccccatcga gaaaaccatc tccaaagcca aagggcagcc ccgagaacca    1080
caggtgtaca ccctgccccc atcccgggat gagctgacca agaaccaggt cagcctgacc    1140
tgcctggtca aaggcttcta tcccagcgac atcgccgtgg agtgggagag caatgggcag    1200
ccggagaaca actacaagac cacgcctccc gtgctggact ccgacggctc cttcttcctc    1260
tacagcaagc tcaccgtgga caagagcagg tggcagcagg ggaacgtctt ctcatgctcc    1320
```

|  |  |
|---|---|
| gtgatgcatg aggctctgca caaccactac acgcagaaga gcctctccct gtctccgggt | 1380 |
| aaatga | 1386 |

<210> SEQ ID NO 51
<211> LENGTH: 702
<212> TYPE: DNA
<213> ORGANISM: Homo sapiens

<400> SEQUENCE: 51

|  |  |
|---|---|
| atgggatgga gctgtatcat cctgttcctc gtggccacag caaccggtgt ccacagcgac | 60 |
| atccagatga cccagtctcc aacctcactg tctgcatctg taggagacag agtcaccatc | 120 |
| acttgtcggg cgagtcaggg tattagcagc tggttaacct ggtatcagca gaaaccagag | 180 |
| aaagccccta agtccctgat ctatgctgca tccagtttgc aaagtggggt cccatcaagg | 240 |
| ttcagcggca gtggatctgg gacagatttc actctcacca tcagcagcct gcagcctgaa | 300 |
| gattttgcaa cttattactg ccaacagtat gatagttacc ctatcacctt cggccaaggg | 360 |
| acacgactgg agattaaacg tacggtggcg gcgccatctg tcttcatctt cccgccatct | 420 |
| gatgagcagt tgaaatctgg aactgcctct gttgtgtgcc tgctgaataa cttctatccc | 480 |
| agagaggcca aagtacagtg gaaggtggat aacgccctcc aatcgggtaa ctcccaggag | 540 |
| agtgtcacag agcaggacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgtt ag | 702 |

<210> SEQ ID NO 52
<211> LENGTH: 1212
<212> TYPE: DNA
<213> ORGANISM: Homo sapiens

<400> SEQUENCE: 52

|  |  |
|---|---|
| ggcctccgcg ccgggttttg gcgcctcccg cgggcgcccc cctcctcacg gcgagcgctg | 60 |
| ccacgtcaga cgaagggcgc agcgagcgtc ctgatccttc cgcccggacg ctcaggacag | 120 |
| cggcccgctg ctcataagac tcggccttag aaccccagta tcagcagaag gacattttag | 180 |
| gacgggactt gggtgactct agggcactgg ttttctttcc agagagcgga acaggcgagg | 240 |
| aaaagtagtc ccttctcggc gattctgcgg agggatctcc gtggggcggt gaacgccgat | 300 |
| gattatataa ggacgcgccg ggtgtggcac agctagttcc gtcgcagccg ggatttgggt | 360 |
| cgcggttctt gtttgtggat cgctgtgatc gtcacttggt gagtagcggg ctgctgggct | 420 |
| ggccggggct ttcgtggccg ccgggccgct cggtgggacg gaagcgtgtg gagagaccgc | 480 |
| caagggctgt agtctgggtc cgcgagcaag gttgccctga actgggggtt gggggagcg | 540 |
| cagcaaaatg gcggctgttc ccgagtcttg aatggaagac gcttgtgagg cgggctgtga | 600 |
| ggtcgttgaa acaaggtggg gggcatggtg gcggcaagaa acccaaggtc ttgaggcctt | 660 |
| cgctaatgcg ggaaagctct tattcgggtg agatgggctg gggcaccatc tggggaccct | 720 |
| gacgtgaagt ttgtcactga ctggagaact cggtttgtcg tctgttgcgg gggcggcagt | 780 |
| tatggcggtg ccgttgggca gtgcaccgt acctttggga gcgcgcgccc tcgtcgtgtc | 840 |
| gtgacgtcac ccgttctgtt ggcttataat gcagggtggg gccacctgcc ggtaggtgtg | 900 |
| cggtaggctt ttctccgtcg caggacgcag ggttcgggcc tagggtaggc tctcctgaat | 960 |
| cgacaggcgc cggacctctg gtgagggag ggataagtga ggcgtcagtt tctttggtcg | 1020 |
| gttttatgta cctatcttct taagtagctg aagctccggt tttgaactat gcgctcgggg | 1080 |

```
ttggcgagtg tgttttgtga agttttttag gcaccttttg aaatgtaatc atttgggtca    1140
atatgtaatt ttcagtgtta gactagtaaa ttgtccgcta aattctggcc gttttttggct   1200 tttttgttag ac                                                        1212

<210> SEQ ID NO 53
<211> LENGTH: 12640
<212> TYPE: DNA
<213> ORGANISM: Artificial Sequence
<220> FEATURE:
<223> OTHER INFORMATION: Description of Artificial Sequence: Synthetic
      pTV-DS-5F11 polynucleotide

<400> SEQUENCE: 53
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ttaaggagcc cttcgcctc    420 gtgcttgagt tgaggcctgg cttgggcgct ggggccgccg cgtgcgaatc tggtggcacc    480
ttcgcgcctg tctcgctgct ttcgataagt ctctagccat ttaaaatttt tgatgacctg    540
ctgcgacgct ttttttctgg caagatagtc ttgtaaatgc gggccaagat cgatctgcac    600 actggtatt cggttttgg ggccgcgggc ggcgacgggg cccgtgcgtc ccagcgcaca     660
tgttcggcga ggcggggcct gcgagcgcgg ccaccgagaa tcggacgggg gtagtctcaa    720
gctggccggc ctgctctggt gcctggcctc gcgccgccgt gtatcgcccc gccctgggcg    780
gcaaggctgg cccggtcggc accagttgcg tgagcgaaa gatggccgct tcccggccct     840
gctgcaggga gctcaaaatg gaggacgcgg cgctcgggag agcgggcggg tgagtcaccc    900
acacaaagga aaagggcctt tccgtcctca gccgtcgctt catgtgactc cacggagtac    960
cgggcgccgt ccaggcacct cgattagttc tcgagctttt ggagtacgtc gtctttaggt   1020
tggggggagg ggttttatgc gatggagttt ccccacactg agtgggtgga gactgaagtt   1080
aggccagctt ggcacttgat gtaattctcc ttggaatttg ccctttttga gtttggatct   1140
tggttcattc tcaagcctca gacagtggtt caaagttttt ttcttccatt tcaggtgtcg   1200
tggaattggc tagagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgg cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
```

```
aaggaccgcg cacctggtgc atgacccgca agcccggtgc ctgacgcccg ccccacgacc    1920
cgcagcgccc gaccgaaagg agcgcacgac cccatggctc cgaccgaagc cgacccgggc    1980
ggccccgccg accccgcacc cgcccccgag gcccaccgac tctagaggat cataatcagc    2040
cataccacat ttgtagaggt tttacttgct ttaaaaaacc tcccacacct ccccctgaac    2100
ctgaaacata aaatgaatgc aattgttgtt gttaacttgt ttattgcagc ttataatggt    2160
tacaaataaa gcaatagcat cacaaatttc acaaataaag cattttttc actgcattct     2220
agttgtggtt tgtccaaact catcaatgta tcttatcatg tctggatcct agcgtttaaa    2280
cttaagcttg gtaccgagct cggatccact agtaatggtt acaaataaag caatagcatc    2340
acaaatttca caaataaagc atttttttca ctgcattcta gttgtggttt gtccaaactc    2400
atcaatgtat cttatcatgt ctgtacgatg tacgggccag atatacgcgc gaggcctccg    2460
cgccgggttt tggcgcctcc cgcgggcgcc cccctcctca cggcgagcgc tgccacgtca    2520
gacgaagggc gcagcgagcg tcctgatcct tccgcccgga cgctcaggac agcggcccgc    2580
tgctcataag actcggcctt agaaccccag tatcagcaga aggacatttt aggacgggac    2640
ttgggtgact ctagggcact ggttttcttt ccagagagcg gaacaggcga ggaaaagtag    2700
tcccttctcg gcgattctgc ggagggatct ccgtggggcg gtgaacgccg atgattatat    2760
aaggacgcgc cgggtgtggc acagctagtt ccgtcgcagc cgggatttgg gtcgcggttc    2820
ttgtttgtgg atcgctgtga tcgtcacttg gtgagtagcg ggctgctggg ctggccgggg    2880
ctttcgtggc cgccgggccg ctcggtggga cggaagcgtg tggagagacc gccaagggct    2940
gtagtctggg tccgcgagca aggttgccct gaactggggg ttgggggag cgcagcaaaa     3000
tggcggctgt tcccgagtct tgaatggaag acgcttgtga ggcgggctgt gaggtcgttg    3060
aaacaaggtg gggggcatgg tgggcggcaa gaacccaagg tcttgaggcc ttcgctaatg    3120
cgggaaagct cttattcggg tgagatgggc tggggcacca tctggggacc ctgacgtgaa    3180
gtttgtcact gactggagaa ctcggtttgt cgtctgttgc gggggcggca gttatggcgg    3240
tgccgttggg cagtgcaccc gtacctttgg gagcgcgcgc cctcgtcgtg tcgtgacgtc    3300
acccgttctg ttggcttata atgcagggtg gggccacctg ccggtaggtg tgcggtaggc    3360
ttttctccgt cgcaggacgc agggttcggg cctagggtag gctctcctga atcgacaggc    3420
gccggacctc tggtgagggg agggataagt gaggcgtcag tttctttggt cggttttatg    3480
tacctatctt cttaagtagc tgaagctccg gttttgaact atgcgctcgg ggttggcgag    3540
tgtgttttgt gaagttttt aggcaccttt tgaaatgtaa tcatttgggt caatatgtaa      3600
ttttcagtgt tagactagta aattgtccgc taaattctgg ccgttttgg ctttttgtt       3660
agacagatct gtttaaactt aagcttgccg ccaccatggg atggagctgt atcatcctgt    3720
tcctcgtggc cacagcaacc ggtgtccaca gcgacatcca gatgacccag tctccaacct    3780
cactgtctgc atctgtagga gacagagtca ccatcacttg tcgggcgagt cagggtatta    3840
gcagctggtt aacctggtat cagcagaaac cagagaaagc ccctaagtcc ctgatctatg    3900
ctgcatccag tttgcaaagt ggggtcccat caaggttcag cggcagtgga tctgggacag    3960
atttcactct caccatcagc agcctgcagc ctgaagattt tgcaacttat tactgccaac    4020
agtatgatag ttaccctatc accttcggcc aagggacacg actggagatt aaacgtacgg    4080
tggcggcgcc atctgtcttc atcttcccgc catctgatga gcagttgaaa tctggaactg    4140
cctctgttgt gtgcctgctg aataacttct atcccagaga ggccaaagta cagtggaagg    4200
```

-continued

```
tggataacgc cctccaatcg ggtaactccc aggagagtgt cacagagcag gacagcaagg    4260
acagcaccta cagcctcagc agcaccctga cgctgagcaa agcagactac gagaaacaca    4320
aagtctacgc ctgcgaagtc acccatcagg gcctgagctc gcccgtcaca aagagcttca    4380
acaggggaga gtgttaggga tccatctaga agggagaagt gcccccacct gctcctcagt    4440
tccagcctga cccctccca tcctttggcc tctgacccctt tttccacagg ggacctaccc    4500
ctattgcggt cctccagctc atctttcacc tcacccccct cctcctcctt ggctttaatt    4560
atgctaatgt tggaggagaa tgaataaata aagtgaatct ttgcacctgt ggtttctctc    4620
tttcctcatt taataattat tatctgttgt tttaccaact actcaatttc tcttataagg    4680
gactaaatat gtagtcatcc taaggcgcat aaccatttat aaaaatcatc cttcattcta    4740
ttttacccta tcatcctctg caagacagtc ctccctcaaa cccacaagcc ttctgtcctc    4800
acagtcccct gggccatcgg accgctatca ggacatagcg ttggctaccc gtgatattgc    4860
tgaagagctt ggcggcgaat gggctgaccg cttcctcgtg ctttacggta tcgccgctcc    4920
cgattcgcag cgcatcgcct tctatcgcct tcttgacgag ttcttctgag cgggactctg    4980
gggttcgaaa tgaccgacca agcgacgccc aacctgccat cacgagattt cgattccacc    5040
gccgccttct atgaaaggtt gggcttcgga atcgttttcc gggacgccgg ctggatgatc    5100
ctccagcgcg ggatctcat gctggagttc ttcgcccacc ccaacttgtt tattgcagct    5160
tataatggtt acaaataaag caatagcatc acaaatttca caaataaagc attttttca    5220 ctgcattcta gttgtggttt gtccaaactc atcaatgtat cttatcatgt ctgtataccg    5280
tcgacctcta gctagagctt ggcgtaatca tggtcatagc tgtttcctgt gtgaaattgt    5340
tatccgctca caattccaca acatacga gccggaagca taagtgtaa agcctggggt    5400 gcctaatgag tgagctaact cacattaatt gcgttgcgct cactgcccgc tttccagtcg    5460
ggaaacctgt cgtgccagct gcattaatga atcggccaac gcgcggggag aggcggtttg    5520
cgtattgggc gctcttccgc ttcctcgctc actgactcgc tgcgctcggt cgttcggctg    5580
cggcgagcgg tatcagctca ctcaaaggcg gtaatacggt tatccacaga atcaggggat    5640
aacgcaggaa agaacatgcg aggcctccgc gccgggtttt ggcgcctccc gcgggcgccc    5700
ccctcctcac ggcgagcgct gccacgtcag acgaagggcg cagcgagcgt cctgatcctt    5760
ccgcccggac gctcaggaca gcggcccgct gctcataaga ctcggcctta gaaccccagt    5820
atcagcagaa ggacatttta ggacgggact tgggtgactc tagggcactg gttttctttc    5880
cagagagcgg aacaggcgag gaaaagtagt cccttctcgg cgattctgcg gagggatctc    5940
cgtggggcgg tgaacgccga tgattatata aggacgcgcc gggtgtggca cagctagttc    6000
cgtcgcagcc gggatttggg tcgcggttct tgtttgtgga tcgctgtgat cgtcacttgg    6060
tgagtagcgg gctgctgggc tggccggggc tttcgtggcc gccgggccgc tcggtgggac    6120
ggaagcgtgt ggagagaccg ccaagggctg tagtctgggt ccgcgagcaa ggttgccctg    6180
aactgggggt tggggggagc gcagcaaaat ggcggctgtt cccgagtctt gaatggaaga    6240
cgcttgtgag gcgggctgtg aggtcgttga acaaggtgg ggggcatggt gggcggcaag    6300
aacccaaggt cttgaggcct tcgctaatgc gggaaagctc ttattcgggt gagatgggct    6360
ggggcaccat ctggggaccc tgacgtgaag tttgtcactg actggagaac tcggtttgtc    6420
gtctgttgcg ggggcggcag ttatggcggt gccgttgggc agtgcacccg tacctttggg    6480 agcgcgcgc ctcgtcgtgt cgtgacgtca cccgttctgt tggcttataa tgcagggtgg    6540
ggccacctgc cggtaggtgt gcggtaggct tttctccgtc gcaggacgca gggttcgggc    6600
```

```
ctagggtagg ctctcctgaa tcgacaggcg ccggacctct ggtgagggga gggataagtg    6660
aggcgtcagt ttctttggtc ggttttatgt acctatcttc ttaagtagct gaagctccgg    6720
ttttgaacta tgcgctcggg gttggcgagt gtgttttgtg aagttttta ggcacctttt     6780 gaaatgtaat catttgggtc aatatgtaat tttcagtgtt agactagtaa attgtccgct    6840
aaattctggc cgttttggc ttttttgtta gacagatctg tttaaactta agcttgccgc     6900
caccatggga tggagctgta tcatcctgtt cctcgtggcc acagcaaccg gtgtccacag    6960
ccaggtgcag ctacagcagt ggggcgcagg actgttgaag ccttcggaga ccctgtccct    7020
cacctgcgct gtctatggtg ggtccttcag tgcttactac tggagctgga tccgccagcc    7080
cccagggaag gggctggagt ggattgggga catcaatcat ggtggaggca ccaactacaa    7140
cccgtccctc aagagtcgag tcaccatatc agtagacacg tccaagaacc agttctccct    7200
gaagctgaac tctgtaaccg ccgcggacac ggctgtgtat tactgtgcga gcctaactgc    7260 ctactgggc cagggaagcc tggtcaccgt ctcctcagct agcaccaagg gcccatcggt     7320 cttcccctg gcaccctcct ccaagagcac ctctgggggc acagcggccc tgggctgcct     7380
ggtcaaggac tacttccccg aaccggtgac ggtgtcgtgg aactcaggcg ccctgaccag    7440
cggcgtgcac accttcccgg ccgtcctaca gtcctcagga ctctactccc tcagcagcgt    7500
ggtgaccgtg ccctccagca gcttgggcac ccagacctac atctgcaacg tgaatcacaa    7560
gcccagcaac accaaggtgg acaagagagt tgagcccaaa tcttgtgaca aaactcacac    7620
atgcccaccg tgcccagcac ctgaactcct ggggggaccg tcagtcttcc tcttccccc    7680 aaaacccaag gacaccctca tgatctcccg gacccctgag gtcacatgcg tggtggtgga    7740
cgtgagccac gaagaccctg aggtcaagtt caactggtac gtggacggcg tggaggtgca    7800
taatgccaag acaaagccgc gggaggagca gtacaacagc acgtaccgtg tggtcagcgt    7860
cctcaccgtc ctgcaccagg actggctgaa tggcaaggag tacaagtgca aggtctccaa    7920
caaagccctc ccagccccca tcgagaaaac catctccaaa gccaaagggc agccccgaga    7980
accacaggtg tacaccctgc ccccatcccg ggatgagctg accaagaacc aggtcagcct    8040
gacctgcctg gtcaaaggct tctatcccag cgacatcgcc gtggagtggg agagcaatgg    8100
gcagccggag aacaactaca agaccacgcc tcccgtgctg gactccgacg gctccttctt    8160
cctctacagc aagctcaccg tggacaagag caggtggcag caggggaacg tcttctcatg    8220
ctccgtgatg catgaggctc tgcacaacca ctacacgcag aagagcctct ccctgtctcc    8280
gggtaaatga gtgcgacggc cggcaaggga tccagggga gtgttagag ggagaagtgc      8340 ccccacctgc tcctcagttc cagcctgacc ccctcccatc ctttggcctc tgaccctttt    8400
tccacagggg acctaccct attgcggtcc tccagctcat ctttcacctc accccctcc     8460 tcctccttgg ctttaattat gctaatgttg gaggagaatg aataaataaa gtgaatcttt    8520
gcacctgtgg tttctctctt tcctcattta ataattatta tctgttgttt taccaactac    8580
tcaatttctc ttataaggga ctaaatatgt agtcatccta aggcgcataa ccatttataa    8640
aaatcatcct tcattctatt ttaccctatc atcctctgca agacagtcct ccctcaaacc    8700
cacaagcctt ctgtcctcac agtcccctgg gccatgtgag caaaaggcca gcaaaggcc     8760 aggaaccgta aaaaggccgc gttgctggcg ttttttccata ggctccgccc cctgacgag    8820 catcacaaaa atcgacgctc aagtcagagg tggcgaaacc cgatagttgc ggccgctcga    8880
gtctagaggg cccgtttaaa cccgctgatc agcctcgact gtgccttcta gttgccagcc    8940
```

```
atctgttgtt tgcccctccc ccgtgccttc cttgaccctg gaaggtgcca ctcccactgt    9000
cctttcctaa taaaatgagg aaattgcatc gcattgtctg agtaggtgtc attctattct    9060 gggggggtggg gtggggcagg acagcaaggg ggaggattgg gaagacaata gcaggcatgc    9120
tggggatgcg gtgggctcta tggcttctga ggcggaaaga accagctggg gctctagggg    9180
gtatccccac gcgccctgta gcggcgcatt aagcgcggcg ggtgtggtgg ttacgcgcag    9240
cgtgaccgct acacttgcca gcgccctagc gcccgctcct ttcgcttttct tcccttcctt    9300 tctcgccacg ttcgcctacc gtcgaatcac cggtaacctt ataagggatt ttgccgattt    9360
cggcctattg gttaaaaaat gagctgattt aacaaaaatt taacgcgaat taattctgtg    9420
gaatgtgtgt cagttagggt gtggaaagtc cccaggctcc ccagcaggca gaagtatgca    9480
aagcatgcat ctcaattagt cagcaaccag gtgtggaaag tccccaggct ccccagcagg    9540
cagaagtatg caaagcatgc atctcaatta gtcagcaacc atagtcccgc ccctaactcc    9600
gcccatcccg cccctaactc cgcccagttc cgcccattct ccgccccatg gctgactaat    9660 ttttttatt tatgcagagg ccgaggccgc ctctgcctct gagctattcc agaagtagtg    9720
aggaggcttt tttggaggcc taggcttttg caaaaagctc ccgggagctt gtatatccat    9780
tttcggatct gatcaagaga caggatgagg atcgtttcgc atgattgaac aagatggatt    9840
gcacgcaggt tctccggccg cttgggtgga gaggctattc ggctatgact gggcacaaca    9900
gacaatcggc tgctctgatg ccgccgtgtt ccggctgtca gcgcaggggc gcccggttct    9960
ttttgtcaag accgacctgt ccggtgccct gaatgaactg caggacgagg cagcgcggct   10020
atcgtggctg gccacgacgg gcgttccttg cgcagctgtg ctcgacgttg tcactgaagc   10080
gggaagggac tggctgctat tgggcgaagt gccggggcag gatctcctgt catctcacct   10140
tgctcctgcc gagaaagtat ccatcatggc tgatgcaatg cggcggctgc atacgcttga   10200
tccggctacc tgcccattcg accaccaagc gaaacatcgc atcgagcgag cacgtactcg   10260 gatgaagcc ggtcttgtcg atcaggatga tctggacgaa gagcatcagg ggctcgcgcc   10320
agccgaactg ttcgccaggc tcaaggcgcg aattcgagct cggtacccgg ggatcctcta   10380
gagtcgacct gcaggcatgc aagcttggcg taatcatggt catagctgtt tcctgtgtga   10440
aattgttatc cgctcacaat tccacacaac atacgagccg gaagcataaa gtgtaaagcc   10500
tggggtgcct aatgagtgag ctaactcaca ttaattgcgt tgcgctcact gcccgctttc   10560
cagtcgggaa acctgtcgtg ccagctgcat taatgaatcg gccaacgcgc ggggagaggc   10620
ggtttgcgta ttgggcgctc ttccgcttcc tcgctcactg actcgctgcg ctcggtcgtt   10680
cggctgcggc gagcggtatc agctcactca aaggcggtaa tacggttatc cacagaatca   10740
ggggataacg caggaaagaa catgtgagca aaaggccagc aaaaggccag gaaccgtaaa   10800
aaggccgcgt tgctggcgtt tttccatagg ctccgccccc ctgacgagca tcacaaaaat   10860
cgacgctcaa gtcagaggtg gcgaaacccg acaggactat aaagatacca ggcgtttccc   10920
cctggaagct ccctcgtgcg ctctcctgtt ccgaccctgc cgcttaccgg atacctgtcc   10980
gcctttctcc cttcgggaag cgtggcgctt tctcatagct cacgctgtag gtatctcagt   11040
tcggtgtagg tcgttcgctc caagctgggc tgtgtgcacg aaccccccgt tcagcccgac   11100
cgctgcgcct tatccggtaa ctatcgtctt gagtccaacc cggtaagaca cgacttatcg   11160
ccactggcag cagccactgg taacaggatt agcagagcga ggtatgtagg cggtgctaca   11220
gagttcttga agtggtggcc taactacggc tacactagaa ggacagtatt tggtatctgc   11280
gctctgctga agccagttac cttcggaaaa agagttggta gctcttgatc cggcaaacaa   11340
```

-continued

```
accaccgctg gtagcggtgg ttttttttgtt tgcaagcagc agattacgcg cagaaaaaaa    11400
ggatctcaag aagatccttt gatcttttct acggggtctg acgctcagtg gaacgaaaac    11460
tcacgttaag ggattttggt catgagatta tcaaaaagga tcttcaccta gatcctttta    11520
aattaaaaat gaagttttaa atcaatctaa agtatatatg agtaaacttg gtctgacagt    11580
taccaatgct taatcagtga ggcacctatc tcagcgatct gtctatttcg ttcatccata    11640
gttgcctgac tccccgtcgt gtagataact acgatacggg agggcttacc atctggcccc    11700
agtgctgcaa tgataccgcg agacccacgc tcaccggctc cagatttatc agcaataaac    11760
cagccagccg aagggccga cgcagaagt ggtcctgcaa ctttatccgc ctccatccag    11820
tctattaatt gttgccggga agctagagta agtagttcgc cagttaatag tttgcgcaac    11880
gttgttgcca ttgctacagg catcgtggtg tcacgctcgt cgtttggtat ggcttcattc    11940
agctccggtt cccaacgatc aaggcgagtt acatgatccc ccatgttgtg caaaaaagcg    12000
gttagctcct tcggtcctcc gatcgttgtc agaagtaagt tggccgcagt gttatcactc    12060
atggttatgg cagcactgca taattctctt actgtcatgc catccgtaag atgcttttct    12120
gtgactggtg agtactcaac caagtcattc tgagaatagt gtatgcggcg accgagttgc    12180
tcttgcccgg cgtcaatacg ggataatacc gcgccacata gcagaacttt aaaagtgctc    12240
atcattggaa aacgttcttc ggggcgaaaa ctctcaagga tcttaccgct gttgagatcc    12300
agttcgatgt aacccactcg tgcacccaac tgatcttcag catcttttac tttcaccagc    12360
gtttctgggt gagcaaaaac aggaaggcaa aatgccgcaa aaaagggaat aagggcgaca    12420
cggaaatgtt gaatactcat actcttcctt tttcaatatt attgaagcat ttatcagggt    12480
tattgtctca tgagcggata catatttgaa tgtatttaga aaataaaca aatagggggtt    12540 ccgcgcacat ttccccgaaa agtgccacct gacgtctaag aaaccattat tatcatgaca    12600
ttaacctata aaaataggcg tatcacgagg ccctttcgtc                         12640
```

<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic Luciferase ORF polynucleotide

<400> SEQUENCE: 54

```
atggaagatg ccaaaaacat taagaagggc ccagcgccat tctacccact cgaagacggg      60
accgccggcg agcagctgca caaagccatg aagcgctacg ccctggtgcc cggcaccatc     120
gcctttaccg acgcacatat cgaggtggac attacctacg ccgagtactt cgagatgagc     180
gttcggctgg cagaagctat gaagcgctat gggctgaata caaaccatcg gatcgtggtg     240
tgcagcgaga atagcttgca gttcttcatg cccgtgttgg gtgccctgtt catcggtgtg     300
gctgtggccc cagctaacga catctacaac gagcgcgagc tgctgaacag catgggcatc     360
agccagccca ccgtcgtatt cgtgagcaag aaagggctgc aaaagatcct caacgtgcaa     420
aagaagctac cgatcataca aaagatcatc atcatggata gcaagaccga ctaccagggc     480
ttccaaagca tgtacacctt cgtgacttcc catttgccac ccggcttcaa cgagtacgac     540
ttcgtgcccg agagcttcga ccgggacaaa accatcgccc tgatcatgaa cagtagtggc     600
agtaccggat tgcccaaggg cgtagcccta ccgcaccgca ccgcttgtgt ccgattcagt     660
catgcccgcg accccatctt cggcaaccag atcatccccg acaccgctat cctcagcgtg     720
```

```
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatcgcca gcggcggggc gccgctcagc    960
aaggaggtag gtgaggccgt ggccaaacgc ttccacctac caggcatccg ccagggctac   1020
ggcctgacag aaacaaccag cgccattctg atcaccccg aaggggacga caagcctggc   1080
gcagtaggca aggtggtgcc cttcttcgag gctaaggtgg tggacttgga caccggtaag   1140
acactgggtg tgaaccagcg cggcgagctg tgcgtccgtg gccccatgat catgagcggc   1200
tacgttaaca accccgaggc tacaaacgct ctcatcgaca aggacggctg gctgcacagc   1260
ggcgacatcg cctactggga cgaggacgag cacttcttca tcgtggaccg gctgaagagc   1320
ctgatcaaat acaagggcta ccaggtagcc ccagccgaac tggagagcat cctgctgcaa   1380
caccccaaca tcttcgacgc cggggtcgcc ggcctgcccg acgacgatgc cggcgagctg   1440
cccgccgcag tcgtcgtgct ggaacacggt aaaaccatga ccgagaagga gatcgtggac   1500
tatgtggcca gccaggttac aaccgccaag aagctgcgcg gtggtgttgt gttcgtggac   1560
gaggtgccta aaggactgac cggcaagttg gacgcccgca gatccgcga gattctcatt   1620 aaggccaaga agggcggcaa gatcgccgtg taa                                 1653

<210> SEQ ID NO 55
<211> LENGTH: 8708
<212> TYPE: DNA
<213> ORGANISM: Artificial Sequence
<220> FEATURE:
<223> OTHER INFORMATION: Description of Artificial Sequence: Synthetic
      pTV-DS-luciferase polynucleotide

<400> SEQUENCE: 55
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ttaaggagcc cttcgcctc    420 gtgcttgagt tgaggcctgg cttgggcgct ggggccgccg cgtgcgaatc tggtggcacc    480
ttcgcgcctg tctcgctgct tcgataagt ctctagccat ttaaaatttt tgatgacctg    540
ctgcgacgct ttttttctgg caagatagtc ttgtaaatgc gggccaagat cgatctgcac    600
actggtattt cggttttttgg ggccgcgggc ggcgacgggg cccgtgcgtc ccagcgcaca    660
tgttcggcga ggcggggcct gcgagcgcgg ccaccgagaa tcggacgggg gtagtctcaa    720
gctggccggc ctgctctggt gcctggcctc gcgccgccgt gtatcgcccc gccctgggcg    780
gcaaggctgg cccggtcggc accagttgcg tgagcggaaa gatggccgct tcccggccct    840
gctgcaggga gctcaaaatg gaggacgcgg cgctcgggag agcgggcggg tgagtcaccc    900
acacaaagga aaagggcctt tccgtcctca gccgtcgctt catgtgactc cacggagtac    960
cgggcgccgt ccaggcacct cgattagttc tcgagctttt ggagtacgtc gtctttaggt   1020
tggggggagg ggttttatgc gatggagttt ccccacactg agtgggtgga gactgaagtt   1080
```

```
aggccagctt ggcacttgat gtaattctcc ttggaatttg cccttttttga gtttggatct    1140 tggttcattc tcaagcctca gacagtggtt caaagttttt ttcttccatt tcaggtgtcg    1200
tggaattggc tagagcttgc atgcctgcag gtcggccgcc acgaccggtg ccgccaccat    1260
cccctgaccc acgcccctga cccctcacaa ggagacgacc ttccatgacc gagtacaagc    1320
ccacggtgcg cctcgccacc cgcgacgacg tcccccgggc cgtacgcacc ctcgccgccg    1380
cgttcgccga ctaccccgcc acgcgccaca ccgtcgaccc ggaccgccac atcgagcggg    1440
tcaccgagct gcaagaactc ttcctcacgc gcgtcgggct cgacatcggc aaggtgtggg    1500
tcgcggacga cggcgccgcg gtggcggtct ggaccacgcc ggagagcgtc gaagcggggg    1560
cggtgttcgc cgagatcggc ccgcgcatgg ccgagttgag cggttcccgg ctggccgcgc    1620
agcaacagat ggaaggcctc ctggcgccgc accggcccaa ggagcccgcg tggttcctgg    1680
ccaccgtcgg cgtctcgccc gaccaccagg gcaagggtct gggcagcgcc gtcgtgctcc    1740
ccggagtgga ggcggccgag cgcgccgggg tgcccgcctt cctggagacc tccgcgcccc    1800
gcaacctccc cttctacgag cggctcggct tcaccgtcac cgccgacgtc gaggtgcccg    1860
aaggaccgcg cacctggtgc atgacccgca agcccggtgc ctgacgcccg ccccacgacc    1920
cgcagcgccc gaccgaaagg agcgcacgac cccatggctc cgaccgaagc cgacccgggc    1980
ggccccgccg accccgcacc cgcccccgag gcccaccgac tctagaggat cataatcagc    2040
cataccacat ttgtagaggt tttacttgct ttaaaaaacc tcccacacct cccctgaac    2100 ctgaaacata aaatgaatgc aattgttgtt gttaacttgt ttattgcagc ttataatggt    2160
tacaaataaa gcaatagcat cacaaatttc acaaataaag catttttttc actgcattct    2220
agttgtggtt tgtccaaact catcaatgta tcttatcatg tctggatcct agcgtttaaa    2280
cttaagcttg gtaccgagct cggatccact agcgatgtac gggccagata tacgcgttga    2340
cattgattat tgactagtta ttaatagtaa tcaattacgg ggtcattagt tcatagccca    2400
tatatggagt tccgcgttac ataacttacg gtaaatggcc cgcctggctg accgcccaac    2460
gacccccgcc cattgacgtc aataatgacg tatgttccca tagtaacgcc aatagggact    2520
ttccattgac gtcaatgggt ggagtattta cggtaaactg cccacttggc agtacatcaa    2580
gtgtatcata tgccaagtac gccccctatt gacgtcaatg acggtaaatg gcccgcctgg    2640
cattatgccc agtacatgac cttatgggac tttcctactt ggcagtacat ctacgtatta    2700
gtcatcgcta ttaccatggt gatgcggttt tggcagtaca tcaatgggcg tggatagcgg    2760
tttgactcac ggggatttcc aagtctccac cccattgacg tcaatgggag tttgttttgg    2820
caccaaaatc aacgggactt tccaaaatgt cgtaacaact ccgccccatt gacgcaaatg    2880
ggcggtaggc gtgtacggtg ggaggtctat ataagcagag ctctctggct aactagagaa    2940
cccactgctt actggcttat cgaaattaat acgactcact ataggagac caagctggc     3000 tagcgctgat atcgatcgcg agcggccgcg aattcactag tgattgcaga attcatggaa    3060
gatgccaaaa acattaagaa gggcccagcg ccattctacc cactcgaaga cgggaccgcc    3120
ggcgagcagc tgcacaaagc catgaagcgc tacgccctgg tgcccggcac catcgccttt    3180
accgacgcac atatcgaggt ggacattacc tacgccgagt acttcgagat gagcgttcgg    3240
ctggcagaag ctatgaagcg ctatgggctg aatacaaacc atcggatcgt ggtgtgcagc    3300
gagaatagct tgcagttctt catgcccgtg ttgggtgccc tgttcatcgg tgtgctgtg    3360 gccccagcta acgacatcta caacgagcgc gagctgctga acagcatggg catcagccag    3420
```

```
cccaccgtcg tattcgtgag caagaaaggg ctgcaaaaga tcctcaacgt gcaaaagaag   3480
ctaccgatca tacaaaagat catcatcatg gatagcaaga ccgactacca gggcttccaa   3540
agcatgtaca ccttcgtgac ttcccatttg ccacccggct tcaacgagta cgacttcgtg   3600
cccgagagct tcgaccggga caaaaccatc gccctgatca tgaacagtag tggcagtacc   3660
ggattgccca agggcgtagc cctaccgcac cgcaccgctt gtgtccgatt cagtcatgcc   3720
cgcgacccca tcttcggcaa ccagatcatc cccgacaccg ctatcctcag cgtggtgcca   3780
tttcaccacg gcttcggcat gttcaccacg ctgggctact tgatctgcgg ctttcgggtc   3840
gtgctcatgt accgcttcga ggaggagcta ttcttgcgca gcttgcaaga ctataagatt   3900
caatctgccc tgctggtgcc cacactattt agcttcttcg ctaagagcac tctcatcgac   3960
aagtacgacc taagcaactt gcacgagatc gccagcggcg gggcgccgct cagcaaggag   4020
gtaggtgagg ccgtggccaa acgcttccac ctaccaggca tccgccaggg ctacggcctg   4080
acagaaacaa ccagcgccat tctgatcacc cccgaagggg acgacaagcc tggcgcagta   4140
ggcaaggtgg tgcccttctt cgaggctaag gtggtggact tggacaccgg taagacactg   4200
ggtgtgaacc agcgcggcga gctgtgcgtc cgtggcccca tgatcatgag cggctacgtt   4260
aacaaccccg aggctacaaa cgctctcatc gacaaggacg ctggctgca cagcggcgac   4320
atcgcctact gggacgagga cgagcacttc ttcatcgtgg accggctgaa gagcctgatc   4380
aaatacaagg ctaccaggt agccccagcc gaactggaga gcatcctgct gcaacacccc   4440
aacatcttcg acgccggggt cgccggcctg cccgacgacg atgccggcga gctgcccgcc   4500
gcagtcgtcg tgctggaaca cggtaaaacc atgaccgaga aggagatcgt ggactatgtg   4560
gccagccagg ttacaaccgc caagaagctg cgcggtggtg ttgtgttcgt ggacgaggtg   4620
cctaaaggac tgaccggcaa gttggacgcc cgcaagatcc gcgagattct cattaaggcc   4680
aagaagggcg gcaagatcgc cgtgtaataa ttctagagtc ggggcggccg gccgcttcga   4740
gcagacatga taagatacat tgatgagttt ggacaaacca actagaat gcagtgaaaa   4800
aaatgcttta tttgtgaaat ttgtgatgct attgctttat ttgtaaccat tataagctgc   4860
aataaacaag ttaacaacaa caattgcatt cattttatgt ttcaggttca gggggaggtg   4920
tgggaggttt tttaaagcgg ccgctcgagt ctagagggcc cgtttaaacc cgctgatcag   4980
cctcgactgt gccttctagt tgccagccat ctgttgtttg cccctccccc gtgccttcct   5040
tgaccctgga aggtgccact cccactgtcc tttcctaata aaatgaggaa attgcatcgc   5100
attgtctgag taggtgtcat tctattctgg ggggtgggt ggggcaggac agcaagggg   5160
aggattggga agacaatagc aggcatgctg gggatgcggt gggctctatg gcttctgagg   5220
cggaaagaac cagctgggc tctaggggt atccccacgc gccctgtagc ggcgcattaa   5280
gcgcggcggg tgtggtggtt acgcgcagcg tgaccgctac acttgccagc gccctagcgc   5340
ccgctccttt cgctttcttc ccttcctttc tcgccacgtt cgccaccgt cgaatcaccg   5400
gtaaccttat aagggatttt gccgatttcg gcctattggt taaaaaatga ctgatttaa   5460
caaaaattta acgcgaatta attctgtgga atgtgtgtca gttagggtgt ggaaagtccc   5520
caggctcccc agcaggcaga agtatgcaaa gcatgcatct caattagtca gcaaccaggt   5580
gtggaaagtc cccaggctcc ccagcaggca gaagtatgca aagcatgcat ctcaattagt   5640
cagcaaccat agtcccgccc ctaactccgc ccatcccgcc ctaactccg cccagttccg   5700
cccattctcc gccccatggc tgactaattt tttttattta tgcagaggcc gaggccgcct   5760
ctgcctctga gctattccag aagtagtgag gaggcttttt tggaggccta ggcttttgca   5820
```

```
aaaagctccc gggagcttgt atatccattt tcggatctga tcaagagaca ggatgaggat    5880
cgtttcgcat gattgaacaa gatggattgc acgcaggttc tccggccgct tgggtggaga    5940
ggctattcgg ctatgactgg gcacaacaga caatcggctg ctctgatgcc gccgtgttcc    6000
ggctgtcagc gcaggggcgc ccggttcttt ttgtcaagac cgacctgtcc ggtgccctga    6060
atgaactgca ggacgaggca gcgcggctat cgtggctggc cacgacgggc gttccttgcg    6120
cagctgtgct cgacgttgtc actgaagcgg aagggactg gctgctattg ggcgaagtgc     6180
cggggcagga tctcctgtca tctcaccttg ctcctgccga aaagtatcc atcatggctg     6240 atgcaatgcg gcggctgcat acgcttgatc cggctacctg cccattcgac caccaagcga    6300
aacatcgcat cgagcgagca cgtactcgga tggaagccgg tcttgtcgat caggatgatc    6360
tggacgaaga gcatcagggg ctcgcgccag ccgaactgtt cgccaggctc aaggcgcgaa    6420
ttcgagctcg gtacccgggg atcctctaga gtcgacctgc aggcatgcaa gcttggcgta    6480
atcatggtca tagctgtttc ctgtgtgaaa ttgttatccg ctcacaattc cacacaacat    6540
acgagccgga agcataaagt gtaaagcctg gggtgcctaa tgagtgagct aactcacatt    6600
aattgcgttg cgctcactgc ccgctttcca gtcgggaaac ctgtcgtgcc agctgcatta    6660
atgaatcggc caacgcgcgg ggagaggcgg tttgcgtatt gggcgctctt ccgcttcctc    6720
gctcactgac tcgctgcgct cggtcgttcg gctgcggcga gcggtatcag ctcactcaaa    6780
ggcggtaata cggttatcca cagaatcagg ggataacgca ggaaagaaca tgtgagcaaa    6840
aggccagcaa aaggccagga accgtaaaaa ggccgcgttg ctggcgtttt tccataggct    6900
ccgcccccct gacgagcatc acaaaaatcg acgctcaagt cagaggtggc gaaacccgac    6960
aggactataa agataccagg cgtttccccc tggaagctcc ctcgtgcgct ctcctgttcc    7020
gaccctgccg cttaccggat acctgtccgc ctttctccct tcgggaagcg tggcgctttc    7080
tcatagctca cgctgtaggt atctcagttc ggtgtaggtc gttcgctcca agctgggctg    7140
tgtgcacgaa ccccccgttc agcccgaccg ctgcgcctta tccggtaact atcgtcttga    7200
gtccaacccg gtaagacacg acttatcgcc actggcagca gccactggta acaggattag    7260
cagagcgagg tatgtaggcg gtgctacaga gttcttgaag tggtggccta actacggcta    7320
cactagaagg acagtatttg gtatctgcgc tctgctgaag ccagttacct tcggaaaaag    7380
agttggtagc tcttgatccg gcaaacaaac caccgctggt agcggtggtt ttttgtttg     7440 caagcagcag attacgcgca gaaaaaaagg atctcaagaa gatcctttga tcttttctac    7500
ggggtctgac gctcagtgga acgaaaactc acgttaaggg attttggtca tgagattatc    7560
aaaaaggatc ttcacctaga tccttttaaa ttaaaaatga agttttaaat caatctaaag    7620
tatatatgag taaacttggt ctgacagtta ccaatgctta atcagtgagg cacctatctc    7680
agcgatctgt ctatttcgtt catccatagt tgcctgactc cccgtcgtgt agataactac    7740
gatacgggag ggcttaccat ctggccccag tgctgcaatg ataccgcgag acccacgctc    7800
accggctcca gatttatcag caataaacca gccagccgga agggccgagc gcagaagtgg    7860
tcctgcaact ttatccgcct ccatccagtc tattaattgt tgccgggaag ctagagtaag    7920
tagttcgcca gttaatagtt tgcgcaacgt tgttgccatt gctacaggca tcgtggtgtc    7980
acgctcgtcg tttggtatgg cttcattcag ctccggttcc caacgatcaa ggcgagttac    8040
atgatccccc atgttgtgca aaaaagcggt tagctccttc ggtcctccga tcgttgtcag    8100
aagtaagttg gccgcagtgt tatcactcat ggttatggca gcactgcata attctcttac    8160
```

```
tgtcatgcca tccgtaagat gctttctgt gactggtgag tactcaacca agtcattctg    8220
agaatagtgt atgcggcgac cgagttgctc ttgcccggcg tcaatacggg ataataccgc    8280
gccacatagc agaactttaa aagtgctcat cattggaaaa cgttcttcgg ggcgaaaact    8340
ctcaaggatc ttaccgctgt tgagatccag ttcgatgtaa cccactcgtg cacccaactg    8400
atcttcagca tctttactt tcaccagcgt ttctgggtga gcaaaacag gaaggcaaaa    8460 tgccgcaaaa aagggaataa gggcgacacg gaaatgttga atactcatac tcttcctttt    8520
tcaatattat tgaagcattt atcagggtta ttgtctcatg agcggataca tatttgaatg    8580
tatttagaaa aataaacaaa taggggttcc gcgcacattt ccccgaaaag tgccacctga    8640
cgtctaagaa accattatta tcatgacatt aacctataaa aataggcgta tcacgaggcc    8700
ctttcgtc                                                            8708
```

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      DPV15b peptide

<400> SEQUENCE: 56

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      DPV1047 peptide

<400> SEQUENCE: 57

Val Lys Arg Gly Leu Lys Leu Arg His Val Arg Pro Arg Val Thr Arg
1               5                   10                  15

Met Asp Val

<210> SEQ ID NO 58
<211> LENGTH: 196
<212> TYPE: PRT
<213> ORGANISM: Artificial Sequence
<220> FEATURE:
<223> OTHER INFORMATION: Description of Artificial Sequence: Synthetic
      DPV15b/I-CreI N75/6xHis protein sequence

<400> SEQUENCE: 58

Met Gly Ala Tyr Asp Leu Arg Arg Arg Glu Arg Gln Ser Arg Leu Arg
1               5                   10                  15

Arg Arg Glu Arg Gln Ser Arg Asn Thr Lys Tyr Asn Lys Glu Phe Leu
            20                  25                  30

Leu Tyr Leu Ala Gly Phe Val Asp Gly Asp Gly Ser Ile Ile Ala Gln
        35                  40                  45

Ile Lys Pro Asn Gln Ser Tyr Lys Phe Lys His Gln Leu Ser Leu Thr
    50                  55                  60

Phe Gln Val Thr Gln Lys Thr Gln Arg Arg Trp Phe Leu Asp Lys Leu
65                  70                  75                  80

```
Val Asp Glu Ile Gly Val Gly Tyr Val Arg Asp Arg Gly Ser Val Ser
            85                  90                  95

Asn Tyr Ile Leu Ser Glu Ile Lys Pro Leu His Asn Phe Leu Thr Gln
            100                 105                 110

Leu Gln Pro Phe Leu Lys Leu Lys Gln Lys Gln Ala Asn Leu Val Leu
            115                 120                 125

Lys Ile Ile Glu Gln Leu Pro Ser Ala Lys Glu Ser Pro Asp Lys Phe
            130                 135                 140

Leu Glu Val Cys Thr Trp Val Asp Gln Ile Ala Leu Asn Asp Ser
145                 150                 155                 160

Lys Thr Arg Lys Thr Thr Ser Glu Thr Val Arg Ala Val Leu Asp Ser
                165                 170                 175

Leu Ser Glu Lys Lys Lys Ser Ser Pro Ala Ala Ala Leu Glu His His
            180                 185                 190

His His His His
        195

<210> SEQ ID NO 59
<211> LENGTH: 12632
<212> TYPE: DNA
<213> ORGANISM: Artificial Sequence
<220> FEATURE:
<223> OTHER INFORMATION: Description of Artificial Sequence: Synthetic
      cGPS custom lacz integration matrix polynucleotide

<400> SEQUENCE: 59
```

| | | |
|---|---|---|
| gaccacaaaa gtgtgatggg tcctctggaa ctggagttgc aggccattgg gagctactgt | 60 |
| gtggctggga actggactta gggcctctgc ccaaacagca aatgggctta actctctcca | 120 |
| gccccaatat tttctagttt taaagttctt tttcacaaaa agaaaaacac caggaagtcc | 180 |
| tactagttat tcagtttgag atataaatag tggtactcca aatgagtcc agcaaatgtt | 240 |
| gaaacgaggt tggaagtctg taatgagat tatgattctg ttggtttgct atacacattt | 300 |
| ctttttaaaat ttttttataa attttattta aattagaaac aatcttattt tacatatcaa | 360 |
| tcccagttca ctctcactcc catcctccca agcccccac caattctccc atccactccc | 420 |
| caaggagggc gaggccttcc atgagggatc atcaaaaaat ctgtcacttg gggcagggcc | 480 |
| taggccctcc tccctgtta tacacatttc tttactgtat cactgtatgt aaagtatata | 540 |
| tacacatacg agttatgtac tatcatataa tactaaattt ttggactttt taatattagt | 600 |
| acatctatag ctatcacatg tttttacctt taaaaatttt tataattgtg tgtgtgtgtg | 660 |
| tgtgtgtgtg tgtgtgtgtg tgtgtgtgtg tgtgtatgta tgtgtatgtg tgtgtatgtg | 720 |
| tgtaaactgt tttctctttg ataggttc ttactgttta gttcagtctg cttggaact | 780 |
| ttctgtatag cccagactga ccttaactca gtattcctcc cccatctgga gattacaggt | 840 |
| atgagccacc atgcccagtc ctgtttttat attgattttg aaaagggtc tcaaatagtt | 900 |
| tagactggct tccaactcac agtgtagctg aggatgacct gaagttctga tgctattgct | 960 |
| tctactggtg tgccattatg cccagtttgc acagttatga ggataaaacc taggaccttg | 1020 |
| ttcctgtgca tactaggcat agactctacc aattaagcta cattcccagc tcccccaggt | 1080 |
| ttactttaaa ggtgataatg ctattctgtt catggatata ccataactga tttaactctg | 1140 |
| tactgttggt agacacttaa gatctccatt attttgcact tagcaggagt ttattagagg | 1200 |
| aaatatgata tatattggca cttgctcagc tttaggcaag tagaaattct gggtcaagta | 1260 |
| aaagatgttt attgaatatt atcatactgc caaattaacc tctaaaaaat ttcataattt | 1320 |

```
tatactacca gtggtatgtg agttcatttt tcctcacaat ctcttctaat attttacatt      1380
agagaaatgc aatttaacca aaattcacca gtcttgttag ctttgaacat tgtatctttt      1440
tatttgtatt tttaaatttc atgatgttat agtatacctg ttcttttatt tgagacagaa      1500
tcttattatg tagccctaag tgacctagta cttactctgc tgttgtacag tatgtccctc      1560
aacccatacc cttcctcctg cctcagcctc cagagtgcta gaattatagg catgtaccat      1620
ggtgcctagc atgtacctgg tttttaaagg tagctggaat tataggcatg taccatgatg      1680
cctagcatgt acctggtttt taaagttagt aagttttaat tttggttgag ctgtgtgttg      1740
gtgtgtaagt ataatctcag cacacagagt tcgagacatg ggttatgagt tactatgcag      1800
cctgggctac atagagggat cctgtgtcac cttccccaac ccccaaaatc ttcccttttgc     1860 catatggaaa acatccccca ctttatttaa tagtttgatt tatgaagcaa gattaccaat      1920 tatgggaca aagaatgtgt cctgtggaag tttaagaagt gtttgttata aaaatataac       1980
tatttggaat cttctattcc tgattttatt tttgtaggac tgaaagactt gcccgagata      2040
aaaagcctga actcaccgcg acgtctgtcg agaagtttct gatcgaaaag ttcgacagcg      2100
tctccgacct gatgcagctc tcggagggcg aagaatctcg tgctttcagc ttcgatgtag      2160
gagggcgtgg atatgtcctg cgggtaaata gctgcgccga tggtttctac aaagatcgtt      2220
atgtttatcg gcactttgca tcggccgcgc tcccgattcc ggaagtgctt gacattgggg      2280
aattcagcga gagcctgacc tattgcatct cccgccgtgc acagggtgtc acgttgcaag      2340
acctgcctga aaccgaactg cccgctgttc tgcagccggt cgcggaggcc atggatgcga      2400
tcgctgcggc cgatcttagc cagacgagcg gttcggccc attcggaccg caaggaatcg       2460
gtcaatacac tacatggcgt gatttcatat gcgcgattgc tgatccccat gtgtatcact      2520
ggcaaactgt gatggacgac accgtcagtg cgtccgtcgc gcaggctctc gatgagctga      2580
tgctttgggc cgaggactgc cccgaagtcc ggcacctcgt gcacgcggat tcggctcca      2640 acaatgtcct gacggacaat ggccgcataa cagcggtcat tgactggagc gaggcgatgt      2700
tcggggattc ccaatacgag gtcgccaaca tcttcttctg gaggccgtgg ttggcttgta      2760
tggagcagca gacgcgctac ttcgagcgga ggcatccgga gcttgcagga tcgccgcggc      2820
tccgggcgta tatgctccgc attggtcttg accaactcta tcagagcttg gttgacggca      2880
atttcgatga tgcagcttgg gcgcagggtc gatgcgacgc aatcgtccga tccggagccg      2940
ggactgtcgg gcgtacacaa atcgcccgca gaagcgcggc cgtctggacc gatggctgtg      3000
tagaagtact cgccgatagt ggaaaccgac gccccagcac tcgtccgagg caaaggaat      3060 agcacgtgct acgagatttc gattccaccg ccgccttcta tgaaaggttg gcttcggaa      3120 tcgttttccg ggacgccggc tggatgatcc tccagcgcgg ggatctcatg ctggagttct      3180
tcgcccaccc caacttgttt attgcagctt ataatggtta caaataaagc aatagcatca      3240
caaatttcac aaataaagca ttttttttcac tgcattctag ttgtggtttg tccaaactca      3300
tcaatgtatc ttatcatgtc tgtataccgt cgacctctag ctagagcttg gcgtaatcat      3360
ggtcatagct gtttcctgtg tgaaattgtt atccgctcac aattccacac aacatacgag      3420
ccggaagcat aaagaatcga attcccgcgg ccgcacgcta gggataacag ggtaatatag      3480
atcgatgtac gggccagata tacgcgttga cattgattat tgactagtta ttaatagtaa      3540
tcaattacgg ggtcattagt tcatagccca tatatggagt tccgcgttac ataacttacg      3600
gtaaatggcc cgcctggctg accgcccaac gacccccgcc cattgacgtc aataatgacg      3660
tatgttccca tagtaacgcc aatagggact ttccattgac gtcaatgggt ggactattta      3720
```

```
cggtaaactg cccacttggc agtacatcaa gtgtatcata tgccaagtac gcccectatt    3780
gacgtcaatg acggtaaatg gcccgcctgg cattatgccc agtacatgac cttatgggac    3840
tttcctactt ggcagtacat ctacgtatta gtcatcgcta ttaccatggt gatgcggttt    3900
tggcagtaca tcaatgggcg tggatagcgg tttgactcac ggggatttcc aagtctccac    3960
cccattgacg tcaatgggag tttgttttgg caccaaaatc aacgggactt tccaaaatgt    4020
cgtaacaact ccgccccatt gacgcaaatg gcggtaggc gtgtacggtg ggaggtctat     4080
ataagcagag ctctctggct aactagagaa cccactgctt actggcttat cgaaattaat    4140
acgactcact atagggagac ccaagctggc tagcgtttaa acttaagctt ggtaccgagc    4200
tcggatccac tagtccagtg tggtggaatt ctgcagatcg aaacgatgat agatcccgtc    4260
gttttacaac gtcgtgactg ggaaaaccct ggcgttaccc aacttaatcg ccttgcagca    4320
catccccctt cgccagctg gcgtaatagc gaagaggccc gcaccgatcg cccttcccaa     4380
cagttgcgca gcctgaatgg cgaatggcgc tttgcctggt ttccggtacc agaagcggtg    4440
ccggaaagct ggctggagtg cgatcttcct gaggccgata ctgtcgtcgt cccctcaaac    4500
tggcagatgc acggttacga tgcgcccatc tacaccaacg taacctatcc cattacggtc    4560
aatccgccgt ttgttcccac ggagaatccg acgggttgtt actcgctcac atttaatgtt    4620
gatgaaagct ggctacagga aggccagacg cgaattattt ttgatggcgt taactcggcg    4680
tttcatctgt ggtgcaacgg gcgctgggtc ggttacggcc aggacagtcg tttgccgtct    4740
gaatttgacc tgagcgcatt tttacgcgcc ggagaaaacc gcctcgcggt gatggtgctg    4800
cgttggagtg acggcagtta tctggaagat caggatatgt ggcggatgag cggcattttc    4860
cgtgacgtct cgttgctgca taaaccgact acacaaatca gcgatttcca tgttgccact    4920
cgctttaatg atgatttcag ccgcgctgta ctggaggctg aagttcagat gtgcggcgag    4980
ttgcgtgact acctacgggt aacagtttct ttatggcagg gtgaaacgca ggtcgccagc    5040
ggcaccgcgc ctttcggcgg tgaaattatc gatgagcgtg gtggttatgc cgatcgcgtc    5100
acactacgtc tgaacgtcga aacccgaaa ctgtggagcg ccgaaatccc gaatctctat     5160
cgtgcggtgg ttgaactgca caccgccgac ggcacgctga ttgaagcaga agcctgcgat    5220
gtcggtttcc gcgaggtgcg gattgaaaat ggtctgctgc tgctgaacgg caagccgttg    5280
ctgattcgag gcgttaaccg tcacgagcat catcctctgc atggtcaggt catggatgag    5340
cagacgatgg tgcaggatat cctgctgatg aagcagaaca actttaacgc cgtgcgctgt    5400
tcgcattatc cgaaccatcc gctgtggtac acgctgtgcg accgctacgg cctgtatgtg    5460
gtggatgaag ccaatattga aacccacggc atggtgccaa tgaatcgtct gaccgatgat    5520
ccgcgctggc taccggcgat gagcgaacgc gtaacgcgaa tggtgcagcg cgatcgtaat    5580
caccccgagtg tgatcatctg gtcgctgggg aatgaatcag ccacggcgc taatcacgac    5640
gcgctgtatc gctggatcaa atctgtcgat ccttcccgcc cggtgcagta tgaaggcggc    5700
ggagccgaca ccacggccac cgatattatt tgcccgatgt acgcgcgcgt ggatgaagac    5760
cagcccttcc cggctgtgcc gaaatggtcc atcaaaaaat ggcttcgct acctggagag     5820
acgcgcccgc tgatcctttg cgaatacgcc cacgcgatgg taacagtct ggcggtttc     5880
gctaaatact ggcaggcgtt tcgtcagtat ccccgtttac agggcggctt cgtctgggac    5940
tgggtggatc agtcgctgat taaatatgat gaaaacggca cccgtggtc ggcttacggc     6000
ggtgattttg gcgatacgcc gaacgatcgc cagttctgta tgaacggtct ggtctttgcc    6060
```

```
gaccgcacgc cgcatccagc gctgacggaa gcaaaacacc agcagcagtt tttccagttc    6120
cgtttatccg ggcaaaccat cgaagtgacc agcgaatacc tgttccgtca tagcgataac    6180
gagctcctgc actggatggt ggcgctggat ggtaagccgc tggcaagcgg tgaagtgcct    6240
ctggatgtcg ctccacaagg taaacagttg attgaactgc tgaactacc gcagccggag     6300
agcgccgggc aactctggct cacagtacgc gtagtgcaac cgaacgcgac cgcatggtca    6360
gaagccgggc acatcagcgc ctggcagcag tggcgtctgg cggaaaacct cagtgtgacg    6420
ctccccgccg cgtcccacgc catcccgcat ctgaccacca gcgaaatgga ttttttgcatc   6480
gagctgggta ataagcgttg gcaatttaac cgccagtcag gctttctttc acagatgtgg    6540
attggcgata aaaacaact gctgacgccg ctgcgcgatc agttcacccg tgcaccgctg     6600
gataacgaca ttggcgtaag tgaagcgacc cgcattgacc ctaacgcctg ggtcgaacgc    6660
tggaaggcgg cgggccatta ccaggccgaa gcagcgttgt tgcagtgcac ggcagataca    6720
cttgctgatg cggtgctgat tacgaccgct cacgcgtggc agcatcaggg gaaaaccta    6780
tttatcagcc ggaaaaccta ccggattgat ggtagtggtc aaatggcgat taccgttgat   6840
gttgaagtgg cgagcgatac accgcatccg gcgcggattg gcctgaactg ccagctggcg    6900
caggtagcag agcgggtaaa ctggctcgga ttagggccgc aagaaaacta tcccgaccgc   6960
cttactgccg cctgttttga ccgctgggat ctgccattgt cagacatgta tacccgtac    7020
gtcttcccga gcgaaaacgg tctgcgctgc gggacgcgcg aattgaatta tggcccacac    7080
cagtggcgcg gcgacttcca gttcaacatc agccgctaca gtcaacagca actgatggaa    7140
accagccatc gccatctgct gcacgcgaa gaaggcacat ggctgaatat cgacggtttc     7200
catatgggga ttggtggcga cgactcctgg agcccgtcag tatcggcgga attccagctg    7260
agcgccggtc gctaccatta ccagttggtc tggtgtcaaa aagcggccgc tcgagtctag    7320
agggcccgtt taaacccgct gatcagcctc gactgtgcct tctagttgcc agccatctgt    7380
tgtttgcccc tcccccgtgc cttccttgac cctggaaggt gccactccca ctgtcctttc     7440
ctaataaaat gaggaaattg catcgcattg tctgagtagg tgtcattcta ttctgggggg   7500
tggggtgggg caggacagca agggggagga ttgggaagac aatagcaggc atgctgggga   7560
tgcggtgggc tctatggctt ctgaggcgga agaaccagc tggggctcta ggggtatcc     7620
ccacgcgccc tgtagcggcg cattaagcgc ggcgggtgtg gtggttacgc gcagcgtgac    7680
cgctacactt gccagcgccc tagcgcccgc tcctttcgct ttcttccctt cctttctcgc    7740
cacgttcgcc ggtttaaact cgaggcgcgc cgctagctcg cgaggccgct gggaggccat    7800
cacattgtgg ccctctgtgt gctgaagggg ggctataaat tctttgctga cctgctggat    7860
tacattaaag cactgaatag aaatagtgat agatccattc ccatgactgt agatttttatc   7920
agactgaaga gctactgtgt aagtataatt cattcataat ttaaaaaata tggcaatcct    7980
agttttgtat gtatttttgt ttgtttgttt ttactttgaa acagtgtttt tctgggtagc    8040
tttggagcct gtcttggaac tctctgctgt agaccagact gacctacaga gatctacctg    8100
cctctgactc ctgagtgctg agattaaacg agtgcaccac cacctgagcc tcatcaactg    8160
aggcttatcc cagttttttt tagaattta gtttgagacc ctctctaact tgctcagact    8220
atccttgaac tcattacata ggctgatcta gaaatttag tcatcttgac tcagtttctc    8280
aagtagctgg gattacaggc aggtgctacc acttctggcc ataattgttg ctgttattat    8340
tcactggtac tttacatcac aacactgtag ttcaagacca acatcaaagt gaatattgtt    8400
tgttagtcac ccaagatgga tttgtactta ctttgcatgg ttttcttt gtcttatttt       8460
```

-continued

```
gacctggatt ttgacttgtt ttatgatact gctcaggcta gtatcaaact ctgtggttca    8520
aataatcctt ctgtcttagc ctcccaaatt ctgggagtac aagcgtgtat caccatacct    8580
gactgtgttt tgatattttc caaaacaact tttaagaatt actgcagagt acagtgacag    8640
agagagatgg ttcatcagtc acaagcactt gtagagaaga ctggggttta gttactggca    8700
cccaaaagat ggctcacagc tatgtagctc cagttccagg ggacctgatg tcctagcctc    8760
cagataaaat aaaaataagt aagttttaca agaattatgg gactggtgag gtggactcag    8820
tagtcaaagg cactggctgc tctttcagag gacctggttc aattcctagc acccacgtgg    8880
tagttcacag ttgtctttaa ctccagtccc agggatctga tgccatcttc tggcctccaa    8940
gggcaccaga cactaacatg gtacacaaac aaatatgcaa cttgaacacc catacacata    9000
ttttaaaaat aaacaatttc tgttgagact tggtgttttc ctgactgtat atgctggtgg    9060
caaataattt ctctggaact aagttgcttt gagagtaatc ctaaattatt tgaagcaaag    9120
tctcattatt aaggttaaca attatttctc agaaaacaga aaccacttt gacctttggc    9180 cacgttacct ttgtcagagt ctgaagtgat gtagaatatt gacaatatga tgaaacaaaa    9240
tgaatgtaat ctttacatgt aaattccatc attcacaatt ttgattgtgt ggcttatttt    9300
ttttattttc attctctctc tttttttttt gagactctat gtagctctta ctgtcttgga    9360
actcactgta tagaccaggc tggtcttgaa ctcagagacc caactgcctc tacctcctga    9420
gtgctgggat tagaggcatg tgccaccact gcctggctaa aatagatatt tattttttaaa    9480 ataaaactgc aggatattat agagaaactt aagtcaccca tattctttt gtttttttgtt    9540 ttttttttgt ttttggtttt tctagacagg gtttctctgg ctttggaggc tgtcctggaa    9600
ctagctcttg tagaccaggc tggtctcgaa ctcacagcct gcctctgcct cccgagtgct    9660
gggattaaag gcgtgggcca ccaacgcctg gctctctttt tggttttta agacaggatt    9720 tctctatgta gctttggagc ctatcctggc actcgatctg gagacggatc cccaggaagc    9780
tcctctgtgt cctcataaac cctaacctcc tctacttgag aggacattcc aatcataggc    9840
tgcccatcca ccctctgtgt cctcctgtta attaggtcac ttaacaaaaa ggaaattggg    9900
taggggtttt tcacagaccg ctttctaagg gtaattttaa aatatctggg aagtcccttc    9960
cactgctgtg ttccagaagt gttggtaaac agcccacaaa tgtcaacagc agaaacatac   10020
aagctgtcag cttgcacaa gggcccaaca ccctgctcat caagaagcac tgtggttgct   10080
gtgttagtaa tgtgcaaaac aggaggcaca ttttccccac ctgtgtaggt tccaaaatat   10140
ctagtgtttt cattttact tggatcagga acccagcact ccactggata agcattatcc   10200
ttatccaaaa cagccttgtg gtcagtgttc atctgctgac tgtcaactgt agcattttt   10260 ggggttacag tttgagcagg atatttggtc ctgtagtttg ctaacacacc ctgcagctcc   10320
aaaggttccc caccaacagc aaaaaaatga aaatttgacc cttgaatggg ttttccagca   10380 ccatttcat gagtttttg tgtccctgaa tgcaagttta acatagcagt tacccccaata   10440 acctcagttt taacagtaac agcttcccac atcaaaatat ttccacaggt taagtcctca   10500
tttaaattag gcaaaggaat tcttgaagac gaaagggcct cgtgatacgc ctatttttat   10560
aggttaatgt catgataata atggtttctt agacgtcagg tggcactttt cggggaaatg   10620
tgcgcggaac ccctatttgt ttatttttct aaatacattc aaatatgtat ccgctcatga   10680
gacaataacc ctgataaatg cttcaataat attgaaaaag gaagagtatg agtattcaac   10740
atttccgtgt cgcccttatt ccctttttg cggcattttg ccttcctgtt tttgctcacc   10800
```

```
cagaaacgct ggtgaaagta aaagatgctg aagatcagtt gggtgcacga gtgggttaca    10860
tcgaactgga tctcaacagc ggtaagatcc ttgagagttt tcgccccgaa gaacgttttc    10920
caatgatgag cacttttaaa gttctgctat gtggcgcggt attatcccgt gttgacgccg    10980
ggcaagagca actcggtcgc cgcatacact attctcagaa tgacttggtt gagtactcac    11040
cagtcacaga aaagcatctt acggatggca tgacagtaag agaattatgc agtgctgcca    11100
taaccatgag tgataacact gcggccaact tacttctgac aacgatcgga ggaccgaagg    11160
agctaaccgc ttttttgcac aacatggggg atcatgtaac tcgccttgat cgttgggaac    11220
cggagctgaa tgaagccata ccaaacgacg agcgtgacac cacgatgcct gcagcaatgg    11280
caacaacgtt gcgcaaacta ttaactggcg aactacttac tctagcttcc cggcaacaat    11340
taatagactg gatggaggcg gataaagttg caggaccact tctgcgctcg gcccttccgg    11400
ctggctggtt tattgctgat aaatctggag ccggtgagcg tgggtctcgc ggtatcattg    11460
cagcactggg gccagatggt aagccctccc gtatcgtagt tatctacacg acggggagtc    11520
aggcaactat ggatgaacga atagacaga tcgctgagat aggtgcctca ctgattaagc    11580
attggtaact gtcagaccaa gtttactcat atatacttta gattgattta aaacttcatt    11640
tttaatttaa aaggatctag gtgaagatcc tttttgataa tctcatgacc aaaatcccct    11700
aacgtgagtt ttcgttccac tgagcgtcag accccgtaga aaagatcaaa ggatcttctt    11760
gagatccttt ttttctgcgc gtaatctgct gcttgcaaac aaaaaaacca ccgctaccag    11820
cggtggtttg tttgccggat caagagctac caactctttt tccgaaggta actggcttca    11880
gcagagcgca gataccaaat actgtccttc tagtgtagcc gtagttaggc caccacttca    11940
agaactctgt agcaccgcct acatacctcg ctctgctaat cctgttacca gtggctgctg    12000
ccagtggcga taagtcgtgt cttaccgggt tggactcaag acgatagtta ccggataagg    12060
cgcagcggtc gggctgaacg gggggttcgt gcacacagcc cagcttggag cgaacgacct    12120
acaccgaact gagatacctac agcgtgagc tatgagaaag cgccacgctt cccgaaggga    12180
gaaaggcgga caggtatccg gtaagcggca gggtcggaac aggagagcgc acgagggagc    12240
ttccagggga aaacgcctgg tatctttata gtcctgtcgg gtttcgccac ctctgacttg    12300
agcgtcgatt tttgtgatgc tcgtcagggg ggcggagcct atggaaaaac gccagcaacg    12360
cggccttttt acgttcctg gccttttgct ggccttttgc tcacatgttc tttcctgcgt    12420
tatcccctga ttctgtggat aaccgtatta ccgcctttga gtgagctgat accgctcgcc    12480
gcagccgaac gaccgagcgc agcgagtcag tgagcgagga agcggaagag cgcctgatgc    12540
ggtattttct ccttacgcat ctgtgcggta tttcacaccg catatggtgc actctcagta    12600
caatctgctc tgatgccgca tagttaagcc ag                                 12632
```

<210> SEQ ID NO 60
<211> LENGTH: 1065
<212> TYPE: DNA
<213> ORGANISM: Artificial Sequence
<220> FEATURE:
<223> OTHER INFORMATION: Description of Artificial Sequence: Synthetic
      Sc MA17-RM2-G19H33 ORF polynucleotide

<400> SEQUENCE: 60

```
atggccaata ccaaatataa caaagagttc ctgctgtacc tggccggctt tgtggacggt     60
gacggtagca tcatcgctca gattaaacca aaccagacgc ataagtttaa acatcagcta    120
agcttgacct ttcgtgtgac tcaaaagacc cagcgccgtt ggtttctgga caaactagtg    180
```

-continued

| | |
|---|---|
| gatgaaattg gcgttggtta cgtatatgat tctggaaccg tttccaatta caatttaagc | 240 |
| gaaatcaagc cgctgcacaa cttcctgact caactgcagc cgtttctgaa actgaaacag | 300 |
| aaacaggcaa acctggttct gaaaattatc gaacagctgc cgtctgcaaa agaatccccg | 360 |
| gacaaattcc tggaagtttg tacctgggtg gatcagattg cagctctgaa cgattctaag | 420 |
| acgcgtaaaa ccacttctga aaccgttcgt gctgtgctgg acagcctgag cgagaagaag | 480 |
| aaatcctccc cggcggccgg tggatctgat aagtataatc aggctctgtc taaatacaac | 540 |
| caagcactgt ccaagtacaa tcaggccctg tctggtggag gcggttccaa caaagagttc | 600 |
| ctgctgtatc ttgctggatt tgtggattct gatggctcca tcattgctca gataaaacca | 660 |
| aatcaatctc acaagttcaa acaccagctc tccttggcct ttcaagtcac tcagaagaca | 720 |
| caaagaaggt ggttcttgga caaattggtt gatgagattg gtgtgggcta tgtcagagac | 780 |
| agaggctctg tgtcagacta catcctgtct gaaattaagc ctcttcataa ctttctcacc | 840 |
| caactgcaac ccttcttgaa gctcaaacag aagcaagcaa atctggtttt gaaaatcatc | 900 |
| tggagactgc catctgccaa ggagtcccct gacaagtttc ttgaagtgtg tacttgggtg | 960 |
| gatcagattg ctgccttgaa tgactccaag accagaaaaa ccacctctga gactgtgagg | 1020 |
| gcagttctgg atagcctctc tgagaagaaa aagtcctctc cttag | 1065 |

<210> SEQ ID NO 61
<211> LENGTH: 6089
<212> TYPE: DNA
<213> ORGANISM: Artificial Sequence
<220> FEATURE:
<223> OTHER INFORMATION: Description of Artificial Sequence: Synthetic
      Sc HPRT expression vector polynucleotide

<400> SEQUENCE: 61

| | |
|---|---|
| atggccaata ccaaatataa caaagagttc ctgctgtacc tggccggctt tgtggacggt | 60 |
| gacggtagca tcatcgctca gattaaacca aaccagacgc ataagtttaa acatcagcta | 120 |
| agcttgacct ttcgtgtgac tcaaaagacc cagcgccgtt ggtttctgga caaactagtg | 180 |
| gatgaaattg gcgttggtta cgtatatgat tctggaaccg tttccaatta caatttaagc | 240 |
| gaaatcaagc cgctgcacaa cttcctgact caactgcagc cgtttctgaa actgaaacag | 300 |
| aaacaggcaa acctggttct gaaaattatc gaacagctgc cgtctgcaaa agaatccccg | 360 |
| gacaaattcc tggaagtttg tacctgggtg gatcagattg cagctctgaa cgattctaag | 420 |
| acgcgtaaaa ccacttctga aaccgttcgt gctgtgctgg acagcctgag cgagaagaag | 480 |
| aaatcctccc cggcggccgg tggatctgat aagtataatc aggctctgtc taaatacaac | 540 |
| caagcactgt ccaagtacaa tcaggccctg tctggtggag gcggttccaa caaagagttc | 600 |
| ctgctgtatc ttgctggatt tgtggattct gatggctcca tcattgctca gataaaacca | 660 |
| aatcaatctc acaagttcaa acaccagctc tccttggcct ttcaagtcac tcagaagaca | 720 |
| caaagaaggt ggttcttgga caaattggtt gatgagattg gtgtgggcta tgtcagagac | 780 |
| agaggctctg tgtcagacta catcctgtct gaaattaagc ctcttcataa ctttctcacc | 840 |
| caactgcaac ccttcttgaa gctcaaacag aagcaagcaa atctggtttt gaaaatcatc | 900 |
| tggagactgc catctgccaa ggagtcccct gacaagtttc ttgaagtgtg tacttgggtg | 960 |
| gatcagattg ctgccttgaa tgactccaag accagaaaaa ccacctctga gactgtgagg | 1020 |
| gcagttctgg atagcctctc tgagaagaaa aagtcctctc cttagtctag agggcccgcg | 1080 |
| gttcgaaggt aagcctatcc ctaaccctct cctcggtctc gattctacgc gtaccggtta | 1140 |

```
gtaatgagtt taaacggggg aggctaactg aaacacggaa ggagacaata ccggaaggaa    1200
cccgcgctat gacggcaata aaaagacaga ataaaacgca cgggtgttgg gtcgtttgtt    1260
cataaacgcg gggttcggtc ccagggctgg cactctgtcg ataccccacc gagacccat     1320 tggggccaat acgcccgcgt ttcttccttt tccccacccc acccccaag ttcgggtgaa     1380 ggcccagggc tcgcagccaa cgtcggggcg gcaggccctg ccatagcaga tctgcgcagc    1440
tggggctcta gggggtatcc ccacgcgccc tgtagcggcg cattaagcgc ggcgggtgtg    1500
gtggttacgc gcagcgtgac cgctacactt gccagcgccc tagcgcccgc tcctttcgct    1560
ttcttccctt cctttctcgc cacgttcgcc ggctttcccc gtcaagctct aaatcggggc    1620 atcccttag  ggttccgatt tagtgcttta cggcacctcg accccaaaaa acttgattag    1680
ggtgatggtt cacgtagtgg gccatcgccc tgatagacgg ttttcgccc tttgacgttg     1740 gagtccacgt tctttaatag tggactcttg ttccaaactg gaacaacact caaccctatc    1800
tcggtctatt cttttgattt ataagggatt tgggattt cggcctattg gttaaaaat       1860 gagctgattt aacaaaaatt taacgcgaat taattctgtg aatgtgtgt cagttagggg     1920 gtggaaagtc cccaggctcc ccagcaggca gaagtatgca aagcatgcat ctcaattagt    1980
cagcaaccag gtgtggaaag tccccaggct ccccagcagg cagaagtatg caaagcatgc    2040
atctcaatta gtcagcaacc atagtcccgc ccctaactcc gcccatcccg ccctaactc     2100 cgcccagttc cgcccattct ccgccccatg gctgactaat ttttttatt tatgcagagg     2160 ccgaggccgc ctctgcctct gagctattcc agaagtagtg aggaggcttt tttggaggcc    2220
taggcttttg caaaaagctc ccgggagctt gtatatccat tttcggatct gatcagcacg    2280
tgttgacaat taatcatcgg catagtatat cggcatagta aatacgaca aggtgaggaa     2340 ctaaaccatg gccaagcctt tgtctcaaga agaatccacc ctcattgaaa gagcaacggc    2400
tacaatcaac agcatcccca tctctgaaga ctacagcgtc gccagcgcag ctctctctag    2460
cgacggccga atcttcactg gtgtcaatgt atatcatttt actgggggac cttgtgcaga    2520
actcgtggtg ctgggcactg ctgctgctgc ggcagctggc aacctgactt gtatcgtcgc    2580
gatcggaaat gagaacaggg gcatcttgag cccctgcgga cggtgccgac aggtgcttct    2640
cgatctgcat cctgggatca aagccatagt gaaggacagt gatggacagc cgacggcagt    2700
tgggattcgt gaattgctgc cctctggtta tgtgtgggag ggctaagcac ttcgtggccg    2760
aggagcagga ctgacacgtg ctacgagatt tcgattccac cgccgccttc tatgaaaggt    2820
tgggcttcgg aatcgttttc cgggacgccg gctggatgat cctccagcgc ggggatctca    2880
tgctggagtt cttcgcccac cccaacttgt ttattgcagc ttataatggt tacaaataaa    2940
gcaatagcat cacaaatttc acaaataaag catttttttc actgcattct agttgtggtt    3000
tgtccaaact catcaatgta tcttatcatg tctgtatacc gtcgacctct agctagagct    3060
tggcgtaatc atggtcatag ctgtttcctg tgtgaaattg ttatccgctc acaattccac    3120
acaacatacg agccggaagc ataaagtgta aagcctgggg tgcctaatga gtgagctaac    3180
tcacattaat tgcgttgcgc tcactgcccg ctttccagtc gggaaacctg tcgtgccagc    3240
tgcattaatg aatcggccaa cgcgcgggga gaggcggttt gcgtattggg cgctcttccg    3300
cttcctcgct cactgactcg ctgcgctcgg tcgttcggct gcggcgagcg gtatcagctc    3360
actcaaaggc ggtaatacgg ttatccacag aatcagggga taacgcagga aagaacatgt    3420
gagcaaaagg ccagcaaaag gccaggaacc gtaaaaaggc cgcgttgctg gcgtttttcc    3480
ataggctccg cccccctgac gagcatcaca aaaatcgacg ctcaagtcag aggtggcgaa    3540
```

```
acccgacagg actataaaga taccaggcgt ttccccctgg aagctccctc gtgcgctctc   3600
ctgttccgac cctgccgctt accggatacc tgtccgcctt tctcccttcg ggaagcgtgg   3660
cgctttctca tagctcacgc tgtaggtatc tcagttcggt gtaggtcgtt cgctccaagc   3720
tgggctgtgt gcacgaaccc cccgttcagc ccgaccgctg cgccttatcc ggtaactatc   3780
gtcttgagtc caacccggta agacacgact tatcgccact ggcagcagcc actggtaaca   3840
ggattagcag agcgaggtat gtaggcggtg ctacagagtt cttgaagtgg tggcctaact   3900
acggctacac tagaagaaca gtatttggta tctgcgctct gctgaagcca gttaccttcg   3960
gaaaaagagt tggtagctct tgatccggca aacaaaccac cgctggtagc ggttttttg    4020
tttgcaagca gcagattacg cgcagaaaaa aaggatctca agaagatcct ttgatctttt   4080
ctacggggtc tgacgctcag tggaacgaaa actcacgtta agggattttg gtcatgagat   4140
tatcaaaaag gatcttcacc tagatccttt taaattaaaa atgaagtttt aaatcaatct   4200
aaagtatata tgagtaaact tggtctgaca gttaccaatg cttaatcagt gaggcaccta   4260
tctcagcgat ctgtctattt cgttcatcca tagttgcctg actccccgtc gtgtagataa   4320
ctacgatacg ggagggctta ccatctggcc ccagtgctgc aatgataccg cgagacccac   4380
gctcaccggc tccagattta tcagcaataa accagccagc cggaagggcc gagcgcagaa   4440
gtggtcctgc aactttatcc gcctccatcc agtctattaa ttgttgccgg gaagctagag   4500
taagtagttc gccagttaat agtttgcgca acgttgttgc cattgctaca ggcatcgtgg   4560
tgtcacgctc gtcgtttggt atggcttcat tcagctccgg ttcccaacga tcaaggcgag   4620
ttacatgatc ccccatgttg tgcaaaaaag cggttagctc cttcggtcct ccgatcgttg   4680
tcagaagtaa gttggccgca gtgttatcac tcatggttat ggcagcactg cataattctc   4740
ttactgtcat gccatccgta agatgctttt ctgtgactgg tgagtactca accaagtcat   4800
tctgagaata gtgtatgcgg cgaccgagtt gctcttgccc ggcgtcaata cgggataata   4860
ccgcgccaca tagcagaact ttaaaagtgc tcatcattgg aaaacgttct tcggggcgaa   4920
aactctcaag gatcttaccg ctgttgagat ccagttcgat gtaacccact cgtgcaccca   4980
actgatcttc agcatctttt actttcacca gcgtttctgg gtgagcaaaa acaggaaggc   5040
aaaatgccgc aaaaaaggga ataagggcga cacggaaatg ttgaatactc atactcttcc   5100
tttttcaata ttattgaagc atttatcagg gttattgtct catgagcgga tacatatttg   5160
aatgtattta gaaaaataaa caaatagggg ttccgcgcac atttccccga aaagtgccac   5220
ctgacgtcga cggatcggga gatctcccga tcccctatgg tgcactctca gtacaatctg   5280
ctctgatgcc gcatagttaa gccagtatct gctccctgct tgtgtgttgg aggtcgctga   5340
gtagtgcgcg agcaaaattt aagctacaac aaggcaaggc ttgaccgaca attgcatgaa   5400
gaatctgctt agggttaggc gttttgcgct gcttcgcgat gtacgggcca gatatacgcg   5460
ttgacattga ttattgacta gttattaata gtaatcaatt acgggtcat tagttcatag    5520
cccatatatg gagttccgcg ttacataact tacggtaaat ggcccgcctg gctgaccgcc   5580
caacgacccc cgcccattga cgtcaataat gacgtatgtt cccatagtaa cgccaatagg   5640
gactttccat tgacgtcaat gggtggagta tttacgtaa actgcccact ggcagtaca    5700
tcaagtgtat catatgccaa gtacgccccc tattgacgtc aatgacggta aatggcccgc   5760
ctggcattat gcccagtaca tgaccttatg gactttcct acttggcagt acatctacgt    5820
attagtcatc gctattacca tggtgatgcg gttttggcag tacatcaatg ggcgtggata   5880
```

| | |
|---|---|
| gcggtttgac tcacggggat ttccaagtct ccaccccatt gacgtcaatg ggagtttgtt | 5940 |
| ttggcaccaa aatcaacggg actttccaaa atgtcgtaac aactccgccc cattgacgca | 6000 |
| aatgggcggt aggcgtgtac ggtgggaggt ctatataagc agagctctct ggctaactag | 6060 |
| agaacccact gcttactggc ttatcgacc | 6089 |

```
<210> SEQ ID NO 62
<211> LENGTH: 5515
<212> TYPE: DNA
<213> ORGANISM: Artificial Sequence
<220> FEATURE:
<223> OTHER INFORMATION: Description of Artificial Sequence: Synthetic
      CD4 KI construct

<400> SEQUENCE: 62
```

| | |
|---|---|
| agccccttcg cctcgtgctt gagttgaggc ctggcttggg cgctggggcc gccgcgtgcg | 60 |
| aatctggtgg caccttcgcg cctgtctcgc tgctttcgat aagtctctag ccatttaaaa | 120 |
| tttttgatga cctgctgcga cgctttttt ctggcaagat agtcttgtaa atgcgggcca | 180 |
| agatcgatct gcacactggt atttcggttt ttggggccgc gggcggcgac ggggcccgtg | 240 |
| cgtcccagcg cacatgttcg gcgaggcggg gcctgcgagc gcggccaccg agaatcggac | 300 |
| gggggtagtc tcaagctggc cggcctgctc tggtgcctgg cctcgcgccg ccgtgtatcg | 360 |
| ccccgccctg gcggcaagg ctggcccggt cggcaccagt tgcgtgagcg gaaagatggc | 420 |
| cgcttcccgg ccctgctgca gggagctcaa aatggaggac gcggcgctcg ggagagcggg | 480 |
| cgggtgagtc acccacacaa aggaaaaggg cctttccgtc ctcagccgtc gcttcatgtg | 540 |
| actccacgga gtaccgggcg ccgtccaggc acctcgatta gttctcgagc ttttggagta | 600 |
| cgtcgtcttt aggttggggg gaggggtttt atgcgatgga gtttccccac actgagtggg | 660 |
| tggagactga agttaggcca gcttggcact tgatgtaatt ctccttggaa tttgcccttt | 720 |
| ttgagtttgg atcttggttc attctcaagc ctcagacagt ggttcaaagt ttttttcttc | 780 |
| catttcaggt gtcgtggaat tggctagagc ttgcatgcct gcaggtcggc cgccacgacc | 840 |
| ggtgccgcca ccatcccctg acccacgccc ctgaccccctc acaaggagac gaccttccat | 900 |
| gaccgagtac aagcccacgg tgcgcctcgc cacccgcgac gacgtccccc gggccgtacg | 960 |
| caccctcgcc gccgcgttcg ccgactaccc cgccacgcgc cacaccgtcg acccggaccg | 1020 |
| ccacatcgag cgggtcaccg agctgcaaga actcttcctc acgcgcgtcg ggctcgacat | 1080 |
| cggcaaggtg tgggtcgcgg acgacggcgc cgcggtggcg gtctggacca cgccggagag | 1140 |
| cgtcgaagcg ggggcggtgt cgccgagat cggcccgcgc atggccgagt tgagcggttc | 1200 |
| ccggctggcc gcgcagcaac agatggaagg cctcctggcg ccgcaccggc caaggagcc | 1260 |
| cgcgtggttc ctggccaccg tcggcgtctc gcccgaccac cagggcaagg gtctgggcag | 1320 |
| cgccgtcgtg ctccccggag tggaggcggc cgagcgcgcc ggggtgcccg ccttcctgga | 1380 |
| gacctccgcg ccccgcaacc tccccttcta cgagcggctc ggcttcaccg tcaccgccga | 1440 |
| cgtcgaggtg cccgaaggac cgcgcacctg gtgcatgacc cgcaagcccg gtgcctgacg | 1500 |
| cccgccccac gacccgcagc gcccgaccga aaggagcgca cgaccccatg gctccgaccg | 1560 |
| aagccgaccc gggcggcccc gccgaccccg caccggcccc cgaggccac cgactctaga | 1620 |
| ggatcataat cagccatacc acatttgtag aggttttact tgctttaaaa aacctcccac | 1680 |
| acctccccct gaacctgaaa cataaaatga atgcaattgt tgttgttaac ttgtttattg | 1740 |
| cagcttataa tggttacaaa taaagcaata gcatcacaaa tttcacaaat aaagcatttt | 1800 |

```
tttcactgca ttctagttgt ggtttgtcca aactcatcaa tgtatcttat catgtctgga   1860
tcctagcgtt taaacttaag cttggtaccg agctcggatc cactagcgat gtacgggcca   1920
gatatacgcg ttgacattga ttattgacta gttattaata gtaatcaatt acgggtcat    1980
tagttcatag cccatatatg gagttccgcg ttacataact tacggtaaat ggcccgcctg   2040
gctgaccgcc caacgacccc cgcccattga cgtcaataat gacgtatgtt cccatagtaa   2100
cgccaatagg gactttccat tgacgtcaat gggtggagta tttacggtaa actgcccact   2160
tggcagtaca tcaagtgtat catatgccaa gtacgccccc tattgacgtc aatgacggta   2220
aatggcccgc ctggcattat gcccagtaca tgaccttatg gactttcct acttggcagt    2280
acatctacgt attagtcatc gctattacca tggtgatgcg gttttggcag tacatcaatg   2340
ggcgtggata gcggtttgac tcacggggat ttccaagtct ccaccccatt gacgtcaatg   2400
ggagtttgtt ttggcaccaa aatcaacggg actttccaaa atgtcgtaac aactccgccc   2460
cattgacgca aatgggcggt aggcgtgtac ggtgggaggt ctatataagc agagctctct   2520
ggctaactag agaacccact gcttactggc ttatcgaaat taatacgact cactataggg   2580
agacccaagc tggctagcgc tgatatggcg tactaccatc accatcacca tcactctaga   2640
tcagaaggag ttcgaaccaa ccggggagtc ccttttaggc acttgcttct ggtgctgcaa   2700
ctggcgctcc tcccagcagc cactcaggga agaaagtgg tgctgggcaa aaaggggat     2760
acagtggaac tgacctgtac agcttcccag aagaagagca tacaattcca ctggaaaaac   2820
tccaaccaga taaagattct gggaaatcag ggctccttct taactaaagg tccatccaag   2880
ctgaatgatc gcgctgactc aagaagaagc ctttgggacc aaggaaactt cccctgatc    2940
atcaagaatc ttaagataga agactcagat acttacatct gtgaagtgga ggaccagaag   3000
gaggaggtgc aattgctagt gttcggattg actgccaact ctgacaccca cctgcttcag   3060
gggcagagcc tgaccctgac cttggagagc cccctggta gtagcccctc agtgcaatgt     3120
aggagtccaa ggggtaaaaa catacagggg gggaagaccc tctccgtgtc tcagctggag   3180
ctccaggata gtggcacctg gacatgcact gtcttgcaga accagaagaa ggtggagttc   3240
aaaatagaca tcgtggtgct agcttttccag aaggcctcca gcatagtcta taagaaagag   3300
ggggaacagg tggagttctc cttcccactc gcctttacag ttgaaaagct gacgggcagt   3360
ggcgagctgt ggtggcaggc ggagagggct tcctcctcca agtcttggat cacctttgac   3420
ctgaagaaca aggaagtgtc tgtaaaacgg gttacccagg accctaagct ccagatgggc   3480
aagaagctcc cgctccacct cacccctgcc caggccttgc ctcagtatgc tggctctgga   3540
aacctcaccc tggcccttga agcgaaaaca ggaaagttgc atcaggaagt gaacctggtg   3600
gtgatgagag ccactcagct ccagaaaaat ttgacctgtg aggtgtgggg acccacctcc   3660
cctaagctga tgctgagctt gaaactggag aacaaggagg caaggtctc gaagcgggag    3720
aaggcggtgt gggtgctgaa ccctgaggcg gggatgtggc agtgtctgct gagtgactcg   3780
ggacaggtcc tgctggaatc caacatcaag gttctgccca tggtccac cccggtgcag     3840
ccaatggccc tgattgtgct ggggggcgtc gccggcctcc tgcttttcat tgggctaggc   3900
atcttcttct gtgtcaggtg ccggcaccga aggcgccaag cagagcggat gtctcagatc   3960
aagagactcc tcagtgagaa gaagacctgc cagtgccctc accggtttca gaagacatgt   4020
agatcgatcg cgagcggccg ctcgagtcta gagggcccgt ttaaaccgc tgatcagcct    4080
cgactgtgcc ttctagttgc cagccatctg ttgtttgccc ctcccccgtg ccttccttga   4140
ccctggaagg tgccactccc actgtccttt cctaataaaa tgaggaaatt gcatcgcatt   4200
```

```
gtctgagtag gtgtcattct attctggggg gtggggtggg gcaggacagc aaggggagg    4260 attgggaaga caatagcagg catgctgggg atgcggtggg ctctatggct tctgaggcgg   4320
aaagaaccag ctggggctct aggggtatc cccacgcgcc ctgtagcggc gcattaagcg    4380
cggcgggtgt ggtggttacg cgcagcgtga ccgctacact tgccagcgcc ctagcgcccg   4440
ctcctttcgc tttcttccct tcctttctcg ccacgttcgc ctaccgtcga atcaccggta   4500
accttataag ggattttgcc gatttcggcc tattggttaa aaaatgagct gatttaacaa   4560
aaatttaacg cgaattaatt ctgtggaatg tgtgtcagtt agggtgtgga agtccccag    4620 gctccccagc aggcagaagt atgcaaagca tgcatctcaa ttagtcagca accaggtgtg   4680
gaaagtcccc aggctcccca gcaggcagaa gtatgcaaag catgcatctc aattagtcag   4740
caaccatagt cccgccccta actccgccca tcccgcccct aactccgccc agttccgccc   4800
attctccgcc ccatggctga ctaatttttt ttatttatgc agaggccgag gccgcctctg   4860
cctctgagct attccagaag tagtgaggag gcttttttgg aggcctaggc ttttgcaaaa   4920
agctcccggg agcttgtata tccatttcg gatctgatca agagacagga tgaggatcgt    4980
ttcgcatgat tgaacaagat ggattgcacg caggttctcc ggccgcttgg gtggagaggc   5040
tattcggcta tgactgggca acagacaa tcggctgctc tgatgccgcc gtgttccggc     5100
tgtcagcgca gggcgcccg gttcttttg tcaagaccga cctgtccggt gccctgaatg     5160
aactgcagga cgaggcagcg cggctatcgt ggctggccac gacgggcgtt ccttgcgcag   5220
ctgtgctcga cgttgtcact gaagcggaa gggactggct gctattgggc gaagtgccgg    5280
ggcaggatct cctgtcatct caccttgctc ctgccgagaa agtatccatc atggctgatg   5340
caatgcggcg gctgcatacg cttgatccgg ctacctgccc attcgaccac caagcgaaac   5400
atcgcatcga gcgagcacgt actcggatgg aagccggtct tgtcgatcag gatgatctgg   5460
acgaagagca tcaggggctc gcgccagccg aactgttcgc caggctcaag gcgcg          5515
```

<210> SEQ ID NO 63
<211> LENGTH: 5370
<212> TYPE: DNA
<213> ORGANISM: Artificial Sequence
<220> FEATURE:
<223> OTHER INFORMATION: Description of Artificial Sequence: Synthetic
      SSTR2 KI construct

<400> SEQUENCE: 63

```
agccccttcg cctcgtgctt gagttgaggc ctggcctggg cgctgggcc gccgcgtgcg      60 aatctggtgg caccttcgcg cctgtctcgc tgctttcgat aagtctctag ccatttaaaa    120 ttttgatga cctgctgcga cgcttttttt ctggcaagat agtcttgtaa atgcgggcca     180
agatcgatct gcacactggt atttcggttt ttggggccgc gggcggcgac ggggcccgtg    240
cgtcccagcg cacatgttcg gcgaggcggg gcctgcgagc gcggccaccg agaatcggac    300 ggggtagtc tcaagctggc cggcctgctc tggtgcctgg cctcgcgccg ccgtgtatcg    360
ccccgccctg gcggcaagg ctggcccggt cggcaccagt tgcgtgagcg aaagatggc     420 cgcttccccgg ccctgctgca gggagctcaa aatggaggac gcggcgctcg ggagagcggg   480
cgggtgagtc acccacacaa aggaaaaggg cctttccgtc ctcagccgtc gcttcatgtg   540
actccacgga gtaccgggcg ccgtccaggc acctcgatta ttctcgagc tttggagta    600 cgtcgtcttt aggttggggg gaggggtttt atgcgatgga gttccccac actgagtggg    660 tggagactga agttaggcca gcttggcact tgatgtaatt ctccttggaa tttgcccttt   720
```

```
ttgagtttgg atcttggttc attctcaagc ctcagacagt ggttcaaagt ttttttcttc    780
catttcaggt gtcgtgagga attggctaag cttgcatgcc tgcaggtcgg ccgccacgac    840
cggtgccgcc accatcccct gacccacgcc cctgacccct cacaaggaga cgaccttcca    900
tgaccgagta caagcccacg gtgcgcctcg ccacccgcga cgacgtcccc cgggccgtac    960
gcaccctcgc cgccgcgttc gccgactacc ccgccacgcg ccacaccgtc gacccggacc   1020
gccacatcga gcgggtcacc gagctgcaag aactcttcct cacgcgcgtc gggctcgaca   1080
tcggcaaggt gtgggtcgcg gacgacggcg ccgcggtggc ggtctggacc acgccggaga   1140
gcgtcgaagc gggggcggtg ttcgccgaga tcggcccgcg catggccgag ttgagcggtt   1200
cccggctggc cgcgcagcaa cagatggaag gcctcctggc gccgcaccgg cccaaggagc   1260
ccgcgtggtt cctggccacc gtcggcgtct cgcccgacca ccagggcaag ggtctgggca   1320
gcgccgtcgt gctccccgga gtggaggcgg ccgagcgcgc cggggtgccc gccttcctgg   1380
agacctccgc gccccgcaac ctccccttct acgagcggct cggcttcacc gtcaccgccg   1440
acgtcgaggt gcccgaagga ccgcgcacct ggtgcatgac ccgcaagccc ggtgcctgac   1500
gcccgcccca cgaccgcag cgcccgaccg aaaggagcgc acgacccat ggctccgacc   1560
gaagccaccc ggggcggccc cgccgacccc gcacccgccc ccgaggccca ccgactctag   1620
aggatcataa tcagccatac cacatttgta gaggttttac ttgctttaaa aaacctccca   1680
cacctccccc tgaacctgaa acataaaatg aatgcaattg ttgttgttaa cttgtttatt   1740
gcagcttata atggttacaa ataaagcaat agcatcacaa atttcacaaa taaagcattt   1800
ttttcactgc attctagttg tggtttgtcc aaactcatca atgtatctta tcatgtctgg   1860
atctagcgtt taaacttaag cttggtaccg agctcggatc cactagcgat gtacgggcca   1920
gatatacgcg ttgacattga ttattgacta gttattaata gtaatcaatt acgggtcat   1980
tagttcatag cccatatatg gagttccgcg ttacataact tacggtaaat ggcccgcctg   2040
gctgaccgcc caacgacccc cgcccattga cgtcaataat gacgtatgtt cccatagtaa   2100
cgccaatagg gactttccat tgacgtcaat gggtggagta tttacggtaa actgcccact   2160
tggcagtaca tcaagtgtat catatgccaa gtacgccccc tattgacgtc aatgacggta   2220
aatggcccgc ctggcattat gcccagtaca tgaccttatg ggactttcct acttggcagt   2280
acatctacgt attagtcatc gctattacca tggtgatgcg gttttggcag tacatcaatg   2340
ggcgtggata gcggtttgac tcacggggat ttccaagtct ccaccccatt gacgtcaatg   2400
ggagtttgtt ttggcaccaa aatcaacggg actttccaaa atgtcgtaac aactccgccc   2460
cattgacgca aatgggcggt aggcgtgtac ggtgggaggt ctatataagc agagctctct   2520
ggctaactag agaacccact gcttactggc ttatcgaaat taatacgact cactataggg   2580
agacccaagc tggctagcac catggacatg gcggatgagc cactcaatgg aagccacaca   2640
tggctatcca ttccatttga cctcaatggc tctgtggtgt caaccaacac ctcaaaccag   2700
acagagccgt actatgacct gacaagcaat gcagtcctca cattcatcta ttttgtggtc   2760
tgcatcattg ggttgtgtgg caacacactt gtcatttatg tcatcctccg ctatgccaag   2820
atgaagacca tcaccaacat ttacatcctc aacctggcca tcgcagatga gctcttcatg   2880
ctgggtctgc ctttcttggc tatgcaggtg gctctggtcc actggccctt tggcaaggcc   2940
atttgccggg tggtcatgac tgtggatggc atcaatcagt tcaccagcat cttctgcctg   3000
acagtcatga gcatcgaccg ataccctggct gtggtccacc ccatcaagtc ggccaagtgg   3060
```

```
aggagacccc ggacggccaa gatgatcacc atggctgtgt ggggagtctc tctgctggtc    3120
atcttgccca tcatgatata tgctgggctc cggagcaacc agtggggag aagcagctgc      3180
accatcaact ggccaggtga atctggggct tggtacacag ggttcatcat ctacactttc    3240
attctggggt tcctggtacc cctcaccatc atctgtcttt gctacctgtt cattatcatc    3300
aaggtgaagt cctctggaat ccgagtgggc tcctctaaga ggaagaagtc tgagaagaag    3360
gtcacccgaa tggtgtccat cgtggtggct gtcttcatct tctgctggct tcccttctac    3420
atattcaacg tttcttccgt ctccatggcc atcagcccca ccccagccct aaaggcatg     3480
tttgactttg tggtggtcct cacctatgct aacagctgtg ccaaccctat cctatatgcc    3540
ttcttgtctg acaacttcaa gaagagcttc cagaatgtcc tctgcttggt caaggtgagc    3600
ggcacagatg atggggagcg gagtgacagt aagcaggaca atcccggct gaatgagacc      3660
acggagaccc agaggaccct cctcaatgga gacctccaaa ccagtatctc aagcttcgaa    3720
ttgggaggtg gcggtagcgg aggtggcggt agcctcgagg attcactggc cgtcgtttta    3780
caacgtcgtg actgggaaaa ccctggcgtt acccaactta atcgccttgc agcacgtccc    3840
cctttcgcca gctggcgtaa tagcgaagag gcccgcaccg atcgctgagc ggccgctcga    3900
gtctagaggg cccgtttaaa cccgctgatc agcctcgact gtgccttcta gttgccagcc    3960
atctgttgtt tgcccctccc ccgtgccttc cttgaccctg gaaggtgcca ctcccactgt    4020
cctttcctaa taaatgagg aaattgcatc gcattgtctg agtaggtgtc attctattct      4080
ggggggtggg gtggggcagg acagcaaggg ggaggattgg gaagacaata gcaggcatgc    4140
tggggatgcg gtgggctcta tggcttctga ggcggaaaga accagctggg gctctagggg    4200
gtatccccac gcgccctgta gcggcgcatt aagcgcggcg ggtgtggtgg ttacgcgcag    4260
cgtgaccgct acacttgcca gcgccctagc gcccgctcct ttcgctttct tcccttcctt    4320
tctcgccacg ttcgcctacc gtcgaatcac cggtaacctt ataagggatt ttgccgattt    4380
cggcctattg gttaaaaaat gagctgattt aacaaaaatt taacgcgaat taattctgtg    4440
gaatgtgtgt cagttagggt gtggaaagtc cccaggctcc ccagcaggca gaagtatgca    4500
aagcatgcat ctcaattagt cagcaaccag gtgtggaaag tccccaggct ccccagcagg    4560
cagaagtatg caaagcatgc atctcaatta gtcagcaacc atagtcccgc ccctaactcc    4620
gcccatcccg cccctaactc cgcccagttc cgcccattct ccgccccatg ctgactaat     4680
ttttttatt tatgcagagg ccgaggccgc ctctgcctct gagctattcc agaagtagtg     4740
aggaggcttt tttggaggcc taggcttttg caaaaagctc ccgggagctt gtatatccat    4800
tttcggatct gatcaagaga caggatgagg atcgtttcgc atgattgaac aagatggatt    4860
gcacgcaggt tctccggccg cttgggtgga gaggctattc ggctatgact gggcacaaca    4920
gacaatcggc tgctctgatg ccgccgtgtt ccggctgtca gcgcaggggc gcccggttct    4980
ttttgtcaag accgacctgt ccggtgccct gaatgaactg caggacgagg cagcgcggct    5040
atcgtggctg gccacgacgg gcgttccttg cgcagctgtg ctcgacgttg tcactgaagc    5100
gggaagggac tggctgctat tgggcgaagt gccggggcag gatctcctgt catctcacct    5160
tgctcctgcc gagaaagtat ccatcatggc tgatgcaatg cggcggctgc atacgcttga    5220
tccggctacc tgcccattcg accaccaagc gaaacatcgc atcgagcgag cacgtactcg    5280
gatggaagcc ggtcttgtcg atcaggatga tctggacgaa gagcatcagg gctcgcgcc    5340
agccgaactg ttcgccaggc tcaaggcgcg                                      5370
```

<210> SEQ ID NO 64
<211> LENGTH: 6789
<212> TYPE: DNA
<213> ORGANISM: Artificial Sequence
<220> FEATURE:
<223> OTHER INFORMATION: Description of Artificial Sequence: Synthetic hATX KI construct

<400> SEQUENCE: 64

```
agcccttcg cctcgtgctt gagttgaggc ctggcttggg cgctggggcc gccgcgtgcg    60
aatctggtgg caccttcgcg cctgtctcgc tgctttcgat aagtctctag ccatttaaaa   120
tttttgatga cctgctgcga cgcttttttt ctggcaagat agtcttgtaa atgcgggcca   180
agatcgatct gcacactggt atttcggttt ttggggccgc gggcggcgac ggggcccgtg   240
cgtcccagcg cacatgttcg gcgaggcggg gcctgcgagc gcggccaccg agaatcggac   300
gggggtagtc tcaagctggc cggcctgctc tggtgcctgg cctcgcgccg ccgtgtatcg   360
ccccgccctg gcggcaagg ctggcccggt cggcaccagt tgcgtgagcg gaaagatggc    420
cgcttcccgg ccctgctgca gggagctcaa aatggaggac gcggcgctcg ggagagcggg   480
cgggtgagtc acccacacaa aggaaaaggg cctttccgtc ctcagccgtc gcttcatgtg   540
actccacgga gtaccgggcg ccgtccaggc acctcgatta gttctcgagc ttttggagta   600
cgtcgtcttt aggttggggg gaggggtttt atgcgatgga gtttccccac actgagtggg   660
tggagactga agttaggcca gcttggcact tgatgtaatt ctccttggaa tttgcccttt   720
ttgagtttgg atcttggttc attctcaagc ctcagacagt ggttcaaagt tttttttcttc  780
catttcaggt gtcgtggaat tggctagagc ttgcatgcct gcaggtcggc cgccacgacc   840
ggtgccgcca ccatcccctg acccacgccc ctgacccctc acaaggagac gaccttccat   900
gaccgagtac aagcccacgg tgcgcctcgc caccgcgac gacgtccccc gggccgtacg    960
caccctcgcc gccgcgttcg ccgactaccc cgccacgcgc cacaccgtcg acccggaccg  1020
ccacatcgag cgggtcaccg agctgcaaga actcttcctc acgcgcgtcg gctcgacat   1080
cggcaaggtg tgggtcgcgg acgacggcgc cgcggtggcg gtctggacca cgccggagag  1140
cgtcgaagcg ggggcggtgt tcgccgagat cggcccgcgc atggccgagt tgagcggttc  1200
ccggctggcc gcgcagcaac agatggaagg cctcctggcg ccgcaccggc caaggagcc   1260
cgcgtggttc ctggccaccg tcggcgtctc gcccgaccac cagggcaagg gtctgggcag  1320
cgccgtcgtg ctccccggag tggaggcggc cgagcgcgcc ggggtgcccg ccttcctgga  1380
gacctccgcg ccccgcaacc tcccttcta cgagcggctc ggcttcaccg tcaccgccga  1440
cgtcgaggtg cccgaaggac cgcgcacctg gtgcatgacc cgcaagcccg tgcctgacg   1500
cccgccccac gacccgcagc gcccgaccga aaggagcgca cgaccccatg ctccgaccg   1560
aagccgaccc gggcggcccc gccgaccccg cacccgcccc cgaggccac cgactctaga   1620
ggatcataat cagccatacc acatttgtag aggtttttact tgctttaaaa acctcccac   1680
acctccccct gaacctgaaa cataaaatga atgcaattgt tgttgttaac ttgtttattg   1740
cagcttataa tggttacaaa taaagcaata gcatcacaaa tttcacaaat aaagcatttt   1800
ttcactgca ttctagttgt ggtttgtcca aactcatcaa tgtatcttat catgtctgga   1860
tcctagcgtt taaacttaag cttggtaccg agctcggatc cactagtaat ggttacaaat  1920
aaagcaatag catcacaaat ttcacaaata aagcattttt tcactgcat tctagttgtg   1980
gtttgtccaa actcatcaat gtatcttatc atgtctgtac gatgtacggg ccagatatac  2040
gcgttgacat tgattattga ctagttatta atagtaatca attacggggt cattagttca  2100
```

```
tagcccatat atggagttcc gcgttacata acttacggta aatggcccgc ctggctgacc    2160
gcccaacgac ccccgcccat tgacgtcaat aatgacgtat gttcccatag taacgccaat    2220
agggactttc cattgacgtc aatgggtgga gtatttacgg taaactgccc acttggcagt    2280
acatcaagtg tatcatatgc caagtacgcc ccctattgac gtcaatgacg gtaaatggcc    2340
cgcctggcat tatgcccagt acatgacctt atgggacttt cctacttggc agtacatcta    2400
cgtattagtc atcgctatta ccatggtgat gcggttttgg cagtacatca atgggcgtgg    2460
atagcggttt gactcacggg gatttccaag tctccacccc attgacgtca atgggagttt    2520
gttttggcac caaaatcaac gggactttcc aaaatgtcgt aacaactccg cccattgac    2580
gcaaatgggc ggtaggcgtg tacggtggga ggtctatata agcagagctc tctggctaac    2640
tagagaaccc actgcttact ggcttatcga aattaatacg actcactata gggagaccca    2700
agctggctag ccaccatggc aaggaggagc tcgttccagt cgtgtcagat aatatccctg    2760
ttcacttttg ccgttggagt caatatctgc ttaggattca ctgcacatcg aattaagaga    2820
gcagaaggat gggaggaagg tcctcctaca gtgctatcag actcccctg gaccaacatc    2880
tccggatctt gcaagggcag gtgctttgaa cttcaagagg ctggacctcc tgattgtcgc    2940
tgtgacaact tgtgtaagag ctataccagt tgctgccatg actttgatga gctgtgtttg    3000
aagacagccc gtggctggga gtgtactaag gacagatgtg gagaagtcag aaatgaagaa    3060
aatgcctgtc actgctcaga ggactgcttg gccaggggag actgctgtac caattaccaa    3120
gtggttttgca aaggagagtc gcattgggtt gatgatgact gtgaggaaat aaaggccgca    3180
gaatgccctg cagggtttgt tcgccctcca ttaatcatct tctccgtgga tggcttccgt    3240
gcatcataca tgaagaaagg cagcaaagtc atgcctaata ttgaaaaact aaggtcttgt    3300
ggcacacact ctccctacat gaggccggtg tacccaacta aaacctttcc taacttatac    3360
actttggcca ctgggctata tccagaatca catggaattg ttggcaattc aatgtatgat    3420
cctgtatttg atgccacttt tcatctgcga gggcgagaga atttaatca tagatggtgg    3480
ggaggtcaac cgctatggat tacagccacc aagcaagggg tgaaagctgg aacattcttt    3540
tggtctgttg tcatccctca cgagcggaga atattaacca tattgcagtg gctcacccctg   3600
ccagatcatg agaggccttc ggtctatgcc ttctattctg agcaacctga tttctctgga    3660
cacaaatatg gcccttttcgg ccctgagatg acaaatcctc tgagggaaat cgacaaaatt    3720
gtggggcaat taatggatgg actgaaacaa ctaaaactgc atcggtgtgt caacgtcatc    3780
tttgtcggag accatggaat ggaagatgtc acatgtgata gaactgagtt cttgagtaat    3840
tacctaacta atgtggatga tattactta gtgcctggaa ctctaggaag aattcgatcc    3900
aaatttagca acaatgctaa atatgacccc aaagccatta ttgccaatct cacgtgtaaa    3960
aaaccagatc agcactttaa gccttacttg aaacagcacc ttcccaaacg tttgcactat    4020
gccaacaaca gaagaattga ggatatccat ttattggtgg aacgcagatg gcatgttgca    4080
aggaaacctt tggatgtttta taagaaacca tcaggaaaat gcttttttcca gggagaccac    4140
ggatttgata acaaggtcaa cagcatgcag actgtttttg taggttatgg cccaacattt    4200
aagtacaaga ctaaagtgcc tccatttgaa acattgaac tttacaatgt tatgtgtgat    4260
ctcctgggat tgaagccagc tcctaataat gggacccatg gaagtttgaa tcatctcctg    4320
cgcactaata ccttcaggcc aaccatgcca gaggaagtta ccagacccaa ttatccaggg    4380
attatgtacc ttcagtctga ttttgacctg ggctgcactt gtgatgataa ggtagagcca    4440
```

```
aagaacaagt tggatgaact caacaaacgg cttcatacaa aagggtctac agaagagaga      4500
cacctcctct atgggcgacc tgcagtgctt tatcggacta gatatgatat cttatatcac      4560
actgactttg aaagtggtta tagtgaaata ttcctaatgc cactctggac atcatatact      4620
gtttccaaac aggctgaggt ttccagcgtt cctgaccatc tgaccagttg cgtccggcct      4680
gatgtccgtg tttctccgag tttcagtcag aactgtttgg cctacaaaaa tgataagcag      4740
atgtcctacg gattcctctt tcctccttat ctgagctctt caccagaggc taaatatgat      4800
gcattccttg taaccaatat ggttccaatg tatcctgctt tcaaacgggt ctggaattat      4860
ttccaaaggg tattggtgaa gaaatatgct cggaaagaa atggagttaa cgtgataagt       4920
ggaccaatct tcgactatga ctatgatggc ttacatgaca cagaagacaa aataaaacag      4980
tacgtggaag gcagttccat tcctgttcca actcactact acagcatcat caccagctgt      5040
ctggatttca ctcagcctgc cgacaagtgt gacggccctc tctctgtgtc ctccttcatc      5100
ctgcctcacc ggcctgacaa cgaggagagc tgcaatagct cagaggacga atcaaaatgg      5160
gtagaagaac tcatgaagat gcacacagct agggtgcgtg acattgaaca tctcaccagc      5220
ctggacttct tccgaaagac cagccgcagc tacccagaaa tcctgacact caagacatac      5280
ctgcatacat atgagagcga gatttaagcg gccgctcgag tctagagggc ccgtttaaac      5340
ccgctgatca gcctcgactg tgccttctag ttgccagcca tctgttgttt gcccctcccc      5400
cgtgccttcc ttgaccctgg aaggtgccac tcccactgtc ctttcctaat aaaatgagga      5460
aattgcatcg cattgtctga gtaggtgtca ttctattctg ggggtgggg tggggcagga       5520
cagcaagggg gaggattggg aagacaatag caggcatgct ggggatgcgg tgggctctat      5580
ggcttctgag gcggaaagaa ccagctgggg ctctaggggg tatccccacg cgccctgtag      5640
cggcgcatta agcgcggcgg gtgtggtggt tacgcgcagc gtgaccgcta cacttgccag      5700
cgccctagcg cccgctcctt tcgctttctt cccttccttt ctcgccacgt tcgcctaccg      5760
tcgaatcacc ggtaacctta aagggattt tgccgatttc ggcctattgg ttaaaaaatg      5820
agctgattta acaaaaattt aacgcgaatt aattctgtgg aatgtgtgtc agttagggtg      5880
tggaaagtcc ccaggctccc cagcaggcag aagtatgcaa agcatgcatc tcaattagtc      5940
agcaaccagg tgtggaaagt ccccaggctc cccagcaggc agaagtatgc aaagcatgca      6000
tctcaattag tcagcaacca tagtcccgcc cctaactccg cccatcccgc ccctaactcc      6060
gcccagttcc gcccattctc cgccccatgg ctgactaatt ttttttattt atgcagaggc      6120
cgaggccgcc tctgcctctg agctattcca gaagtagtga ggaggctttt ttggaggcct      6180
aggcttttgc aaaaagctcc cgggagcttg tatatccatt ttcggatctg atcaagagac      6240
aggatgagga tcgtttcgca tgattgaaca agatggattg cacgcaggtt ctccggccgc      6300
ttgggtggag aggctattcg gctatgactg gcacaacag acaatcggct gctctgatgc       6360
cgccgtgttc cggctgtcag cgcaggggcg cccggttctt tttgtcaaga ccgacctgtc      6420
cggtgccctg aatgaactgc aggacgaggc agcgcggcta tcgtggctgg ccacgacggg      6480
cgttccttgc gcagctgtgc tcgacgttgt cactgaagcg ggaagggact ggctgctatt      6540
gggcgaagtg ccggggcagg atctcctgtc atctcacctt gctcctgccg agaaagtatc      6600
catcatggct gatgcaatgc ggcggctgca tacgcttgat ccggctacct gcccattcga      6660
ccaccaagcg aaacatcgca tcgagcgagc acgtactcgg atggaagccg gtcttgtcga      6720
tcaggatgat ctggacgaag agcatcaggg gctcgcgcca gccgaactgt tcgccaggct      6780
caaggcgcg                                                             6789
```

<210> SEQ ID NO 65
<211> LENGTH: 5250
<212> TYPE: DNA
<213> ORGANISM: Artificial Sequence
<220> FEATURE:
<223> OTHER INFORMATION: Description of Artificial Sequence: Synthetic hMT1 KI construct

<400> SEQUENCE: 65

```
agcccctccg cctcgtgctt gagttgaggc ctggcttggg cgctggggcc gccgcgtgcg      60
aatctggtgg caccttcgcg cctgtctcgc tgctttcgat aagtctctag ccatttaaaa     120
ttttttgatga cctgctgcga cgcttttttt ctggcaagat agtcttgtaa atgcgggcca     180
agatcgatct gcacactggt atttcggttt ttggggccgc gggcggcgac ggggcccgtg     240
cgtcccagcg cacatgttcg gcgaggcggg gcctgcgagc gcggccaccg agaatcggac     300
gggggtagtc tcaagctggc cggcctgctc tggtgcctgg cctcgcgccg ccgtgtatcg     360
ccccgccctg ggcggcaagg ctggcccggt cggcaccagt tgcgtgagcg aaagatggc     420
cgcttcccgg ccctgctgca gggagctcaa aatggaggac gcggcgctcg ggagagcggg     480
cgggtgagtc acccacacaa aggaaaaggg cctttccgtc ctcagccgtc gcttcatgtg     540
actccacgga gtaccgggcg ccgtccaggc acctcgatta gttctcgagc ttttggagta     600
cgtcgtcttt aggttggggg gaggggtttt atgcgatgga gtttccccac actgagtggg     660
tggagactga agttaggcca gcttggcact tgatgtaatt ctccttggaa tttgcccttt     720
ttgagtttgg atcttggttc attctcaagc ctcagacagt ggttcaaagt ttttttcttc     780
catttcaggt gtcgtggaat tggctagagc ttgcatgcct gcaggtcggc cgccacgacc     840
ggtgccgcca ccatcccctg acccacgccc ctgaccctc acaaggagac gaccttccat      900
gaccgagtac aagcccacgg tgcgcctcgc cacccgcgac gacgtccccc gggccgtacg     960
cacccctcgcc gccgcgttcg ccgactaccc gccacgcgc cacaccgtcg acccggaccg    1020
ccacatcgag cgggtcaccg agctgcaaga actcttcctc acgcgcgtcg gctcgacat     1080
cggcaaggtg tgggtcgcgg acgacggcgc cgcggtggcg gtctggacca cgccggagag    1140
cgtcgaagcg ggggcggtgt cgcccgagat cggccccgcg atggccgagt tgagcggttc    1200
ccggctggcc gcgcagcaac agatggaagg cctcctggcg ccgcaccggc caaggagcc    1260
cgcgtggttc ctggccaccg tcggcgtctc gcccgaccac cagggcaagg gtctgggcag    1320
cgccgtcgtg ctccccggag tggaggcggc cgagcgcgcc ggggtgcccg ccttcctgga    1380
gacctccgcg ccccgcaacc tcccttcta cgagcggctc ggcttcaccg tcaccgccga    1440
cgtcgaggtg cccgaaggac cgcgcacctg gtgcatgacc cgcaagcccg gtgcctgacg    1500
cccgccccac gacccgcagc gcccgaccga aggagcgca cgacccatg gctccgaccg    1560
aagccgaccc gggcggcccc gccgaccccg caccgccccc gaggcccac cgactctaga    1620
ggatcataat cagccatacc acatttgtag aggttttact tgctttaaaa aacctcccac    1680
acctccccct gaacctgaaa cataaaatga atgcaattgt tgttgttaac ttgtttattg    1740
cagcttataa tggttacaaa taaagcaata gcatcacaaa tttcacaaat aaagcatttt    1800
tttcactgca ttctagttgt ggtttgtcca aactcatcaa tgtatcttat catgtctgga    1860
tcctagcgtt taaacttaag cttggtaccg agctcggatc cactagtaat ggttacaaat    1920
aaagcaatag catcacaaat ttcacaaata aagcattttt ttcactgcat tctagttgtg    1980
gtttgtccaa actcatcaat gtatcttatc atgtctgtac gatgtacggg ccagatatac    2040
```

-continued

```
gcgttgacat tgattattga ctagttatta atagtaatca attacggggt cattagttca   2100
tagcccatat atggagttcc gcgttacata acttacggta aatggcccgc ctggctgacc   2160
gcccaacgac ccccgcccat tgacgtcaat aatgacgtat gttcccatag taacgccaat   2220
agggactttc cattgacgtc aatgggtgga gtatttacgg taaactgccc acttggcagt   2280
acatcaagtg tatcatatgc caagtacgcc ccctattgac gtcaatgacg gtaaatggcc   2340
cgcctggcat tatgcccagt acatgacctt atgggacttt cctacttggc agtacatcta   2400
cgtattagtc atcgctatta ccatggtgat gcggttttgg cagtacatca atgggcgtgg   2460
atagcggttt gactcacggg gatttccaag tctccacccc attgacgtca atgggagttt   2520
gttttggcac caaaatcaac gggactttcc aaaatgtcgt aacaactccg ccccattgac   2580
gcaaatgggc ggtaggcgtg tacggtggga ggtctatata agcagagctc tctggctaac   2640
tagagaaccc actgcttact ggcttatcga aattaatacg actcactata gggagaccca   2700
agctggctag ccaccatgca gggcaacggc agcgcgctgc caacgcctc ccagcccgtg   2760
ctccgcgggg acggcgcgcg gccctcgtgg ctggcgtccg ccctggcctg cgtcctcatc   2820
ttcaccatcg tggtggacat cctgggcaac ctcctggtca tcctgtcggt gtatcggaac   2880
aagaagctca ggaacgccgg caacatcttt gtggtgagct tagcggtggc agacctggtg   2940
gtggccattt atccgtaccc gttggtgctg atgtcgatat ttaacaacgg gtggaacctg   3000
ggctatctgc actgccaagt cagtgggttc ctgatgggcc tgagcgtcat cggctccata   3060
ttcaacatca ccggcatcgc catcaaccgc tactgctaca tctgccacag tctcaagtac   3120
gacaaactgt acagcagcaa gaactccctc tgctacgtgc tcctcatatg gctcctgacg   3180
ctggcggccg tcctgcccaa cctccgtgca gggactctcc agtacgaccc gaggatctac   3240
tcgtgcacct tcgcccagtc cgtcagctcc gcctacacca tcgccgtggt ggttttccac   3300
ttcctcgtcc ccatgatcat agtcatcttc tgttacctga gaatatggat cctggttctc   3360
caggtcagac agagggtgaa acctgaccgc aaacccaaac tgaaaccaca ggacttcagg   3420
aattttgtca ccatgtttgt ggttttttgtc ctttttgcca tttgctgggc tcctctgaac   3480
ttcattggcc tggccgtggc ctctgacccc gccagcatgg tgcctaggat cccagagtgg   3540
ctgtttgtgg ccagttacta catggcgtat ttcaacagct gcctcaatgc cattatatac   3600
gggctactga accaaaattt caggaaggaa tacaggagaa ttatagtctc gctctgtaca   3660
gccagggtgt tctttgtgga cagctctaac gacgtggccg atagggttaa atggaaaccg   3720
tctccactga tgaccaacaa taatgtagta aaggtggact ccgtttaagc ggccgctcga   3780
gtctagaggg cccgtttaaa cccgctgatc agcctcgact gtgccttcta gttgccagcc   3840
atctgttgtt tgcccctccc ccgtgccttc cttgaccctg gaaggtgcca ctcccactgt   3900
cctttcctaa taaaatgagg aaattgcatc gcattgtctg agtaggtgtc attctattct   3960
ggggggtggg gtggggcagg acagcaaggg ggaggattgg gaagacaata gcaggcatgc   4020
tggggatgcg gtgggctcta tggcttctga ggcggaaaga accagctggg gctctagggg   4080
gtatccccac gcgccctgta gcggcgcatt aagcgcggcg ggtgtggtgg ttacgcgcag   4140
cgtgaccgct acacttgcca gcgccctagc gcccgctcct ttcgctttct tcccttcctt   4200
tctcgccacg ttcgccgtacc gtcgaatcac cggtaacctt ataagggatt ttgccgattt   4260
cggcctattg gttaaaaaat gagctgattt aacaaaaatt taacgcgaat taattctgtg   4320
gaatgtgtgt cagttagggt gtggaaagtc cccaggctcc ccagcaggca gaagtatgca   4380
```

```
aagcatgcat ctcaattagt cagcaaccag gtgtggaaag tccccaggct ccccagcagg      4440
cagaagtatg caaagcatgc atctcaatta gtcagcaacc atagtcccgc ccctaactcc      4500
gcccatcccg cccctaactc cgcccagttc cgcccattct ccgccccatg gctgactaat      4560
tttttttatt tatgcagagg ccgaggccgc ctctgcctct gagctattcc agaagtagtg      4620
aggaggcttt tttggaggcc taggcttttg caaaaagctc ccgggagctt gtatatccat      4680
tttcggatct gatcaagaga caggatgagg atcgtttcgc atgattgaac aagatggatt      4740
gcacgcaggt tctccggccg cttgggtgga gaggctattc ggctatgact gggcacaaca      4800
gacaatcggc tgctctgatg ccgccgtgtt ccggctgtca gcgcagggc gcccggttct        4860 ttttgtcaag accgacctgt ccggtgccct gaatgaactg caggacgagg cagcgcggct      4920
atcgtggctg gccacgacgg gcgttccttg cgcagctgtg ctcgacgttg tcactgaagc      4980
gggaagggac tggctgctat tgggcgaagt gccggggcag gatctcctgt catctcacct      5040
tgctcctgcc gagaaagtat ccatcatggc tgatgcaatg cggcggctgc atacgcttga      5100
tccggctacc tgcccattcg accaccaagc gaaacatcgc atcgagcgag cacgtactcg      5160
gatggaagcc ggtcttgtcg atcaggatga tctggacgaa gagcatcagg gctcgcgcc       5220 agccgaactg ttcgccaggc tcaaggcgcg                                       5250
```

<210> SEQ ID NO 66
<211> LENGTH: 5286
<212> TYPE: DNA
<213> ORGANISM: Artificial Sequence
<220> FEATURE:
<223> OTHER INFORMATION: Description of Artificial Sequence: Synthetic
      hMT2 KI construct

<400> SEQUENCE: 66

```
agccccttcg cctcgtgctt gagttgaggc ctggcttggg cgctggggcc gccgcgtgcg        60
aatctggtgg caccttcgcg cctgtctcgc tgctttcgat aagtctctag ccatttaaaa      120
tttttgatga cctgctgcga cgcttttttt ctggcaagat agtcttgtaa atgcgggcca      180
agatcgatct gcacactggt atttcggttt ttggggccgc gggcggcgac ggggcccgtg      240
cgtcccagcg cacatgttcg gcgaggcggg gcctgcgagc gcggccaccg agaatcggac      300
gggggtagtc tcaagctggc cggcctgctc tggtgcctgg cctcgcgccg ccgtgtatcg      360
ccccgccctg ggcggcaagg ctggcccggt cggcaccagt tgcgtgagcg aaagatggc       420 cgcttcccgg ccctgctgca gggagctcaa aatggaggac gcggcgctcg ggagagcggg      480
cgggtgagtc acccacacaa aggaaaaggg cctttccgtc ctcagccgtc gcttcatgtg      540
actccacgga gtaccgggcg ccgtccaggc acctcgatta gttctcgagc ttttggagta      600
cgtcgtcttt aggttggggg gaggggtttt atgcgatgga gttcccca    actgagtggg      660 tggagactga agttaggcca gcttggcact tgatgtaatt ctccttggaa tttgcccttt      720
ttgagtttgg atcttggttc attctcaagc ctcagacagt ggttcaaagt ttttttcttc      780
catttcaggt gtcgtggaat tggctagagc ttgcatgcct gcaggtcggc cgccacgacc      840
ggtgccgcca ccatcccctg acccacgccc ctgacccctc acaaggagac gaccttccat      900
gaccgagtac aagcccacgg tgcgcctcgc cacccgcgac gacgtccccc gggccgtacg      960 cacccctcgcc gccgcgttcg ccgactaccc cgccacgcgc cacaccgtcg acccggaccg    1020
ccacatcgag cgggtcaccg agctgcaaga actcttcctc acgcgcgtcg gctcgacat     1080 cggcaaggtg tgggtcgcgg acgacggcgc cgcggtggcg gtctggacca cgccggagag    1140
```

```
cgtcgaagcg ggggcggtgt tcgccgagat cggcccgcgc atggccgagt tgagcggttc    1200
ccggctggcc gcgcagcaac agatggaagg cctcctggcg ccgcaccggc caaggagcc     1260 cgcgtggttc ctggccaccg tcggcgtctc gcccgaccac cagggcaagg gtctgggcag    1320
cgccgtcgtg ctccccggag tggaggcggc cgagcgcgcc ggggtgcccg ccttcctgga    1380
gacctccgcg ccccgcaacc tcccttcta cgagcggctc ggcttcaccg tcaccgccga    1440
cgtcgaggtg cccgaaggac cgcgcacctg gtgcatgacc cgcaagcccg gtgcctgacg    1500
cccgccccac gacccgcagc gcccgaccga aaggagcgca cgaccccatg gctccgaccg    1560
aagccgaccc gggcggcccc gccgaccccg cacccgcccc cgaggcccac cgactctaga    1620
ggatcataat cagccatacc acatttgtag aggtttact tgctttaaaa aacctcccac     1680
acctccccct gaacctgaaa cataaaatga atgcaattgt tgttgttaac ttgtttattg    1740
cagcttataa tggttacaaa taaagcaata gcatcacaaa tttcacaaat aaagcatttt    1800
tttcactgca ttctagttgt ggtttgtcca aactcatcaa tgtatcttat catgtctgga    1860
tcctagcgtt taaacttaag cttggtaccg agctcggatc cactagtaat ggttacaaat    1920
aaagcaatag catcacaaat ttcacaaata aagcattttt ttcactgcat tctagttgtg    1980
gtttgtccaa actcatcaat gtatcttatc atgtctgtac gatgtacggg ccagatatac    2040
gcgttgacat tgattattga ctagttatta atagtaatca attacggggt cattagttca    2100
tagcccatat atggagttcc gcgttacata acttacggta atggcccgc ctggctgacc     2160 gcccaacgac ccccgcccat tgacgtcaat aatgacgtat gttcccatag taacgccaat    2220
agggactttc cattgacgtc aatgggtgga gtatttacgg taaactgccc acttggcagt    2280
acatcaagtg tatcatatgc caagtacgcc ccctattgac gtcaatgacg gtaaatggcc    2340
cgcctggcat tatgcccagt acatgacctt atgggacttt cctacttggc agtacatcta    2400
cgtattagtc atcgctatta ccatggtgat gcggttttgg cagtacatca atgggcgtgg    2460
atagcggttt gactcacggg gatttccaag tctccacccc attgacgtca atgggagttt    2520
gttttggcac caaaatcaac gggactttcc aaaatgtcgt aacaactccg ccccattgac    2580
gcaaatgggc ggtaggcgtg tacggtggga ggtctatata agcagagctc tctggctaac    2640
tagagaaccc actgcttact ggcttatcga aattaatacg actcactata gggagaccca    2700
agctggctag ccaccatgtc agagaacggc tccttcgcca actgctgcga ggcgggcggg    2760
tgggcagtgc gcccgggctg gtcggggcct ggcagcgcgc ggcctccag  gaccctcga    2820 cctccctggg tggctccagc gctgtccgcg gtgctcatcg tcaccaccgc cgtggacgtc    2880
gtgggcaacc tcctggtgat cctctccgtg ctcaggaacc gcaagctccg gaacgcaggt    2940
aatttgttct tggtgagtct ggcattggct gacctggtgg tggccttcta ccctacccg     3000 ctaatcctcg tggccatctt ctatgacggc tgggccctgg gggaggagca ctgcaaggcc    3060
agcgcctttg tgatgggcct gagcgtcatc ggctctgtct tcaatatcac tgccatcgcc    3120
attaaccgct actgctacat ctgccacagc atggcctacc accgaatcta ccggcgctgg    3180 cacaccccctc tgcacatctg cctcatctgg ctcctcaccg tggtggcctt gctgcccaac    3240
ttctttgtgg ggtccctgga gtacgaccca cgcatctatt cctgcacctt catccagacc    3300
gccagcaccc agtacacggc ggcagtggtg gtcatccact cctcctcccc tatcgctgtc    3360
gtgtccttct gctacctgcg catctgggtg ctggtgcttc aggcccgcag gaaagccaag    3420
ccagagagca ggctgtgcct gaagcccagc gacttgcgga gctttctaac catgtttgtg    3480
gtgtttgtga tctttgccat ctgctgggct ccacttaact gcatcggcct cgctgtggcc    3540
```

```
atcaaccccc aagaaatggc tccccagatc cctgaggggc tatttgtcac tagctactta    3600
ctggcttatt tcaacagctg cctgaatgcc attgtctatg gctcttgaa ccaaaacttc     3660 cgcagggaat acaagaggat cctcttggcc ctttggaacc cacggcactg cattcaagat    3720
gcttccaagg gcagccacgc ggaggggctg cagagcccag ctccacccat cattggtgtg    3780
cagcaccagg cagatgctct ctaggcggcc gctcgagtct agagggcccg tttaaacccg    3840
ctgatcagcc tcgactgtgc cttctagttg ccagccatct gttgtttgcc ctcccccgt     3900 gccttccttg accctggaag gtgccactcc cactgtcctt tcctaataaa atgaggaaat    3960
tgcatcgcat tgtctgagta ggtgtcattc tattctgggg ggtggggtgg ggcaggacag    4020 caaggggag gattgggaag acaatagcag gcatgctggg gatgcggtgg gctctatggc     4080
ttctgaggcg gaaagaacca gctggggctc taggggggtat ccccacgcgc cctgtagcgc   4140
cgcattaagc gcggcgggtg tggtggttac gcgcagcgtg accgctacac ttgccagcgc    4200
cctagcgccc gctcctttcg ctttcttccc ttcctttctc gccacgttcg cctaccgtcg    4260
aatcaccggt aaccttataa gggattttgc cgatttcggc ctattggtta aaaaatgagc    4320
tgatttaaca aaaatttaac gcgaattaat tctgtggaat gtgtgtcagt tagggtgtgg    4380
aaagtcccca ggctccccag caggcagaag tatgcaaagc atgcatctca attagtcagc    4440
aaccaggtgt ggaaagtccc caggctcccc agcaggcaga agtatgcaaa gcatgcatct    4500
caattagtca gcaaccatag tcccgcccct aactccgccc atcccgcccc taactccgcc    4560
cagttccgcc cattctccgc cccatggctg actaattttt tttatttatg cagaggccga    4620
ggccgcctct gcctctgagc tattccagaa gtagtgagga ggcttttttg gaggcctagg    4680
cttttgcaaa aagctcccgg gagcttgtat atccattttc ggatctgatc aagagacagg    4740
atgaggatcg tttcgcatga ttgaacaaga tggattgcac gcaggttctc cggccgcttg    4800
ggtggagagg ctattcggct atgactgggc acaacagaca atcggctgct ctgatgccgc    4860
cgtgttccgg ctgtcagcgc aggggcgccc ggttcttttt gtcaagaccg acctgtccgg    4920
tgccctgaat gaactgcagg acgaggcagc gcggctatcg tggctggcca cgacgggcgt    4980
tccttgcgca gctgtgctcg acgttgtcac tgaagcggga aggactggc tgctattggg     5040 cgaagtgccg gggcaggatc tcctgtcatc tcaccttgct cctgccgaga aagtatccat    5100
catggctgat gcaatgcggc ggctgcatac gcttgatccg gctacctgcc cattcgacca    5160
ccaagcgaaa catcgcatcg agcgagcacg tactcggatg aagccggtc ttgtcgatca     5220 ggatgatctg gacgaagagc atcaggggct cgcgccagcc gaactgttcg ccaggctcaa    5280
ggcgcg                                                              5286
```

<210> SEQ ID NO 67
<211> LENGTH: 9944
<212> TYPE: DNA
<213> ORGANISM: Artificial Sequence
<220> FEATURE:
<223> OTHER INFORMATION: Description of Artificial Sequence: Synthetic 5F11 KI construct

<400> SEQUENCE: 67

```
agccccttcg cctcgtgctt gagttgaggc ctggcttggg cgctggggcc gccgcgtgcg     60
aatctggtgg caccttcgcg cctgtctcgc tgctttcgat aagtctctag ccatttaaaa    120 ttttgatga cctgctgcga cgcttttttt ctggcaagat agtcttgtaa atgcgggcca     180
agatcgatct gcacactggt atttcggttt ttggggccgc gggcggcgac ggggcccgtg    240
```

```
cgtcccagcg cacatgttcg gcgaggcggg gcctgcgagc gcggccaccg agaatcggac      300
gggggtagtc tcaagctggc cggcctgctc tggtgcctgg cctcgcgccg ccgtgtatcg      360
ccccgccctg ggcggcaagg ctggcccggt cggcaccagt tgcgtgagcg gaaagatggc      420
cgcttcccgg ccctgctgca gggagctcaa aatggaggac gcggcgctcg ggagagcggg      480
cgggtgagtc acccacacaa aggaaaaggg cctttccgtc ctcagccgtc gcttcatgtg      540
actccacgga gtaccgggcg ccgtccaggc acctcgatta gttctcgagc ttttggagta      600
cgtcgtcttt aggttggggg gagggggtttt atgcgatgga gtttccccac actgagtggg      660
tggagactga agttaggcca gcttggcact tgatgtaatt ctccttggaa tttgcccttt      720
ttgagtttgg atcttggttc attctcaagc ctcagacagt ggttcaaagt ttttttcttc      780
catttcaggt gtcgtggaat tggctagagc ttgcatgcct gcaggtcggc cgccacgacc      840
ggtgccgcca ccatcccctg acccacgccc ctgaccccctc acaaggagac gaccttccat      900
gaccgagtac aagcccacgg tgcgcctcgc cacccgcgac gacgtccccc gggccgtacg      960
caccctcgcc gccgcgttcg ccgactaccc cgccacgcgc cacaccgtcg acccggaccg     1020
ccacatcgag cgggtcaccg agctgcaaga actcttcctc acgcgcgtcg ggctcgacat     1080
cggcaaggtg tgggtcgcgg acgacggcgc cgcggtggcg gtctggacca cgccggagag     1140
cgtcgaagcg ggggcggtgt tcgccgagat cggcccgcgc atggccgagt tgagcggttc     1200
ccggctggcc gcgcagcaac agatggaagg cctcctggcg ccgcaccggc ccaaggagcc     1260
cgcgtggttc ctggccaccg tcggcgtctc gcccgaccac cagggcaagg gtctgggcag     1320
cgccgtcgtg ctccccggag tggaggcggc cgagcgcgcc ggggtgcccg ccttcctgga     1380
gacctccgcg ccccgcaacc tccccttcta cgagcggctc ggcttcaccg tcaccgccga     1440
cgtcgaggtg cccgaaggac cgcgcacctg gtgcatgacc cgcaagcccg gtgcctgacg     1500
cccgccccac gacccgcagc gcccgaccga aaggagcgca cgaccccatg gctccgaccg     1560
aagccgaccc gggcggcccc gccgaccccg caccccgcccc cgaggccccac cgactctaga     1620 ggatcataat cagccatacc acatttgtag aggttttact tgctttaaaa aacctcccac     1680
acctccccct gaacctgaaa cataaaatga atgcaattgt tgttgttaac ttgtttattg     1740
cagcttataa tggttacaaa taaagcaata gcatcacaaa tttcacaaat aaagcatttt     1800
tttcactgca ttctagttgt ggtttgtcca aactcatcaa tgtatcttat catgtctgga     1860
tcctagcgtt taaacttaag cttggtaccg agctcggatc cactagtaat ggttacaaat     1920
aaagcaatag catcacaaat ttcacaaata aagcattttt ttcactgcat tctagttgtg     1980
gtttgtccaa actcatcaat gtatcttatc atgtctgtac gatgtacggg ccagatatac     2040
gcgcgaggcc tccgcgccgg gttttggcgc ctcccgcggg cgcccccctc ctcacggcga     2100
gcgctgccac gtcagacgaa gggcgcagcg agcgtcctga tccttccgcc cggacgctca     2160
ggacagcggc ccgctgctca taagactcgg ccttagaacc ccagtatcag cagaaggaca     2220
ttttaggacg ggacttgggt gactctaggg cactggtttt cttccagag agcggaacag     2280 gcgaggaaaa gtagtccctt ctcggcgatt ctgcggaggg atctccgtgg ggcggtgaac     2340
gccgatgatt atataaggac gcgccgggtg tggcacagct agttccgtcg cagccgggat     2400
ttgggtcgcg gttcttgttt gtggatcgct gtgatcgtca cttggtgagt agcgggctgc     2460
tgggctggcc ggggctttcg tggccgccgg gccgctcggt gggacggaag cgtgtggaga     2520
gaccgccaag ggctgtagtc tgggtccgcg agcaaggttg ccctgaactg ggggttgggg     2580
```

```
ggagcgcagc aaaatggcgg ctgttcccga gtcttgaatg gaagacgctt gtgaggcggg    2640
ctgtgaggtc gttgaaacaa ggtgggggc atggtgggcg gcaagaaccc aaggtcttga    2700
ggccttcgct aatgcgggaa agctcttatt cgggtgagat gggctggggc accatctggg    2760
gaccctgacg tgaagtttgt cactgactgg agaactcggt ttgtcgtctg ttgcgggggc    2820
ggcagttatg gcggtgccgt tgggcagtgc accgtacct ttgggagcgc gcgccctcgt     2880
cgtgtcgtga cgtcacccgt tctgttggct tataatgcag ggtggggcca cctgccggta    2940
ggtgtgcggt aggcttttct ccgtcgcagg acgcagggtt cgggcctagg gtaggctctc    3000
ctgaatcgac aggcgccgga cctctggtga ggggagggga aagtgaggcg tcagtttctt    3060
tggtcggttt tatgtaccta tcttcttaag tagctgaagc tccggttttg aactatgcgc    3120
tcggggttgg cgagtgtgtt ttgtgaagtt ttttaggcac cttttgaaat gtaatcattt    3180
gggtcaatat gtaattttca gtgttagact agtaaattgt ccgctaaatt ctggccgttt    3240
ttggcttttt tgttagacag atctgtttaa acttaagctt gccgccacca tgggatggag    3300
ctgtatcatc ctgttcctcg tggccacagc aaccggtgtc cacagcgaca tccagatgac    3360
ccagtctcca acctcactgt ctgcatctgt aggagacaga gtcaccatca cttgtcgggc    3420
gagtcagggt attagcagct ggttaacctg gtatcagcag aaaccagaga aagcccctaa    3480
gtccctgatc tatgctgcat ccagtttgca aagtggggtc ccatcaaggt tcagcggcag    3540
tggatctggg acagatttca ctctcaccat cagcagcctg cagcctgaag attttgcaac    3600
ttattactgc caacagtatg atagttaccc tatcaccttc ggccaaggga cacgactgga    3660
gattaaacgt acggtggcgg cgccatctgt cttcatcttc ccgccatctg atgagcagtt    3720
gaaatctgga actgcctctg ttgtgtgcct gctgaataac ttctatccca gagaggccaa    3780
agtacagtgg aaggtggata acgccctcca atcgggtaac tcccaggaga gtgtcacaga    3840
gcaggacagc aaggacagca cctacagcct cagcagcacc ctgacgctga gcaaagcaga    3900
ctacgagaaa cacaaagtct acgcctgcga agtcacccat cagggcctga gctcgcccgt    3960
cacaaagagc ttcaacaggg gagagtgtta gggatccatc tagaagggag aagtgccccc    4020
acctgctcct cagttccagc ctgacccct cccatccttt ggcctctgac cttttttcca    4080
caggggacct accctatttg cggtcctcca gctcatcttt cacctcaccc cctcctcct     4140 ccttggcttt aattatgcta atgttggagg agaatgaata aataaagtga atctttgcac    4200
ctgtggtttc tctctttcct catttaataa ttattatctg ttgttttacc aactactcaa    4260
tttctcttat aagggactaa atatgtagtc atcctaaggc gcataaccat ttataaaaat    4320
catccttcat tctattttac cctatcatcc tctgcaagac agtcctccct caaacccaca    4380
agccttctgt cctcacagtc ccctgggcca tcggaccgct atcaggacat agcgttggct    4440
acccgtgata ttgctgaaga gcttggcggc gaatgggctg accgcttcct cgtgctttac    4500
ggtatcgccg ctcccgattc gcagcgcatc gccttctatc gccttcttga cgagttcttc    4560
tgagcgggac tctggggttc gaaatgaccg accaagcgac gcccaacctg ccatcacgag    4620
atttcgattc caccgccgcc ttctatgaaa ggttgggctt cggaatcgtt ttccgggacg    4680
ccggctggat gatcctccag cgcgggatc tcatgctgga gttcttcgcc cacccccaact    4740 tgtttattgc agcttataat ggttacaaat aaagcaatag catcacaaat ttcacaaata    4800
aagcattttt ttcactgcat tctagttgtg gtttgtccaa actcatcaat gtatcttatc    4860
atgtctgtat accgtcgacc tctagctaga gcttggcgta atcatggtca tagctgtttc    4920
ctgtgtgaaa ttgttatccg ctcacaattc cacacaacat acgagccgga agcataaagt    4980
```

```
gtaaagcctg gggtgcctaa tgagtgagct aactcacatt aattgcgttg cgctcactgc   5040
ccgctttcca gtcgggaaac ctgtcgtgcc agctgcatta atgaatcggc caacgcgcgg   5100
ggagaggcgg tttgcgtatt gggcgctctt ccgcttcctc gctcactgac tcgctgcgct   5160
cggtcgttcg gctgcggcga gcggtatcag ctcactcaaa ggcggtaata cggttatcca   5220
cagaatcagg ggataacgca ggaaagaaca tgcgaggcct ccgcgccggg ttttggcgcc   5280
tcccgcgggc gcccccctcc tcacggcgag cgctgccacg tcagacgaag gcgcagcga   5340 gcgtcctgat ccttccgccc ggacgctcag gacagcggcc cgctgctcat aagactcggc   5400
cttagaaccc cagtatcagc agaaggacat tttaggacgg gacttgggtg actctagggc   5460
actggttttc tttccagaga gcggaacagg cgaggaaaag tagtcccttc tcggcgattc   5520
tgcggaggga tctccgtggg gcggtgaacg ccgatgatta tataaggacg cgccgggtgt   5580
ggcacagcta gttccgtcgc agccgggatt tgggtcgcgg ttcttgtttg tggatcgctg   5640
tgatcgtcac ttggtgagta gcgggctgct gggctggccg gggctttcgt ggccgccggg   5700
ccgctcggtg ggacggaagc gtgtggagag accgccaagg gctgtagtct gggtccgcga   5760
gcaaggttgc cctgaactgg gggttggggg gagcgcagca aaatggcggc tgttcccgag   5820
tcttgaatgg aagacgcttg tgaggcgggc tgtgaggtcg ttgaaacaag gtggggggca   5880
tggtgggcgg caagaaccca aggtcttgag gccttcgcta atgcgggaaa gctcttattc   5940
gggtgagatg ggctggggca ccatctgggg accctgacgt gaagtttgtc actgactgga   6000
gaactcggtt tgtcgtctgt tgcggggcg gcagttatgg cggtgccgtt gggcagtgca   6060
cccgtacctt tgggagcgcg cgccctcgtc gtgtcgtgac gtcacccgtt ctgttggctt   6120
ataatgcagg gtggggccac ctgccggtag gtgtgcggta ggcttttctc cgtcgcagga   6180
cgcagggttc gggcctaggg taggctctcc tgaatcgaca ggcgccggac ctctggtgag   6240
gggagggata agtgaggcgt cagtttcttt ggtcggtttt atgtacctat cttcttaagt   6300
agctgaagct ccggttttga actatgcgct cggggttggc gagtgtgttt tgtgaagttt   6360
tttaggcacc tttgaaatg taatcatttg ggtcaatatg taattttcag tgttagacta   6420
gtaaattgtc cgctaaattc tggccgtttt tggctttttt gttagacaga tctgtttaaa   6480
cttaagcttg ccgccaccat gggatggagc tgtatcatcc tgttcctcgt ggccacagca   6540
accggtgtcc acagccaggt gcagctacag cagtggggcg caggactgtt gaagccttcg   6600
gagaccctgt ccctcacctg cgctgtctat ggtgggtcct tcagtgctta ctactggagc   6660
tggatccgcc agccccaagg gaaggggctg gagtggattg ggacatcaa tcatggtgga   6720 ggcaccaact acaacccgtc cctcaagagt cgagtcacca tatcagtaga cacgtccaag   6780
aaccagttct ccctgaagct gaactctgta accgccgcgg acacggctgt gtattactgt   6840
gcgagcctaa ctgcctactg gggccaggga agcctggtca ccgtctcctc agctagcacc   6900
aagggcccat cggtcttccc cctggcaccc tcctccaaga gcacctctgg gggcacagcg   6960
gccctgggct gcctggtcaa ggactacttc cccgaaccgg tgacggtgtc gtggaactca   7020
ggcgccctga ccagcggcgt gcacaccttc ccggccgtcc tacagtcctc aggactctac   7080
tccctcagca gcgtggtgac cgtgcccctcc agcagcttgg gcacccagac ctacatctgc   7140
aacgtgaatc acaagcccag caacaccaag gtggacaaga gagttgagcc caaatcttgt   7200
gacaaaactc acacatgccc accgtgccca gcacctgaac tcctggggg accgtcagtc   7260 ttcctcttcc ccccaaaacc caaggacacc ctcatgatct cccggacccc tgaggtcaca   7320
```

```
tgcgtggtgg tggacgtgag ccacgaagac cctgaggtca agttcaactg gtacgtggac    7380
ggcgtggagg tgcataatgc caagacaaag ccgcgggagg agcagtacaa cagcacgtac    7440
cgtgtggtca gcgtcctcac cgtcctgcac caggactggc tgaatggcaa ggagtacaag    7500
tgcaaggtct ccaacaaagc cctcccagcc cccatcgaga aaaccatctc caaagccaaa    7560
gggcagcccc gagaaccaca ggtgtacacc ctgcccccat cccgggatga gctgaccaag    7620
aaccaggtca gcctgacctg cctggtcaaa ggcttctatc ccagcgacat cgccgtggag    7680
tgggagagca atgggcagcc ggagaacaac tacaagacca cgcctcccgt gctggactcc    7740
gacggctcct tcttcctcta cagcaagctc accgtggaca agagcaggtg gcagcagggg    7800
aacgtcttct catgctccgt gatgcatgag gctctgcaca accactacac gcagaagagc    7860
ctctccctgt ctccgggtaa atgagtgcga cggccggcaa gggatccagg ggagagtgtt    7920
agagggagaa gtgcccccac ctgctcctca gttccagcct gacccctcc catcctttgg    7980 cctctgaccc ttttcccaca ggggacctac ccctattgcg gtcctccagc tcatctttca    8040
cctcaccccc ctcctcctcc ttggctttaa ttatgctaat gttggaggag aatgaataaa    8100
taaagtgaat ctttgcacct gtggtttctc tctttcctca tttaataatt attatctgtt    8160
gttttaccaa ctactcaatt tctcttataa gggactaaat atgtagtcat cctaaggcgc    8220
ataaccattt ataaaaatca tccttcattc tattttaccc tatcatcctc tgcaagacag    8280
tcctccctca aacccacaag cctctgtgcc tcacagtccc ctgggccatg tgagcaaaag    8340
gccagcaaaa ggccaggaac cgtaaaaagg ccgcgttgct ggcgtttttc cataggctcc    8400
gcccccctga cgagcatcac aaaaatcgac gctcaagtca gaggtggcga acccgatag    8460 ttgcggccgc tcgagtctag agggcccgtt taaacccgct gatcagcctc gactgtgcct    8520
tctagttgcc agccatctgt tgtttgcccc tcccccgtgc cttccttgac cctggaaggt    8580
gccactccca ctgtcctttc ctaataaaat gaggaaattg catcgcattg tctgagtagg    8640
tgtcattcta ttctgggggg tggggtgggg caggacagca agggggagga ttgggaagac    8700
aatagcaggc atgctgggga tgcggtgggc tctatggctt ctgaggcgga agaaccagc    8760 tggggctcta gggggtatcc ccacgcgccc tgtagcggcg cattaagcgc ggcgggtgtg    8820
gtggttacgc gcagcgtgac cgctacactt gccagcgccc tagcgcccgc tcctttcgct    8880
ttcttccctt cctttctcgc cacgttcgcc ggctttcccc gtcaagctct aaatcgggg    8940 gatttttgccg atttcggcct attggttaaa aaatgagctg atttaacaaa aatttaacgc    9000
gaattaattc tgtggaatgt gtgtcagtta gggtgtggaa agtccccagg ctccccagca    9060
ggcagaagta tgcaaagcat gcatctcaat tagtcagcaa ccaggtgtgg aaagtccca    9120 ggctccccag caggcagaag tatgcaaagc atgcatctca attagtcagc aaccatagtc    9180
ccgcccctaa ctccgcccat cccgcccta actccgccca gttccgccca ttctccgcc    9240 catggctgac taatttttt tattatatgca gaggccgagg ccgcctctgc ctctgagcta    9300
ttccagaagt agtgaggagg cttttttgga ggcctaggct tttgcaaaaa gctcccggga    9360
gcttgtatat ccattttcgg atctgatcaa gagacaggat gaggatcgtt tcgcatgatt    9420
gaacaagatg gattgcacgc aggttctccg gccgcttggg tggagaggct attcggctat    9480
gactgggcac aacagacaat cggctgctct gatgccgccg tgttccggct gtcagcgcag    9540
gggcgcccgg ttctttttgt caagaccgac ctgtccggtg ccctgaatga actgcaggac    9600
gaggcagcgc ggctatcgtg gctggccacg acgggcgttc cttgcgcagc tgtgctcgac    9660
gttgtcactg aagcgggaag ggactggctg ctattgggcg aagtgccggg gcaggatctc    9720
```

| | |
|---|---|
| ctgtcatctc accttgctcc tgccgagaaa gtatccatca tggctgatgc aatgcggcgg | 9780 |
| ctgcatacgc ttgatccggc tacctgccca ttcgaccacc aagcgaaaca tcgcatcgag | 9840 |
| cgagcacgta ctcggatgga agccggtctt gtcgatcagg atgatctgga cgaagagcat | 9900 |
| caggggctcg cgccagccga actgttcgcc aggctcaagg cgcg | 9944 |

<210> SEQ ID NO 68
<211> LENGTH: 6012
<212> TYPE: DNA
<213> ORGANISM: Artificial Sequence
<220> FEATURE:
<223> OTHER INFORMATION: Description of Artificial Sequence: Synthetic
      Luciferase KI construct

<400> SEQUENCE: 68

| | |
|---|---|
| agccccttcg cctcgtgctt gagttgaggc ctggcttggg cgctggggcc gccgcgtgcg | 60 |
| aatctggtgg caccttcgcg cctgtctcgc tgctttcgat aagtctctag ccatttaaaa | 120 |
| ttttgatga cctgctgcga cgcttttttt ctggcaagat agtcttgtaa atgcgggcca | 180 |
| agatcgatct gcacactggt atttcggttt ttggggccgc gggcggcgac ggggcccgtg | 240 |
| cgtcccagcg cacatgttcg gcgaggcggg gcctgcgagc gcggccaccg agaatcggac | 300 |
| gggggtagtc tcaagctggc cggcctgctc tggtgcctgg cctcgcgccg ccgtgtatcg | 360 |
| ccccgccctg ggcggcaagg ctggcccggt cggcaccagt tgcgtgagcg gaaagatggc | 420 |
| cgcttcccgg ccctgctgca gggagctcaa aatggaggac gcggcgctcg ggagagcggg | 480 |
| cgggtgagtc acccacacaa aggaaaaggg cctttccgtc ctcagccgtc gcttcatgtg | 540 |
| actccacgga gtaccgggcg ccgtccaggc acctcgatta gttctcgagc ttttggagta | 600 |
| cgtcgtcttt aggttggggg gaggggtttt atgcgatgga gtttccccac actgagtggg | 660 |
| tggagactga agttaggcca gcttggcact tgatgtaatt ctccttggaa tttgcccttt | 720 |
| ttgagtttgg atcttggttc attctcaagc ctcagacagt ggttcaaagt ttttttcttc | 780 |
| catttcaggt gtcgtggaat tggctagagc ttgcatgcct gcaggtcggc cgccacgacc | 840 |
| ggtgccgcca ccatcccctg acccacgccc ctgaccccct caaggagac gaccttccat | 900 |
| gaccgagtac aagcccacgg tgcgcctcgc cacccgcgac gacgtccccc gggccgtacg | 960 |
| caccctcgcc gccgcgttcg ccgactaccc cgccacgcgc cacaccgtcg acccggaccg | 1020 |
| ccacatcgag cgggtcaccg agctgcaaga actcttcctc acgcgcgtcg ggctcgacat | 1080 |
| cggcaaggtg tgggtcgcgg acgacggcgc cgcggtggcg gtctggacca cgccggagag | 1140 |
| cgtcgaagcg ggggcggtgt tcgccgagat cggcccgcgc atggccgagt tgagcggttc | 1200 |
| ccggctggcc gcgcagcaac agatggaagg cctcctggcg ccgcaccggc caaggagcc | 1260 |
| cgcgtggttc ctggccaccg tcggcgtctc gcccgaccac cagggcaagg gtctgggcag | 1320 |
| cgccgtcgtg ctccccggag tggaggcggc cgagcgcgcc ggggtgcccg ccttcctgga | 1380 |
| gacctccgcg ccccgcaacc tccccttcta cgagcggctc ggcttcaccg tcaccgccga | 1440 |
| cgtcgaggtg cccgaaggac cgcgcacctg gtgcatgacc cgcaagcccg gtgcctgacg | 1500 |
| cccgccccac gaccccgcag ccccgaccga aaggagcgca cgaccccatg ctccgaccg | 1560 |
| aagccgaccc gggcggcccc gccgaccccg cacccgcccc cgaggcccac cgactctaga | 1620 |
| ggatcataat cagccatacc acatttgtag aggttttact tgctttaaaa aacctcccac | 1680 |
| acctccccct gaacctgaaa cataaaatga atgcaattgt tgttgttaac ttgtttattg | 1740 |
| cagcttataa tggttacaaa taaagcaata gcatcacaaa tttcacaaat aaagcatttt | 1800 |

```
tttcactgca ttctagttgt ggtttgtcca aactcatcaa tgtatcttat catgtctgga    1860
tcctagcgtt taaacttaag cttggtaccg agctcggatc cactagcgat gtacgggcca    1920
gatatacgcg ttgacattga ttattgacta gttattaata gtaatcaatt acggggtcat    1980
tagttcatag cccatatatg gagttccgcg ttacataact tacggtaaat ggcccgcctg    2040
gctgaccgcc caacgacccc cgcccattga cgtcaataat gacgtatgtt cccatagtaa    2100
cgccaatagg gactttccat tgacgtcaat gggtggagta tttacggtaa actgcccact    2160
tggcagtaca tcaagtgtat catatgccaa gtacgccccc tattgacgtc aatgacggta    2220
aatggcccgc ctggcattat gcccagtaca tgaccttatg ggactttcct acttggcagt    2280
acatctacgt attagtcatc gctattacca tggtgatgcg gttttggcag tacatcaatg    2340
ggcgtggata gcggtttgac tcacggggat ttccaagtct ccaccccatt gacgtcaatg    2400
ggagtttgtt ttggcaccaa atcaacggg actttccaaa atgtcgtaac aactccgccc    2460
cattgacgca aatgggcggt aggcgtgtac ggtgggaggt ctatataagc agagctctct    2520
ggctaactag agaacccact gcttactggc ttatcgaaat taatacgact cactataggg    2580
agacccaagc tggctagcgc tgatatcgat cgcgagcggc cgcgaattca ctagtgattg    2640
cagaattcat ggaagatgcc aaaaacatta agaagggccc agcgccattc tacccactcg    2700
aagacgggac cgccggcgag cagctgcaca aagccatgaa gcgctacgcc ctggtgcccg    2760
gcaccatcgc ctttaccgac gcacatatcg aggtggacat tacctacgcc gagtacttcg    2820
agatgagcgt tcggctggca gaagctatga acgctatgg gctgaataca aaccatcgga    2880
tcgtggtgtg cagcgagaat agcttgcagt tcttcatgcc cgtgttgggt gccctgttca    2940
tcggtgtggc tgtggcccca gctaacgaca tctacaacga gcgcgagctg ctgaacagca    3000
tgggcatcag ccagcccacc gtcgtattcg tgagcaagaa agggctgcaa aagatcctca    3060
acgtgcaaaa gaagctaccg atcatacaaa agatcatcat catggatagc aagaccgact    3120
accagggctt ccaaagcatg tacaccttcg tgacttccca tttgccaccc ggcttcaacg    3180
agtacgactt cgtgcccgag agcttcgacc gggacaaaac catcgccctg atcatgaaca    3240
gtagtggcag taccggattg cccaagggcg tagccctacc gcaccgcacc gcttgtgtcc    3300
gattcagtca tgcccgcgac cccatcttcg gcaaccagat catccccgac accgctatcc    3360
tcagcgtggt gccatttcac cacggcttcg gcatgttcac cacgctgggc tacttgatct    3420
gcggctttcg ggtcgtgctc atgtaccgct tcgaggagga gctattcttg cgcagcttgc    3480
aagactataa gattcaatct gccctgctgg tgcccacact atttagcttc ttcgctaaga    3540
gcactctcat cgacaagtac gacctaagca acttgcacga gatcgccagc ggcggggcgc    3600
cgctcagcaa ggaggtaggt gaggccgtgg ccaaacgctt ccacctacca ggcatccgcc    3660
agggctacgg cctgacagaa acaaccagcg ccattctgat caccccgaa ggggacgaca    3720 agcctggcgc agtaggcaag gtggtgccct tcttcgaggc taaggtggtg acttggaca    3780 ccggtaagac actgggtgtg aaccagcgcg gcgagctgtg cgtccgtggc cccatgatca    3840
tgagcggcta cgttaacaac cccgaggcta caaacgctct catcgacaag acggctggc    3900 tgcacagcgg cgacatcgcc tactgggacg aggacgagca cttcttcatc gtggaccggc    3960
tgaagagcct gatcaaatac aagggctacc aggtagcccc agccgaactg gagagcatcc    4020
tgctgcaaca ccccaacatc ttcgacgcg ggtcgccgg cctgcccgac gacgatgccg    4080
gcgagctgcc cgccgcagtc gtcgtgctgg aacacggtaa aaccatgacc gagaaggaga    4140
```

```
tcgtggacta tgtggccagc caggttacaa ccgccaagaa gctgcgcggt ggtgttgtgt    4200
tcgtggacga ggtgcctaaa ggactgaccg gcaagttgga cgcccgcaag atccgcgaga    4260
ttctcattaa ggccaagaag ggcggcaaga tcgccgtgta ataattctag agtcggggcg    4320
gccggccgct tcgagcagac atgataagat acattgatga gtttggacaa accacaacta    4380
gaatgcagtg aaaaaaatgc tttatttgtg aaatttgtga tgctattgct ttatttgtaa    4440
ccattataag ctgcaataaa caagttaaca acaacaattg cattcatttt atgtttcagg    4500
ttcaggggga ggtgtgggag gttttttaaa gcggccgctc gagtctagag ggcccgttta    4560
aacccgctga tcagcctcga ctgtgccttc tagttgccag ccatctgttg tttgcccctc    4620
ccccgtgcct tccttgaccc tggaaggtgc cactcccact gtcctttcct aataaaatga    4680
ggaaattgca tcgcattgtc tgagtaggtg tcattctatt ctggggggtg gggtggggca    4740
ggacagcaag ggggaggatt gggaagacaa tagcaggcat gctggggatg cggtgggctc    4800
tatggcttct gaggcggaaa gaaccagctg gggctctagg gggtatcccc acgcgccctg    4860
tagcggcgca ttaagcgcgg cgggtgtggt ggttacgcgc agcgtgaccg ctacacttgc    4920
cagcgcccta gcgcccgctc ctttcgcttt cttcccttcc tttctcgcca cgttcgccta    4980
ccgtcgaatc accggtaacc ttataaggga ttttgccgat tcggcctat tggttaaaaa    5040 atgagctgat ttaacaaaaa tttaacgcga attaattctg tggaatgtgt gtcagttagg    5100
gtgtggaaag tccccaggct ccccagcagg cagaagtatg caaagcatgc atctcaatta    5160
gtcagcaacc aggtgtggaa agtccccagg ctccccagca ggcagaagta tgcaaagcat    5220
gcatctcaat tagtcagcaa ccatagtccc gcccctaact ccgcccatcc cgcccctaac    5280
tccgcccagt tccgcccatt ctccgcccca tggctgacta attttttttta tttatgcaga    5340 ggccgaggcc gcctctgcct ctgagctatt ccagaagtag tgaggaggct ttttttggagg    5400 cctaggcttt tgcaaaaagc tcccgggagc ttgtatatcc attttcggat ctgatcaaga    5460
gacaggatga ggatcgtttc gcatgattga acaagatgga ttgcacgcag gttctccggc    5520
cgcttgggtg gagaggctat tcggctatga ctgggcacaa cagacaatcg gctgctctga    5580
tgccgccgtg ttccggctgt cagcgcaggg gcgcccggtt cttttttgtca agaccgacct    5640 gtccggtgcc ctgaatgaac tgcaggacga ggcagcgcgg ctatcgtggc tggccacgac    5700
gggcgttcct tgcgcagctg tgctcgacgt tgtcactgaa gcgggaaggg actggctgct    5760
attgggcgaa gtgccggggc aggatctcct gtcatctcac cttgctcctg ccgagaaagt    5820
atccatcatg gctgatgcaa tgcggcggct gcatacgctt gatccggcta cctgcccatt    5880
cgaccaccaa gcgaaacatc gcatcgagcg agcacgtact cggatggaag ccggtcttgt    5940
cgatcaggat gatctggacg aagagcatca ggggctcgcg ccagccgaac tgttcgccag    6000
gctcaaggcg cg                                                       6012
```

<210> SEQ ID NO 69
<211> LENGTH: 9
<212> TYPE: PRT
<213> ORGANISM: Unknown
<220> FEATURE:
<223> OTHER INFORMATION: Description of Unknown: "LAGLIDADG" motif

<400> SEQUENCE: 69

Leu Ala Gly Leu Ile Asp Ala Asp Gly
1               5

<210> SEQ ID NO 70

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 70

His His His His His His
1               5
```